United States Patent
Burns et al.

(10) Patent No.: US 11,267,826 B2
(45) Date of Patent: Mar. 8, 2022

(54) PENICILLIN-BINDING PROTEIN INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Guo-Hua Chu, Exton, PA (US); Randy W. Jackson, Livingston, MT (US); Jodie Hamrick, New Holland, PA (US); Matthew Lucas, Malvern, PA (US); Steven A. Boyd, Mars, PA (US); Jiangchao Yao, Princeton, NJ (US); Eugen F. Mesaros, Wallingford, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 15 days.

(21) Appl. No.: 16/616,382

(22) PCT Filed: May 25, 2018

(86) PCT No.: PCT/US2018/034660
§ 371 (c)(1),
(2) Date: Nov. 22, 2019

(87) PCT Pub. No.: WO2018/218154
PCT Pub. Date: Nov. 29, 2018

(65) Prior Publication Data
US 2020/0102331 A1    Apr. 2, 2020

Related U.S. Application Data

(60) Provisional application No. 62/511,613, filed on May 26, 2017, provisional application No. 62/582,870, filed on Nov. 7, 2017.

(51) Int. Cl.
*C07F 5/02* (2006.01)
*A61K 45/06* (2006.01)

(52) U.S. Cl.
CPC .............. *C07F 5/025* (2013.01); *A61K 45/06* (2013.01)

(58) Field of Classification Search
CPC ..................................................... C07F 5/025
See application file for complete search history.

(56) References Cited

U.S. PATENT DOCUMENTS

| | | | |
|---|---|---|---|
| 4,427,690 A | 1/1984 | Cole et al. | |
| 7,271,186 B1 | 9/2007 | Shoichet et al. | |
| 7,714,159 B2 | 5/2010 | Pickersgill et al. | |
| 8,283,467 B2 | 10/2012 | Ammoscato et al. | |
| 8,680,136 B2 | 3/2014 | Hirst et al. | |
| 9,101,638 B2 | 8/2015 | Reddy et al. | |
| 9,511,142 B2 | 12/2016 | Burns et al. | |
| 9,642,869 B2 | 5/2017 | Reddy et al. | |
| 9,802,966 B2 | 10/2017 | Burns et al. | |
| 9,963,467 B2 | 5/2018 | Reddy et al. | |
| 10,206,937 B2 | 2/2019 | Reddy et al. | |
| 10,479,805 B2 | 11/2019 | Wu et al. | |
| 10,889,600 B2 | 1/2021 | Amann et al. | |
| 2009/0156518 A1 | 6/2009 | Zhang | |
| 2010/0056478 A1 | 3/2010 | Desarbre et al. | |
| 2010/0120715 A1 | 5/2010 | Burns et al. | |
| 2010/0286092 A1 | 11/2010 | Burns et al. | |
| 2010/0292185 A1 | 11/2010 | Burns et al. | |
| 2010/0317621 A1 | 12/2010 | Burns et al. | |
| 2011/0294777 A1 | 12/2011 | Blizzard et al. | |
| 2012/0040932 A1 | 2/2012 | Hirst et al. | |
| 2014/0171390 A1 | 6/2014 | Burns et al. | |
| 2014/0194385 A1 | 7/2014 | Reddy et al. | |
| 2014/0194386 A1 | 7/2014 | Burns et al. | |
| 2015/0094472 A1 | 4/2015 | Hecker et al. | |
| 2015/0291630 A1 | 10/2015 | Burns et al. | |
| 2015/0361107 A1 | 12/2015 | Trout | |
| 2015/0361108 A1 | 12/2015 | Burns et al. | |
| 2017/0073360 A1 | 3/2017 | Burns et al. | |
| 2017/0281639 A1 | 10/2017 | Kawasaki et al. | |
| 2017/0342092 A1 | 11/2017 | Burns et al. | |
| 2018/0002351 A1 | 1/2018 | Hecker et al. | |
| 2018/0273552 A1 | 9/2018 | Burns et al. | |
| 2020/0055877 A1 | 2/2020 | Burns et al. | |

(Continued)

FOREIGN PATENT DOCUMENTS

| CN | 1965838 A | 5/2007 |
|---|---|---|
| CN | 105801610 A | 7/2016 |

(Continued)

OTHER PUBLICATIONS

Germs: Understand and protect against bacteria, viruses and infection, PreventBacterialInfection, 2020. Available at https://www.mayoclinic.org/diseases-conditions/infectious-diseases/in-depth/germs/art-20045289#:-:text=Warding%20off%20germs%20and%20infection&text=You%20can%20prevent%20infections%20through ,vaccinations%2C%20and%20taking%20appropriate%20medications (Mar. 5, 2020).

Hardy et al. The Chemistry of Some 2-Aminothiazol-4-ylacetic Acid Derivatives and the Synthesis of Derived Penicillins. J Chem Soc Perkin Trans 1:1227-1235 (1984).

(Continued)

*Primary Examiner* — Noble E Jarrell

(74) *Attorney, Agent, or Firm* — Wilson Sonsini Goodrich & Rosati

(57) ABSTRACT

Described herein are certain boron-containing compounds, compositions, preparations and their use as modulators of the transpeptidase function of bacterial penicillin-binding proteins and as antibacterial agents. In some embodiments, the compounds described herein inhibit penicillin-binding proteins. In certain embodiments, the compounds described herein are useful in the treatment of bacterial infections.

20 Claims, No Drawings

(56) References Cited

U.S. PATENT DOCUMENTS

| | | |
|---|---|---|
| 2020/0157123 A1 | 5/2020 | Burns et al. |
| 2020/0317698 A1 | 10/2020 | Burns et al. |
| 2021/0163506 A1 | 6/2021 | Amann et al. |
| 2021/0198288 A1 | 7/2021 | Burns et al. |

FOREIGN PATENT DOCUMENTS

| | | |
|---|---|---|
| KR | 20130064004 A | 6/2013 |
| RU | 2012107163 A | 9/2013 |
| WO | WO-2005004799 A2 | 1/2005 |
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2012021455 A1 | 2/2012 |
| WO | WO-2013014497 A1 | 1/2013 |
| WO | WO-2013053372 A1 | 4/2013 |
| WO | WO-2013092979 A1 | 6/2013 |
| WO | WO-2013122888 A2 | 8/2013 |
| WO | WO-2014086664 A1 | 6/2014 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015157618 A1 | 10/2015 |
| WO | WO-2015171398 A1 | 11/2015 |
| WO | WO-2015171430 A1 | 11/2015 |
| WO | WO-2015179308 A1 | 11/2015 |
| WO | WO-2015191907 A1 | 12/2015 |
| WO | WO-2016003929 A1 | 1/2016 |
| WO | WO-2016100043 A1 | 6/2016 |
| WO | WO-2017001655 A1 | 1/2017 |
| WO | WO-2017044828 A1 | 3/2017 |
| WO | WO-2017100537 A1 | 6/2017 |
| WO | WO-2018027062 A1 | 2/2018 |
| WO | WO-2018165048 A1 | 9/2018 |
| WO | WO-2018218154 A1 | 11/2018 |
| WO | WO-2018218190 A1 | 11/2018 |
| WO | WO-2019165374 A1 | 8/2019 |
| WO | WO-2019185016 A1 | 10/2019 |
| WO | WO-2019223791 A1 | 11/2019 |
| WO | WO-2019226931 A1 | 11/2019 |
| WO | WO-2020056048 A1 | 3/2020 |
| WO | WO-2020112542 A1 | 6/2020 |
| WO | WO-2020205932 A1 | 10/2020 |
| WO | WO-2021108023 A1 | 6/2021 |

OTHER PUBLICATIONS

Krajnc et al., Bicyclic boronate VNRX-5133 inhibits metallo- and serine-beta-lactamases . Journal of Medicinal Chemistry 62(18):8544-8556 (2019).

PCT/US2020/052439 International Search Report and Written Opinion dated Dec. 31, 2020.

U.S. Appl. No. 16/616,294 Office Action dated Feb. 8, 2021.

U.S. Appl. No. 16/616,294 Office Action dated Jun. 18, 2021.

Zhou et al. Trigonelline: A Plant Alkaloid With Therapeutic Potential for Diabetes and Central Nervous System Disease. Curr Med Chem 19(21):3523-3531 (2012).

Contreras-Martel et al. Structure-guided design of cell wall biosynthesis inhibitors that overcome β-lactam resistance in *Staphylococcus aureus* (MRSA). ACS Chem Biol 6(7):943-951 (2011).

Inglis et al. Synthesis and evaluation of 3-(dihydroxyboryl)benzoic acids as D,D-carboxypeptidase R39 inhibitors. J Med Chem 52:6097-6106 (2009).

Woon et al. Structure guided development of potent reversibly binding penicillin binding protein inhibitors. ACS Med Chem Lett 2(1):219-223 (2011).

Burns et al. CAPLUS AN 2014-1130723 (1 pg.) (2014).

Eidam et al. Design, synthesis, crystal structures, and antimicrobial activity of sulfonamide boronic acids as β-lactamase inhibitors. J. Med. Chem. 53(21):7852-7863 (2010).

Ishikura et al. Synthesis and structure-activity relationships of 7 beta-[(Z)-2-(2-aminothiazol-4-yl)-3-(substituted)-2-propenoyl-amino]-3-desacetoxymethylcephalosporins. J. Antibiotics 47:453-465 (1994).

Martin et al. Rational design and synthesis of a highly effective transition state analog inhibitor of the RTEM-1 β-lactamase. Tetrahedron Lett. 36:8399-8402 (1995).

Matteson. Boronic esters in asymmetric synthesis. J Org Chem 78:10009-10023 (2013).

Matteson et al. Synthesis of 1-amino-2-phenylethane-1-boronic acid derivatives. Organometallics 3:614-18 (1984).

Morandi et al. Structure-based optimization of cephalothin-analogue boronic acids as β-lactamase inhibitors. Bioorg. Med. Chem. 16(3):1195-1205 (2008) (Epub: Nov. 7, 2007).

Ness et al. Structure-based design guides the improved efficacy of deacylation transition state analogue inhibitors of TEM-1 β-lactamase. Biochemistry 39(18):5312-5321 (2000).

PCT/US2018/034660 International Search Report and Written Opinion dated Sep. 14, 2018.

PCT/US2018/034722 International Search Report and Written Opinion dated Sep. 14, 2018.

PCT/US2019/033813 International Search Report and Written Opinion dated Sep. 10, 2019.

Powers et al. Structure-based approach for binding site identification on AmpC β-lactamase. J. Med. Chem. 45(15):3222-3234 (2002).

Powers et al. Structures of ceftazidime and its transition-state analogue in complex with AmpC β-lactamase: implications for resistance mutations and inhibitor design. Biochemistry 40(31):9207-9214 (2001).

Pub Chem Substance Record for SID 197433672. https://pubchem.ncbi.nim.nih/substance/197433672. Created Aug. 18, 2014. Retrieved Jan. 10, 2017 (5 pgs).

Reddy et al. Caplus 2014:1118372 (2014) (2 pgs.).

Watkins et al. Novel β-lactamase inhibitors: a therapeutic hope against the scourge of multi-drug resistance. © Dec. 24, 2013. Accessed Jul. 7, 2018. (18 pgs) (2013).

Weston et al. Structure-based enhancement of boronic acid-based inhibitors of AmpC β-lactamase. J. Med. Chem. 41(23):4577-4586 (1998).

Winkler et al. Design and exploration of novel boronic acid inhibitors reveals important interactions with a clavulanic acid-resistant sulfhydryl-variable (SHV) β-lactamase. J Med Chem 56:1084-1097 (2013) (Publication Date (Web): Dec. 19, 2012).

PENICILLIN-BINDING PROTEIN INHIBITORS

CROSS-REFERENCE TO RELATED APPLICATIONS

This application is a U.S. National Stage entry of International Application No. PCT/US18/034660, filed May 25, 2018, which claims the benefit of U.S. Provisional Application Ser. No. 62/511,613 filed May 26, 2017, and U.S. Provisional Application Ser. No. 62/582,870 filed Nov. 7, 2017, which are hereby incorporated by reference in their entirety.

STATEMENT AS TO FEDERALLY SPONSORED RESEARCH

This invention was made with the support of the United States government under SBIR Grant number 5R43AI094827 by the National Institutes of Health (NIH). The government has certain rights in the invention.

BACKGROUND OF THE INVENTION

Antibiotics are the most effective drugs for curing bacteria-related infectious diseases clinically. They are incredibly valuable therapeutic options that are currently losing efficacy due to the evolution and spread of drug resistance genes, leading to multidrug resistance bacterial organisms. Among the different classes of antibiotics, the penicillin-binding protein-targeting beta-lactams (e.g. penicillins, cephalosporins, and carbapenems) are the most widely used antibiotic class because they have a strong bactericidal effect and low associated toxicity.

Penicillin Binding Proteins (PBPs) are a family of essential bacterial enzymes involved in the synthesis of peptidoglycan, the major structural polymer found in the bacterial cell wall. Beta-lactam antibiotics bind with high affinity to PBPs and inhibit their transpeptidase function, resulting in disruption of peptidoglycan cell wall synthesis and rapid cell lysis of actively dividing bacteria. As there are no close mammalian homologues to PBPs, and beta-lactams are well-regarded for their safety and efficacy, PBPs represent an ideal target for antibacterials.

SUMMARY OF THE INVENTION

Described herein are compounds that inhibit the activity of penicillin-binding proteins, the bacterial enzyme class targeted by the beta lactam antibiotics and do provide significant antibacterial activity in vitro.

In one aspect, provided herein are compounds of Formula (IIa) or (IIb), or a pharmaceutically acceptable salt, solvate, stereoisomer, tautomer, N-oxide, dimer, or trimer thereof:

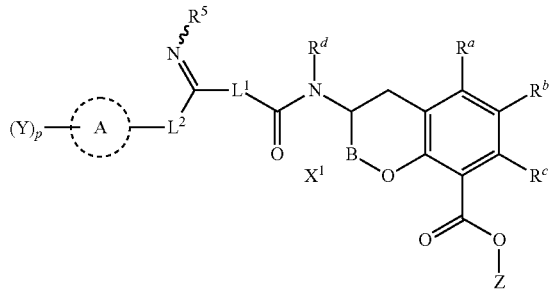

Formula (IIa)

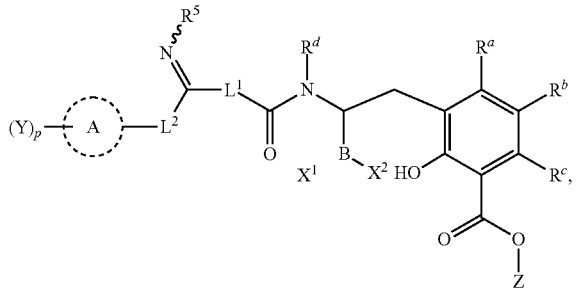

Formula (IIb)

wherein:
L$^1$ is —(CR$^1$R$^2$)$_n$—;
L$^2$ is —(CR$^1$R$^2$)$_m$—;
Ring A is cycloalkyl, heterocycloalkyl, aryl, or heteroaryl;
each R$^1$ and R$^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl;
R$^5$ is —OR$^{10}$, —NR$^{11}$R$^{12}$, —S(=O)$_{0,1,2}$R$^{13}$;
R$^{10}$ is hydrogen, optionally substituted alkyl, optionally substituted cycloalkyl, optionally substituted heterocycloalkyl, optionally substituted aryl, optionally substituted heteroaryl, —(CR$^{40d}$R$^{41d}$)$_v$NR$^{42d}$R$^{43d}$, —(CR$^{40d}$R$^{41d}$)$_v$C(=O)NR$^{42d}$R$^{43d}$, —(CR$^{40d}$R$^{41d}$)$_v$C(=O)NR$^{42d}$(CR$^{40d}$R$^{41d}$)$_w$NR$^{42d}$C(=O)R$^{44d}$, —(CR$^{40d}$R$^{41d}$)$_v$C(=O)NR$^{42d}$(CR$^{40d}$R$^{41d}$)$_w$NR$^{42d}$R$^{43d}$, —(CR$^{40d}$R$^{41d}$)$_v$C(=O)NR$^{42d}$(CR$^{40d}$R$^{41d}$)$_w$NR$^{42d}$(CR$^{40d}$R$^{41d}$)$_w$NR$^{42d}$R$^{43d}$, —(CR$^{40d}$R$^{41d}$)$_v$C(=O)NR$^{42d}$(CR$^{40d}$R$^{41d}$)$_v$C(=O)OH, —(CR$^{40d}$R$^{41d}$)$_v$C(=O)NR$^{42d}$(CR$^{40d}$R$^{41d}$)$_v$C(=O)OR$^{44d}$, —(CR$^{40d}$R$^{41d}$)$_v$NR$^{42d}$C(=O)R$^{44d}$, —(CR$^{40d}$R$^{41d}$)$_v$NR$^{42d}$S(=O)$_{0,1,2}$R$^{44d}$, —(CR$^{40d}$R$^{41d}$)$_v$OR$^{44d}$, —(CR$^{40d}$R$^{41d}$)$_v$OH, —(CR$^{40d}$R$^{41d}$)$_v$OR$^{44d}$, —(CR$^{40d}$R$^{41d}$)$_v$C(=O)OH, —(CR$^{40d}$R$^{41d}$)$_v$C(=O)OR$^{44d}$, —(CR$^{40d}$R$^{41d}$)$_v$heteroaryl, or —(CR$^{40d}$R$^{41d}$)$_v$heterocycloalkyl.
R$^{11}$ and R$^{12}$ are independently hydrogen, —S(=O)$_2$R$^{44e}$, —S(=O)$_2$NR$^{42e}$R$^{43e}$, optionally substituted alkyl, optionally substituted cycloalkyl, optionally substituted heterocycloalkyl, optionally substituted aryl, or optionally substituted heteroaryl; or
R$^{11}$ and R$^{12}$ are taken together with the nitrogen to which they are attached to form an optionally substituted heterocycloalkyl;
R$^{13}$ is optionally substituted alkyl, optionally substituted cycloalkyl, optionally substituted heterocycloalkyl, optionally substituted aryl, or optionally substituted heteroaryl;
each R$^{20}$ and R$^{21}$ are independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40d}$, $R^{41d}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40d}$ and $R^{41d}$, or $R^{50}$ and $R^{51}$ are taken together with the carbon atom to which they are attached form an optionally substituted cycloalkyl; or two $R^{30}$, two $R^{40d}$, or two $R^{50}$ on adjacent carbons are taken together to form an alkenyl; or two $R^{30}$ and two $R^{31}$, two $R^{40d}$ and two $R^{41d}$, or two $R^{50}$ and two $R^{51}$ on adjacent carbons are taken together to form an alkynyl;

$R^{32}$, $R^{33}$, $R^{42d}$, $R^{43d}$, $R^{42e}$, $R^{43e}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, $R^{42d}$ and $R^{43d}$, $R^{42e}$ and $R^{43e}$, or $R^{52}$ and $R^{53}$ are taken together with the nitrogen to which they are attached to form an optionally substituted heterocycloalkyl;

$R^{34}$, $R^{44d}$, $R^{44e}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_v$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoakyl, —O(CR$^{30}$R$^{31}$)$_w$NR$^{32}$-heteroaryl, —O(CR$^{30}$R$^{31}$)$_w$NR$^{32}$-heterocycoakyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C —(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$ S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C (=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$ (CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_w$heteroaryl, —NR$^{32}$(CR$^{30}$R$^{31}$)$_w$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O (CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O) NR$^{32}$(CR$^{30}$R$^{31}$)$_w$NR$^{32}$R$^{33}$, —(CR$^{30}$R$^{31}$)$_v$C(=O)NR$^{32}$ (CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_w$N(R$^{32}$)C(=O)OR$^{34}$, —(CR$^{30}$R$^{31}$)$_v$N (R$^{32}$)C(=O)NR$^{32}$R$^{33}$, —(CR$^{30}$R$^{31}$)$_v$N(R$^{32}$)C(=O)(CR$^{30}$R$^{31}$)$_w$NR$^{32}$R$^{33}$, —(CR$^{30}$R$^{31}$)$_v$N(R$^{32}$) S(=O)$_{0,1,2}$R$^{34}$, —(CR$^{30}$R$^{31}$)$_v$N(R$^{32}$) S(=O)$_{0,1,2}$NR$^{32}$R$^{33}$, —(CR$^{30}$R$^{31}$)$_v$ S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$) NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_v$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S (=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$) NR$^{32}$R$^{33}$, —S(=O)$_{0,1,2}$(CR$^{30}$R$^{31}$)$_w$N(R$^{32}$)C(=NR$^{36}$) NR$^{32}$R$^{33}$, —S(=O)$_{0,1,2}$(CR$^{30}$R$^{31}$)$_v$C(=NR$^{36}$)NR$^{32}$C (=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5;

provided that the compound is not: (Z)-3-(2-(2-aminothiazol-4-yl)-2-(hydroxyimino)acetamido)-2-hydroxy-3,4-dihydro-2H-benzo[e][1,2]oxaborinine-8-carboxylic acid/(Z)-3-(2-(2-(2-aminothiazol-4-yl)-2-(hydroxyimino)acetamido)-2-boronoethyl)-2-hydroxybenzoic acid; (Z)-3-(2-(2-aminothiazol-4-yl)-2-(((2-carboxypropan-2-yl)oxy)imino)acetamido)-2-hydroxy-3,4-dihydro-2H-benzo[e][1,2]oxaborinine-8-carboxylic acid/ (Z)-5-(2-(2-aminothiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(((2-carboxypropan-2-yl)oxy)imino)acetamido)-2-hydroxy-3,4-dihydro-2H-benzo[e][1,2]oxaborinine-8-carboxylic acid/(Z)-5-(2-(2-(2-aminoacetamido)thiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(methoxyimino)acetamido)-2-hydroxy-3,4-dihydro-2H-benzo[e][1,2]oxaborinine-8-carboxylic acid/(Z)-3-(2-(2-(2-aminoacetamido)thiazol-4-yl)-2-(methoxyimino)acetamido)-2-boronoethyl)-2-hydroxybenzoic acid; (Z)-3-(2-(2-(2,6-diaminohexanamido)thiazol-4-yl)-2-(methoxyimino)acetamido)-2-hydroxy-3,4-dihydro-2H-benzo[e][1,2]oxaborinine-8-carboxylic acid/(Z)-3-(2-borono-2-(2-(2-(2,6-diaminohexanamido)thiazol-4-yl)-2-(methoxyimino)acetamido)ethyl)-2-hydroxybenzoic acid; or (Z)-3-(2-(4-(aminomethyl)phenyl)-2-(hydroxyimino)acetamido)-2-hydroxy-3,4-dihydro-2H-benzo[e][1,2]oxaborinine-8-carboxylic acid/(Z)-3-(2-(2-(4-(aminomethyl)phenyl)-2-(hydroxyimino)acetamido)-2-boronoethyl)-2-hydroxybenzoic acid.

Also provided herein are compounds of Formula (IIIa) or (IIIb), or a pharmaceutically acceptable salt, solvate, stereoisomer, tautomer, N-oxide, dimer, or trimer thereof:

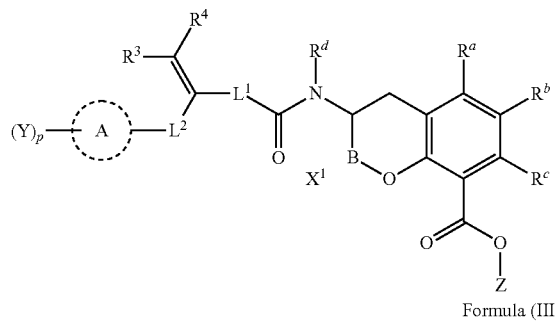

Formula (IIIa)

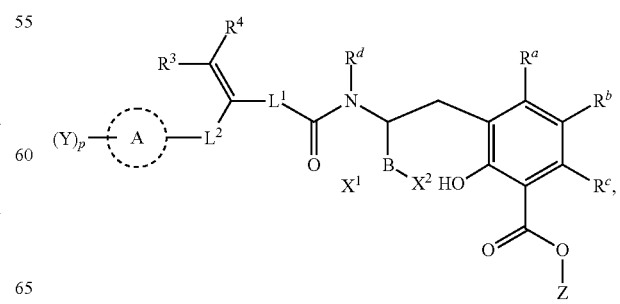

Formula (IIIb)

wherein:

$L^1$ is $-(CR^1R^2)_n-$;

$L^2$ is $-(CR^1R^2)_m-$;

Ring A is cycloalkyl, heterocycloalkyl, aryl, or heteroaryl;

each $R^1$ and $R^2$ are independently hydrogen, halogen, optionally substituted alkyl, $-OH$, $-OR^{34}$, $-SR^{35}$, $-NR^{32}R^{33}$, $-NR^{32}C(=O)R^{34}$, $-C(=O)NR^{32}R^{33}$, $-NR^{32}S(=O)_2R^{34}$, $-C(=O)OH$, $-C(=O)OR^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^3$ and $R^4$ are independently hydrogen, halogen, optionally substituted alkyl, optionally substituted cycloalkyl, optionally substituted heterocycloalkyl, optionally substituted aryl, optionally substituted heteroaryl, $-C(=O)OH$, $-C(=O)OR^{44a}$, $-(CR^{40a}R^{41a})_vC(=O)OH$, $-(CR^{40a}R^{41a})_vC(=O)OR^{44a}$, $-(CR^{40a}R^{41a})_vOH$, or $-(CR^{40a}R^{41a})_vOR^{44a}$; or $R^3$ and $R^4$ are taken together with the carbon atom to which they are attached to form optionally substituted cycloalkyl or an optionally substituted heterocycloalkyl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40a}$, $R^{41a}$, $R^5$, and $R^{51}$ are independently hydrogen, halogen, optionally substituted alkyl, optionally substituted cycloalkyl, optionally substituted heterocycloalkyl, optionally substituted aryl, optionally substituted heteroaryl, $-OH$, $-OR^{24}$, $-SR^{25}$, $-NR^{22}R^{23}$, $-NR^{22}C(=O)R^{24}$, $-C(=O)NR^{22}R^{23}$, $-NR^{22}S(=O)_2R^{24}$, $-C(=O)OH$, or $-C(=O)OR^{24}$; or $R^{30}$ and $R^{31}$, $R^{40a}$ and $R^{41a}$, or $R^{50}$ and $R^{51}$ are taken together with the carbon atom to which they are attached form an optionally substituted cycloalkyl; or two $R^{30}$, two $R^{40a}$, or two $R^{50}$ on adjacent carbons are taken together to form an alkenyl; or two $R^{30}$ and two $R^{31}$, two $R^{40a}$ and two $R^{41a}$, or two $R^{50}$ and two $R^{51}$ on adjacent carbons are taken together to form an alkynyl;

$R^{32}$, $R^{33}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, $-CN$, $-OH$, $-S(=O)_2R^{24}$, $-S(=O)_2NR^{22}R^{23}$, or $-C(=O)R^{24}$; or $R^{32}$ and $R^{33}$ or $R^{52}$ and $R^{53}$ are taken together with the nitrogen to which they are attached to form an optionally substituted heterocycloalkyl;

$R^{34}$, $R^{44a}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, $-OH$, $-OR^{24}$, $-CN$, $-NO_2$, $-NR^{22}R^{23}$, or optionally substituted alkyl;

Z is hydrogen, $R^{61}$, $-(R^{60})_qOR^6$, $-(R^{60})_qO(R^{60})_qOR^{61}$, $-R^{60}OC(=O)R^6$, $-R^{60}OC(=O)OR^6$, $-R^{60}OC(=O)NHR^{61}$, $-R^{60}OC(=O)N(R^{61})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently $-CH_2-$, $-CH(CH_3)-$, $-C(CH_3)_2-$, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, optionally substituted heteroaryl, $-OH$, $-OR^{54}$, $-O(CR^{50}R^{51})_wNR^{52}R^{53}$, $-O(CR^{50}R^{51})_wOH$, $-O(CR^{50}R^{51})_wOR^{54}$, $-O(CR^{50}R^{51})_vC(=O)OH$, $-O(CR^{50}R^{51})_vC(=O)OR^{54}$, $-O(CR^{50}R^{51})_vC(=O)NR^{52}R^{53}$, $-NR^{52}R^{53}$, $-NR^{52}(CR^{50}R^{51})_wNR^{52}R^{53}$, $-NR^{52}(CR^{50}R^{51})_vC(=O)OH$, $-NR^{52}(CR^{50}R^{51})_vC(=O)OR^{54}$, $-NR^{52}(CR^{50}R^{51})_vC(=O)NR^{52}R^{53}$, $-NR^{52}S(=O)_{1,2}R^{54}$, $-S(=O)_{1,2}R^{54}$, $-SR^{55}$, $-S(CR^{50}R^{51})_wNR^{52}C(=NR^{56})NR^{52}R^{53}$, $-S(CR^{50}R^{51})_wNR^{52}CR^{50}(=NR^{56})$, $-S(CR^{50}R^{51})_vC(=NR^{56})NR^{52}R^{53}$, $-S(CR^{50}R^{51})_wOH$, $-S(CR^{50}R^{51})_wOR^{54}$, $-S(CR^{50}R^{51})_wNR^{52}R^{53}$, $-S(CR^{50}R^{51})_vC(=O)OH$, $-S(CR^{50}R^{51})_vC(=O)OR^{54}$, $-S(CR^{50}R^{51})_vC(=O)NR^{52}R^{53}$, $-C(=O)H$, $-C(=O)R^{54}$, $-C(=O)OH$, $-C(=O)OR^{54}$, $-C(=O)NR^{52}R^{53}$, $-(CR^{50}R^{51})_vN(R^{52})(CR^{50}R^{51})_vC(=O)OH$, $-(CR^{50}R^{51})_vOH$, $-(CR^{50}R^{51})_vOR^{54}$, $-(CR^{50}R^{51})_vC(=O)OH$, $-(CR^{50}R^{51})_vC(=O)OR^{54}$, $-(CR^{50}R^{51})_vC(=O)NR^{52}R^{53}$, $-(CR^{50}R^{51})_vOC(=O)R^{54}$, $-(CR^{50}R^{51})_vSR^{55}$, $-(CR^{50}R^{51})_vNR^{52}C(=NR^{56})$, $-(CR^{50}R^{51})_vNR^{52}R^{53}$, $-(CR^{50}R^{51})_vC(=NR^{56})NR^{52}R^{53}$, $-(CR^{50}R^{51})_vC(=O)NR^{52}R^{53}$, $-(CR^{50}R^{51})_v$heterocycloalkyl, or $-(CR^{50}R^{51})_v$heteroaryl;

$R^d$ is hydrogen, $-CN$, $-OH$, $-S(=O)_2R^{24}$, $-S(=O)_2NR^{22}R^{23}$, $-(CR^{20}R^{21})_vC(=O)OH$, $-C(=O)R^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently $-OH$, $-OR^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-$NR^{32}R^{33}$, -heterocycloalkyl-$NR^{32}R^{33}$, -heteroaryl-$N(R^{32})C(=NR^{32})NR^{32}R^{33}$, -heterocycloalkyl-$N(R^{32})C(=NR^{32})NR^{32}R^{33}$, —OH, —$OR^{34}$, —$O(CR^{30}R^{31})_w OH$, —$O(CR^{30}R^{31})_w OR^{34}$, —$O(CR^{30}R^{31})_w NR^{32}R^{33}$, —$O(CR^{30}R^{31})_w NR^{32}C(=O)R^{34}$, —$O(CR^{30}R^{31})_w NR^{32}C(=O)OR^{34}$, —$O(CR^{30}R^{31})_w NR^{32}C(=O)NR^{32}R^{33}$, —$O(CR^{30}R^{31})_w C(=O)NR^{32}R^{33}$, —$O(CR^{30}R^{31})_w NR^{32}S(=O)_{0,1,2}R^{34}$, —$O(CR^{30}R^{31})_w NR^{32}S(=O)_{0,1,2}NR^{32}R^{33}$, —$O(CR^{30}R^{31})_w S(=O)_{0,1,2}R^{34}$, —$O(CR^{30}R^{31})_w S(=O)_{0,1,2}NR^{32}R^{33}$, —$O(CR^{30}R^{31})_v C(=NR^{36})NR^{32}R^{33}$, —$O(CR^{30}R^{31})_w N(R^{32})C(=NR^{36})R^{34}$, —$O(CR^{30}R^{31})_v C(=NR^{36})NR^{32}C(=NR^{36})NR^{32}R^{33}$, —$O(CR^{30}R^{31})_w N(R^{32})C(=NR^{36})NR^{32}R^{33}$, —$O(CR^{30}R^{31})_w S(=O)_{0,1,2}R^{34}$, —$O(CR^{30}R^{31})_w S(=O)_{0,1,2}NR^{32}R^{33}$, —$OC(=O)R^{34}$, —$OC(=O)(CR^{30}R^{31})_v NR^{32}R^{33}$, —$OC(=O)NR^{32}R^{33}$, —$OC(=O)OR^{34}$, —$OC(=O)NR^{32}(CR^{30}R^{31})_w NR^{32}R^{33}$, —O-heteroaryl, —O-heterocycloalkyl, —$O(CR^{30}R^{31})_v$heteroaryl, —$O(CR^{30}R^{31})_v$heterocycoakyl, —$O(CR^{30}R^{31})_w NR^{32}$-heteroaryl, —$O(CR^{30}R^{31})_w NR^{32}$-heterocycoakyl, —$O(CR^{30}R^{31})_w O$-heterocycloalkyl, —$NR^{32}R^{33}$, —$NR^{32}(CR^{30}R^{31})_w NR^{32}R^{33}$, —$NR^{32}(CR^{30}R^{31})_w OH$, —$NR^{32}(CR^{30}R^{31})_w OR^{34}$, —$NR^{32}C(=O)R^{34}$, —$NR^{32}C(=O)OR^{34}$, —$N(R^{32})C(=O)(CR^{30}R^{31})_v NR^{32}R^{33}$, —$NR^{32}C(=O)NR^{32}R^{33}$, —$NR^{32}C(=O)NR^{32}(CR^{30}R^{31})_w NR^{32}R^{33}$, —$NR^{32}(CR^{30}R^{31})_v S(=O)_{0,1,2}R^{34}$, —$NR^{32}(CR^{30}R^{31})_w S(=O)_{0,1,2}NR^{32}R^{33}$, —$NR^{32}(CR^{30}R^{31})_w NR^{32}R^{33}S(=O)_{0,1,2}R^{34}$, —$NR^{32}(CR^{30}R^{31})_w NR^{32}S(=O)_{0,1,2}NR^{32}R^{33}$, —$NR^{32}C(=NR^{36})NR^{32}R^{33}$, —$N(R^{32})C(=NR^{36})R^{34}$, —$NR^{32}(CR^{30}R^{31})_w N(R^{32})C(=NR^{36})R^{34}$, —$NR^{32}(CR^{30}R^{31})_v C(=NR^{36})NR^{32}R^{33}$, —$NR^{32}(CR^{30}R^{31})_w N(R^{32})C(=NR^{36})NR^{32}R^{33}$, —$NR^{32}(CR^{30}R^{31})_w NR^{32}C(=O)NR^{32}R^{33}$, —$NR^{32}(CR^{30}R^{31})_w NR^{32}C(=O)OR^{34}$, —$NR^{32}S(=O)_{0,1,2}R^{34}$, —$NR^{32}(CR^{30}R^{31})_v CO_2H$, —$NR^{32}(CR^{30}R^{31})_v CO_2R^{34}$, —$NR^{32}(CR^{30}R^{31})_v C(=O)NR^{32}R^{33}$, —$N(R^{32})$-heteroaryl-$NR^{32}R^{33}$, —$N(R^{32})$-heterocycloalkyl-$NR^{32}R^{33}$, —$NR^{32}(CR^{30}R^{31})_v$heteroaryl, —$NR^{32}(CR^{30}R^{31})_v$heterocycloalkyl, —$NR^{32}(CR^{30}R^{31})_w NR^{32}$-heteroaryl, —$NR^{32}(CR^{30}R^{31})_w NR^{32}$-heterocycoakyl, —CN, —$(CR^{30}R^{31})_v CN$, —$(CR^{30}R^{31})_v NR^{32}R^{33}$, —$(CR^{30}R^{31})_v OH$, —$(CR^{30}R^{31})_v OR^{34}$, —$(CR^{30}R^{31})_v OC(=O)R^{34}$, —$(CR^{30}R^{31})_v OC(=O)NR^{32}R^{33}$, —$(CR^{30}R^{31})_v O(CR^{30}R^{31})_w OR^{34}$, —$(CR^{30}R^{31})_v O(CR^{30}R^{31})_w OH$, —$(CR^{30}R^{31})_v O(CR^{30}R^{31})_w NR^{32}R^{33}$, —$(CR^{30}R^{31})_v NR^{32}(CR^{30}R^{31})_w OH$, —$(CR^{30}R^{31})_v NR^{32}(CR^{30}R^{31})_w OR^{34}$, —$(CR^{30}R^{31})_v C(=O)NR^{32}R^{33}$, —$(CR^{30}R^{31})_v C(=O)NR^{32}(CR^{30}R^{31})_w NR^{32}R^{33}$, —$(CR^{30}R^{31})_v C(=O)NR^{32}(CR^{30}R^{31})_w OR^{34}$, —$(CR^{30}R^{31})_v N(R^{32})C(=O)R^{34}$, —$(CR^{30}R^{31})_v N(R^{32})C(=O)OR^{34}$, —$(CR^{30}R^{31})_v N(R^{32})C(=O)NR^{32}R^{33}$, —$(CR^{30}R^{31})_v N(R^{32})C(=O)(CR^{30}R^{31})_v NR^{32}R^{33}$, —$(CR^{30}R^{31})_v N(R^{32})S(=O)_{0,1,2}R^{34}$, —$(CR^{30}R^{31})_v N(R^{32})S(=O)_{0,1,2}NR^{32}R^{33}$—$(CR^{30}R^{31})_v S(=O)_{0,1,2}NR^{32}R^{33}$, —$(CR^{30}R^{31})_v N(R^{32})CH(=NR^{36})$, —$(CR^{30}R^{31})_v N(R^{32})C(=NR^{36})R^{34}$, —$(CR^{30}R^{31})_v C(=NR^{36})NR^{32}R^{33}$, —$(CR^{30}R^{31})_v N(R^{32})C(=NR^{36})NR^{32}R^{33}$, —$(CR^{30}R^{31})_v C(=NR^{36})NR^{32}C(=NR^{36})NR^{32}R^{33}$, —$(CR^{30}R^{31})_v$heteroaryl-$NR^{32}R^{33}$, —$(CR^{30}R^{31})_v$heterocycloalkyl-$NR^{32}R^{33}$, —$(CR^{30}R^{31})_v$heteroaryl-$N(R^{32})C(=NR^{36})NR^{32}R^{33}$, —$(CR^{30}R^{31})_v$heterocycloalkyl-$N(R^{32})C(=NR^{36})NR^{32}R^{33}$, —$(CR^{30}R^{31})_v$heteroaryl, —$(CR^{30}R^{31})_v$heterocycloalkyl, —$C(=O)OH$, —$C(=O)OR^{34}$, —$C(=O)NR^{32}R^{33}$, —$C(=O)NR^{32}(CR^{30}R^{31})_w NR^{32}R^{33}$, —$C(=O)NR^{32}(CR^{30}R^{31})_w OH$, —$C(=O)NR^{32}(CR^{30}R^{31})_w OR^{34}$, —$C(=NR^{36})NR^{32}R^{33}$, —$C(=NR^{36})NR^{32}C(=O)R^{34}$, —$S(=O)_{1,2}R^{34}$, —$SR^{35}$, —$S(=O)_{0,1,2}(CR^{30}R^{31})_w NR^{32}R^{33}$, —$S(=O)_{0,1,2}(CR^{30}R^{31})_w OH$, —$S(=O)_{0,1,2}(CR^{30}R^{31})_w OR^{34}$, —$S(=O)_{0,1,2}NR^{32}R^{33}$, —$S(=O)_{0,1,2}NR^{32}(CR^{30}R^{31})_w NR^{32}R^{33}$, —$S(=O)_{0,1,2}(CR^{30}R^{31})_w N(R^{32})C(=NR^{36})R^{34}$, —$S(=O)_{0,1,2}(CR^{30}R^{31})_v C(=NR^{36})NR^{32}R^{33}$, —$S(=O)_{0,1,2}(CR^{30}R^{31})_w N(R^{32})C(=NR^{36})NR^{32}R^{33}$, —$S(=O)_{0,1,2}(CR^{30}R^{31})_v C(=NR^{36})NR^{32}C(=NR^{36})NR^{32}R^{33}$, —$Si(R^{34})_3$, —$NR^{32}R^{33}R^{34+}Q^-$, —$(CR^{30}R^{31})_v NR^{32}R^{33}R^{34+}Q^-$, —$NR^{32}(CR^{30}R^{31})_w NR^{32}R^{33}R^{34+}Q^-$, —$NR^{32}R^{34+}(CR^{30}R^{31})_w NR^{32}R^{33}R^{34+}Q^-_2$, —$(CR^{30}R^{31})_v(T)^+Q^-$, or —$O(CR^{30}R^{31})_w NR^{32}R^{33}R^{34+}Q^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5.

Also provided herein are compounds of Formula (IVa) or (IVb), or a pharmaceutically acceptable salt, solvate, stereoisomer, tautomer, N-oxide, dimer, or trimer thereof:

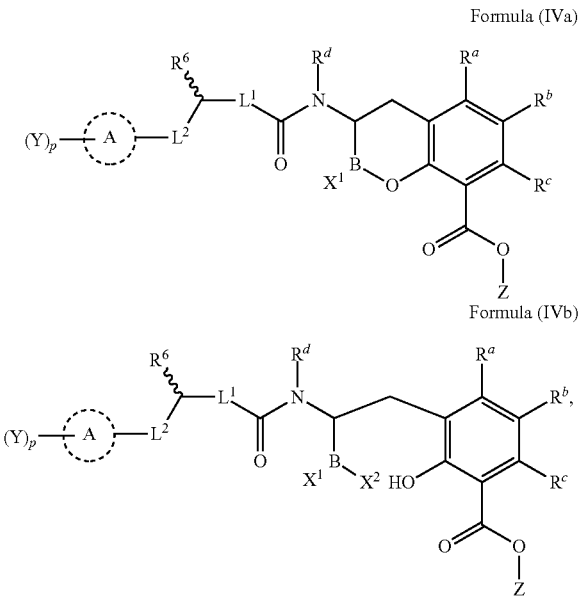

Formula (IVa)

Formula (IVb)

wherein:
$L^1$ is —$(CR^1R^2)_n$—;
$L^2$ is —$(CR^1R^2)_m$—;
Ring A is cycloalkyl, heterocycloalkyl, aryl, or heteroaryl;

each $R^1$ and $R^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^6$ is optionally substituted alkyl, —(CR$^{40b}$R$^{41b}$)$_v$C(=O)OR$^{44b}$, or —(CR$^{40b}$R$^{41b}$)$_v$C(=O)OH;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40b}$, $R^{41b}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40b}$ and $R^{41b}$, or $R^{50}$ and $R^{51}$ are taken together with the carbon atom to which they are attached form an optionally substituted cycloalkyl; or two $R^{30}$, two $R^{40b}$, or two $R^{50}$ on adjacent carbons are taken together to form an alkenyl; or two $R^{30}$ and two $R^{31}$, two $R^{40b}$ and two $R^{41b}$, or two $R^{50}$ and two $R^{51}$ on adjacent carbons are taken together to form an alkynyl;

$R^{32}$, $R^{33}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$ or $R^{52}$ and $R^{53}$ are taken together with the nitrogen to which they are attached to form an optionally substituted heterocycloalkyl;

$R^{34}$, $R^{44b}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$ —S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoakyl, —O(CR$^{30}$R$^{31}$)$_w$NR$^{32}$-heteroaryl, —O(CR$^{30}$R$^{31}$)$_w$NR$^{32}$-heterocycoakyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_w$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$ heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5;

provided that the compound is not 2-hydroxy-3-(3-hydroxy-2-(4-((2-(methylamino)ethyl)amino)cyclohexyl)propanamido)-3,4-dihydro-2H-benzo[e][1,2]oxaborinine-8-carboxylic acid/3-(2-borono-2-(3-hydroxy-2-(4-((2-(methylamino)ethyl)amino)cyclohexyl)propanamido)ethyl)-2-hydroxybenzoic acid.

Also disclosed herein is a pharmaceutical composition comprising a compound of Formula (IIa)-(IVa) or (IIb)-(IVb) and a pharmaceutically acceptable excipient.

Also disclosed herein is a method of treating a bacterial infection in a subject, comprising administering to the subject an effective amount of a compound of Formula (IIa)-(IVa) or (IIb)-(IVb), or a pharmaceutically acceptable salt, solvate, stereoisomer, tautomer, N-oxide, dimer, or trimer thereof, or a pharmaceutical composition comprising a compound of Formula (IIa)-(IVa) or (IIb)-(IVb) and a pharmaceutically acceptable excipient.

Also disclosed herein is method of inhibiting a bacterial penicillin binding protein in a human infected with a bacterial infection, comprising contacting said bacterial penicillin binding protein with an effective amount of compound of Formula (Ia)-(IVa) or (Ib)-(IVb), or a pharmaceutically acceptable salt, solvate, stereoisomer, tautomer, N-oxide, dimer, or trimer thereof, or a pharmaceutical composition comprising a compound of Formula (Ia)-(IVa) or (Ib)-(IVb) and a pharmaceutically acceptable excipient.

Also disclosed herein is method of inhibiting a bacterial penicillin binding protein in a human infected with a bacterial infection, comprising contacting said bacterial penicillin binding protein with an effective amount of a compound of Formula (Ia) or Formula (Ib), or a pharmaceutically acceptable salt, solvate, stereoisomer, tautomer, N-oxide, dimer, or trimer thereof:

Formula (Ia)

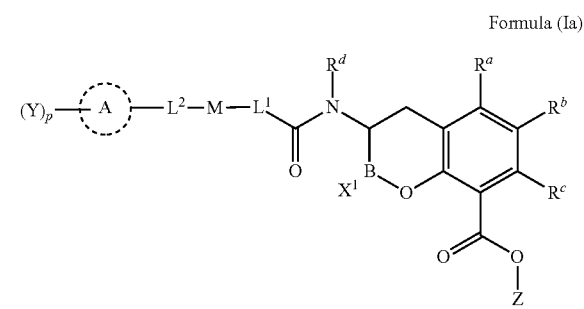

-continued

Formula (Ib)

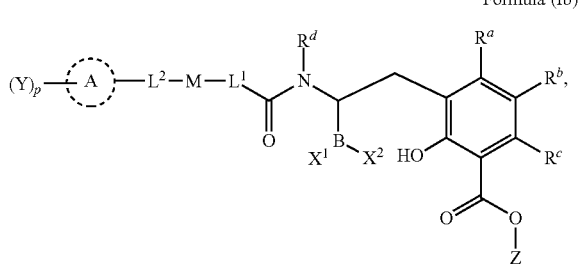

wherein:
L$^1$ is —(CR$^1$R$^2$)$_n$—;
L$^2$ is —(CR$^1$R$^2$)$_m$—;
Ring A is cycloalkyl, heterocycloalkyl, aryl, or heteroaryl;
M is

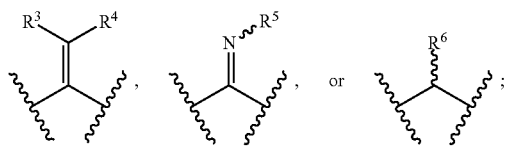

each R$^1$ and R$^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or R$^1$ and R$^2$ are taken together with the carbon to which they are attached to form an optionally substituted cycloalkyl;

R$^3$ and R$^4$ are independently hydrogen, halogen, optionally substituted alkyl, optionally substituted cycloalkyl, optionally substituted heterocycloalkyl, optionally substituted aryl, optionally substituted heteroaryl, —C(=O)OH, —C(=O)OR$^{44a}$, —(CR$^{40a}$R$^{41a}$)$_v$C(=O)OH, —(CR$^{40a}$R$^{41a}$)C(=O)OR$^{44a}$, —(CR$^{40a}$R$^{41a}$)$_v$OH, or —(CR$^{40a}$R$^{41a}$)$_v$OR$^{44a}$; or R$^3$ and R$^4$ are taken together with the carbon atom to which they are attached to form optionally substituted cycloalkyl or an optionally substituted heterocycloalkyl;

R$^5$ is —OR$^{10}$, —NR$^{11}$R$^{12}$, —S(=O)$_{0,1,2}$R$^{13}$;
R$^6$ is optionally substituted alkyl, —(CR$^{40b}$R$^{41b}$)$_v$C(=O)OR$^{44b}$, or —(CR$^{40b}$R$^{41b}$)$_v$C(=O)OH;
R$^{10}$ is hydrogen, optionally substituted alkyl, optionally substituted cycloalkyl, optionally substituted heterocycloalkyl, optionally substituted aryl, optionally substituted heteroaryl, —(CR$^{40d}$R$^{41d}$)$_v$NR$^{42d}$R$^{43d}$, —(CR$^{40d}$R$^{41d}$)$_v$C(=O)NR$^{42d}$R$^{43d}$, —(CR$^{40d}$R$^{41d}$)$_v$C(=O)NR$^{42d}$(CR$^{40d}$R$^{41d}$)$_w$NR$^{42d}$C(=O)R$^{44d}$, —(CR$^{40d}$R$^{41d}$)$_v$C(=O)NR$^{42d}$(CR$^{40d}$R$^{41d}$)$_w$NR$^{42d}$R$^{43d}$, —(CR$^{40d}$R$^{41d}$)$_v$C(=O)NR$^{42d}$(CR$^{40d}$R$^{41d}$)$_w$NR$^{42d}$(CR$^{40d}$R$^{41d}$)$_w$NR$^{42d}$R$^{43d}$, —(CR$^{40d}$R$^{41d}$)$_v$C(=O)NR$^{42d}$(CR$^{40d}$R$^{41d}$)$_v$C(=O)OH, —(CR$^{40d}$R$^{41d}$)$_v$C(=O)NR$^{42d}$(CR$^{40d}$R$^{41d}$)$_v$C(=O)OR$^{44d}$, —(CR$^{40d}$R$^{41d}$)$_v$NR$^{42d}$C(=O)R$^{44d}$, —(CR$^{40d}$R$^{41d}$)$_v$NR$^{42d}$S(=O)$_{0,1,2}$R$^{44d}$, —(CR$^{40d}$R$^{41d}$)$_v$OH, —(CR$^{40d}$R$^{41d}$)$_v$OR$^{44d}$, —(CR$^{40d}$R$^{41d}$)$_v$C(=O)OH, —(CR$^{40d}$R$^{41d}$)$_v$C(=O)OR$^{44d}$, —(CR$^{40d}$R$^{41d}$)$_v$heteroaryl, or —(CR$^{40d}$R$^{41d}$)$_v$heterocycloalkyl.

R$^{11}$ and R$^{12}$ are independently hydrogen, —S(=O)$_2$R$^{44e}$, —S(=O)$_2$NR$^{42e}$R$^{43e}$, optionally substituted alkyl, optionally substituted cycloalkyl, optionally substituted heterocycloalkyl, optionally substituted aryl, or optionally substituted heteroaryl; or R$^{11}$ and R$^{12}$ are taken together with the nitrogen to which they are attached to form an optionally substituted heterocycloalkyl;

R$^{13}$ is optionally substituted alkyl, optionally substituted cycloalkyl, optionally substituted heterocycloalkyl, optionally substituted aryl, or optionally substituted heteroaryl;

each R$^{20}$ and R$^{21}$ are independently hydrogen, halogen, or optionally substituted alkyl;

R$^{22}$ and R$^{23}$ are independently hydrogen or optionally substituted alkyl; or R$^{22}$ and R$^{23}$ are taken together with the nitrogen to which they are attached to form an optionally substituted heterocycloalkyl;

R$^{24}$ is optionally substituted alkyl, optionally substituted cycloalkyl, optionally substituted heterocycloalkyl, optionally substituted aryl, or optionally substituted heteroaryl;

R$^{25}$ is hydrogen, optionally substituted alkyl, optionally substituted cycloalkyl, optionally substituted heterocycloalkyl, optionally substituted aryl, optionally substituted heteroaryl;

each R$^{30}$, R$^{31}$, R$^{40a}$, R$^{40b}$, R$^{40d}$, R$^{41a}$, R$^{41b}$, R$^{41d}$, R$^{50}$, and R$^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$ or R$^{30}$ and R$^{31}$, R$^{40a}$ and R$^{41a}$, R$^{40b}$ and R$^{41b}$, R$^{40d}$ and R$^{41d}$, or R$^{50}$ and R$^{51}$ are taken together with the carbon atom to which they are attached form an optionally substituted cycloalkyl; or two R$^{30}$, two R$^{40a}$, two R$^{40b}$, two R$^{40d}$, or two R$^{50}$ on adjacent carbons are taken together to form an alkenyl; or two R$^{30}$ and two R$^{31}$, two R$^{40a}$ and two R$^{41a}$, two R$^{40b}$ and two R$^{41b}$, two R$^{40d}$ and two R$^{41d}$, or two R$^{50}$ and two R$^{51}$ on adjacent carbons are taken together to form an alkynyl;

R$^{32}$, R$^{33}$, R$^{42d}$, R$^{42e}$, R$^{43d}$, R$^{43e}$, R$^{52}$, or R$^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or R$^{32}$ and R$^{33}$, R$^{42d}$ and R$^{43d}$, R$^{42e}$ and R$^{43e}$, or R$^{52}$ and R$^{53}$ are taken together with the nitrogen to which they are attached to form an optionally substituted heterocycloalkyl;

R$^{34}$, R$^{44a}$, R$^{44b}$, R$^{44d}$, R$^{44e}$, or R$^{54}$ are independently optionally substituted alkyl, optionally substituted cycloalkyl, optionally substituted heterocycloalkyl, optionally substituted aryl, or optionally substituted heteroaryl;

R$^{35}$ and R$^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^6$, —R$^{60}$OC(=O)OR$^6$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_v$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$OR$^{54}$, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_v$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoakyl, —O(CR$^{30}$R$^{31}$)$_w$NR$^{32}$-heteroaryl, —O(CR$^{30}$R$^{31}$)$_w$NR$^{32}$-heterocycoakyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_w$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_v$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR³²(CR³⁰R³¹)ᵥᵥOR³⁴, —C(=NR³⁶)NR³²R³³, —C(=NR³⁶)NR³²C(=O)R³⁴, —S(=O)₁,₂R³⁴, —SR³⁵, —S(=O)₀,₁,₂(CR³⁰R³¹)ᵥᵥNR³²R³³, —S(=O)₀,₁,₂(CR³⁰R³¹)ᵥᵥOH, —S(=O)₀,₁,₂(CR³⁰R³¹)ᵥᵥOR³⁴, —S(=O)₀,₁,₂NR³²R³³, —S(=O)₀,₁,₂NR³²(CR³⁰R³¹)ᵥᵥNR³²R³³, —S(=O)₀,₁,₂(CR³⁰R³¹)ᵥᵥN(R³²)C(=NR³⁶)R³⁴, —S(=O)₀,₁,₂(CR³⁰R³¹)ᵥC(=NR³⁶)NR³²R³³, —S(=O)₀,₁,₂(CR³⁰R³¹)ᵥᵥN(R³²)C(=NR³⁶)NR³²R³³, —S(=O)₀,₁,₂(CR³⁰R³¹)ᵥC(=NR³⁶)NR³²C(=NR³⁶)NR³²R³³, —Si(R³⁴)₃, —NR³²R³³R³⁴⁺Q⁻, —(CR³⁰R³¹)ᵥNR³²R³³R³⁴⁺Q⁻, —NR³²(CR³⁰R³¹)ᵥᵥNR³²R³³R³⁴⁺Q⁻, —NR³²R³⁴⁺(CR³⁰R³¹)ᵥᵥNR³²R³³R³⁴⁺Q⁻₂, —(CR³⁰R³¹)ᵥ(T)⁺Q⁻, or —O(CR³⁰R³¹)ᵥᵥNR³²R³³R³⁴⁺Q⁻;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Over the decades of clinical use of beta-lactam antibiotics, bacteria have evolved resistance mechanisms that compromise beta-lactam utility, including production of easily transferable, broad-spectrum beta-lactamases that are able to efficiently hydrolyze the beta lactam ring. These enzymes, now counting >1300 variants, have spread throughout Enterobacteriaceae. The rapid spread of this mechanism of bacterial resistance severely limits beta-lactam therapeutic options.

Novel non-beta-lactam compounds that inhibit the transpeptidase function of PBPs and are not degraded by beta-lactamases would represent a major advance in the treatment of resistant bacterial infections, essentially circumventing >70 years of bacterial evolution to protect the function of the penicillin-binding proteins in cell wall biosynthesis. The present invention is directed to certain boron-based compounds (boronic acids and cyclic boronic acid esters) which are PBP inhibitors and antibacterial compounds. The compounds and their pharmaceutically acceptable salts are useful for the treatment of bacterial infections, particularly antibiotic resistant bacterial infections. Some embodiments include compounds, compositions, pharmaceutical compositions, use, and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins, and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase.

"Amino" refers to the —NH₂ substituent.
"Oxo" refers to the =O substituent.
"Oxime" refers to the =N—OH substituent.
"Thioxo" refers to the =S substituent.
"Alkyl" refers to a linear or branched hydrocarbon chain, which is fully saturated. Alkyl may have from one to thirty carbon atoms. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. An alkyl comprising up to 6 carbons is a $C_1$-$C_6$ alkyl. Alkyl groups include, but are not limited to, $C_1$-$C_{30}$ alkyl, $C_1$-$C_{20}$ alkyl, $C_1$-$C_5$ alkyl, $C_1$-$C_{10}$ alkyl, $C_1$-$C_5$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_5$ alkyl, and $C_5$-$C_{12}$ alkyl. In some embodiments, the alkyl group is $C_1$-$C_6$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, and the like. Representative linear alkyl groups include, but are not limited to, methyl, ethyl, n-propyl, n-butyl, n-pentyl and the like. In certain embodiments, an alkyl group is optionally substituted by one or more of the following substituents: halogen, cyano, nitro, oxo, thioxo, imino, oximo, trimethylsilyl, —OR$^e$, —SR$^e$, —OC(O)—R$^e$, —N(R$^e$)$_2$, —C(O)R$^e$, —C(O)OR$^e$, —C(O)N(R$^e$)$_2$, —N(R$^e$)C(O)OR$^f$, —OC(O)—NR$^e$R$^f$, —N(R$^e$)C(O)R$^f$, —N(R$^e$)S(O)$_t$R$^f$ (where t is 1 or 2), —S(O)$_t$OR$^e$ (where t is 1 or 2), —S(O)$_t$R$^f$ (where t is 1 or 2), —S(O)$_t$N(R$^e$)$_2$ (where t is 1 or 2), aryl (optionally substituted as defined below), heteroaryl (optionally substituted as defined below), cycloalkyl (optionally substituted as defined below), and heterocycloalkyl (optionally substituted as defined below); where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, the alkyl is substituted with an optionally substituted aryl to form an optionally substituted aralkyl. In some embodiments, the alkyl is substituted with an optionally substituted heteroaryl to form an optionally substituted heteroarylalkyl. In some embodiments, the alkyl is substituted with an optionally substituted cycloalkyl to form an optionally substituted cycloalkylalkyl. In some embodiments, the alkyl is substituted with an optionally substituted heterocycloalkyl to form an optionally substituted heterocycloalkylalkyl. In some embodiments, an alkyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to a straight or branched hydrocarbon chain, containing at least one carbon-carbon double bond. In certain embodiments, alkenyl comprises two to twelve (C$_2$-C$_{12}$ alkenyl) carbon atoms, or two to eight carbon atoms (C$_2$-C$_8$ alkenyl), or two to six carbon atoms (C$_2$-C$_6$ alkenyl) or two to four carbon atoms (C$_2$-C$_4$ alkenyl). The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Alkenyl may be attached to the rest of the molecule by a double bond, e.g., =CH$_2$, =CH(CH$_2$)$_3$CH$_3$. In certain embodiments, an alkenyl group is optionally substituted by one or more of the following substituents: halo, cyano, nitro, oxo, thioxo, imino, oximo, trimethylsilyl, —OR$^e$, —SR$^e$, —OC(O)—R$^e$, —N(R$^e$)$_2$, —C(O)R$^e$, —C(O)OR$^e$, —C(O)N(R$^e$)$_2$, —N(R$^e$)C(O)OR$^f$, —OC(O)—NR$^e$R$^f$, —N(R$^e$)C(O)R$^f$, —N(R$^e$)S(O)$_t$R$^f$ (where t is 1 or 2), —S(O)$_t$OR$^e$ (where t is 1 or 2), —S(O)$_t$R$^f$ (where t is 1 or 2) —S(O)$_t$N(R$^e$)$_2$ (where t is 1 or 2), aryl, heteroaryl, cycloalkyl, and heterocycloalkyl; where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkenyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —CF$_3$, —OH, —OMe, —NH$_2$, or —NO$_2$. In some embodiments, the alkenyl is optionally substituted with oxo, halogen, —CN, —CF$_3$, —OH, or —OMe. In some embodiments, the alkenyl is optionally substituted with halogen.

"Alkynyl" refers to a straight or branched hydrocarbon chain group, containing at least one carbon-carbon triple bond. In certain embodiments, alkynyl comprises two to twelve (C$_2$-C$_{12}$ alkynyl) carbon atoms, or two to eight carbon atoms (C$_2$-C$_8$ alkynyl), or two to six carbon atoms (C$_2$-C$_6$ alkynyl) or two to four carbon atoms (C$_2$-C$_4$ alkynyl). The alkynyl may be attached to the rest of the molecule by a single bond, for example, ethynyl, propynyl, butynyl, pentynyl, hexynyl, and the like. In certain embodiments, an alkynyl group is optionally substituted by one or more of the following substituents: halo, cyano, nitro, oxo, thioxo, imino, oximo, trimethylsilanyl, —OR$^e$, —SR$^e$, —OC(O)—R$^e$, —N(R$^e$)$_2$, —C(O)R$^e$, —C(O)OR$^e$, —C(O)N(R$^e$)$_2$, —N(R$^e$)C(O)OR$^f$, —OC(O)—NR$^e$R$^f$, —N(R$^e$)C(O)R$^f$, —N(R$^e$)S(O)$_t$R$^f$ (where t is 1 or 2), —S(O)$_t$OR$^e$ (where t is 1 or 2), —S(O)$_t$R$^f$ (where t is 1 or 2) —S(O)$_t$N(R$^e$)$_2$ (where t is 1 or 2), aryl, heteroaryl, cycloalkyl, and heterocycloalkyl; where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkynyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —CF$_3$, —OH, —OMe, —NH$_2$, or —NO$_2$. In some embodiments, the alkynyl is optionally substituted with oxo, halogen, —CN, —CF$_3$, —OH, or —OMe. In some embodiments, the alkynyl is optionally substituted with halogen.

"Alkylene" or "alkylene chain" refers to a straight or branched divalent hydrocarbon chain linking the rest of the molecule to a radical group, consisting solely of carbon and hydrogen, containing no unsaturation and having, for example, from one to twelve carbon atoms (C$_1$-C$_{12}$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (C$_1$-C$_8$ alkylene), or one to five carbon atoms (C$_1$-C$_5$ alkylene), or one to four carbon atoms (C$_1$-C$_4$ alkylene), or one to three carbon atoms (C$_1$-C$_3$ alkylene), or one to two carbon atoms (C$_1$-C$_2$ alkylene). In other embodiments, an alkylene comprises one carbon atom (C$_1$ alkylene), or two carbon atoms (C$_2$ alkylene). In certain embodiments, an alkylene comprises two to five carbon atoms (e.g., C$_2$-C$_5$ alkylene). In certain embodiments, an alkylene chain is optionally substituted by one or more of the following substituents: halo, cyano, nitro, oxo, thioxo, imino, oximo, trimethylsilyl, —OR$^e$, —SR$^e$, —OC(O)—R$^e$, —N(R$^e$)$_2$, —C(O)R$^e$, —C(O)OR$^e$, —C(O)N(R$^e$)$_2$, —N(R$^e$)C(O)OR$^f$, —OC(O)—NR$^e$R$^f$, —N(R$^e$)C(O)R$^f$, —N(R$^e$)S(O)$_t$R$^f$ (where t is 1 or 2), —S(O)$_t$OR$^e$ (where t is 1 or 2), —S(O)$_t$R$^f$ (where t is 1 or 2) —S(O)$_t$N(R$^e$)$_2$ (where t is 1 or 2), aryl, heteroaryl, cycloalkyl, and heterocycloalkyl; where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkylene group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkylene is optionally substituted with oxo, halogen, —CN, —CF$_3$, —OH, —OMe, —NH$_2$, or —NO$_2$. In some embodiments, the alkylene is optionally substituted with oxo, halogen, —CN, —CF$_3$, —OH, or —OMe. In some embodiments, the alkylene is optionally substituted with halogen.

"Alkoxy" refers to a radical of the formula —O-alkyl where alkyl is as defined herein. Unless stated otherwise specifically in the specification, an alkoxy group may be optionally substituted as described above for alkyl.

"Aryl" refers to an aromatic monocyclic hydrocarbon or aromatic multicyclic hydrocarbon ring system by removing a hydrogen atom from a ring carbon atom. Aryl may include cycles with six to eighteen carbon atoms, where at least one of the rings in the ring system is aromatic, i.e., it contains a cyclic, delocalized (4n+2) π-electron system in accordance with the Hückel theory. In some embodiments, the aryl is a monocyclic, bicyclic, tricyclic or tetracyclic ring system, which may include fused ring system (when fused with a cycloalkyl or heterocycloalkyl ring, the aryl is bonded through an aromatic ring atom). In some embodiments, the aryl is a 6 to 10-membered aryl. In some embodiments, the aryl is a 6-membered aryl. In some embodiments, the aryl is a 10-membered aryl. The ring system from which aryl groups are derived include, but are not limited to, groups such as benzene, fluorene, indane, indene, tetralin and naphthalene. In certain embodiments, an aryl group is optionally substituted by one or more of the following substituents: alkyl, alkenyl, alkynyl, halogen, fluoroalkyl, hydroxyalkyl, aminoalkyl, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —R$^g$—OR$^e$, —R$^g$C(=NR$^e$)N(R$^e$)$_2$, —R$^g$—OC(O)—R$^e$, —R$^g$—OC(O)—OR$^e$, —R$^g$—OC(O)—N(R$^e$)$_2$, —R$^g$—N(R$^e$)$_2$, —R$^g$—C(O)R$^e$, —R$^g$—C(O)OR$^e$, —R$^g$—C(O)N(R$^e$)$_2$, —R$^g$—O—R$^h$—C(O)N(R$^e$)$_2$, —R$^g$—N(R$^e$)C(O)OR$^e$, —R$^g$—N(R$^e$)C(O)R$^e$, —R$^g$—N(R$^e$)S(O)$_t$R$^e$ (where t is 1 or 2), —R$^g$—S(O)$_t$OR$^e$ (where t is 1 or 2), —R$^g$—S(O)$_t$R$^e$ (where t is 1 or 2), and —R$^g$—S(O)$_t$N(R$^e$)$_2$ (where t is 1 or 2), where each R$^e$ is independently hydrogen, alkyl, fluoroalkyl, cycloalkyl, cycloalkylalkyl, aryl, aralkyl, heterocycloalkyl (optionally substituted with one or more alkyl groups), heterocycloalkylalkyl, heteroaryl or heteroarylalkyl, or two R$^e$ attached to the same nitrogen atom are combined to form a heterocycloalkyl, each R$^g$ is independently a direct bond or a straight or branched alkylene or alkenylene chain, and R$^h$ is a straight or branched alkylene or alkenylene chain, and where each of the above substituents is unsubstituted unless otherwise indicated. In some embodiments, an aryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the aryl is optionally substituted with halogen, —CN, -Me, -Et, —CF$_3$, —OH, —OMe, —NH$_2$, —NO$_2$, or cyclopropyl. In some embodiments, the aryl is optionally substituted with oxo, halogen, —CN, -Me, -Et, —CF$_3$, —OH, —OMe, or cyclopropyl. In some embodiments, the aryl is optionally substituted with halogen.

"Aryloxy" refers to a radical bonded through an oxygen atom of the formula —O-aryl, where aryl is as described above.

"Aralkyl" refers to a radical of the formula —R$^h$-aryl where R$^h$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Boronate ester" refers to —B(OR$^k$)$_2$ wherein each R$^k$ are independently hydrogen, optionally substituted alkyl, optionally substituted cycloalkyl, optionally substituted heterocycloalkyl, optionally substituted aryl, optionally substituted heteroaryl, (poly ethylene glycol) ethyl, or an optionally substituted saccharide provided that they are not both hydrogen. In some embodiments, each R$^k$ is alkyl. In some embodiments, two R$^k$ may be taken together with the atom to which they are attached to form an optionally substituted heterocycle or a cyclic boronate ester. In some embodiments, the cyclic boronate ester is formed from pinanediol, pinacol, 1,2-ethanediol, 1,3-propanediol, 1,2-propanediol, 2,3-butanediol, 1,2-diisopropylethandiol, 5,6-decanediol, 1,2-dicyclohexylethanediol, diethanolamine, 1,2-diphenyl-1,2-ethanediol, 2,6,6-trimethylbicyclo[3.1.1]heptane-2,3-diol, or (1 S,2S,3R,5S)-2,6,6-trimethylbicyclo[3.1.1]heptane-2,3-diol.

"Cycloalkyl" refers to a saturated or partially unsaturated, monocyclic or polycyclic hydrocarbon. In certain embodiments, the cycloalkyl includes fused (when fused with an aryl or a heteroaryl ring, the cycloalkyl is bonded through a non-aromatic ring atom) or bridged ring systems. In certain embodiments, the cycloalkyl comprises from three to twenty carbon atoms (C$_3$-C$_{20}$ cycloalkyl), or three to ten carbon atoms (C$_3$-C$_{10}$ cycloalkyl), or three to eight carbon atoms (C$_3$-C$_8$ cycloalkyl), or three to six carbon atoms (C$_3$-C$_6$ cycloalkyl). In some embodiments, the cycloalkyl is a 3- to 6-membered cycloalkyl. In some embodiments, the cycloalkyl is a 3- to 8-membered cycloalkyl. Examples of monocyclic cycloalkyls include, e.g., cyclopropyl, cyclobutyl, cyclopentyl, cyclohexyl, cycloheptyl, and cyclooctyl. Polycyclic cycloalkyl include, for example, adamantyl, norbornyl (i.e., bicyclo[2.2.1]heptanyl), norbornenyl, decalinyl, 7,7-dimethyl-bicyclo[2.2.1]heptanyl, and the like. In certain embodiments, the cycloalkyl is optionally substituted by one or more substituents independently selected from alkyl, alkenyl, alkynyl, halogen, fluoroalkyl, hydroxyalkyl, aminoalkyl, oxo, thioxo, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —R$^g$—OR$^e$, —R$^g$C(=NR$^e$)N(R$^e$)$_2$, —R$^g$—OC(O)—R$^e$, —R$^g$—OC(O)—OR$^e$, —R$^g$—OC(O)—N(R$^e$)$_2$, —R$^g$—N(R$^e$)$_2$, —R$^g$—C(O)R$^e$, —R$^g$—C(O)OR$^e$, —R$^g$—C(O)N(R$^e$)$_2$, —R$^g$—O—R$^h$—C(O)N(R$^e$)$_2$, —R$^g$—N(R$^e$)C(O)OR$^e$, —R$^g$—N(R$^e$)C(O)R$^e$, —R$^g$—N(R$^e$)S(O)$_t$R$^e$ (where t is 1 or 2), —R$^g$—S(O)$_t$OR$^e$ (where t is 1 or 2), —R$^g$—S(O)$_t$R$^e$ (where t is 1 or 2) and —R$^g$—S(O)$_t$N(R$^e$)$_2$ (where t is 1 or 2), where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^g$ is independently a direct bond or a straight or branched alkylene or alkenylene chain, and R$^h$ is a straight or branched alkylene or alkenylene chain, and where each of the above substituents is unsubstituted unless otherwise indicated. In some embodiments, a cycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the cycloalkyl is optionally substituted with oxo, halogen, —CN, -Me, -Et, —CF$_3$, —OH, —OMe, —NH$_2$, —NO$_2$, or cyclopropyl. In some embodiments, the cycloalkyl is optionally substituted with oxo, halogen, —CN, -Me, -Et, —CF$_3$, —OH, —OMe, or cyclopropyl. In some embodiments, the cycloalkyl is optionally substituted with halogen.

"Cycloalkylalkyl" refers to a radical of the formula —R$^h$-cycloalkyl where R$^h$ is an alkylene chain as defined above. The alkylene chain and the cycloalkyl radical are optionally substituted as described above.

"Halo" or "halogen" refers to bromo, chloro, fluoro, or iodo. In some embodiments, halogen refers to chloro or fluoro.

"Heterocycloalkyl" refers to a saturated or partially unsaturated ring that comprises two to twenty carbon atoms and at least one heteroatom. In certain embodiments, the heteroatoms are independently selected from N, O, Si, P, B, and S atoms. In certain embodiments, the heteroatoms are independently selected from N, O, and S atoms. The heterocycloalkyl may be selected from monocyclic or bicyclic, fused (when fused with an aryl or a heteroaryl ring, the heterocycloalkyl is bonded through a non-aromatic ring atom) or bridged ring systems. The heteroatoms in the heterocycloalkyl are optionally oxidized. One or more nitrogen atoms, if present, are optionally quaternized. The heterocycloalkyl is partially or fully saturated. The heterocycloalkyl is attached to the rest of the molecule through any atom of the heterocycloalkyl, valence permitting, such as any carbon or nitrogen atoms of the heterocycloalkyl. In certain embodiments, the heterocycloalkyl comprises from two to twenty carbon atoms (C$_2$-C$_{20}$ heterocycloalkyl), or two to ten carbon atoms (C$_2$-C$_{10}$ heterocycloalkyl), or two to eight carbon atoms (C$_2$-C$_8$ heterocycloalkyl), or two to six carbon atoms (C$_2$-C$_6$ heterocycloalkyl). In some embodiments, the heterocycloalkyl is a 3- to 6-membered heterocycloalkyl. In some embodiments, the heterocycloalkyl is a 3- to 8-membered heterocycloalkyl. In some embodiments, the heterocycloalkyl is a 5- to 6-membered heterocycloalkyl. In some embodiments, the heterocycloalkyl is a 5-membered heterocycloalkyl. In some embodiments, the heterocycloalkyl is a 6-membered heterocycloalkyl. Examples of heterocycloalkyl include, but are not limited to, azetidinyl, aziridyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. In some embodiments, the heterocycloalkyl is piperazinyl. In certain embodiments, a heterocycloalkyl group is optionally substituted by one or more of the following substituents selected from alkyl, alkenyl, alkynyl, halogen, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^g$—OR$^e$, —R$^g$C(=NR$^e$)N(R$^e$)$_2$, —R$^g$—OC(O)—R$^e$, —R$^g$—OC(O)—OR$^e$, —R$^g$—OC(O)—N(R$^e$)$_2$, —R$^g$—N (R$^e$)$_2$, —R$^g$—C(O)R$^e$, —R$^g$—C(O)OR$^e$, —R$^g$—C(O) N(R$^e$)$_2$, —R$^g$—O—R$^h$—C(O)N(R$^e$)$_2$, —R$^g$—N(R$^e$)C(O) OR$^e$, —R$^g$—N(R$^e$)C(O)R$^e$, —R$^g$—N(R$^e$)S(O)$_t$R$^e$ (where t is 1 or 2), —R$^g$—S(O)$_t$OR$^e$ (where t is 1 or 2), —R$^g$—S (O)$_t$R$^e$ (where t is 1 or 2) and —R$^g$—S(O)$_t$N(R$^e$)$_2$ (where t is 1 or 2), where each R$^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^g$ is independently a direct bond or a straight or branched alkylene or alkenylene chain, and R$^h$ is a straight or branched alkylene or alkenylene chain, and where each of the above substituents is unsubstituted unless otherwise indicated. In some embodiments, a heterocycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the heterocycloalkyl is optionally substituted with oxo, halogen, —CN, -Me, -Et, —CF$_3$, —OH, —OMe, —NH$_2$, —NO$_2$, or cyclopropyl. In some embodiments, the heterocycloalkyl is optionally substituted with oxo, halogen, —CN, -Me, -Et, —CF$_3$, —OH, —OMe, or cyclopropyl. In some embodiments, the heterocycloalkyl is optionally substituted with halogen.

"Heterocycloalkylalkyl" refers to a radical of the formula —R$^h$-heterocycloalkyl where R$^h$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heteroaryl" refers to a 5- to 14-membered ring system comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl is a 5-membered heteroaryl. In some embodiments, the heteroaryl is a 6-membered heteroaryl. In some embodiments, the heteroaryl is a monocyclic, bicyclic, tricyclic or tetracyclic ring system, which may include fused ring systems (when fused with a cycloalkyl or heterocycloalkyl ring, the heteroaryl is bonded through an aromatic ring atom); and the nitrogen, carbon or sulfur atoms in the heteroaryl may be optionally oxidized; the nitrogen atom may be optionally quaternized. In some embodiments, the heteroaryl is a 5- to 10-membered heteroaryl. In some embodiments, the heteroaryl is a 5-membered heteroaryl. In some embodiments, the heteroaryl is a 6-membered heteroaryl. In some embodiments, the heteroaryl is a 10-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted by one or more of the following substituents selected from alkyl, alkenyl, alkynyl, halogen, fluoroalkyl, hydroxyalkyl, aminoalkyl, haloalkenyl, haloalkynyl, cyano, nitro, aryl, aralkyl, aralkenyl, alkynyl, cycloalkyl, cycloalkylalkyl, heterocycloalkyl, heterocycloalkylalkyl, heteroaryl, heteroarylalkyl, $-R^g-OR^e$, $-R^gC(=NR^e)N(R^e)_2$, $-R^g-OC(O)-R^e$, $-R^g-OC(O)-OR^e$, $-R^g-OC(O)-N(R^e)_2$, $-R^g-N(R^e)_2$, $-R^g-C(O)R^e$, $-R^g-C(O)OR^e$, $-R^g-C(O)N(R^e)_2$, $-R^g-O-R^h-C(O)N(R^e)_2$, $-R^g-N(R^e)C(O)OR^e$, $-R^g-N(R^e)C(O)R^e$, $-R^g-N(R^e)S(O)_tR^e$ (where t is 1 or 2), $-R^g-S(O)_tOR^e$ (where t is 1 or 2), $-R^g-S(O)_tR^e$ (where t is 1 or 2) and $-R^g-S(O)_tN(R^e)_2$ (where t is 1 or 2), where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^g$ is independently a direct bond or a straight or branched alkylene or alkenylene chain, and $R^h$ is a straight or branched alkylene or alkenylene chain, and where each of the above substituents is unsubstituted unless otherwise indicated. In some embodiments, a heteroaryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the heteroaryl is optionally substituted with halogen, —CN, -Me, -Et, —CF$_3$, —OH, —OMe, —NH$_2$, —NO$_2$, or cyclopropyl. In some embodiments, the heteroaryl is optionally substituted with halogen, —CN, -Me, -Et, —CF$_3$, —OH, —OMe, or cyclopropyl. In some embodiments, the heteroaryl is optionally substituted with halogen.

"Heteroarylalkyl" refers to a radical of the formula —$R^h$-heteroaryl, where $R^h$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

Compounds

Described herein are compounds that modulate the activity of beta-lactamase. In some embodiments, the compounds described herein inhibit beta-lactamase. In some embodiments, the compounds described herein inhibit penicillin binding protein. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula (Ia) or Formula (Ib), or a pharmaceutically acceptable salt, solvate, stereoisomer, tautomer, N-oxide, dimer, or trimer thereof:

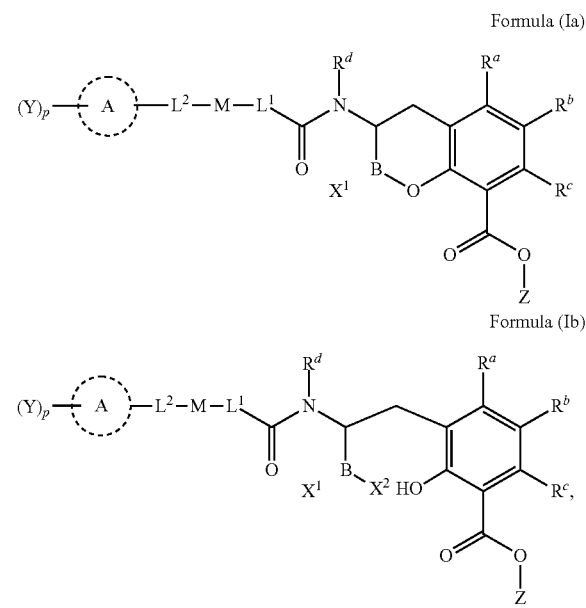

wherein:
L$^1$ is —(CR$^1$R$^2$)$_n$—;
L$^2$ is —(CR$^1$R$^2$)$_m$—;
Ring A is cycloalkyl, heterocycloalkyl, aryl, or heteroaryl;
M is

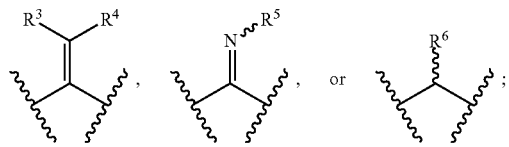

each R$^1$ and R$^2$ are independently hydrogen, halogen, optionally substituted alkyl, —OH, —OR$^{34}$, —SR$^{35}$, —$NR^{32}R^{33}$, —$NR^{32}C(=O)R^{34}$, —$C(=O)NR^{32}R^{33}$, —$NR^{32}S(=O)_2R^{34}$, —$C(=O)OH$, —$C(=O)OR^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^3$ and $R^4$ are independently hydrogen, halogen, optionally substituted alkyl, optionally substituted cycloalkyl, optionally substituted heterocycloalkyl, optionally substituted aryl, optionally substituted heteroaryl, —$C(=O)OH$, —$C(=O)OR^{44a}$, —$(CR^{40a}R^{41a})_vC(=O)OH$, —$(CR^{40a}R^{41a})_vC(=O)OR^{44a}$, —$(CR^{40a}R^{41a})_vOH$, or —$(CR^{40a}R^{41a})_vOR^{44a}$; or $R^3$ and $R^4$ are taken together with the carbon atom to which they are attached to form optionally substituted cycloalkyl or an optionally substituted heterocycloalkyl;

$R^5$ is —$OR^{10}$, —$NR^{11}R^{12}$, —$S(=O)_{0,1,2}R^{13}$;

$R^6$ is optionally substituted alkyl, —$(CR^{40b}R^{41b})_vC(=O)OR^{44b}$, or —$(CR^{40b}R^{41b})_vC(=O)OH$;

$R^{10}$ is hydrogen, optionally substituted alkyl, optionally substituted cycloalkyl, optionally substituted heterocycloalkyl, optionally substituted aryl, optionally substituted heteroaryl, —$(CR^{40d}R^{41d})_vNR^{42d}R^{43d}$, —$(CR^{40d}R^{41d})_vC(=O)NR^{42d}R^{43d}$, —$(CR^{40d}R^{41d})_vC(=O)NR^{42d}(CR^{40d}R^{41d})C_wNR^{42d}C(=O)R^{44d}$, —$(CR^{40d}R^{41d})_vC(=O)NR^{42d}(CR^{40d}R^{41d})_wNR^{42d}R^{43d}$, —$(CR^{40d}R^{41d})_vC(=O)NR^{42d}(CR^{40d}R^{41d})_wNR^{42d}(CR^{40d}R^{41d})_wNR^{42d}R^{43d}$, —$(CR^{40d}R^{41d})_vC(=O)NR^{42d}(CR^{40d}R^{41d})_vC(=O)OH$, —$(CR^{40d}R^{41d})_vC(=O)NR^{42d}(CR^{40d}R^{41d})_vC(=O)OR^{44d}$, —$(CR^{40d}R^{41d})_vNR^{42d}C(=O)R^{44d}$, —$(CR^{40d}R^{41d})_vNR^{42d}S(=O)_{0,1,2}R^{44d}$, —$(CR^{40d}R^{41d})_vOH$, —$(CR^{40d}R^{41d})_vOR^{44d}$, —$(CR^{40d}R^{41d})_vC(=O)OH$, —$(CR^{40d}R^{41d})_vC(=O)OR^{44d}$, —$(CR^{40d}R^{41d})_v$heteroaryl, or —$(CR^{40d}R^{41d})_v$heterocycloalkyl.

$R^{11}$ and $R^{12}$ are independently hydrogen, —$S(=O)_2R^{44e}$, —$S(=O)_2NR^{42e}R^{43e}$, optionally substituted alkyl, optionally substituted cycloalkyl, optionally substituted heterocycloalkyl, optionally substituted aryl, or optionally substituted heteroaryl; or $R^{11}$ and $R^{12}$ are taken together with the nitrogen to which they are attached to form an optionally substituted heterocycloalkyl;

$R^{13}$ is optionally substituted alkyl, optionally substituted cycloalkyl, optionally substituted heterocycloalkyl, optionally substituted aryl, or optionally substituted heteroaryl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40a}$, $R^{40b}$, $R^{40d}$, $R^{41a}$, $R^{41b}$, $R^{41d}$, $R^5$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —$OR^{24}$, —$SR^{25}$, —$NR^{22}R^{23}$, —$NR^{22}C(=O)R^{24}$, —$C(=O)NR^{22}R^{23}$, —$NR^{22}S(=O)_2R^{24}$, —$C(=O)OH$, or —$C(=O)OR^{24}$ or $R^{30}$ and $R^{31}$, $R^{40a}$ and $R^{41a}$, $R^{40b}$ and $R^{41b}$, $R^{40d}$ and $R^{41d}$, or $R^{50}$ and $R^{51}$ are taken together with the carbon atom to which they are attached form an optionally substituted cycloalkyl; or two $R^{30}$, two $R^{40a}$, two $R^{40b}$, two $R^{40d}$, or two $R^{50}$ on adjacent carbons are taken together to form an alkenyl; or two $R^{30}$ and two $R^{31}$, two $R^{40a}$ and two $R^{41a}$, two $R^{40b}$ and two $R^{41b}$, two $R^{40d}$ and two $R^{41d}$, or two $R^{50}$ and two $R^{51}$ on adjacent carbons are taken together to form an alkynyl;

$R^{32}$, $R^{33}$, $R^{42d}$, $R^{42e}$, $R^{43d}$, $R^{43e}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —$S(=O)_2R^{24}$, —$S(=O)_2NR^{22}R^{23}$, or —$C(=O)R^{24}$; or $R^{32}$ and $R^{33}$, $R^{42d}$ and $R^{43d}$, $R^{42e}$ and $R^{43e}$, or $R^{52}$ and $R^{53}$ are taken together with the nitrogen to which they are attached to form an optionally substituted heterocycloalkyl;

$R^{34}$, $R^{44a}$, $R^{44b}$, $R^{44d}$, $R^{44e}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —$OR^{24}$, —CN, —$NO_2$, —$NR^{22}R^{23}$, or optionally substituted alkyl;

Z is hydrogen, $R^{61}$, —$(R^{60})_qOR^{61}$, —$(R^{60})_qO(R^{60})_qOR^{61}$, —$R^{60}OC(=O)R^{61}$, —$R^{60}OC(=O)OR^{61}$, —$R^{60}OC(=O)NHR^{61}$, —$R^{60}OC(=O)N(R^{61})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —$CH_2$—, —$CH(CH_3)$—, —$C(CH_3)_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —$OR^{54}$, —$O(CR^{50}R^{51})_wNR^{52}R^{53}$, —$O(CR^{50}R^{51})_wOH$, —$O(CR^{50}R^{51})_wOR^{54}$, —$O(CR^{50}R^{51})_vC(=O)OH$, —$O(CR^{50}R^{51})_vC(=O)$ OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$C$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

R$^X$ is optionally substituted alkyl or optionally substituted cycloalkyl;

X$^1$ and X$^2$ are independently —OH, —OR$^X$, or F; or

X$^1$ and X$^2$ are taken together with the boron atom to which they are attached to form a cyclic boronate ester; each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_w$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)N$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoalkyl, —O(CR$^{30}$R$^{31}$)$_w$NR$^{32}$-heteroaryl, —O(CR$^{30}$R$^{31}$)$_w$NR$^{32}$-heterocycoalkyl, —O(CR$^{30}$R$^{31}$)$_w$O-heterocycoalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$S(=O)$_{0,1,2}$R$^{34}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_w$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$—(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycoakyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-{}_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

In some embodiments of a compound of Formula (Ia) or (Ib), M is

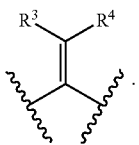

In some embodiments of a compound of Formula (Ia) or (Ib), M is

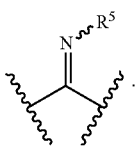

In some embodiments of a compound of Formula (Ia) or (Ib), M is

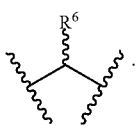

Also disclosed herein is a compound of Formula (IIa) or (IIb), or a pharmaceutically acceptable salt, solvate, stereoisomer, tautomer, N-oxide, dimer, or trimer thereof:

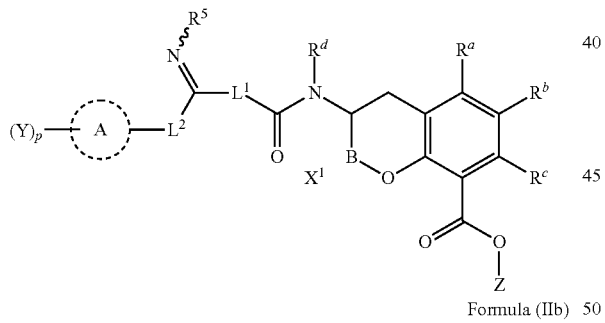

Formula (IIa)

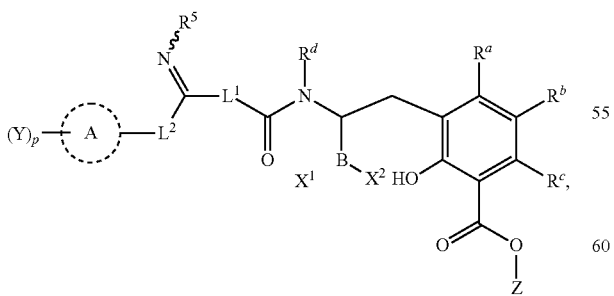

Formula (IIb)

wherein:
$L^1$ is $-(CR^1R^2)_n-$;
$L^2$ is $-(CR^1R^2)_m-$;
Ring A is cycloalkyl, heterocycloalkyl, aryl, or heteroaryl;

each $R^1$ and $R^2$ are independently hydrogen, halogen, optionally substituted alkyl, $-OH$, $-OR^{34}$, $-SR^{35}$, $-NR^{32}R^{33}$, $-NR^{32}C(=O)R^{34}$, $-C(=O)NR^{32}R^{33}$, $-NR^{32}S(=O)_2R^{34}$, $-C(=O)OH$, $-C(=O)OR^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^5$ is $-OR^{10}$, $-NR^{11}R^{12}$, $-S(=O)_{0,1,2}R^{13}$;

$R^{10}$ is hydrogen, optionally substituted alkyl, optionally substituted cycloalkyl, optionally substituted heterocycloalkyl, optionally substituted aryl, optionally substituted heteroaryl, $-(CR^{40d}R^{41d})_vNR^{42d}R^{43d}$, $-(CR^{40d}R^{41d})_vC(=O)NR^{42d}R^{43d}$, $-(CR^{40d}R^{41d})_vC(=O)NR^{42d}(CR^{40d}R^{41d})_wNR^{42d}C(=O)R^{44d}$, $-(CR^{40d}R^{41d})_vC(=O)NR^{42d}(CR^{40d}R^{41d})_wNR^{42d}R^{43d}$, $-(CR^{40d}R^{41d})_vC(=O)NR^{42d}(CR^{40d}R^{41d})_wNR^{42d}(CR^{40d}R^{41d})_wNR^{42d}R^{43d}$, $-(CR^{40d}R^{41d})_vC(=O)NR^{42d}(CR^{40d}R^{41d})_vC(=O)OH$, $-(CR^{40d}R^{41d})_vC(=O)NR^{42d}(CR^{40d}R^{41d})_vC(=O)OR^{44d}$, $-(CR^{40d}R^{41d})_vNR^{42d}C(=O)R^{44d}$, $-(CR^{40d}R^{41d})_vNR^{42d}S(=O)_{0,1,2}R^{44d}$, $-(CR^{40d}R^{41d})_vOR^{44d}$, $-(CR^{40d}R^{41d})_vOH$, $-(CR^{40d}R^{41d})_vC(=O)OH$, $-(CR^{40d}R^{41d})_vC(=O)OR^{44d}$, $-(CR^{40d}R^{41d})_v$heteroaryl, or $-(CR^{40d}R^{41d})_v$heterocycloalkyl;

$R^{11}$ and $R^{12}$ are independently hydrogen, $-S(=O)_2R^{44e}$, $-S(=O)_2NR^{42e}R^{43e}$, optionally substituted alkyl, optionally substituted cycloalkyl, optionally substituted heterocycloalkyl, optionally substituted aryl, or optionally substituted heteroaryl; or $R^{11}$ and $R^{12}$ are taken together with the nitrogen to which they are attached to form an optionally substituted heterocycloalkyl;

$R^{13}$ is optionally substituted alkyl, optionally substituted cycloalkyl, optionally substituted heterocycloalkyl, optionally substituted aryl, or optionally substituted heteroaryl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40d}$, $R^{41d}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, $-OH$, $-OR^{24}$, $-SR^{25}$, $-NR^{22}R^{23}$, $-NR^{22}C(=O)R^{24}$, $-C(=O)NR^{22}R^{23}$, $-NR^{22}S(=O)_2R^{24}$, $-C(=O)OH$, or $-C(=O)OR^{24}$; or $R^{30}$ and $R^{31}$, $R^{40d}$ and $R^{41d}$, or $R^{50}$ and $R^{51}$ are taken together with the carbon atom to which they are attached form an optionally substituted cycloalkyl; or two $R^{30}$, two $R^{40d}$, or two $R^{50}$ on adjacent carbons are taken together to form an alkenyl; or two $R^{30}$ and two $R^{31}$, two $R^{40d}$ and two $R^{41d}$, or two $R^{50}$ and two $R^{51}$ on adjacent carbons are taken together to form an alkynyl;

$R^{32}$, $R^{33}$, $R^{42d}$, $R^{43d}$, $R^{42e}$, $R^{43e}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S($=$O)$_2$R$^{24}$, —S($=$O)$_2$NR$^{22}$R$^{23}$, or —C($=$O)R$^{24}$; or $R^{32}$ and $R^{33}$, $R^{42d}$ and $R^{43d}$, $R^{42e}$ and $R^{43e}$, or $R^{52}$ and $R^{53}$ are taken together with the nitrogen to which they are attached to form an optionally substituted heterocycloalkyl;

$R^{34}$, $R^{44d}$, $R^{44e}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC($=$O)R$^{61}$, —R$^{60}$OC($=$O)OR$^{61}$, —R$^{60}$OC($=$O)NHR$^{61}$, —R$^{60}$OC($=$O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C($=$O)OH, —O(CR$^{50}$R$^{51}$)$_v$C($=$O)OR$^{54}$, —O(CR$^{50}$R$^{51}$)$_v$C($=$O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C($=$O)OH, —NR$^{52}$(CR$^{50}$R$^{51}$)$_v$C($=$O)OR$^{54}$, —NR$^{52}$(CR$^{50}$R$^{51}$)$_v$C($=$O)NR$^{52}$R$^{53}$, —NR$^{52}$S($=$O)$_{1,2}$R$^{54}$, —S($=$O)$_{1,2}$R$^{54}$, —SR$^{55}$, —S(CR$^{50}$R$^{51}$)$_v$NR$^{52}$C($=$NR$^{56}$)NR$^{52}$R$^{53}$, —S(CR$^{50}$R$^{51}$)$_v$NR$^{52}$CR$^{50}$($=$NR$^{56}$), —S(CR$^{50}$R$^{51}$)$_v$C($=$NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C($=$O)OH, —S(CR$^{50}$R$^{51}$)$_v$C($=$O)OR$^{54}$, —S(CR$^{50}$R$^{51}$)$_v$C($=$O)NR$^{52}$R$^{53}$, —C($=$O)H, —C($=$O)R$^{54}$, —C($=$O)OH, —C($=$O)OR$^{54}$, —C($=$O)NR$^{52}$R$^{53}$, —C($=$O)(CR$^{50}$R$^{51}$)$_v$N(R$^{52}$)(CR$^{50}$R$^{51}$)$_v$C($=$O)OH, —(CR$^{50}$R$^{51}$)$_v$OH, —(CR$^{50}$R$^{51}$)$_v$OR$^{54}$, —(CR$^{50}$R$^{51}$)$_v$C($=$O)OH, —(CR$^{50}$R$^{51}$)$_v$C($=$O)OR$^{54}$, —(CR$^{50}$R$^{51}$)$_v$C($=$O)NR$^{52}$R$^{53}$, —(CR$^{50}$R$^{51}$)$_v$OC($=$O)R$^{54}$, —(CR$^{50}$R$^{51}$)$_v$NR$^{52}$C($=$NR$^{56}$), —(CR$^{50}$R$^{51}$)$_v$SR$^{55}$, —(CR$^{50}$R$^{51}$)$_v$NR$^{52}$R$^{53}$, —(CR$^{50}$R$^{51}$)$_v$C($=$NR$^{56}$)NR$^{52}$R$^{53}$, —(CR$^{50}$R$^{51}$)$_v$C($=$O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S($=$O)$_2$R$^{24}$, —S($=$O)$_2$NR$^{22}$R$^{23}$, —(CR$^{20}$R$^{21}$)$_v$C($=$O)OH, —C($=$O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C($=$NR$^{32}$)NR$^{32}$R$^{33}$, -heterocycloalkyl-N(R$^{32}$)C($=$NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C($=$O)R$^{34}$, —O(CR$^{30}$R$^{31}$)$_w$NR$^{32}$C($=$O)OR$^{34}$, —O(CR$^{30}$R$^{31}$)$_w$NR$^{32}$C($=$O)NR$^{32}$R$^{33}$, —O(CR$^{30}$R$^{31}$)$_w$C($=$O)NR$^{32}$R$^{33}$, —O(CR$^{30}$R$^{31}$)$_w$NR$^{32}$S($=$O)$_{0,1,2}$R$^{34}$, —O(CR$^{30}$R$^{31}$)$_w$NR$^{32}$S($=$O)$_{0,1,2}$NR$^{32}$R$^{33}$, —O(CR$^{30}$R$^{31}$)$_w$S($=$O)$_{0,1,2}$R$^{34}$, —O(CR$^{30}$R$^{31}$)$_w$S($=$O)$_{0,1,2}$NR$^{32}$R$^{33}$, —O(CR$^{30}$R$^{31}$)$_v$C($=$NR$^{36}$)NR$^{32}$R$^{33}$, —O(CR$^{30}$R$^{31}$)$_v$N(R$^{32}$)C($=$NR$^{36}$)R$^{34}$, —O(CR$^{30}$R$^{31}$)$_v$C($=$NR$^{36}$)NR$^{32}$C($=$NR$^{36}$)NR$^{32}$R$^{33}$, —O(CR$^{30}$R$^{31}$)$_w$N(R$^{32}$)C($=$NR$^{36}$)NR$^{32}$R$^{33}$, —O(CR$^{30}$R$^{31}$)$_w$S($=$O)$_{0,1,2}$R$^{34}$, —O(CR$^{30}$R$^{31}$)$_w$S($=$O)$_{0,1,2}$NR$^{32}$R$^{33}$, —OC($=$O)R$^{34}$, —OC($=$O)(CR$^{30}$R$^{31}$)$_w$NR$^{32}$R$^{33}$, —OC($=$O)NR$^{32}$R$^{33}$, —OC($=$O)OR$^{34}$, —OC($=$O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoakyl, —O(CR$^{30}$R$^{31}$)$_w$NR$^{32}$-heteroaryl, —O(CR$^{30}$R$^{31}$)$_w$NR$^{32}$-heterocycoakyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C($=$O)R$^{34}$, —NR$^{32}$C($=$O)OR$^{34}$, —N(R$^{32}$)C($=$O)(CR$^{30}$R$^{31}$)$_v$NR$^{32}$R$^{33}$, —NR$^{32}$C($=$O)NR$^{32}$R$^{33}$, —NR$^{32}$C($=$O)NR$^{32}$(CR$^{30}$R$^{31}$)$_w$NR$^{32}$R$^{33}$, —NR$^{32}$(CR$^{30}$R$^{31}$)$_w$S($=$O)$_{0,1,2}$R$^{34}$, —NR$^{32}$(CR$^{30}$R$^{31}$)$_w$S($=$O)$_{0,1,2}$NR$^{32}$R$^{33}$, —NR$^{32}$(CR$^{30}$R$^{31}$)$_w$NR$^{32}$R$^{33}$S($=$O)$_{0,1,2}$R$^{34}$, —NR$^{32}$(CR$^{30}$R$^{31}$)$_w$NR$^{32}$S($=$O)$_{0,1,2}$NR$^{32}$R$^{33}$, —NR$^{32}$C($=$NR$^{36}$)NR$^{32}$R$^{33}$, —N(R$^{32}$)C($=$NR$^{36}$)R$^{34}$, —NR$^{32}$(CR$^{30}$R$^{31}$)$_w$N(R$^{32}$)C($=$NR$^{36}$)R$^{34}$, —NR$^{32}$(CR$^{30}$R$^{31}$)$_v$C($=$NR$^{36}$)NR$^{32}$R$^{33}$, —NR$^{32}$(CR$^{30}$R$^{31}$)$_w$N(R$^{32}$)C($=$NR$^{36}$)NR$^{32}$R$^{33}$, —NR$^{32}$(CR$^{30}$R$^{31}$)$_w$NR$^{32}$C($=$O)NR$^{32}$R$^{33}$, —NR$^{32}$(CR$^{30}$R$^{31}$)$_w$NR$^{32}$C($=$O)OR$^{34}$, —NR$^{32}$S($=$O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C($=$O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC($=$O)R$^{34}$, —(CR$^{30}$R$^{31}$)$_v$OC($=$O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O —(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_w$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_v$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_v$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_v$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-{}_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, orthiazol-3-yl;

Q is a pharmaceutically acceptable counterion;

n is 0-3;

m is 0-3;

p is 0-3;

each q is independently 2-6;

each v is independently 1-5; and each w is independently 2-5.

In some embodiments of a compound of Formula (Ia), (IIa), (Ib) or (IIb), the compound is not: (Z)-3-(2-(2-aminothiazol-4-yl)-2-(hydroxyimino)acetamido)-2-hydroxy-3,4-dihydro-2H-benzo[e][1,2]oxaborinine-8-carboxylic acid/(Z)-3-(2-(2-(2-aminothiazol-4-yl)-2-(hydroxyimino)acetamido)-2-boronoethyl)-2-hydroxybenzoic acid; (Z)-3-(2-(2-(2-aminothiazol-4-yl)-2-(((2-carboxypropan-2-yl)oxy)imino)acetamido)-2-hydroxy-3,4-dihydro-2H-benzo[e][1,2]oxaborinine-8-carboxylic acid/(Z)-5-(2-aminothiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(((2-carboxypropan-2-yl)oxy)imino)acetamido)-2-hydroxy-3,4-dihydro-2H-benzo[e][1,2]oxaborinine-8-carboxylic acid/(Z)-5-(2-(2-aminoacetamido)thiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(methoxyimino)acetamido)-2-hydroxy-3,4-dihydro-2H-benzo[e][1,2]oxaborinine-8-carboxylic acid/(Z)-3-(2-(2-(2-(2-aminoacetamido)thiazol-4-yl)-2-(methoxyimino)acetamido)-2-boronoethyl)-2-hydroxybenzoic acid; (Z)-3-(2-(2-(2,6-diaminohexanamido)thiazol-4-yl)-2-(methoxyimino)acetamido)-2-hydroxy-3,4-dihydro-2H-benzo[e][1,2]oxaborinine-8-carboxylic acid/(Z)-3-(2-borono-2-(2-(2-(2,6-diaminohexanamido)thiazol-4-yl)-(methoxyimino)acetamido)ethyl)-2-hydroxybenzoic acid; or (Z)-3-(2-(4-(aminomethyl)phenyl)-2-(hydroxyimino)acetamido)-2-hydroxy-3,4-dihydro-2H-benzo[e][1,2]oxaborinine-8-carboxylic acid/(Z)-3-(2-(2-(4-(aminomethyl)phenyl)-2-(hydroxyimino)acetamido)-2-boronoethyl)-2-hydroxybenzoic acid.

In some embodiments of a compound of Formula (Ia), (IIa), (Ib) or (IIb), R$^5$ is —OR$^{10}$.

In some embodiments of a compound of Formula (Ia), (IIa), (Ib) or (IIb), R$^{10}$ is not hydrogen.

In some embodiments of a compound of Formula (Ia), (IIa), (Ib) or (IIb), R$^{10}$ is not —CH$_3$. In some embodiments of a compound of Formula (Ia), (IIa), (Ib) or (IIb), R$^{10}$ is not —C(CH$_3$)$_2$C(=O)OH. In some embodiments of a compound of Formula (Ia), (IIa), (Ib) or (IIb), R$^{10}$ is not hydrogen when Ring A is thiazole. In some embodiments of a compound of Formula (Ia), (IIa), (Ib) or (IIb), R$^{10}$ is not hydrogen when Ring A is benzene. In some embodiments of a compound of Formula (Ia), (IIa), (Ib) or (IIb), R$^{10}$ is not hydrogen when Y is NH$_2$. In some embodiments of a compound of Formula (Ia), (IIa), (Ib) or (IIb), R$^{10}$ is not hydrogen when Y is —CH$_2$NH$_2$. In some embodiments of a compound of Formula (Ia), (IIa), (Ib) or (IIb), R$^{10}$ is not —CH$_3$ when Y is —NHC(=O)CH$_2$NH$_2$. In some embodiments of a compound of Formula (Ia), (IIa), (Ib) or (IIb), R$^{10}$ is not —CH$_3$ when Y is —NHC(=O)CH(NH$_2$)CH$_2$CH$_2$CH$_2$CH$_2$NH$_2$. In some embodiments of a compound of Formula (Ia), (IIa), (Ib) or (IIb), R$^{10}$ is not —CH$_3$ when Ring A is thiazole. In some embodiments of a compound of Formula (Ia), (IIa), (Ib) or (IIb), R$^{10}$ is not —C(CH$_3$)$_2$C(=O)OH when Y is —NHC(=O)CH$_2$NH$_2$. In some embodiments of a compound of Formula (Ia), (IIa), (Ib) or (IIb), R$^{10}$ is not —C(CH$_3$)$_2$C(=O)OH when Y is —NH$_2$. In some embodiments of a compound of Formula (Ia), (IIa), (Ib) or (IIb), R$^{10}$ is not —C(CH$_3$)$_2$C(=O)OH when Ring A is thiazole.

In some embodiments of a compound of Formula (Ia), (IIa), (Ib) or (IIb), R$^{10}$ is hydrogen, optionally substituted alkyl, optionally substituted heterocycloalkyl, —(CR$^{40d}$R$^{41d}$)$_v$NR$^{42d}$R$^{43d}$, —(CR$^{40d}$R$^{41d}$)$_v$C(=O)NR$^{42d}$R$^{43d}$, —(CR$^{40d}$R$^{41d}$)$_v$C(=O)NR$^{42d}$(CR$^{40d}$R$^{41d}$)$_w$NR$^{42d}$R$^{43d}$, —(CR$^{40d}$R$^{41d}$)$_v$C(=O)NR$^{42d}$(CR$^{40d}$R$^{41d}$)$_v$C(=O)OH, —(CR$^{42d}$R$^{43d}$)$_v$C(=O)NR$^{42d}$(CR$^{40d}$R$^{41d}$)$_w$NR$^{42d}$C(=O)R$^{44d}$, —(CR$^{40d}$R$^{41d}$)$_v$C(=O)NR$^{42d}$(CR$^{40d}$R$^{41d}$)$_w$R$^{42d}$(CR$^{40d}$R$^{41d}$)$_w$NR$^{42d}$R$^{43d}$, —(CR$^{40d}$R$^{41d}$)$_w$NR$^{42d}$C(=O)R$^{44d}$, —(CR$^{40d}$R$^{41d}$)$_v$NR$^{42d}$S(=O)$_{0,1,2}$R$^{44d}$, —(CR$^{40d}$R$^{41d}$)$_v$OH, —(CR$^{40d}$R$^{41d}$)$_v$OR$^{44d}$, —(CR$^{40d}$R$^{41d}$)$_v$C(=O)OH, —(CR$^{40d}$R$^{41d}$)$_v$C(=O)OR$^{44d}$, or —(CR$^{40d}$R$^{41d}$)$_v$heterocycloalkyl. In some embodiments of a compound of Formula (Ia), (IIa), (Ib) or (IIb), R$^{10}$ is alkyl optionally substituted with aryl, heteroaryl, cycloalkyl, or heterocycloalkyl; each of which optionally substituted with alkyl, halogen, or cyano. In some embodiments of a compound of Formula (Ia), (IIa), (Ib) or (IIb), R$^{10}$ is heterocycloalkyl optionally substituted with alkyl, halogen, or cyano. In some embodiments of a compound of Formula (Ia), (IIa), (Ib) or (IIb), R$^{10}$ is C$_2$-C$_6$ alkyl, optionally substituted heterocycloalkyl, —(CR$^{40d}$R$^{41d}$)$_v$C(=O)NR$^{42d}$(CR$^{40d}$R$^{41d}$)$_v$C(=O)OH, —(CR$^{40d}$R$^{41d}$)$_v$NR$^{42d}$R$^{43d}$, —(CR$^{40d}$R$^{41d}$)$_v$C(=O)NR$^{42d}$R$^{43d}$, —(CR$^{40d}$R$^{41d}$)$_v$C(=O)NR$^{42d}$(CR$^{40d}$R$^{41d}$)$_w$NR$^{42d}$R$^{43d}$, —(CR$^{42d}$R$^{43d}$)$_v$C(=O)

$-NR^{42d}(CR^{40d}R^{41d})_w NR^{42d}C(=O)R^{44d}$, $-(CR^{40d}R^{41d})_v C(=O)NR^{42d}(CR^{40d}R^{41d})_w R^{42d}(CR^{40d}R^{41d})_w NR^{42d}R^{43d}$, $-(CR^{40d}R^{41d})_v NR^{42d}C(=O)R^{44d}$, $-(CR^{40d}R^{41d})_v NR^{42d}S(=O)_{0,1,2}R^{44d}$, $-(CR^{40d}R^{41d})_v OH$, $-(CR^{40d}R^{41d})_v OR^{44d}$, $-(CR^{40d}R^{41d})_v C(=O)OH$, $-(CR^{40d}R^{41d})_v C(=O)OR^{44d}$, or $-(CR^{40d}R^{41d})_v$ heterocycloalkyl; provided that $R^{10}$ is not $-C(CH_3)_2 C(=O)OH$.

In some embodiments of a compound of Formula (Ia), (IIa), (Ib) or (IIb), $R^{10}$ is hydrogen. In some embodiments of a compound of Formula (Ia), (IIa), (Ib) or (IIb), $R^{10}$ is alkyl, haloalky, hydroxyalkyl, or aminoalkyl. In some embodiments of a compound of Formula (Ia), (IIa), (Ib) or (IIb), $R^{10}$ is $-(CR^{40d}R^{41d})_v C(=O)NR^{42d}R^{43d}$. In some embodiments of a compound of Formula (Ia), (IIa), (Ib) or (IIb), $R^{10}$ is $-(CR^{40d}R^{41d})_v C(=O)NR^{42d}(CR^{40d}R^{41d})_v C(=O)OH$. In some embodiments of a compound of Formula (Ia), (IIa), (Ib) or (IIb), $R^{10}$ is $-(CR^{40d}R^{41d})_v C(=O)NR^{42d}(CR^{40d}R^{41d})_w NR^{42d}(CR^{4d}R^{41d})_w NR^{42d}R^{43d}$ In some embodiments of a compound of Formula (Ia), (IIa), (Ib) or (IIb), $R^{10}$ is $-(CR^{40d}R^{41d})_v C(=O)OH$. In some embodiments of a compound of Formula (Ia), (IIa), (Ib) or (IIb), $R^{10}$ is $-(CR^{40d}R^{41d})_v NR^{42d}C(=O)R^{44d}$. In some embodiments of a compound of Formula (Ia), (IIa), (Ib) or (IIb), $R^{10}$ is $-(CR^{40d}R^{41d})_v OR^{44d}$. In some embodiments of a compound of Formula (Ia), (IIa), (Ib) or (IIb), $-(CR^{40d}R^{41d})_v NR^{42d}S(=O)_{0,1,2}R^{44d}$. In some embodiments of a compound of Formula (Ia), (IIa), (Ib) or (IIb), $R^{10}$ is $-(CR^{40d}R^{41d})_v$ heterocycloalkyl. In some embodiments of a compound of Formula (Ia), (IIa), (Ib) or (IIb), $R^{10}$ is optionally substituted heterocycloalkyl.

In some embodiments of a compound of Formula (Ia), (IIa), (Ib) or (IIb), $R^{10}$ is as defined above, $R^{40d}$ and $R^{41d}$ are independently hydrogen, fluoro, chloro, bromo, $-OH$, alkyl, hydroxyalkyl, aminoalkyl, haloalkyl, or $-C(=O)OH$. In some embodiments of a compound of Formula (Ia), (IIa), (Ib) or (IIb), $R^{40d}$ and $R^{41d}$ are hydrogen. In some embodiments of a compound of Formula (Ia), (IIa), (Ib) or (IIb), $R^{40d}$ and $R^{41d}$ are independently hydrogen or alkyl. In some embodiments of a compound of Formula (Ia), (IIa), (Ib) or (IIb), $R^{40d}$ and $R^{41d}$ are independently hydrogen or $-C(=O)OH$. In some embodiments of a compound of Formula (Ia), (IIa), (Ib) or (IIb), $R^{40d}$ and $R^{41d}$ are independently hydrogen or $-OH$.

In some embodiments of a compound of Formula (Ia), (IIa), (Ib) or (IIb), $R^{10}$ is as defined above and $R^{42d}$ and $R^{43d}$ are independently hydrogen, alkyl, optionally substituted aryl, optionally substituted cycloalkyl, or optionally substituted heterocycloalkyl; or $R^{42d}$ and $R^{43d}$ are taken together with the nitrogen to which they are attached to form an optionally substituted heterocycloalkyl. In some embodiments of a compound of Formula (Ia), (IIa), (Ib) or (IIb), $R^{10}$ is as defined above and $R^{42d}$ and $R^{43d}$ are hydrogen. In some embodiments of a compound of Formula (Ia), (IIa), (Ib) or (IIb), $R^{10}$ is as defined above and $R^{42d}$ and $R^{43d}$ are independently hydrogen or alkyl. In some embodiments of a compound of Formula (Ia), (IIa), (Ib) or (IIb), $R^{10}$ is as defined above and $R^{42d}$ and $R^{43d}$ are independently hydrogen or heterocycloalkyl optionally substituted with alkyl, halogen, or cyano. In some embodiments of a compound of Formula (Ia), (IIa), (Ib) or (IIb), $R^{10}$ is as defined above and $R^{42d}$ and $R^{43d}$ are independently hydrogen or cycloalkyl optionally substituted with alkyl, halogen, or cyano. In some embodiments of a compound of Formula (Ia), (IIa), (Ib) or (IIb), $R^{10}$ is as defined above and $R^{42d}$ and $R^{43d}$ are independently hydrogen or aryl optionally substituted with alkyl, halogen, or cyano. In some embodiments of a compound of Formula (Ia), (IIa), (Ib) or (IIb), $R^{10}$ is as defined above and $R^{42d}$ and $R^{43d}$ are taken together with the nitrogen to which they are attached to form a heterocycloalkyl optionally substituted with alkyl, halogen, or cyano.

In some embodiments of a compound of Formula (Ia), (IIa), (Ib) or (IIb), $R^{10}$ is as defined above and $R^{44d}$ is optionally substituted alkyl or optionally substituted aryl. In some embodiments of a compound of Formula (Ia), (IIa), (Ib) or (IIb), $R^{10}$ is as defined above and $R^{44d}$ is alkyl. In some embodiments of a compound of Formula (Ia), (IIa), (Ib) or (IIb), $R^{10}$ is as defined above and $R^{44d}$ is aryl, optionally substituted with alkyl, halogen, cyano, $-C(=NH)NH_2$, $-C(=NH)NH$-alkyl, $-C(=NH)NH$-aryl, $-C(=NH)NH$-heteroaryl, $-C(=NH)NH$-cycloalkyl, or $-C(=NH)NH$-heterocycloalkyl.

In some embodiments of a compound of Formula (Ia), (IIa), (Ib) or (IIb), $R^{10}$ is as defined above and v is 1. In some embodiments of a compound of Formula (Ia), (IIa), (Ib) or (IIb), $R^{10}$ is as defined above and v is 2. In some embodiments of a compound of Formula (Ia), (IIa), (Ib) or (IIb), $R^{10}$ is as defined above and v is 3. In some embodiments of a compound of Formula (Ia), (IIa), (Ib) or (IIb), $R^{10}$ is as defined above and v is 4. In some embodiments of a compound of Formula (Ia), (IIa), (Ib) or (IIb), $R^{10}$ is as defined above and v is 5. In some embodiments of a compound of Formula (Ia), (IIa), (Ib) or (IIb), $R^{10}$ is as defined above and w is 2. In some embodiments of a compound of Formula (Ia), (IIa), (Ib) or (IIb), $R^{10}$ is as defined above and w is 3. In some embodiments of a compound of Formula (Ia), (IIa), (Ib) or (IIb), $R^{10}$ is as defined above and w is 4. In some embodiments of a compound of Formula (Ia), (IIa), (Ib) or (IIb), $R^{10}$ is as defined above and w is 5.

In some embodiments of a compound of Formula (Ia), (IIa), (Ib) or (IIb), $R^{10}$ is

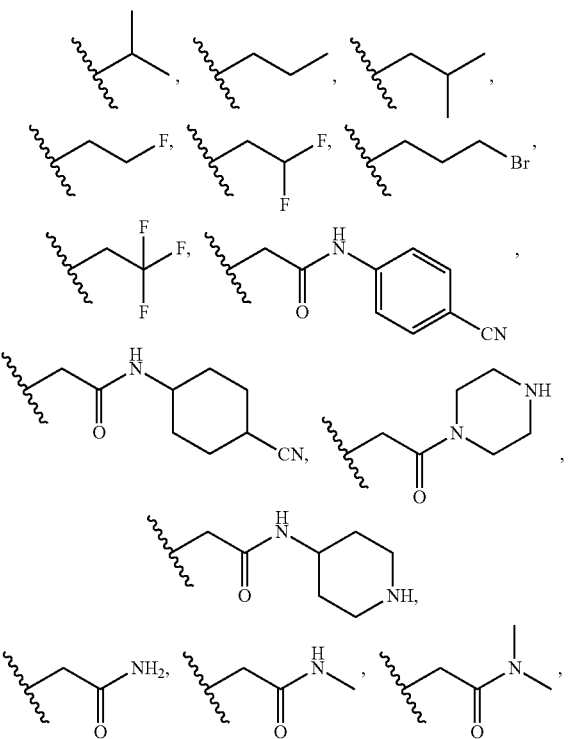

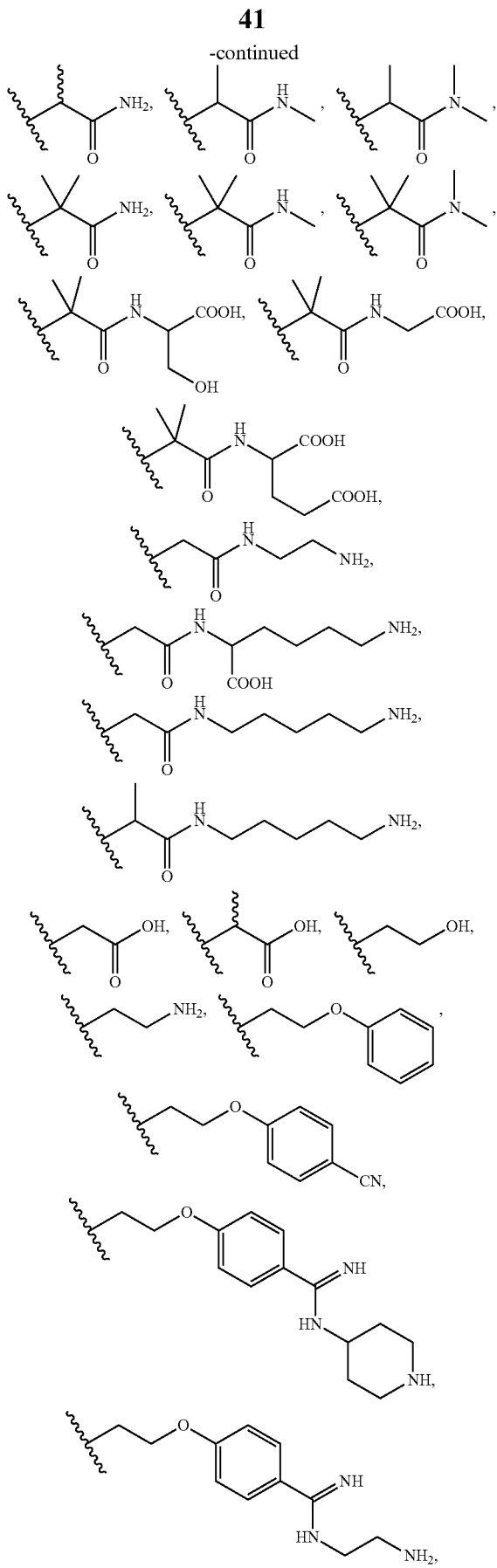

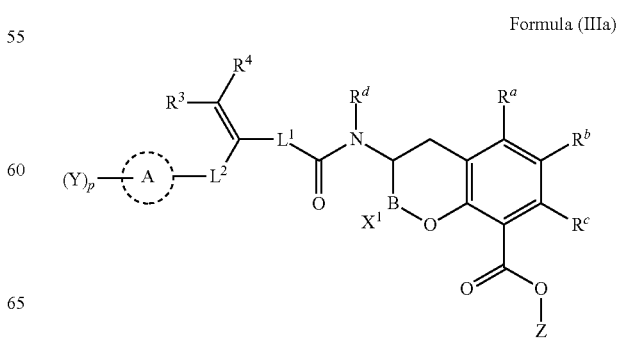

In some embodiments of a compound of Formula (Ia), (IIa), (Ib) or (IIb), $R^5$ is $-NR^{11}R^{12}$. In some embodiments of a compound of Formula (Ia), (IIa), (Ib) or (IIb), $R^{11}$ and $R^{12}$ are hydrogen. In some embodiments of a compound of Formula (Ia), (IIa), (Ib) or (IIb), $R^{11}$ and $R^{12}$ are taken together with the nitrogen to which they are attached to form a heterocycloalkyl optionally substituted with alkyl, halogen, or cyano.

In some embodiments of a compound of Formula (Ia), (IIa), (Ib) or (IIb), $R^5$ is $-S(=O)_{0,1,2}R^{13}$. In some embodiments of a compound of Formula (Ia), (IIa), (Ib) or (IIb), $R^5$ is $-SR^{13}$. In some embodiments of a compound of Formula (Ia), (IIa), (Ib) or (IIb), $R^5$ is $-S(=O)R^{13}$. In some embodiments of a compound of Formula (Ia), (IIa), (Ib) or (IIb), $R^5$ is $-S(=O)_2R^{13}$. In some embodiments of a compound of Formula (Ia), (IIa), (Ib) or (IIb), $R^5$ is as defined above and $R^{13}$ is optionally substituted alkyl.

Also disclosed herein is a compound of Formula (IIIa) or (IIIb), or a pharmaceutically acceptable salt, solvate, stereoisomer, tautomer, N-oxide, dimer, or trimer thereof:

Formula (IIIa)

-continued

Formula (IIIb)

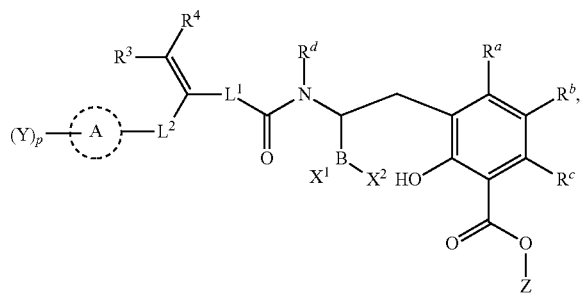

wherein:
L¹ is —(CR¹R²)$_n$—;
L² is —(CR¹R²)$_m$—;
Ring A is cycloalkyl, heterocycloalkyl, aryl, or heteroaryl;
each R¹ and R² are independently hydrogen, halogen, optionally substituted alkyl, —OH, —OR³⁴, —SR³⁵, —NR³²R³³, —NR³²C(=O)R³⁴, —C(=O)NR³²R³³, —NR³²S(=O)₂R³⁴, —C(=O)OH, —C(=O)OR³⁴, optionally substituted cycloalkyl, optionally substituted heterocycloalkyl, optionally substituted aryl, or optionally substituted heteroaryl; or
R¹ and R² are taken together with the carbon to which they are attached to form an optionally substituted cycloalkyl;
R³ and R⁴ are independently hydrogen, halogen, optionally substituted alkyl, optionally substituted cycloalkyl, optionally substituted heterocycloalkyl, optionally substituted aryl, optionally substituted heteroaryl, —C(=O)OH, —C(=O)OR⁴⁴ᵃ, —(CR⁴⁰ᵃR⁴¹ᵃ)$_v$C(=O)OH, —(CR⁴⁰ᵃR⁴¹ᵃ)$_v$C(=O)OR⁴⁴ᵃ, —(CR⁴⁰ᵃR⁴¹ᵃ)$_v$OH, or —(CR⁴⁰ᵃR⁴¹ᵃ)$_v$OR⁴⁴ᵃ; or
R³ and R⁴ are taken together with the carbon atom to which they are attached to form optionally substituted cycloalkyl or an optionally substituted heterocycloalkyl;
each R²⁰ and R²¹ are independently hydrogen, halogen, or optionally substituted alkyl;
R²² and R²³ are independently hydrogen or optionally substituted alkyl; or
R²² and R²³ are taken together with the nitrogen to which they are attached to form an optionally substituted heterocycloalkyl;
R²⁴ is optionally substituted alkyl, optionally substituted cycloalkyl, optionally substituted heterocycloalkyl, optionally substituted aryl, or optionally substituted heteroaryl;
R²⁵ is hydrogen, optionally substituted alkyl, optionally substituted cycloalkyl, optionally substituted heterocycloalkyl, optionally substituted aryl, optionally substituted heteroaryl;
each R³⁰, R³¹, R⁴⁰ᵃ, R⁴⁰ᵇ, R⁵, and R⁵¹ are independently hydrogen, halogen, optionally substituted alkyl, optionally substituted cycloalkyl, optionally substituted heterocycloalkyl, optionally substituted aryl, optionally substituted heteroaryl, —OH, —OR²⁴, —SR²⁵, —NR²²R²³, —NR²²C(=O)R²⁴, —C(=O)NR²²R²³, —NR²²S(=O)₂R²⁴, —C(=O)OH, or —C(=O)OR²⁴; or
R³⁰ and R³¹, R⁴⁰ᵃ and R⁴¹ᵃ, or R⁵⁰ and R⁵¹ are taken together with the carbon atom to which they are attached form an optionally substituted cycloalkyl; or two R³⁰, two R⁴⁰ᵃ, or two R⁵⁰ on adjacent carbons are taken together to form an alkenyl; or
two R³⁰ and two R³¹, two R⁴⁰ᵃ and two R⁴¹ᵃ, or two R⁵⁰ and two R⁵¹ on adjacent carbons are taken together to form an alkynyl;
R³², R³³, R⁵², or R⁵³ are independently hydrogen, optionally substituted alkyl, optionally substituted cycloalkyl, optionally substituted heterocycloalkyl, optionally substituted aryl, optionally substituted heteroaryl, (polyethylene-glycol)-ethyl, optionally substituted saccharide, —CN, —OH, —S(=O)₂R²⁴, —S(=O)₂NR²²R²³, or —C(=O)R²⁴; or
R³² and R³³ or R⁵² and R⁵³ are taken together with the nitrogen to which they are attached to form an optionally substituted heterocycloalkyl;
R³⁴, R⁴⁴ᵃ, or R⁵⁴ are independently optionally substituted alkyl, optionally substituted cycloalkyl, optionally substituted heterocycloalkyl, optionally substituted aryl, or optionally substituted heteroaryl;
R³⁵ and R⁵⁵ are independently hydrogen, optionally substituted alkyl, optionally substituted cycloalkyl, optionally substituted heterocycloalkyl, optionally substituted aryl, optionally substituted heteroaryl;
R³⁶ and R⁵⁶ are independently hydrogen, —OH, —OR²⁴, —CN, —NO₂, —NR²²R²³, or optionally substituted alkyl;
Z is hydrogen, R⁶¹, —(R⁶⁰)$_q$OR⁶¹, —(R⁶⁰)$_q$O(R⁶⁰)$_q$OR⁶¹, —R⁶⁰OC(=O)R⁶¹, —R⁶⁰OC(=O)OR⁶¹, —R⁶⁰OC(=O)NHR⁶¹, —R⁶⁰OC(=O)N(R⁶¹)₂, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;
each R⁶⁰ is independently —CH₂—, —CH(CH₃)—, —C(CH₃)₂—, or optionally substituted 1,1'-cyclopropylene;
each R⁶¹ is independently optionally substituted alkyl, optionally substituted cycloalkyl, optionally substituted heterocycloalkyl, optionally substituted aryl, or optionally substituted heteroaryl; or
two R⁶¹ are taken together with the nitrogen to which they are attached to form an optionally substituted heterocycloalkyl;
Rᵃ, Rᵇ, and Rᶜ are independently hydrogen, halogen, cyano, optionally substituted alkyl, optionally substituted cycloalkyl, optionally substituted heterocycloalkyl, optionally substituted aryl, optionally substituted heteroaryl, —OH, —OR⁵⁴, —O(CR⁵⁰R⁵¹)$_w$NR⁵²R⁵³, —O(CR⁵⁰R⁵¹)$_w$OH, —O(CR⁵⁰R⁵¹)$_w$OR⁵⁴, —O(CR⁵⁰R⁵¹)$_v$C(=O)OH, —O(CR⁵⁰R⁵¹)$_v$C(=O)OR⁵⁴, —O(CR⁵⁰R⁵¹)$_v$C(=O)NR⁵²R⁵³, —NR⁵²R⁵³, —NR⁵²(CR⁵⁰R⁵¹)$_w$NR⁵²R⁵³, —NR⁵²(CR⁵⁰R⁵¹)$_v$C(=O)OH, —NR⁵²(CR⁵⁰R⁵¹)$_v$C(=O)OR⁵⁴, —NR⁵²(CR⁵⁰R⁵¹)$_v$C(=O)NR⁵²R⁵³, —NR⁵²S(=O)$_{1,2}$R⁵⁴, —S(=O)$_{1,2}$R⁵⁴, —SR⁵⁵, —S(CR⁵⁰R⁵¹)$_v$NR⁵²C(=NR⁵⁶)NR⁵²R⁵³, —S(CR⁵⁰R⁵¹)$_v$NR⁵²CR⁵⁰(=NR⁵⁶), —S(CR⁵⁰R⁵¹)$_v$C(=NR⁵⁶)NR⁵²R⁵³, —S(CR⁵⁰R⁵¹)$_w$OH, —S(CR⁵⁰R⁵¹)$_w$OR⁵⁴, —S(CR⁵⁰R⁵¹)$_w$NR⁵²R⁵³, —S(CR⁵⁰R⁵¹)$_v$C(=O)OH, —S(CR⁵⁰R⁵¹)$_v$C(=O)OR⁵⁴, —S(CR⁵⁰R⁵¹)$_v$C(=O)NR⁵²R⁵³, —C(=O)H, —C(=O)R⁵⁴, —C(=O)OH, —C(=O)OR⁵⁴, —C(=O)NR⁵²R⁵³, —(CR⁵⁰R⁵¹)$_v$N(R⁵²)(CR⁵⁰R⁵¹)$_v$C(=O)OH, —(CR⁵⁰R⁵¹)$_v$OH, —(CR⁵⁰R⁵¹)$_v$OR⁵⁴, —(CR⁵⁰R⁵¹)$_v$C(=O)OH, —(CR⁵⁰R⁵¹)$_v$C(=O)OR⁵⁴, —(CR⁵⁰R⁵¹)$_v$C(=O)

$NR^{52}R^{53}$, $-(CR^{50}R^{51})_vOC(=O)R^{54}$, $-(CR^{50}R^{51})_vSR^{55}$, $-(CR^{50}R^{51})_vNR^{52}C(=NR^{56})NR^{52}R^{53}$, $-(CR^{50}R^{51})_vC(=NR^{56})NR^{52}R^{53}$, $-(CR^{50}R^{51})_vC(=O)NR^{52}R^{53}$, $-(CR^{50}R^{51})_v$heterocycloalkyl, or $-(CR^{50}R^{51})_v$heteroaryl;

$R^d$ is hydrogen, $-CN$, $-OH$, $-S(=O)_2R^{24}$, $-S(=O)_2NR^{22}R^{23}$, $-(CR^{20}R^{21})_vC(=O)OH$, $-C(=O)R^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently $-OH$, $-OR^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-$NR^{32}R^{33}$, -heterocycloalkyl-$NR^{32}R^{33}$, -heteroaryl-$N(R^{32})C(=NR^{32})NR^{32}R^{33}$, -heterocycloalkyl-$N(R^{32})C(=NR^{32})NR^{32}R^{33}$, $-OH$, $-OR^{34}$, $-O(CR^{30}R^{31})_wOH$, $-O(CR^{30}R^{31})_wOR^{34}$, $-O(CR^{30}R^{31})_wNR^{32}R^{33}$, $-O(CR^{30}R^{31})_wNR^{32}C(=O)R^{34}$, $-O(CR^{30}R^{31})_wNR^{32}C(=O)OR^{34}$, $-O(CR^{30}R^{31})_wNR^{32}C(=O)NR^{32}R^{33}$, $-O(CR^{30}R^{31})_wC(=O)NR^{32}R^{33}$, $-O(CR^{30}R^{31})_wNR^{32}S(=O)_{0,1,2}R^{34}$, $-O(CR^{30}R^{31})_wNR^{32}S(=O)_{0,1,2}NR^{32}R^{33}$, $-O(CR^{30}R^{31})_wS(=O)_{0,1,2}R^{34}$, $-O(CR^{30}R^{31})_wS(=O)_{0,1,2}NR^{32}R^{33}$, $-O(CR^{30}R^{31})_vC(=NR^{36})NR^{32}R^{33}$, $-O(CR^{30}R^{31})_wN(R^{32})C(=NR^{36})R^{34}$, $-O(CR^{30}R^{31})_vC(=NR^{36})NR^{32}C(=NR^{36})NR^{32}R^{33}$, $-O(CR^{30}R^{31})_wN(R^{32})C(=NR^{36})NR^{32}R^{33}$, $-O(CR^{30}R^{31})_wS(=O)_{0,1,2}R^{34}$, $-O(CR^{30}R^{31})_vS(=O)_{0,1,2}NR^{32}R^{33}$, $-OC(=O)R^{34}$, $-OC(=O)(CR^{30}R^{31})_vNR^{32}R^{33}$, $-OC(=O)NR^{32}R^{33}$, $-OC(=O)OR^{34}$, $-OC(=O)NR^{32}(CR^{30}R^{31})_wNR^{32}R^{33}$, $-O$-heteroaryl, $-O$-heterocycloalkyl, $-O(CR^{30}R^{31})_v$heteroaryl, $-O(CR^{30}R^{31})_v$heterocycoakyl, $-O(CR^{30}R^{31})_wNR^{32}$-heteroaryl, $-O(CR^{30}R^{31})_wNR^{32}$-heterocycoakyl, $-O(CR^{30}R^{31})_w$O-heterocycloalkyl, $-NR^{32}R^{33}$, $-NR^{32}(CR^{30}R^{31})_wNR^{32}R^{33}$, $-NR^{32}(CR^{30}R^{31})_wOH$, $-NR^{32}(CR^{30}R^{31})_wOR^{34}$, $-NR^{32}C(=O)R^{34}$, $-NR^{32}C(=O)OR^{34}$, $-N(R^{32})C(=O)(CR^{30}R^{31})_vNR^{32}R^{33}$, $-NR^{32}C(=O)NR^{32}R^{33}$, $-NR^{32}C(=O)NR^{32}(CR^{30}R^{31})_wNR^{32}R^{33}$, $-NR^{32}(CR^{30}R^{31})_wS(=O)_{0,1,2}R^{34}$, $-NR^{32}(CR^{30}R^{31})_wS(=O)_{0,1,2}NR^{32}R^{33}$, $-NR^{32}(CR^{30}R^{31})_wNR^{32}R^{33}S(=O)_{0,1,2}R^{34}$, $-NR^{32}(CR^{30}R^{31})_wNR^{32}S(=O)_{0,1,2}NR^{32}R^{33}$, $-NR^{32}C(=NR^{36})NR^{32}R^{33}$, $-N(R^{32})C(=NR^{36})R^{34}$, $-NR^{32}(CR^{30}R^{31})_wN(R^{32})C(=NR^{36})R^{34}$, $-NR^{32}(CR^{30}R^{31})_vC(=NR^{36})NR^{32}R^{33}$, $-NR^{32}(CR^{30}R^{31})_wN(R^{32})C(=NR^{36})NR^{32}R^{33}$, $-NR^{32}(CR^{30}R^{31})_wNR^{32}C(=O)NR^{32}R^{33}$, $-NR^{32}(CR^{30}R^{31})_wNR^{32}C(=O)OR^{34}$, $-NR^{32}S(=O)_{0,1,2}R^{34}$, $-NR^{32}(CR^{30}R^{31})_vCO_2H$, $-NR^{32}(CR^{30}R^{31})_vCO_2R^{34}$, $-NR^{32}(CR^{30}R^{31})_vC(=O)NR^{32}R^{33}$, $-N(R^{32})$-heteroaryl-$NR^{32}R^{33}$, $-N(R^{32})$-heterocycloalkyl-$NR^{32}R^{33}$, $-NR^{32}(CR^{30}R^{31})_v$heteroaryl, $-NR^{32}(CR^{30}R^{31})_v$heterocycloalkyl, $-NR^{32}(CR^{30}R^{31})_wNR^{32}$-heteroaryl, $-NR^{32}(CR^{30}R^{31})_wNR^{32}$-heterocycoakyl, $-CN$, $-(CR^{30}R^{31})_vCN$, $-(CR^{30}R^{31})_wNR^{32}R^{33}$, $-(CR^{30}R^{31})_vOH$, $-(CR^{30}R^{31})_vOR^{34}$, $-(CR^{30}R^{31})_vOC(=O)R^{34}$, $-(CR^{30}R^{31})_vOC(=O)NR^{32}R^{33}$, $-(CR^{30}R^{31})_vO(CR^{30}R^{31})_wOR^{34}$, $-(CR^{30}R^{31})_vO(CR^{30}R^{31})_wOH$, $-(CR^{30}R^{31})_vO(CR^{30}R^{31})_wNR^{32}R^{33}$, $-(CR^{30}R^{31})_vNR^{32}(CR^{30}R^{31})_wOH$, $-(CR^{30}R^{31})_wNR^{32}(CR^{30}R^{31})_wOR^{34}$, $-(CR^{30}R^{31})_vC(=O)NR^{32}R^{33}$, $-(CR^{30}R^{31})_vC(=O)NR^{32}(CR^{30}R^{31})_wNR^{32}R^{33}$, $-(CR^{30}R^{31})_vC(=O)NR^{32}(CR^{30}R^{31})_wOR^{34}$, $-(CR^{30}R^{31})_vN(R^{32})C(=O)R^{34}$, $-(CR^{30}R^{31})_vN(R^{32})C(=O)OR^{34}$, $-(CR^{30}R^{31})_vN(R^{32})C(=O)(CR^{30}R^{31})_wNR^{32}R^{33}$, $-(CR^{30}R^{31})_vN(R^{32})C(=O)(CR^{30}R^{31})_wNR^{32}R^{33}$, $-(CR^{30}R^{31})_vN(R^{32})S(=O)_{0,1,2}R^{34}$, $-(CR^{30}R^{31})_vN(R^{32})S(=O)_{0,1,2}NR^{32}R^{33}$, $-(CR^{30}R^{31})_vS(=O)_{0,1,2}NR^{32}R^{33}$, $-(CR^{30}R^{31})_vS(=O)_{0,1,2}(CR^{30}R^{31})_wNR^{32}R^{33}$, $-(CR^{30}R^{31})_vNR^{32}(CR^{30}R^{31})_wNR^{32}R^{33}$, $-(CR^{30}R^{31})_vN(R^{32})CH(=NR^{36})$, $-(CR^{30}R^{31})_vN(R^{32})C(=NR^{36})R^{34}$, $-(CR^{30}R^{31})_vC(=NR^{36})NR^{32}R^{33}$, $-(CR^{30}R^{31})_vN(R^{32})C(=NR^{36})NR^{32}R^{33}$, $-(CR^{30}R^{31})_vC(=NR^{36})NR^{32}C(=NR^{36})NR^{32}R^{33}$, $-(CR^{30}R^{31})_v$heteroaryl-$NR^{32}R^{33}$, $-(CR^{30}R^{31})_v$heterocycloalkyl-$NR^{32}R^{33}$, $-(CR^{30}R^{31})_v$heteroaryl-$N(R^{32})C(=NR^{36})NR^{32}R^{33}$, $-(CR^{30}R^{31})_v$heterocycloalkyl-$N(R^{32})C(=NR^{36})NR^{32}R^{33}$, $-(CR^{30}R^{31})_v$heteroaryl, $-(CR^{30}R^{31}$heterocycloalkyl, $-C(=O)OH$, $-C(=O)OR^{34}$, $-C(=O)NR^{32}R^{33}$, $-C(=O)NR^{32}(CR^{30}R^{31})_wNR^{32}R^{33}$, $-C(=O)NR^{32}(CR^{30}R^{31})_wOH$, $-C(=O)NR^{32}(CR^{30}R^{31})_wOR^{34}$, $-C(=NR^{36})NR^{32}R^{33}$, $-C(=NR^{36})NR^{32}C(=O)R^{34}$, $-S(=O)_{1,2}R^{34}$, $-SR^{35}$, $-S(=O)_{0,1,2}(CR^{30}R^{31})_vNR^{32}R^{33}$, $-S(=O)_{0,1,2}(CR^{30}R^{31})_wOH$, $-S(=O)_{0,1,2}(CR^{30}R^{31})_wOR^{34}$, $-S(=O)_{0,1,2}NR^{32}R^{33}$, $-S(=O)_{0,1,2}NR^{32}(CR^{30}R^{31})_wNR^{32}R^{33}$, $-S(=O)_{0,1,2}(CR^{30}R^{31})_wN(R^{32})C(=NR^{36})R^{34}$, $-S(=O)_{0,1,2}(CR^{30}R^{31})_vC(=NR^{36})NR^{32}R^{33}$, $-S(=O)_{0,1,2}(CR^{30}R^{31})_wN(R^{32})C(=NR^{36})NR^{32}R^{33}$, $-S(=O)_{0,1,2}(CR^{30}R^{31})_vC(=NR^{36})NR^{32}C(=NR^{36})NR^{32}R^{33}$, $-Si(R^{34})_3$, $-NR^{32}R^{33}R^{34+}Q^-$, $-(CR^{30}R^{31})NR^{32}R^{33}R^{34+}Q^-$, $-NR^{32}(CR^{30}R^{31})_wNR^{32}R^{33}R^{34+}Q^-$, $-NR^{32}R^{34+}(CR^{30}R^{31})_wNR^{32}R^{33}R^{34+}Q^-_2$, $-(CR^{30}R^{31})_v(T)^+Q^-$, or $-O(CR^{30}R^{31})_wNR^{32}R^{33}R^{34+}Q^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

In some embodiments of a compound of Formula (Ia), (IIIa), (Ib) or (IIIb), $R^3$ and $R^4$ are independently hydrogen, alkyl, optionally substituted heteroaryl, $-C(=)OH$, $-(CR^{40a}R^{41a})_vC(O)OH$, or $-(CR^{40a}R^{41a})_vOH$. In some embodiments of a compound of Formula (Ia), (IIIa), (Ib) or (IIIb), $R^3$ and $R^4$ are independently hydrogen, alkyl, heteroaryl, $-C(=O)OH$, $-(CR^{40a}R^{41a})_vC(=O)OH$, or $-(CR^{40a}R^{41a})_vOH$. In some embodiments of a compound of Formula (Ia), (IIIa), (Ib) or (IIIb), $R^3$ and $R^4$ are as defined above and $R^{40a}$ and $R^{41a}$ are independently hydrogen or alkyl. In some embodiments of a compound of Formula (Ia), (IIIa), (Ib) or (IIIb), $R^3$ and $R^4$ are as defined above and v is 1 or 2.

Also disclosed herein is a compound of Formula (IVa) or (IVb), or a pharmaceutically acceptable salt, solvate, stereoisomer, tautomer, N-oxide, dimer, or trimer thereof:

Formula (IVa)

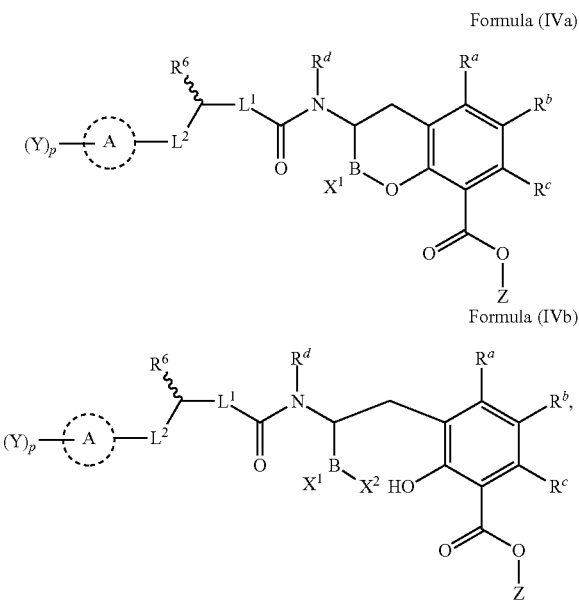

Formula (IVb)

wherein:
L¹ is —(CR¹R²)$_n$—;
L² is —(CR¹R²)$_m$—;
Ring A is cycloalkyl, heterocycloalkyl, aryl, or heteroaryl;
each R¹ and R² are independently hydrogen, halogen, optionally substituted alkyl, —OH, —OR³⁴, —SR³⁵, —NR³²R³³, —NR³²C(=O)R³⁴, —C(=O)NR³²R³³, —NR³²S(=O)₂R³⁴, —C(=O)OH, —C(=O)OR³⁴, optionally substituted cycloalkyl, optionally substituted heterocycloalkyl, optionally substituted aryl, or optionally substituted heteroaryl; or
R¹ and R² are taken together with the carbon to which they are attached to form an optionally substituted cycloalkyl;
R⁶ is optionally substituted alkyl, —(CR⁴⁰ᵇR⁴¹ᵇ)$_v$C(=O)OR⁴⁴ᵇ, or —(CR⁴⁰ᵇR⁴¹ᵇ)$_v$C(=O)OH;
each R²⁰ and R²¹ are independently hydrogen, halogen, or optionally substituted alkyl;
R²² and R²³ are independently hydrogen or optionally substituted alkyl; or
R²² and R²³ are taken together with the nitrogen to which they are attached to form an optionally substituted heterocycloalkyl;
R²⁴ is optionally substituted alkyl, optionally substituted cycloalkyl, optionally substituted heterocycloalkyl, optionally substituted aryl, or optionally substituted heteroaryl;
R²⁵ is hydrogen, optionally substituted alkyl, optionally substituted cycloalkyl, optionally substituted heterocycloalkyl, optionally substituted aryl, optionally substituted heteroaryl;
each R³⁰, R³¹, R⁴⁰ᵇ, R⁴¹ᵇ, R⁵⁰, and R⁵¹ are independently hydrogen, halogen, optionally substituted alkyl, optionally substituted cycloalkyl, optionally substituted heterocycloalkyl, optionally substituted aryl, optionally substituted heteroaryl, —OH, —OR²⁴, —SR²⁵, —NR²²R²³, —NR²²C(=O)R²⁴, —C(=O)NR²²R²³, —NR²²S(=O)₂R²⁴, —C(=O)OH, or —C(=O)OR²⁴; or
R³⁰ and R³¹, R⁴⁰ᵇ and R⁴¹ᵇ, or R⁵⁰ and R⁵¹ are taken together with the carbon atom to which they are attached form an optionally substituted cycloalkyl; or two R³⁰, two R⁴⁰ᵇ, or two R⁵⁰ on adjacent carbons are taken together to form an alkenyl; or
two R³⁰ and two R³¹, two R⁴⁰ᵇ and two R⁴¹ᵇ, or two R⁵⁰ and two R⁵¹ on adjacent carbons are taken together to form an alkynyl;
R³², R³³, R⁵², or R⁵³ are independently hydrogen, optionally substituted alkyl, optionally substituted cycloalkyl, optionally substituted heterocycloalkyl, optionally substituted aryl, optionally substituted heteroaryl, (polyethylene-glycol)-ethyl, optionally substituted saccharide, —CN, —OH, —S(=O)₂R²⁴, —S(=O)₂NR²²R²³, or —C(=O)R²⁴; or
R³² and R³³ or R⁵² and R⁵³ are taken together with the nitrogen to which they are attached to form an optionally substituted heterocycloalkyl;
R³⁴, R⁴⁴ᵇ, or R⁵⁴ are independently optionally substituted alkyl, optionally substituted cycloalkyl, optionally substituted heterocycloalkyl, optionally substituted aryl, or optionally substituted heteroaryl;
R³⁵ and R⁵⁵ are independently hydrogen, optionally substituted alkyl, optionally substituted cycloalkyl, optionally substituted heterocycloalkyl, optionally substituted aryl, optionally substituted heteroaryl;
R³⁶ and R⁵⁶ are independently hydrogen, —OH, —OR²⁴, —CN, —NO₂, —NR²²R²³, or optionally substituted alkyl;
Z is hydrogen, R⁶¹, —(R⁶⁰)$_q$OR⁶¹, —(R⁶⁰)$_q$O(R⁶⁰)$_q$OR⁶¹, —R⁶⁰OC(=O)R⁶¹, —R⁶⁰OC(=O)OR⁶¹, —R⁶⁰OC(=O)NHR⁶¹, —R⁶⁰OC(=O)N(R⁶¹)₂, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;
each R⁶⁰ is independently —CH₂—, —CH(CH₃)—, —C(CH₃)₂—, or optionally substituted 1,1'-cyclopropylene;
each R⁶¹ is independently optionally substituted alkyl, optionally substituted cycloalkyl, optionally substituted heterocycloalkyl, optionally substituted aryl, or optionally substituted heteroaryl; or
two R⁶¹ are taken together with the nitrogen to which they are attached to form an optionally substituted heterocycloalkyl;
Rᵃ, Rᵇ, and Rᶜ are independently hydrogen, halogen, cyano, optionally substituted alkyl, optionally substituted cycloalkyl, optionally substituted heterocycloalkyl, optionally substituted aryl, optionally substituted heteroaryl, —OH, —OR⁵⁴, —O(CR⁵⁰R⁵¹)$_w$NR⁵²R⁵³, —O(CR⁵⁰R⁵¹)$_w$OH, —O(CR⁵⁰R⁵¹)$_w$OR⁵⁴, —O(CR⁵⁰R⁵¹)$_v$C(=O)OH, —O(CR⁵⁰R⁵¹)$_v$C(=O)OR⁵⁴, —O(CR⁵⁰R⁵¹)$_v$C(=O)NR⁵²R⁵³, —NR⁵²R⁵³, —NR⁵²(CR⁵⁰R⁵¹)$_w$NR⁵²R⁵³, —NR⁵²(CR⁵⁰R⁵¹)$_v$C(=O)OH, —NR⁵²(CR⁵⁰R⁵¹)$_w$C(=O)OR⁵⁴, —NR⁵²(CR⁵⁰R⁵¹)$_v$C(=O)NR⁵²R⁵³, —NR⁵²S(=O)$_{1,2}$R⁵⁴, —S(=O)$_{1,2}$R⁵⁴, —SR⁵⁵, —S(CR⁵⁰R⁵¹)$_v$NR⁵²C(=NR⁵⁶)NR⁵²R⁵³, —S(CR⁵⁰R⁵¹)$_v$NR⁵²CR⁵⁰(=NR⁵⁶), —S(CR⁵⁰R⁵¹)$_v$C(=NR⁵⁶)NR⁵²R⁵³, —S(CR⁵⁰R⁵¹)$_w$OH, —S(CR⁵⁰R⁵¹)$_w$OR⁵⁴, —S(CR⁵⁰R⁵¹)$_w$NR⁵²R⁵³, —S(CR⁵⁰R⁵¹)$_v$C(=O)OH, —S(CR⁵⁰R⁵¹)$_v$C(=O)OR⁵⁴, —S(CR⁵⁰R⁵¹)$_v$C(=O)NR⁵²R⁵³, —C(=O)H, —C(=O)R⁵⁴, —C(=O)OH, —C(=O)OR⁵⁴, —C(=O)NR⁵²R⁵³, —(CR⁵⁰R⁵¹)$_v$N(R⁵²)(CR⁵⁰R⁵¹)$_v$C(=O)OH, —(CR⁵⁰R⁵¹)$_v$OH, —(CR⁵⁰R⁵¹)$_v$OR⁵⁴, —(CR⁵⁰R⁵¹)$_v$C(=O)OH, —(CR⁵⁰R⁵¹)$_v$C(=O)OR⁵⁴, —(CR⁵⁰R⁵¹)$_v$C(=O)

NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

R$^X$ is optionally substituted alkyl or optionally substituted cycloalkyl;

X$^1$ and X$^2$ are independently —OH, —OR$^X$, or F; or

X$^1$ and X$^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycoakyl, —O(CR$^{30}$R$^{31}$)$_w$NR$^{32}$-heteroaryl, —O(CR$^{30}$R$^{31}$)$_w$NR$^{32}$-heterocycoakyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycoakyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_w$NR$^{32}$(CR$^{30}$R$^{31}$)$_w$OH, —(CR$^{30}$R$^{31}$)$_w$NR$^{32}$(CR$^{30}$R$^{31}$)$_w$OR$^{34}$, —(CR$^{30}$R$^{31}$)$_w$C(=O)NR$^{32}$R$^{33}$, —(CR$^{30}$R$^{31}$)$_w$C(=O)NR$^{32}$(CR$^{30}$R$^{31}$)$_w$OR$^{34}$, —(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_v$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_v$NR$^{32}$R$^{33}$, —S(=O)$_{0,1,2}$(CR$^{30}$R$^{31}$)$_v$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, orthiazol-3-yl;

Q is a pharmaceutically acceptable counterion;

n is 0-3;

m is 0-3;

p is 0-3;

each q is independently 2-6;

each v is independently 1-5; and each w is independently 2-5.

In some embodiments of a compound of Formula (Ia), (IVa), (Ib) or (IVb), the compound is not 2-hydroxy-3-(3-hydroxy-2-(4-((2-(methylamino)ethyl)amino)cyclohexyl)propanamido)-3,4-dihydro-2H-benzo[e][1,2]oxaborinine-8-carboxylic acid/3-(2-borono-2-(3-hydroxy-2-(4-((2-(methylamino)ethyl)amino)cyclohexyl)propanamido)ethyl)-2-hydroxybenzoic acid.

In some embodiments of a compound of Formula (Ia), (IVa), (Ib) or (IVb), R$^6$ is not —CH$_2$OH. In some embodiments of a compound of Formula (Ia), (IVa), (Ib) or (IVb), R$^6$ is not —CH$_2$OH when Ring A is cyclohexane. In some embodiments of a compound of Formula (Ia), (IVa), (Ib) or (IVb), R$^6$ is not —CH$_2$OH when Y is —NHCH$_2$CH$_2$NHCH$_3$. In some embodiments of a compound of Formula (Ia), (IVa), (Ib) or (IVb), Ring A is not cyclohexyl when Y is —NHCH$_2$CH$_2$NHCH$_3$.

In some embodiments of a compound of Formula (Ia), (IVa), (Ib) or (IVb), R$^6$ is —(CR$^{40b}$R$^{41b}$)$_v$C(=O)OH. In some embodiments of a compound of Formula (Ia), (IVa), (Ib) or (IVb), R$^6$ is as defined above and R$^{40b}$ and R$^{41b}$ are independently hydrogen or alkyl. In some of a compound of Formula (Ia), (IVa), (Ib) or (IVb), $R^6$ is as defined above and v is 1 or 2.

In some embodiments of a compound of Formula (Ia)-(IVa) or (Ib)-(IVb), Ring A is cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In some embodiments of a compound of Formula (Ia)-(IVa) or (Ib)-(IVb), Ring A is cyclopropane, cyclobutane, cyclopentane, or cyclohexane. In some embodiments of a compound of Formula (Ia)-(IVa) or (Ib)-(IVb), Ring A is not cyclohexane.

In some embodiments of a compound of Formula (Ia)-(IVa) or (Ib)-(IVb), Ring A is azetidine, aziridine, oxirane, oxetane, thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, or 2,3,4,7-tetrahydro-1,3-oxazepine. In some embodiments of a compound of Formula (Ia)-(IVa) or (Ib)-(IVb), Ring A is pyrrolidine, piperidine, morpholine, or piperazine. In some embodiments of a compound of Formula (Ia)-(IVa) or (Ib)-(IVb), Ring A is a 5-membered heterocycloalkyl bearing at least one nitrogen atom. In some embodiments of a compound of Formula (Ia)-(IVa) or (Ib)-(IVb), Ring A is a 5-membered heterocycloalkyl bearing at least one oxygen atom. In some embodiments of a compound of Formula (Ia)-(IVa) or (Ib)-(IVb), Ring A is a 5-membered heterocycloalkyl bearing at least one oxygen atom and one nitrogen atom.

In some embodiments of a compound of Formula (Ia)-(IVa) or (Ib)-(IVb), Ring A is benzene, naphthalene, pyridine, pyrimidine, pyrazine, pyridazine, triazine, thiophene, furan, pyrrole, pyrazole, triazole, tetrazole, imidazole, thiazole, isothiazole, oxazole, isoxazole, indole, thiadiazole, oxadiazole, indazole, azaindole, azaindazole, indolizine, imidazopyridine, pyrazolo-pyridine, thiazolo-pyridine, pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine, napthyridine, pyrido-pyrimidine, pyrido-pyrazine, pyridopyridazine, isoxazolo-pyridine, or oxazolo-pyridine. In some embodiments of a compound of Formula (Ia)-(IVa) or (Ib)-(IVb), Ring A is benzene, pyridine, thiazole, triazole, tetrazole, oxadiazole, or thiadiazole. In some embodiments of a compound of Formula (Ia)-(IVa) or (Ib)-(IVb), Ring A is benzene, pyridine, thiazole, triazole, tetrazole, imidazole, oxadiazole, or thiadiazole. In some embodiments of a compound of Formula (Ia)-(IVa) or (Ib)-(IVb), Ring A is thiazole. In some embodiments of a compound of Formula (Ia)-(IVa) or (Ib)-(IVb), Ring A is not thiazole. In some embodiments of a compound of Formula (Ia)-(IVa) or (Ib)-(IVb), Ring A is not benzene.

In some embodiments of a compound of Formula (Ia)-(IVa) or (Ib)-(IVb), Ring A is a 5-membered heteroaryl bearing at least two nitrogen atoms. In some embodiments of a compound of Formula (Ia)-(IVa) or (Ib)-(IVb), Ring A is a 5-membered heteroaryl bearing at least three nitrogen atoms. In some embodiments of a compound of Formula (Ia)-(IVa) or (Ib)-(IVb), Ring A is a 5-membered heteroaryl bearing four nitrogen atoms. In some embodiments of a compound of Formula (Ia)-(IVa) or (Ib)-(IVb), Ring A is a 5-membered heteroaryl bearing only nitrogen atoms as heteroatoms. In some embodiments of a compound of Formula (Ia)-(IVa) or (Ib)-(IVb), Ring A is a 5-membered heteroaryl bearing at least one oxygen atom. In some embodiments of a compound of Formula (Ia)-(IVa) or (Ib)-(IVb), Ring A is a 5-membered heteroaryl bearing at least one sulfur atom.

In some embodiments of a compound of Formula (Ia)-(IVa) or (Ib)-(IVb),

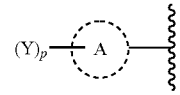

is selected from:

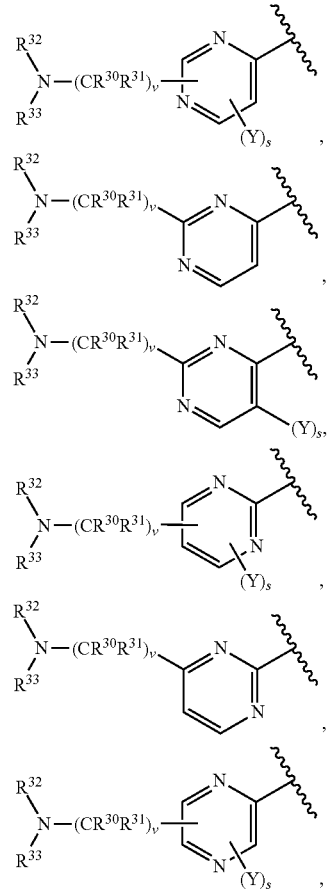

-continued
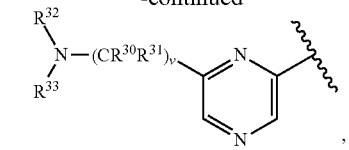
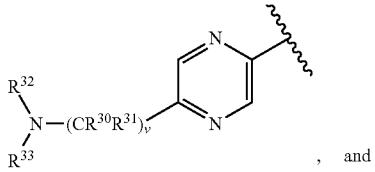, and
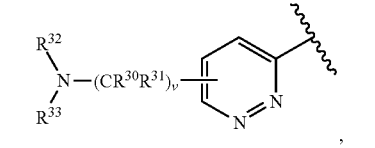
wherein s is 0-2.
In some embodiments of a compound of Formula (Ia)-(IVa) or (Ib)-(IVb),
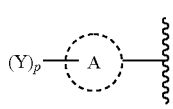
is selected from:
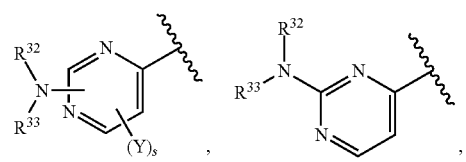
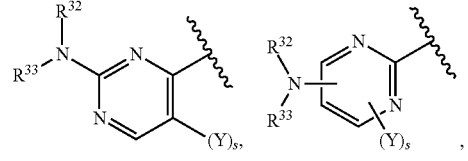
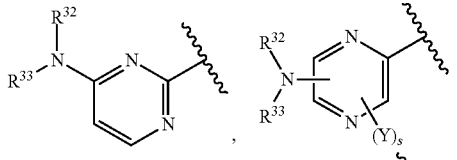
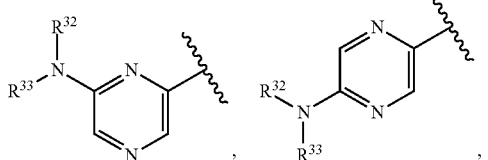, and
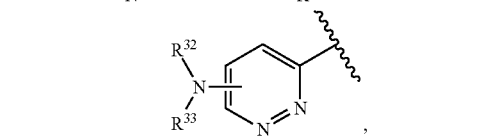
wherein s is 0-2.
In some embodiments of a compound of Formula (Ia)-(IVa) or (Ib)-(IVb),
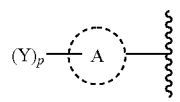
is selected from:
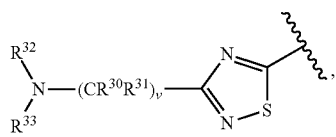,
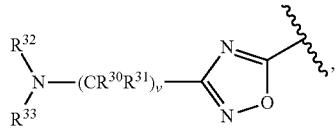,
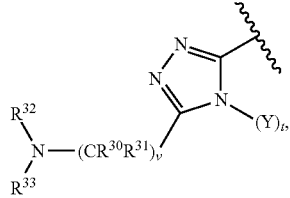,
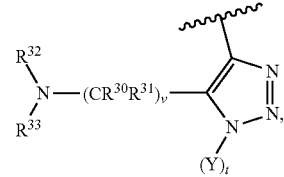,
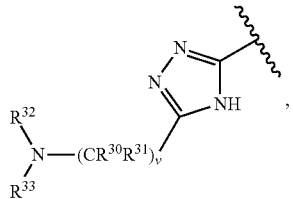,
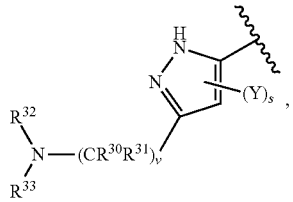,
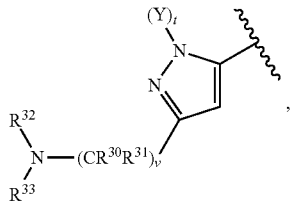,
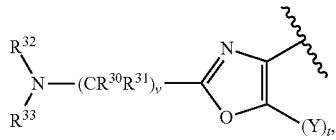, -continued

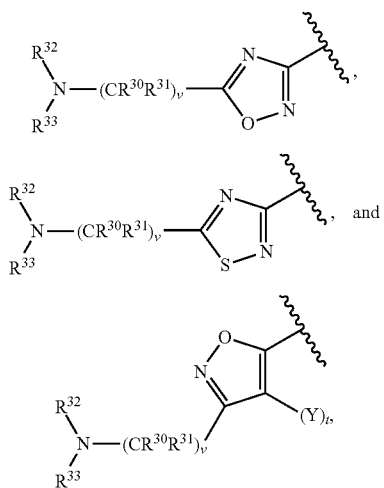

wherein s is 0-2 and t is 0-1.

In some embodiments of a compound of Formula (Ia)-(IVa) or (Ib)-(IVb), $(Y)_p$—A— is selected from:

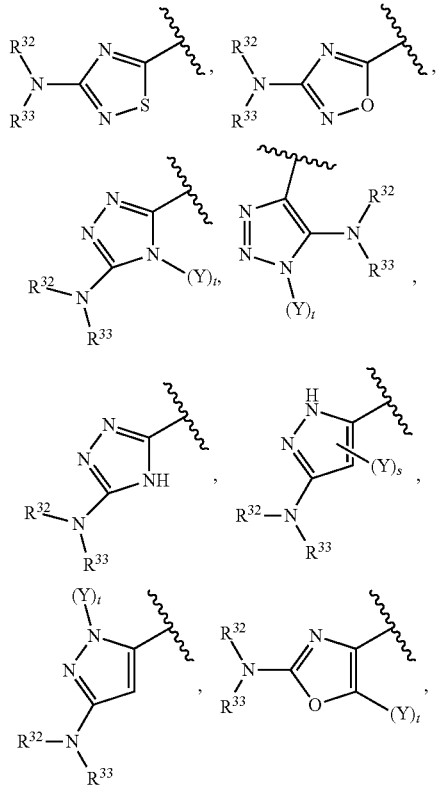

-continued

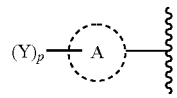

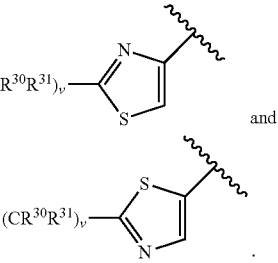

wherein s is 0-2 and t is 0-1.

In some embodiments of a compound of Formula (Ia)-(IVa) or (Ib)-(IVb), $(Y)_p$—A— is selected from:

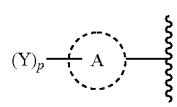

In some embodiments of a compound of Formula (Ia)-(IVa) or (Ib)-(IVb), $(Y)_p$—A— is selected from:

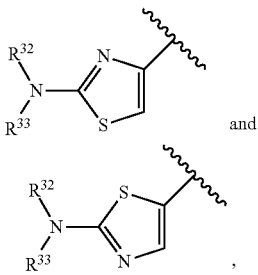

In some embodiments of a compound of Formula (Ia)-(IVa) or (Ib)-(IVb),

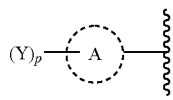

is selected from:

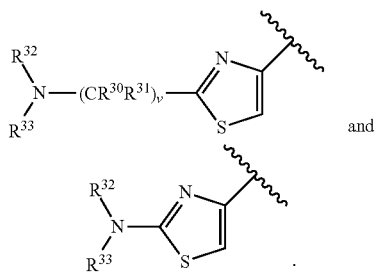

and

In some embodiments of a compound of Formula (Ia)-(IVa) or (Ib)-(IVb), $R^a$, $R^b$, and $R^c$ are independently hydrogen, optionally substituted alkyl, fluoro, chloro, —OH, —OR$^{54}$, —C(=O)H, —C(=O)OH, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$C(=O)OH, —(CR$^{50}$R$^{51}$)$_v$C(=O)OR$^{54}$, or —(CR$^{50}$R$^{51}$)$_v$heterocycloalkyl. In some embodiments of a compound of Formula (Ia)-(IVa) or (Ib)-(IVb), $R^a$, $R^b$, and $R^c$ are independently hydrogen, fluoro, chloro, optionally substituted alkyl, —(CR$^{50}$R$^{51}$)$_v$C(=O)OH, or —(CR$^{50}$R$^{51}$)$_v$heterocycloalkyl. In some embodiments of a compound of Formula (Ia)-(IVa) or (Ib)-(IVb), $R^a$, $R^b$, and $R^c$ are hydrogen.

In some embodiments of a compound of Formula (Ia)-(IVa) or (Ib)-(IVb), at least one of $R^a$, $R^b$, and $R^c$ is halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl.

In some embodiments of a compound of Formula (Ia)-(IVa) or (Ib)-(IVb), at least one of $R^a$, $R^b$, or $R^c$ is optionally substituted alkyl, fluoro, chloro, —OH, —OR$^{54}$, —C(=O)H, —C(=O)OH, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$C(=O)OH, or —(CR$^{50}$R$^{51}$)$_v$C(=O)OR$^{54}$, or —(CR$^{50}$R$^{51}$)$_v$heterocycloalkyl. In some embodiments of a compound of Formula (Ia)-(IVa) or (Ib)-(IVb), at least one of $R^a$, $R^b$, or $R^c$ is alkyl optionally substituted with heterocycloalkyl (optionally substituted with optionally substituted alkyl). In some embodiments of a compound of Formula (Ia)-(IVa) or (Ib)-(IVb), at least one of $R^a$, $R^b$, or $R^c$ is —(CR$^{50}$R$^{51}$)$_v$heterocycloalkyl optionally substituted with optionally substituted alkyl.

In some embodiments of a compound of Formula (Ia)-(IVa) or (Ib)-(IVb), $R^a$, $R^b$, or $R^c$ are defined as above, $R^{50}$ and $R^{51}$ are independently hydrogen or optionally substituted alkyl; or two $R^{50}$ on adjacent carbon form an alkenyl; $R^{52}$ and $R^{53}$ are independently hydrogen or optionally substituted alkyl; or $R^{52}$ and $R^{53}$ are taken together with the nitrogen to which they are attached to form an optionally substituted heterocycloalkyl; $R^{54}$ is optionally substituted alkyl; $R^{55}$ is hydrogen or optionally substituted alkyl; $R^{56}$ is hydrogen or optionally substituted alkyl; each v is independently 1 or 2; and each w is independently 2 or 3.

In some embodiments of a compound of Formula (Ia)-(IVa) or (Ib)-(IVb), $R^a$ is hydrogen. In some embodiments of a compound of Formula (Ia)-(IVa) or (Ib)-(IVb), $R^b$ is hydrogen. In some embodiments of a compound of Formula (Ia)-(IVa) or (Ib)-(IVb), $R^c$ is hydrogen. In some embodiments of a compound of Formula (Ia)-(IVa) or (Ib)-(IVb), $R^a$ is not hydrogen. In some embodiments of a compound of Formula (Ia)-(IVa) or (Ib)-(IVb), $R^b$ is not hydrogen. In some embodiments of a compound of Formula (Ia)-(IVa) or (Ib)-(IVb), $R^c$ is not hydrogen. In some embodiments of a compound of Formula (Ia)-(IVa) or (Ib)-(IVb), $R^a$ and $R^b$ are hydrogen. In some embodiments of a compound of Formula (Ia)-(IVa) or (Ib)-(IVb), $R^a$ and $R^c$ are hydrogen. In some embodiments of a compound of Formula (Ia)-(IVa) or (Ib)-(IVb), $R^b$ and $R^c$ are hydrogen.

In some embodiments of a compound of Formula (Ia)-(IVa) or (Ib)-(IVb), $X^1$ is —OH and $X^2$ is —OH when present. In some embodiments of a compound of Formula (Ia)-(IVa) or (Ib)-(IVb), $X^1$ and $X^2$ are taken together with the boron atom to which they are attached to form a cyclic boronate ester.

In some embodiments of a compound of Formula (Ia)-(IVa) or (Ib)-(IVb), $R^d$ is hydrogen or alkyl. In some embodiments of a compound of Formula (Ia)-(IVa) or (Ib)-(IVb), $R^d$ is hydrogen. In some embodiments of a compound of Formula (Ia)-(IVa) or (Ib)-(IVb), $R^d$ is alkyl.

In some embodiments of a compound of Formula (Ia)-(IVa) or (Ib)-(IVb), n is 0. In some embodiments of a compound of Formula (Ia)-(IVa) or (Ib)-(IVb), n is 1. In some embodiments of a compound of Formula (Ia)-(IVa) or (Ib)-(IVb), n is 2. In some embodiments of a compound of Formula (Ia)-(IVa) or (Ib)-(IVb), n is 3. In some embodiments of a compound of Formula (Ia)-(IVa) or (Ib)-(IVb), m is 0. In some embodiments of a compound of Formula (Ia)-(IVa) or (Ib)-(IVb), m is 1. In some embodiments of a compound of Formula (Ia)-(IVa) or (Ib)-(IVb), m is 2. In some embodiments of a compound of Formula (Ia)-(IVa) or (Ib)-(IVb), m is 3. In some embodiments of a compound of Formula (Ia)-(IVa) or (Ib)-(IVb), n is 0 or 1 and m is 0 or 1. In some embodiments of a compound of Formula (Ia)-(IVa) or (Ib)-(IVb), n is 0 and m is 0. In some embodiments of a compound of Formula (Ia)-(IVa) or (Ib)-(IVb), n is 0 and m is 1. In some embodiments of a compound of Formula (Ia)-(IVa) or (Ib)-(IVb), n is 1 and m is 0. In some embodiments of a compound of Formula (Ia)-(IVa) or (Ib)-(IVb), n is 2 and m is 0. In some embodiments of a compound of Formula (Ia)-(IVa) or (Ib)-(IVb), n is 0 and m is 2.

In some embodiments of a compound of Formula (Ia)-(IVa) or (Ib)-(IVb), each $R^1$ and $R^2$ are independently hydrogen, —OH, fluoro, chloro, bromo, or optionally substituted alkyl.

In some embodiments of a compound of Formula (Ia)-(IVa) or (Ib)-(IVb), each $R^1$ and $R^2$ are independently hydrogen, fluoro, chloro, bromo, or optionally substituted alkyl. In some embodiments of a compound of Formula (Ia)-(IVa) or (Ib)-(IVb), each $R^1$ and $R^2$ are hydrogen.

In some embodiments of a compound of Formula (Ia)-(IVa) or (Ib)-(IVb), Z is hydrogen. In some embodiments of a compound of Formula (Ia)-(IVa) or (Ib)-(IVb), Z is $R^{61}$; and $R^{61}$ is optionally substituted alkyl. In some embodiments of a compound of Formula (Ia)-(IVa) or (Ib)-(IVb), Z is —$R^{60}$OC(=O)$R^{61}$ or —$R^{60}$OC(=O)O$R^{61}$; $R^{60}$ is —CH$_2$— or —CH(CH$_3$)—; and $R^{61}$ is optionally substituted alkyl, optionally substituted cycloalkyl, or optionally substituted heterocycloalkyl.

In some embodiments of a compound of Formula (Ia)-(IVa) or (Ib)-(IVb), at least one Y is halogen, alkyl, optionally substituted heteroaryl, —OH, —O$R^{34}$, —O(C$R^{30}$$R^{31}$)$_w$OH, —O(C$R^{30}$$R^{31}$)$_w$O$R^{34}$, —O(C$R^{30}$$R^{31}$)$_w$N$R^{32}$$R^{33}$, —O(C$R^{30}$$R^{31}$)$_w$N$R^{32}$C(=O)$R^{34}$, —O(C$R^{30}$$R^{31}$)$_w$N$R^{32}$C(=O)O$R^{34}$, —O(C$R^{30}$$R^{31}$)$_w$N$R^{32}$C(=O)N$R^{32}$$R^{33}$, —O(C$R^{30}$$R^{31}$)$_w$C(=O)N$R^{32}$$R^{33}$, —O(C$R^{30}$$R^{31}$)$_v$C(=N$R^{36}$)N$R^{32}$$R^{33}$, —O(C$R^{30}$$R^{31}$)$_w$N($R^{32}$)C(=N$R^{36}$)$R^{34}$, —O(C$R^{30}$$R^{31}$)$_v$C(=N$R^{36}$)N$R^{32}$C(=N$R^{36}$)N$R^{32}$$R^{33}$, —O(C$R^{30}$$R^{31}$)$_w$N($R^{32}$)C(=N$R^{36}$)N$R^{32}$$R^{33}$, —N$R^{32}$(C$R^{30}$$R^{31}$)$_w$N$R^{32}$$R^{33}$, —N$R^{32}$(C$R^{30}$$R^{31}$)$_w$OH, —N$R^{32}$(C$R^{30}$$R^{31}$)$_w$O$R^{34}$, —N$R^{32}$C(=O)$R^{34}$, —N$R^{32}$C(=O)O$R^{34}$, —N($R^{32}$)C(=O)(C$R^{30}$$R^{31}$)$_v$N$R^{32}$$R^{33}$, —N$R^{32}$C(=O)N$R^{32}$$R^{33}$, —N$R^{32}$C(=O)N$R^{32}$(C$R^{30}$$R^{31}$)$_w$N$R^{32}$$R^{33}$, —N$R^{32}$C(=N$R^{36}$)N$R^{32}$$R^{33}$, —N($R^{32}$)C(=N$R^{36}$)$R^{34}$, —N$R^{32}$(C$R^{30}$$R^{31}$)$_w$N($R^{32}$)C(=N$R^{36}$)$R^{34}$, —N$R^{32}$(C$R^{30}$$R^{31}$)$_v$C(=N$R^{36}$)N$R^{32}$$R^{33}$, —N$R^{32}$(C$R^{30}$$R^{31}$)$_w$N($R^{32}$)C(=N$R^{36}$)N$R^{32}$$R^{33}$, —N$R^{32}$(C$R^{30}$$R^{31}$)$_w$N$R^{32}$C(=O)N$R^{32}$$R^{33}$, —N$R^{32}$(C$R^{30}$$R^{31}$)$_w$N$R^{32}$C(=O)O$R^{34}$, —N$R^{32}$(C$R^{30}$$R^{31}$)$_v$CO$_2$H, —N$R^{32}$(C$R^{30}$$R^{31}$)$_v$CO$_2$$R^{34}$, —N$R^{32}$(C$R^{30}$$R^{31}$)$_v$C(=O)N$R^{32}$$R^{33}$, —N($R^{32}$)-heteroaryl-N$R^{32}$$R^{33}$, —N($R^{32}$)-heterocycloalkyl-N$R^{32}$$R^{33}$, —N$R^{32}$(C$R^{30}$$R^{31}$)$_v$heteroaryl, —N$R^{32}$(C$R^{30}$$R^{31}$)$_v$heterocycloalkyl, —CN, —(C$R^{30}$$R^{31}$)$_v$CN, —(C$R^{30}$$R^{31}$)$_v$N$R^{32}$$R^{33}$, —(C$R^{30}$$R^{31}$)$_v$OH, —(C$R^{30}$$R^{31}$)$_v$O$R^{34}$, —(C$R^{30}$$R^{31}$)$_v$OC(=O)$R^{34}$, —(C$R^{30}$$R^{31}$)$_v$OC(=O)N$R^{32}$$R^{33}$, —(C$R^{30}$$R^{31}$)$_v$O(C$R^{30}$$R^{31}$)$_w$O$R^{34}$, —(C$R^{30}$$R^{31}$)$_v$O(C$R^{30}$$R^{31}$)$_w$OH, —(C$R^{30}$$R^{31}$)$_v$O(C$R^{30}$$R^{31}$)$_w$N$R^{32}$$R^{33}$, —(C$R^{30}$$R^{31}$)$_v$N$R^{32}$(C$R^{30}$$R^{31}$)$_w$OH, —(C$R^{30}$$R^{31}$)$_v$N$R^{32}$(C$R^{30}$$R^{31}$)$_w$O$R^{34}$, —(C$R^{30}$$R^{31}$)$_v$C(=O)N$R^{32}$$R^{33}$, —(C$R^{30}$$R^{31}$)$_v$C(=O)N$R^{32}$(C$R^{30}$$R^{31}$)$_w$N$R^{32}$$R^{33}$, —(C$R^{30}$$R^{31}$)$_v$C(=O)N$R^{32}$(C$R^{30}$$R^{31}$)$_w$O$R^{34}$, —(C$R^{30}$$R^{31}$)$_v$N($R^{32}$)C(=O)$R^{34}$, —(C$R^{30}$$R^{31}$)$_v$N($R^{32}$)C(=O)O$R^{34}$, —(C$R^{30}$$R^{31}$)$_v$N($R^{32}$)C(=O)N$R^{32}$$R^{33}$, —(C$R^{30}$$R^{31}$)$_v$N($R^{32}$)C(=O)(C$R^{30}$$R^{31}$)$_w$N$R^{32}$$R^{33}$, —(C$R^{30}$$R^{31}$)$_v$N$R^{32}$(C$R^{30}$$R^{31}$)$_w$N$R^{32}$$R^{33}$, —(C$R^{30}$$R^{31}$)$_v$N($R^{32}$)CH(=N$R^{36}$), —(C$R^{30}$$R^{31}$)$_v$N($R^{32}$)C(=N$R^{36}$)$R^{34}$, —(C$R^{30}$$R^{31}$)$_v$C(=N$R^{36}$)N$R^{32}$$R^{33}$, —(C$R^{30}$$R^{31}$)$_v$N($R^{32}$)C(=N$R^{36}$)N$R^{32}$$R^{33}$, —(C$R^{30}$$R^{31}$)$_v$C(=N$R^{36}$)N$R^{32}$C(=N$R^{36}$)N$R^{32}$$R^{33}$, —(C$R^{30}$$R^{31}$)$_v$heteroaryl-N$R^{32}$$R^{33}$, —C(=O)OH, —C(=O)O$R^{34}$, —C(=O)N$R^{32}$$R^{33}$, —C(=O)N$R^{32}$(C$R^{30}$$R^{31}$)$_w$N$R^{32}$$R^{33}$, —C(=O)N$R^{32}$(C$R^{30}$$R^{31}$)$_w$OH, —C(=O)N$R^{32}$(C$R^{30}$$R^{31}$)$_w$O$R^{34}$, —C(=N$R^{36}$)N$R^{32}$$R^{33}$, —C(=N$R^{36}$)N$R^{32}$C(=O)$R^{34}$, or S$R^{35}$.

In some embodiments of a compound of Formula (Ia)-(IVa) or (Ib)-(IVb), at least one Y is halogen, alkyl, optionally substituted heteroaryl, —OH, —O$R^{34}$, —N$R^{32}$$R^{33}$, —N$R^{32}$(C$R^{30}$$R^{31}$)$_w$N$R^{32}$$R^{33}$, —N$R^{32}$(C$R^{30}$$R^{31}$)$_w$OH, —N$R^{32}$(C$R^{30}$$R^{31}$)$_w$O$R^{34}$, —N$R^{32}$C(=O)$R^{34}$, —N$R^{32}$C(=O)O$R^{34}$, —N($R^{32}$)C(=O)(C$R^{30}$$R^{31}$)$_v$N$R^{32}$$R^{33}$, —N$R^{32}$C(=O)N$R^{32}$$R^{33}$, —N$R^{32}$C(=O)N$R^{32}$(C$R^{30}$$R^{31}$)$_w$N$R^{32}$$R^{33}$, —N$R^{32}$C(=N$R^{36}$)N$R^{32}$$R^{33}$, —N($R^{32}$)C(=N$R^{36}$)$R^{34}$, —N$R^{32}$(C$R^{30}$$R^{31}$)$_w$N($R^{32}$)C(=N$R^{36}$)$R^{34}$, —N$R^{32}$(C$R^{30}$$R^{31}$)$_v$C(=N$R^{36}$)N$R^{32}$$R^{33}$, —N$R^{32}$(C$R^{30}$$R^{31}$)$_w$N($R^{32}$)C(=N$R^{36}$)N$R^{32}$$R^{33}$, —N$R^{32}$(C$R^{30}$$R^{31}$)$_w$N$R^{32}$C(=O)N$R^{32}$$R^{33}$, —N$R^{32}$(C$R^{30}$$R^{31}$)$_w$N$R^{32}$C(=O)O$R^{34}$, —N$R^{32}$(C$R^{30}$$R^{31}$)$_v$CO$_2$H, —N$R^{32}$(C$R^{30}$$R^{31}$)$_v$CO$_2$$R^{34}$, —N$R^{32}$(C$R^{30}$$R^{31}$)$_v$C(=O)N$R^{32}$$R^{33}$, —N$R^{32}$(C$R^{30}$$R^{31}$)$_v$heteroaryl, —N$R^{32}$(C$R^{30}$$R^{31}$)$_v$heterocycloalkyl, —(C$R^{30}$$R^{31}$)$_v$N$R^{32}$$R^{33}$, —(C$R^{30}$$R^{31}$)$_v$OC(=O)N$R^{32}$$R^{33}$, —(C$R^{30}$$R^{31}$)$_v$O(C$R^{30}$$R^{31}$)$_w$N$R^{32}$$R^{33}$, —(C$R^{30}$$R^{31}$)$_v$C(=O)N$R^{32}$$R^{33}$, —(C$R^{30}$$R^{31}$)$_v$C(=O)N$R^{32}$(C$R^{30}$$R^{31}$)$_w$N$R^{32}$$R^{33}$, —(C$R^{30}$$R^{31}$)$_v$C(=O)N$R^{32}$(C$R^{30}$$R^{31}$)$_w$O$R^{34}$, —(C$R^{30}$$R^{31}$)$_v$N($R^{32}$)C(=O)$R^{34}$, —(C$R^{30}$$R^{31}$)$_v$N($R^{32}$)C(=O)O$R^{34}$, —(C$R^{30}$$R^{31}$)$_v$N($R^{32}$)C(=O)N$R^{32}$$R^{33}$, —(C$R^{30}$$R^{31}$)$_v$N($R^{32}$)C(=O)(C$R^{30}$$R^{31}$)$_w$N$R^{32}$$R^{33}$, —(C$R^{30}$$R^{31}$)$_v$N$R^{32}$(C$R^{30}$$R^{31}$)$_w$N$R^{32}$$R^{33}$, —(C$R^{30}$$R^{31}$)$_v$N($R^{32}$)CH(=N$R^{36}$), —(C$R^{30}$$R^{31}$)$_v$N($R^{32}$)C(=N$R^{36}$)$R^{34}$, —(C$R^{30}$$R^{31}$)$_v$C(=N$R^{36}$)N$R^{32}$$R^{33}$, —(C$R^{30}$$R^{31}$)$_v$N($R^{32}$)C(=N$R^{36}$)N$R^{32}$$R^{33}$, —(C$R^{30}$$R^{31}$)$_v$C(=N$R^{36}$)N$R^{32}$C(=N$R^{36}$)N$R^{32}$$R^{33}$, —(C$R^{30}$$R^{31}$)$_v$heteroaryl-N$R^{32}$$R^{33}$, —C(=O)OH, —C(=O)O$R^{34}$, —C(=O)N$R^{32}$$R^{33}$, —C(=O)N$R^{32}$(C$R^{30}$$R^{31}$)$_w$N$R^{32}$$R^{33}$, —C(=O)N$R^{32}$(C$R^{30}$$R^{31}$)$_w$OH, —C(=O)N$R^{32}$(C$R^{30}$$R^{31}$)$_w$O$R^{34}$, —C(=N$R^{36}$)N$R^{32}$$R^{33}$, —C(=N$R^{36}$)N$R^{32}$C(=O)$R^{34}$, or S$R^{35}$.

In some embodiments of a compound of Formula (Ia)-(IVa) or (Ib)-(IVb), at least one Y is halogen, optionally substituted heteroaryl, —N$R^{32}$$R^{33}$, —OH, —O$R^{34}$, —N$R^{32}$(C$R^{30}$$R^{31}$)$_w$N$R^{32}$$R^{33}$, —N$R^{32}$C(=N$R^{36}$)N$R^{32}$$R^{33}$, —(C$R^{30}$$R^{31}$)$_v$N$R^{32}$$R^{33}$, —S$R^{35}$, —N$R^{32}$(C$R^{31}$$R^{31}$)$_v$CO$_2$H, —N$R^{32}$(C$R^{30}$$R^{31}$)$_v$C(=O)N$R^{32}$$R^{33}$, or —N$R^{32}$(C$R^{30}$$R^{31}$)$_v$heteroaryl; or two Ys taken together with the atoms to which they are attached form an optionally substituted heterocycloalkyl. In some embodiments of a compound of Formula (Ia)-(IVa) or (Ib)-(IVb), at least one of Y is —N$R^{32}$$R^{33}$. In some embodiments of a compound of Formula (Ia)-(IVa) or (Ib)-(IVb), at least one of Y is —(C$R^{30}$$R^{31}$)$_v$N$R^{32}$$R^{33}$. In some embodiments of a compound of Formula (Ia)-(IVa) or (Ib)-(IVb), at least one of Y is —N$R^{32}$(C$R^{30}$$R^{31}$)$_w$N$R^{32}$$R^{33}$.

In some embodiments of a compound of Formula (Ia)-(IVa) or (Ib)-(IVb), two Ys taken together with the atoms to which they are attached form an optionally substituted cycloalkyl or an optionally substituted heterocycloalkyl. In some embodiments of a compound of Formula (Ia)-(IVa) or (Ib)-(IVb), two Ys taken together with the atoms to which they are attached form a heterocycloalkyl optionally substituted with alkyl or halogen.

In some embodiments of a compound of Formula (Ia)-(IVa) or (Ib)-(IVb), Y is defined as above and $R^{30}$ and $R^{31}$ are independently hydrogen or optionally substituted alkyl; or two $R^{30}$ on adjacent carbon form an alkenyl. In some embodiments of a compound of Formula (Ia)-(IVa) or (Ib)-(IVb), Y is defined as above and $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl. In some embodiments of a compound of Formula (Ia)-(IVa) or (Ib)-(IVb), Y is defined as above and $R^{34}$ is optionally substituted alkyl. In some embodiments of a compound of Formula (Ia)-(IVa) or (Ib)-(IVb), Y is defined as above and $R^{35}$ is hydrogen or optionally substituted alkyl. In some embodiments of a compound of Formula (Ia)-(IVa) or (Ib)-(IVb), Y is defined as above and $R^{36}$ is hydrogen or optionally substituted alkyl. In some embodiments of a compound of Formula (Ia)-(IVa) or (Ib)-(IVb), Y is defined as above and each v is independently 1 or 2. In some embodiments of a compound of Formula (Ia)-(IVa) or (Ib)-(IVb) Y is defined as above and each w is independently 2 or 3.

In some embodiments of a compound of Formula (Ia)-(IVa) or (Ib)-(IVb), Y is defined as above, $R^{30}$ and $R^{31}$ are independently hydrogen or optionally substituted alkyl; or two $R^{30}$ on adjacent carbon form an alkenyl; $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl; $R^{34}$ is optionally substituted alkyl; $R^{35}$ is hydrogen or optionally substituted alkyl; $R^{36}$ is hydrogen or optionally substituted alkyl; each v is independently 1 or 2; and each w is independently 2 or 3.

In some embodiments of a compound of Formula (Ia)-(IVa) or (Ib)-(IVb), at least one of Y is not —$NR^{32}R^{33}$. In some embodiments of a compound of Formula (Ia)-(IVa) or (Ib)-(IVb), at least one of Y is not —$N(R^{32})C(=O)(CR^{30}R^{31})_vNR^{32}R^{33}$. In some embodiments of a compound of Formula (Ia)-(IVa) or (Ib)-(IVb), at least one of Y is not —$(CR^{30}R^{31})_vNR^{32}R^{33}$. In some embodiments of a compound of Formula (Ia)-(IVa) or (Ib)-(IVb), at least one of Y is not, —$NR^{32}(CR^{30}R^{31})_wNR^{32}R^{33}$. In some embodiments of a compound of Formula (Ia)-(IVa) or (Ib)-(IVb), at least one Y is not —$NH_2$. In some embodiments of a compound of Formula (Ia)-(IVa) or (Ib)-(IVb), at least one Y is not —$CH_2NH_2$. In some embodiments of a compound of Formula (Ia)-(IVa) or (Ib)-(IVb), at least one Y is not —$NHC(=O)CH_2NH_2$. In some embodiments of a compound of Formula (Ia)-(IVa) or (Ib)-(IVb), at least one Y is not —$NHC(=O)CH(NH_2)CH_2CH_2CH_2CH_2NH_2$. In some embodiments of a compound of Formula (Ia)-(IVa) or (Ib)-(IVIb), at least one Y is not —$NHCH_2CH_2NHCH_3$.

In some embodiments of a compound of Formula (Ia)-(IVa) or (Ib)-(IVb), each Y is defined by the inclusion of non-hydrogen atoms. In some embodiments, each Y comprises at least 1, 2, 3, 4, 5, 6, 7, 8, 9, 10, 12, 14, 16, 18, 20, 24, 28, 32, 36, 40, 50, or 60 non-hydrogen atoms. In some embodiments of a compound of Formula (Ia)-(IVa) or (Ib)-(IVb), each Y comprises fewer than 50, 40, 36, 32, 28, 24, 20, 18, 16, 14, 12, 10, 9, 8, 7, 6, 5, 4, 3 or 2 non-hydrogen atoms. In some embodiments of a compound of Formula (Ia)-(IVa) or (Ib)-(IVb), each Y is independently a group comprising 1-50 non-hydrogen atoms. In some embodiments of a compound of Formula (Ia)-(IVa) or (Ib)-(IVb), non-hydrogen atoms are atoms generally found in organic molecules. In some embodiments of a compound of Formula (Ia)-(IVa) or (Ib)-(IVb), non-hydrogen atoms are atoms selected from the group consisting of halogen, C, N, O, S, and P. In some embodiments of a compound of Formula (Ia)-(IVa) or (Ib)-(IVb), each Y is independently a group comprising 1-50 non-hydrogen atoms selected from the group consisting of halogen, C, N, O, S, and P. In some embodiments of a compound of Formula (Ia)-(IVa) or (Ib)-(IVb), each Y is independently a group comprising 1-50 non-hydrogen atoms selected from the group consisting of halogen, C, N, and O.

In some embodiments of a compound of Formula (Ia)-(IVa) or (Ib)-(IVb), each Y is defined by its molecular formula. In some embodiments of a compound of Formula (Ia)-(IVa) or (Ib)-(IVb), each Y has the formula $C_aH_bN_cO_d$; wherein each a is independently 0-30; each b is independently 1-69; each c is independently 1-8; and each d is independently 0-10. In some embodiments of a compound of Formula (Ia)-(IVa) or (Ib)-(IVb), each Y has the formula $C_aH_bN_cO_d$; wherein each a is independently 0-10; each b is independently 1-25; each c is independently 1-4; and each d is independently 0-3. In some embodiments of a compound of Formula (Ia)-(IVa) or (Ib)-(IVb), each c is 2. In some embodiments of a compound of Formula (Ia)-(IVa) or (Ib)-(IVb), each c is at least 2.

In some embodiments of a compound of Formula (Ia)-(IVa) or (Ib)-(IVb), each Y is defined by its molecular weight. In some embodiments of a compound of Formula (Ia)-(IVa) or (Ib)-(IVb), each Y has a molecular weight of less than 500, 450, 400, 350, 300, 250, 200, 190, 180, 170, 160, 150, 140, 130, 120, 110, 100, 90, 80, 75, 70, or 50 daltons. In some embodiments of a compound of Formula (Ia)-(IVa) or (Ib)-(IVb), each Y has a molecular weight of less than 200 daltons. In some embodiments of a compound of Formula (Ia)-(IVa) or (Ib)-(IVb), each Y has a molecular weight of less than 150 daltons. In some embodiments of a compound of Formula (Ia)-(IVa) or (Ib)-(IVb), each Y has a molecular weight between 30 and 280 daltons.

In some embodiments of a compound of Formula (Ia)-(IVa) or (Ib)-(IVb), p is 0, 1, or 2.

In some embodiments of a compound of Formula (Ia)-(IVa) or (Ib)-(IVb), p is 0. In some embodiments of a compound of Formula (Ia)-(IVa) or (Ib)-(IVb), p is 1. In some embodiments of a compound of Formula (Ia)-(IVa) or (Ib)-(IVb), p is 2. In some embodiments of a compound of Formula (Ia)-(IVa) or (Ib)-(IVb), p is 3.

In some embodiments of a compound of Formula (Ia)-(IVa) or (Ib)-(IVb), v is 1. In some embodiments of a compound of Formula (Ia)-(IVa) or (Ib)-(IVb), v is 2. In some embodiments of a compound of Formula (Ia)-(IVa) or (Ib)-(IVb), v is 3. In some embodiments of a compound of Formula (Ia)-(IVa) or (Ib)-(IVb), v is 4. In some embodiments of a compound of Formula (Ia)-(IVa) or (Ib)-(IVb), v is 5.

In some embodiments of a compound of Formula (Ia)-(IVa) or (Ib)-(IVb), w is 2. In some embodiments of a compound of Formula (Ia)-(IVa) or (Ib)-(IVb), w is 3. In some embodiments of a compound of Formula (Ia)-(IVa) or (Ib)-(IVb), w is 4. In some embodiments of a compound of Formula (Ia)-(IVa) or (Ib)-(IVb), w is 5.

Preparation of Compounds

Described herein are compounds of Formula (Ia)-(IVa) or (Ib)-(IVb) that inhibit the activity of penicillin-binding proteins, and processes for their preparation. Also described herein are pharmaceutically acceptable salt, solvate, stereoisomer, tautomer, N-oxide, dimer, or trimer of compounds of Formula (Ia)-(IVa) or (Ib)-(IVb).

Compounds of Formula (Ia)-(IVa) or (Ib)-(IVb) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography, and the like. Such materials may be characterized using conventional means, including physical constants and spectral data.

Further Forms of Compounds Disclosed Herein
Isomers/Stereoisomers

In some embodiments, due to the oxophilic nature of the boron atom, the compounds described herein may convert to, or exist in equilibrium with, alternate forms, particularly in milieu that contain water (aqueous solution, plasma, etc.). Accordingly, the compounds described herein may exist in an equilibrium between the "closed" cyclic form shown in Formula (Ia), (IIa), (IIIa), or (IVa) and the "open" acyclic form shown in Formula (Ib), (IIb), (IIIb), or (IVb). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof.

In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Compounds described herein may be prepared as a single isomer or a mixture of isomers.

Tautomers

In some situations, compounds described herein exist as tautomers. The compounds described herein include all possible tautomers within the formulas described herein. A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

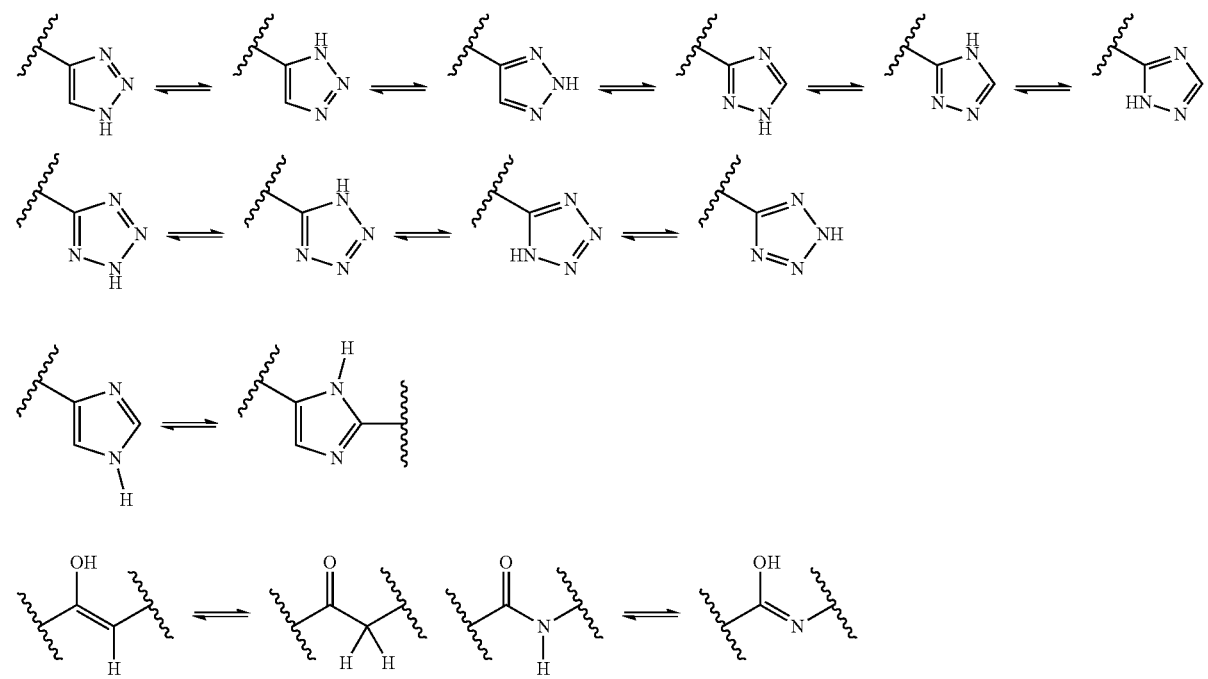

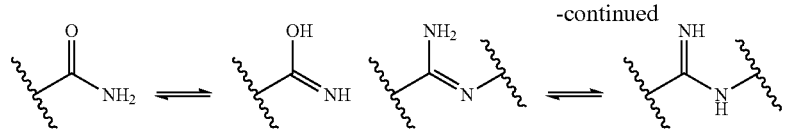

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. In some embodiments, other acids, such as oxalic, while not in themselves pharmaceutically acceptable, are employed in the preparation of salts useful as intermediates in obtaining the compounds described herein and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Pharmaceutical Compositions/Formulations

In another aspect, provided herein are pharmaceutical compositions comprising a compound of Formula (Ia)-(IVa) or (Ib)-(IVb) as described herein, or a pharmaceutically acceptable salt, solvate, stereoisomer, tautomer, N-oxide, dimer, or trimer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds of Formula (Ia)-(IVa) or (Ib)-(IVb) are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (Ia)-(IVa) or (Ib)-(IVb) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Combination Treatment

The compounds of Formula (Ia)-(IVa) or (Ib)-(IVb) may be used in combination with one or more antibiotics in the treatment of bacterial infections. Such antibiotics may be administered, by a route and in an amount commonly used therefore, contemporaneously or sequentially with a compound of Formula (Ia)-(IVa) or (Ib)-(IVb). When a compound of Formula (Ia)-(IVa) or (Ib)-(IVb) is used contemporaneously with one or more antibiotic, a pharmaceutical composition in unit dosage form containing such other drugs and the compound of the present invention is preferred. However, the combination therapy may also include therapies in which the compound of Formula (Ia)-(IVa) or (Ib)-(IVb) and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound of Formula (Ia)-(IVa) or (Ib)-(IVb). In some embodiments, a pharmaceutical composition comprising a compound of Formula (Ia)-(IVa) or (Ib)-(IVb) further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds of Formula (Ia)-(IVa) or (Ib)-(IVb) are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathinebenzylpenicillin, benzathinephenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, and ticarcillin. Penems include, but are not limited to, faropenem. Carbapenems include, but are not limited to, biapenem, ertapenem, doripenem, imipenem, meropenem, and panipenem. Cephalosporins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftarolinefosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, and loracarbef. Monobactams include, but are not limited to, aztreonam, carumonam, nocardicinA, and tigemonam.

Methods

The present disclosure also provides methods for inhibiting bacterial growth, such methods comprising contacting a bacterial cell culture, or a bacterially infected cell culture, tissue, or organism, with a penicillin-binding protein inhibitor of Formula (Ia)-(IVa) or (Ib)-(IVb). Preferably, the bacteria to be inhibited by administration of a penicillin-binding protein inhibitor of Formula (Ia)-(IVa) or (Ib)-(IVb) are bacteria that are resistant to beta-lactam antibiotics. The term "resistant" is well-understood by those of ordinary skill in the art (see, e.g., Payne et al., *Antimicrobial Agents and Chemotherapy* 38 767-772 (1994), Hanaki et al., *Antimicrobial Agents and Chemotherapy* 30 1120-1126 (1995)). In some embodiments, the penicillin-binding protein inhibitor of Formula (Ia)-(IVa) or (Ib)-(IVb) is used to treat a bacterial infection that is resistant to beta-lactam antibiotic. In some embodiments, the penicillin-binding protein inhibitor of Formula (Ia)-(IVa) or (Ib)-(IVb) is used to treat a bacterial infection that has developed beta-lactamase enzymes.

These methods are useful for inhibiting bacterial growth in a variety of contexts. In certain embodiments, a compound of Formula (Ia)-(IVa) or (Ib)-(IVb) is administered to an experimental cell culture in vitro to prevent the growth of beta-lactam resistant bacteria. In some embodiments, a compound of Formula (Ia)-(IVa) or (Ib)-(IVb) is administered to a mammal, including a human, to prevent the growth of beta-lactam resistant bacteria in vivo. The method according to this embodiment comprises administering a therapeutically effective amount of a penicillin-binding protein inhibitor of Formula (Ia)-(IVa) or (Ib)-(IVb) for a therapeutically effective period of time to a mammal, including a human. Preferably, the penicillin-binding protein inhibitor of Formula (Ia)-(IVa) or (Ib)-(IVb) is administered in the form of a pharmaceutical composition as described above.

In another aspect provided herein are methods of treating a bacterial infection, which method comprises administering to a subject a pharmaceutical composition comprising a compound of Formula (Ia)-(IVa) or (Ib)-(IVb), or a pharmaceutically acceptable salt thereof, and a pharmaceutically acceptable excipient. In some embodiments, the methods of treating a bacterial infection in a subject comprises administering to the subject a pharmaceutical composition as described herein. In some embodiments, the bacterial infection is an upper or lower respiratory tract infection, a urinary tract infection, an intra-abdominal infection, or a skin infection. In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonasmaltophilia, Burkholderiacepacia, Aeromonashydrophila, Escherichia coli, Citrobacterfreundii, Salmonella typhimurium, Salmonella typhi, Salmonella paratyphi, Salmonella enteritidis, Shigelladysenteriae, Shigellaflexneri, Shigellasonnei, Enterobacter cloacae, Enterobacter aerogenes, Klebsiella pneumoniae, Klebsiellaoxytoca, Serratiamarcescens, Francisellatularensis, Morganellamorganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilusinfluenzae, Haemophilusparainfluenzae, Haemophilushaemolyticus, Haemophilusparahaemolyticus, Haemophilusducreyi, Pasteurellamultocida, Pasteurellahaemolytica, Branhamellacatarrhalis, Helicobacter pylori, Campylobacter fetus, Campylobacter jejuni, Campylobacter coli, Borreliaburgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroidesfragilis, Bacteroidesdistasonis, Bacteroides*3452A homology group, *Bacteroidesvulgatus, Bacteroidesovalus, Bacteroidesthetaiotaomicron, Bacteroidesuniformis, Bacteroideseggerthii, Bacteroidessplanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In some embodiments, the infection that is treated or prevented comprises a bacteria that includes *Pseudomonas aeruginosa, Pseudomonas fluorescens, Stenotrophomonasmaltophilia, Escherichia coli, Citrobacterfreundii, Salmonella typhimurium, Salmonella typhi, Salmonella paratyphi, Salmonella enteritidis, Shigelladysenteriae, Shigellaflexneri, Shigellasonnei, Enterobacter cloacae, Enterobacter aerogenes, Klebsiella pneumoniae, Klebsiellaoxytoca, Serratiamarcescens, Acinetobacter calcoaceticus, Acinetobacter haemolyticus, Yersinia enterocolitica, Yersinia pestis, Yersinia pseudotuberculosis, Yersinia intermedia, Haemophilusinfluenzae, Haemophilusparainfluenzae, Haemophilushaemolyticus, Haemophilusparahaemolyticus, Helicobacter pylori, Campylobacter fetus, Campylobacterjejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroidesfragilis, Bacteroidesvulga-* tus, *Bacteroidesovalus, Bacteroidesthetaiotaomicron, Bacteroidesuniformis, Bacteroideseggerthii,* or *Bacteroidessplanchnicus.*

In some embodiments of the methods described herein, the compound of Formula (Ia)-(IVa) or (Ib)-(IVb) is not administered with a β-lactam antibiotic. In some embodiments of the methods described herein, the compound of Formula (Ia)-(IVa) or (Ib)-(IVb) is not administered with a β-lactamase inhibitor. In some embodiments of the methods described herein, the compound of Formula (Ia)-(IVa) or (Ib)-(IVb) is not administered with a combination of a β-lactam antibiotic and a β-lactamase inhibitor.

EXAMPLES

General Examples for the Preparation of Compounds of Formula (Ia)-(IVa) or (Ib)-(IVb)

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). The use of protective groups may be as described in methodology compendia such as *Greene's Protective Groups in Organic Synthesis*, Fourth Edition. John Wiley & Sons, Inc. 2006.

Certain compounds of Formula I (Scheme 1) are prepared from the corresponding functional-group-protected boronic acid esters A by treatment with a Lewis acid in a solvent such as dichloromethane, at a temperature between −78° C. and 0° C. followed by an aqueous quench.

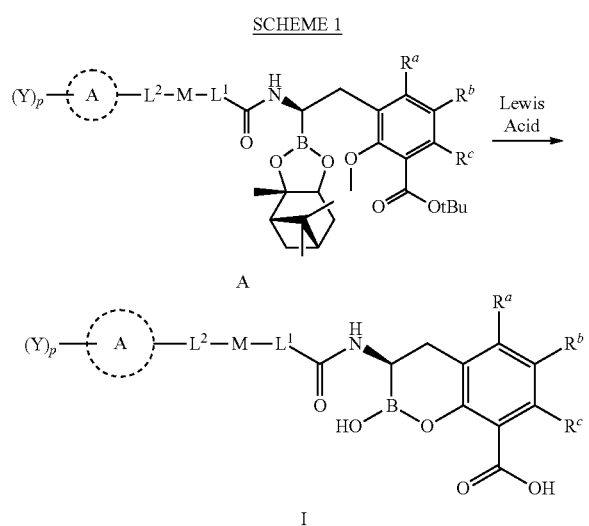

SCHEME 1

Amide intermediates A may be prepared according to the route outlined in Scheme 2. Chloro-boronates B, prepared by methods described previously (e.g. see WO2014089365), is reacted with silylamine bases such as lithium hexamethyldisilazide, and the intermediate silylamine is treated with carboxylic acids C under amide coupling conditions (such as with carbodiimide dehydrating reagents, HATU, or other coupling reagents) to provide protected amides A. Alternatively, the above silylamine intermediate is allowed to react with acid chlorides to provide A. Carboxylic acids (C) or acid chlorides (D) may be obtained from commercial sources, prepared according to known methods in the literature, or prepared by a number of different reaction sequences. Formation of the acid chloride (D) involves treatment of (C) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (E) involves treatment of (C) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (F) involves treatment of (C) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

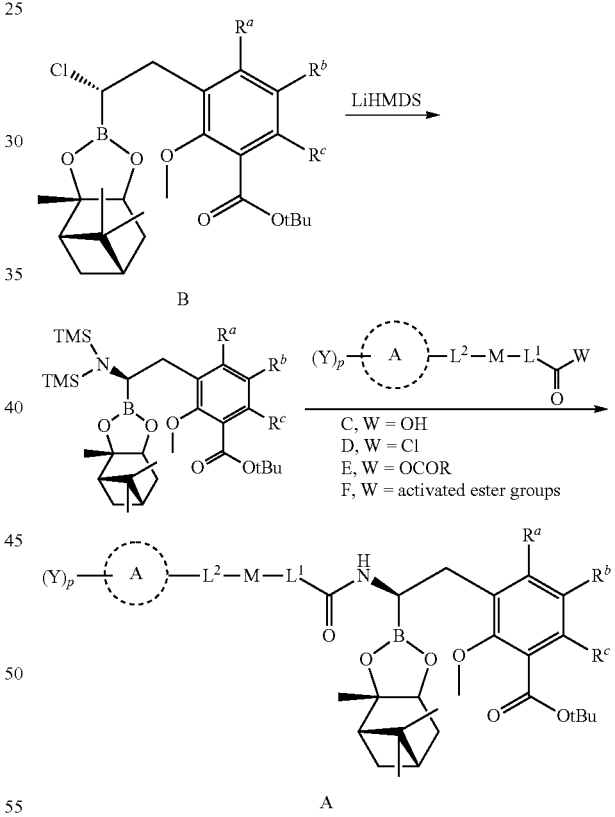

SCHEME 2

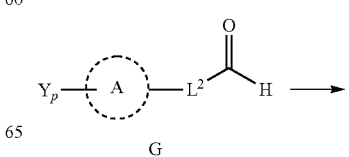

SCHEME 3

73

-continued

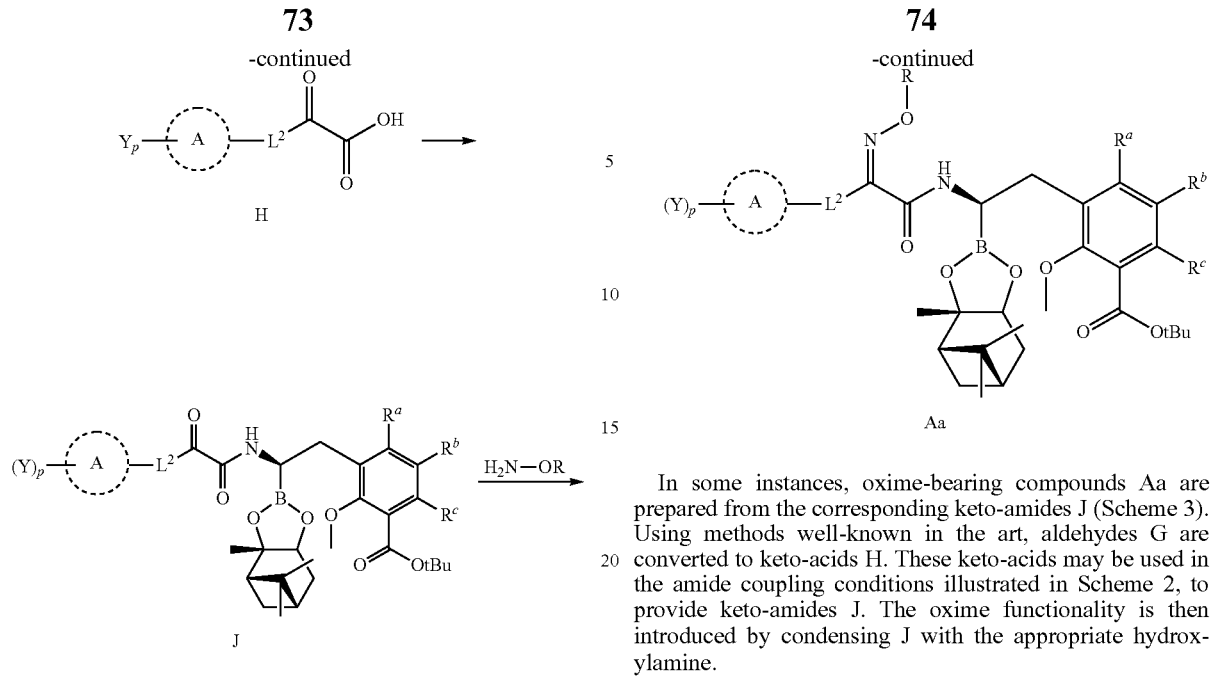

74

-continued

Aa

In some instances, oxime-bearing compounds Aa are prepared from the corresponding keto-amides J (Scheme 3). Using methods well-known in the art, aldehydes G are converted to keto-acids H. These keto-acids may be used in the amide coupling conditions illustrated in Scheme 2, to provide keto-amides J. The oxime functionality is then introduced by condensing J with the appropriate hydroxylamine.

SCHEME 4

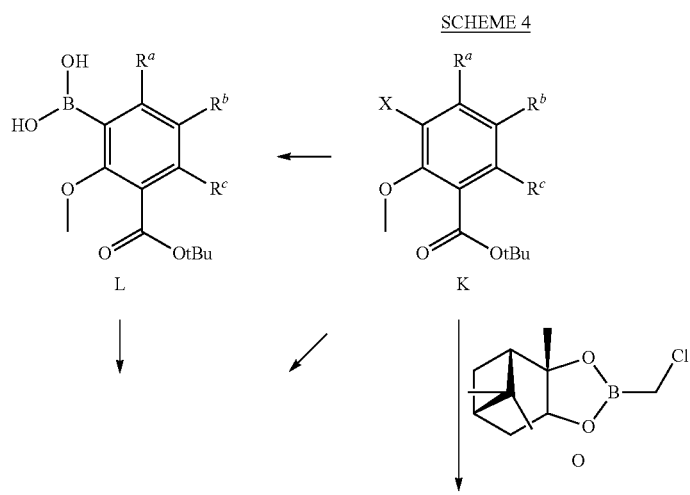

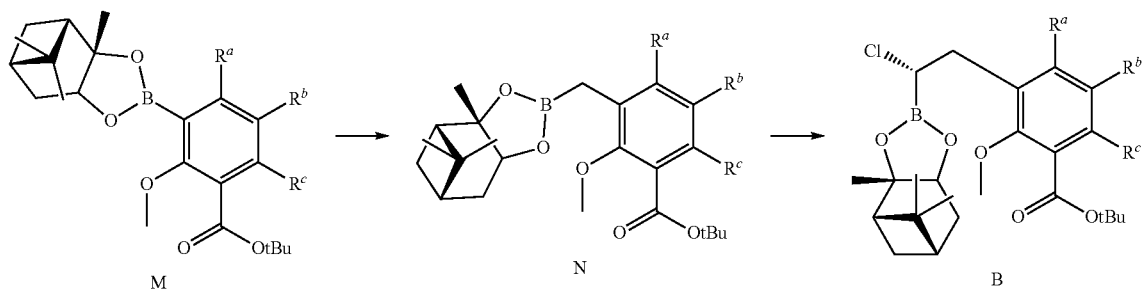

Chloroboronates B may be prepared from aryl halides or aryl triflates K (X=Br, I or OTf) in the manner described in Scheme 4. Compounds K (X=Br, I or OTf) may be converted into boronic acids L by treatment with alkyl lithium reagents, for example n-butyllithium, and then quenching the intermediate aryllithium species with trialkylboronates, followed by aqueous work-up. The boronic acids L may be converted into protected boronate esters M by treatment with 1,2-diols, such as (+)-pinanediol or pinacol. Alternatively, aryl halides K may be converted to boronate esters M by transition-metal-catalyzed reaction with diboron compounds, for example bis[(+)-pinanediolato]diboron and palladium catalysts. Two sequential Matteson reactions, as described previously, provide chloroboronates B bearing a wide range of substituents $R^a$, $R^b$, and $R^c$. Another variant consists of reaction of K with chloromethyl boronate J and isopropylmagnesium chloride to provide desired intermediate N directly.

While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

General Method A: Deprotection with Boron Trichloride or Boron Tribromide

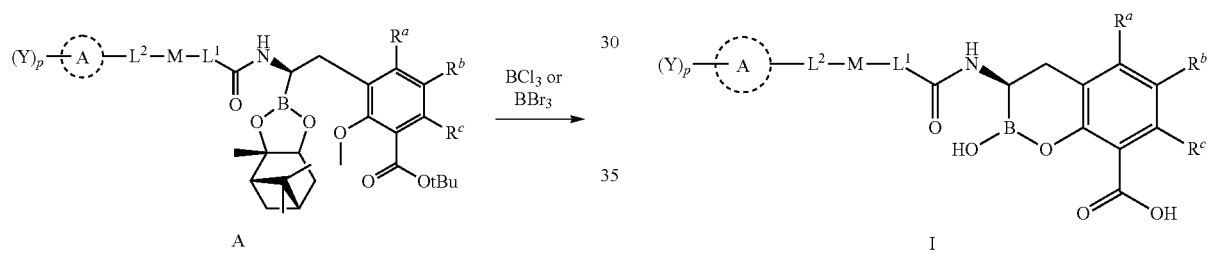

To a solution of the protected precursor A (0.4 mmol) in anhydrous DCM (15 mL) at −78° C. under argon was added dropwise BCl$_3$ or BBr$_3$ (1.0 M in DCM, 2.4-4 mL, 2.4-4 mmol, 6-10 equiv). The reaction mixture was allowed to slowly warmed to 0° C. over 1 h, and stirred between 0-5 OC for an additional 1-2 h, then quenched with water (2 mL) and methanol (20 mL), evaporated to remove DCM, washed with hexane, and concentrated to a volume of ~4-5 mL. The crude product was purified by reverse phase preparative HPLC and dried using lyophilization to afford the product I.

General Method B: Deprotection with Aluminum Chloride

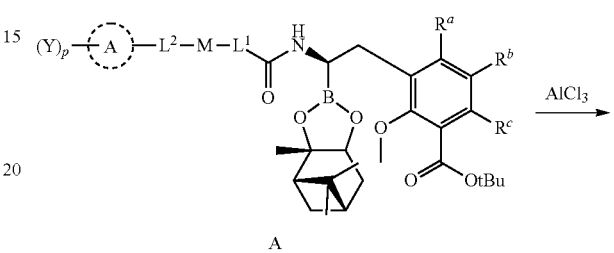

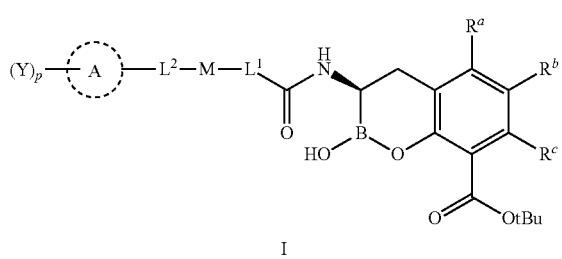

To a solution of the protected precursor A (0.4 mmol) in anhydrous DCM (15 mL) was added AlCl$_3$ (535 mg, 4 mmol, 10 equiv) in one portion at RT. The reaction mixture was stirred at RT for 24 h, then quenched with water (2 mL) and methanol (20 mL), evaporated to remove DCM, and washed with hexane, and concentrated to a volume of ~4-5 mL. The crude product was purified by reverse phase preparative HPLC and dried using lyophilization to afford the product I.

General Method C: Conversion of Chloro-Boronates to Amides

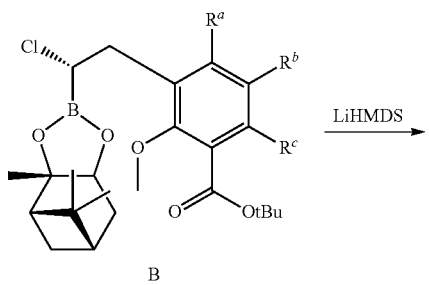

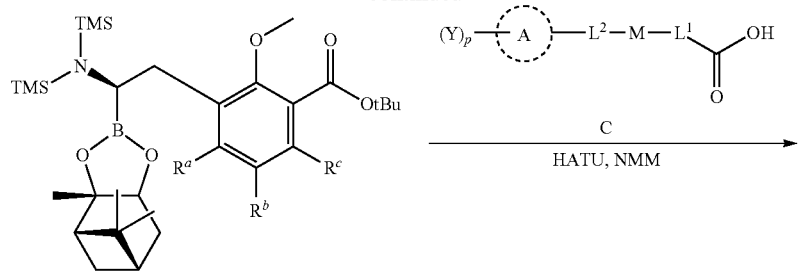

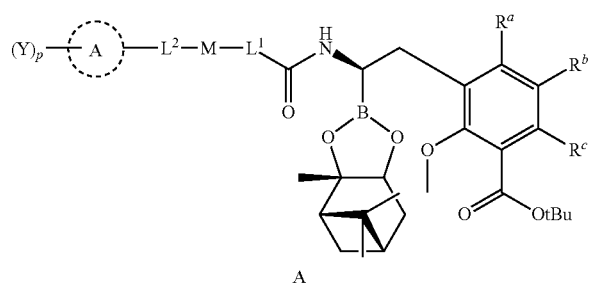

To a solution of the chloride B (4 mmol) in anhydrous THF (16 mL) was added dropwise LiHMDS (1.0 M in THF, 4.5 mL, 4.5 mmol) at −60° C. under argon. The reaction mixture was allowed to slowly warmed to 0° C. over 45 min, and stirred at RT for an additional 2 h.

In a separate flask was charged the carboxylic acid C (4.2 mmol) and anhydrous DMA (20 mL), to this mixture was added HATU (1.68 g, 4.4 mmol) followed by NMM (0.49 mL, 4.4 mmol). The reaction mixture was stirred at RT for 2 h, at which time the solution from the above reaction was added to the flask, and the reaction mixture was stirred at RT overnight, then diluted with EtOAc, washed with water, brine, and dried over $Na_2SO_4$, concentrated in vacuo to afford the crude product, which was purified by flash chromatography on silica gel (hexane-EtOAc, 20:1-1:1, or hexane-acetone, 10:1-1:1, or DCM-MeOH, 30:1-10:1) to afford the product A.

SYNTHETIC EXAMPLES

Example 1: (R,Z)-3-(2-(2-aminothiazol-4-yl)-2-(methoxyimino)acetamido)-2-hydroxy-3,4-dihydro-2H-benzo[e][1,2]oxaborinine-8-carboxylic Acid

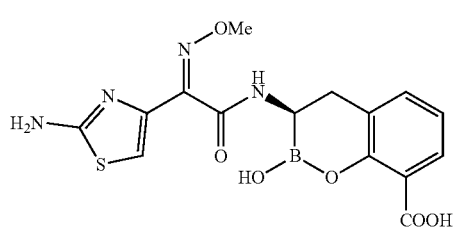

Step 1. Synthesis of (Z)-2-(2-((tert-butoxycarbonyl)amino)thiazol-4-yl)-2-(methoxyimino)acetic Acid

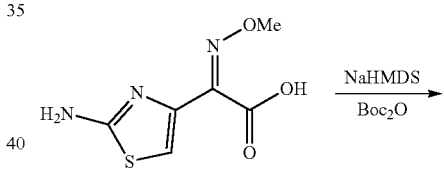

To a solution of (Z)-2-(2-aminothiazol-4-yl)-2-(methoxyimino)acetic acid (3.04 g, 15.1 mmol) in THF (85 mL) and DMF (26 mL) was added NaHMDS (8.33 g, 45.4 mmol) at 0° C. under argon. After 20 min, $Boc_2O$ (3.3 g, 15.1 mmol) was added, and the reaction mixture was stirred for 3.5 h, then diluted with EtOAc, washed with 0.3 N HCl, brine, dried with $Na_2SO_4$, and concentrated in vacuo. To the residue was added hexane, the solid was collected by filtration and washed with hexane and dried in vacuo to yield the product, 1.08 g. ESI-MS m/z 302 (MH)⁺.

Step 2. Synthesis of tert-butyl 3-(2-((Z)-2-(2-((tert-butoxycarbonyl)amino)thiazol-4-yl)-2-(methoxyimino)acetamido)-2-((3aS,4S,6R)-3a,5,5-trimethylhexahydro-4,6-methanobenzo[d][1,3,2]dioxaborol-2-yl)ethyl)-2-methoxybenzoate

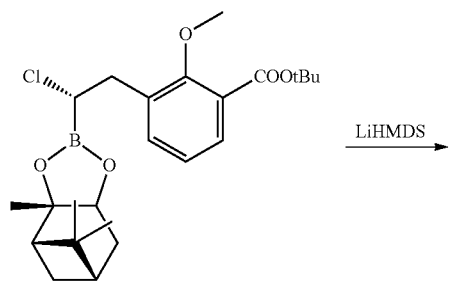

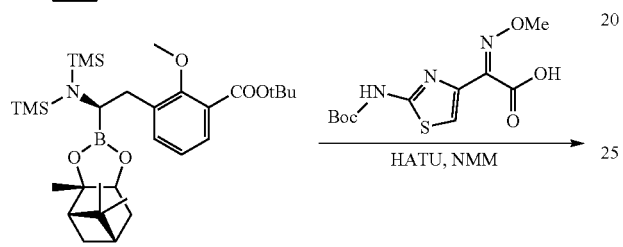

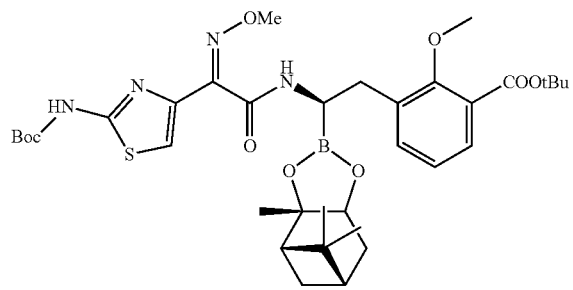

By following General Method C, the chloride (prepared as previous reported, WO2014089365) was treated with LiHMDS, and then coupled with the acid from Step 1 in the presence of HATU and NMM, yielding the product. ESI-MS m/z 713 (MH)+.

Step 3. Synthesis of (R,Z)-3-(2-(2-aminothiazol-4-yl)-2-(methoxyimino)acetamido)-2-hydroxy-3,4-dihydro-2H-benzo[e][1,2]oxaborinine-8-carboxylic Acid

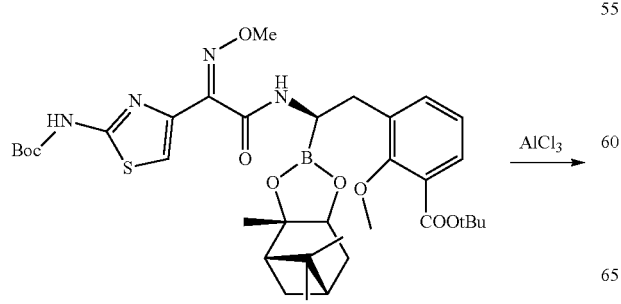

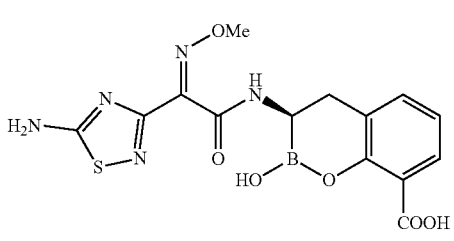 [SMILES: CO/N=C(\C(=O)N[C@H]1Cc2cccc(C(=O)O)c2OB1O)c1nsc(N)n1]

By following General Method B, the desired product was obtained. ESI-MS m/z 391 (MH)+.

Example 2: (R,Z)-3-(2-(5-amino-1,2,4-thiadiazol-3-yl)-2-(methoxyimino)acetamido)-2-hydroxy-3,4-dihydro-2H-benzo[e][1,2]oxaborinine-8-carboxylic Acid

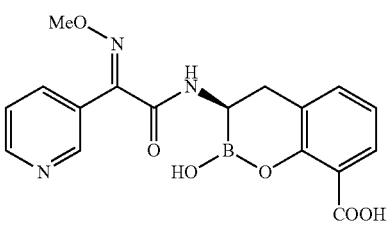 [SMILES: CO/N=C(/C(=O)N[C@H]1Cc2cccc(C(=O)O)c2OB1O)c1cccnc1]

By following the same reaction procedures as described in Example 1, except in Step 1 using 2-(5-amino-1,2,4-thiadiazol-3-yl)-2-(methoxyimino)acetic acid instead of 2-amino-alpha-(methoxyimino)-4-thiazoleacetic acid as starting material, the target compound was prepared. ESI-MS m/z 392 (MH)+.

Example 3: (R,E)-2-hydroxy-3-(2-(methoxyimino)-2-(pyridin-3-yl)acetamido)-3,4-dihydro-2H-benzo[e][1,2]oxaborinine-8-carboxylic Acid

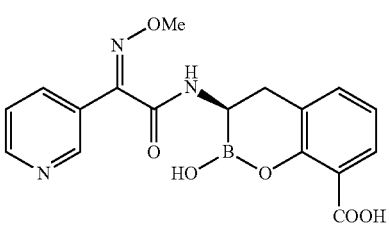 [SMILES: CO/N=C(\C(=O)N[C@H]1Cc2cccc(C(=O)O)c2OB1O)c1cccnc1]

Example 4: (R,Z)-2-hydroxy-3-(2-(methoxyimino)-2-(pyridin-3-yl)acetamido)-3,4-dihydro-2H-benzo[e][1,2]oxaborinine-8-carboxylic Acid

Step 1. Synthesis of 2-hydroxy-2-pyridin-3-yl)acetonitrile

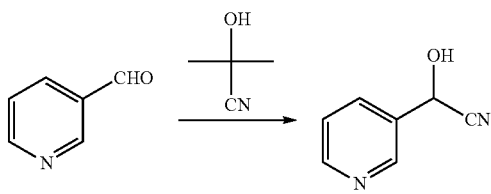

To 3-pyridinecarboxaldehyde (5.35 g, 50 mmol) was added acetone cyanohydrins (6.85 mL, 75 mmol) followed by iPr$_2$NEt (0.13 mL, 0.75 mmol) at 0° C., the reaction mixture was stirred for 1 h, then evaporated to remove acetone, added more acetone cyanohydrins (1 mL) and iPr$_2$NEt (0.1 mL), stirred in ice bath for an additional 1.5 h. The reaction mixture was purified by flash chromatography on silica gel (hexane-EtOAc, 10:1-0:100) to afford the product, 5 g, which was contaminated with some aldehyde. ESI-MS m/z 135 (MH)$^+$.

Step 2. Synthesis of methyl 2-hydroxy-2-(pyridin-3-yl)acetate

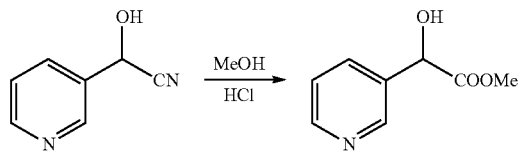 [SMILES: "MeOH" ; N#CC(O)c1cccnc1 ; Cl ; COC(=O)C(O)c1cccnc1]

The above product (9.8 g, 73.1 mmol) was dissolved in 3 N methanolic HCl (180 mL), stirred at RT overnight, concentrated in vacuo. To the residue was added saturated aqueous NaHCO$_3$, extracted with DCM. The organic extracts were dried over Na$_2$SO$_4$, concentrated in vacuo to afford the crude product, which was purified by flash chromatography on silica gel (hexane-acetone, 4:1-1:2) to afford the product, 8 g. ESI-MS m/z 168 (MH)$^+$.

Step 3. Synthesis of methyl 2-oxo-2-(pyridin-3-yl)acetate

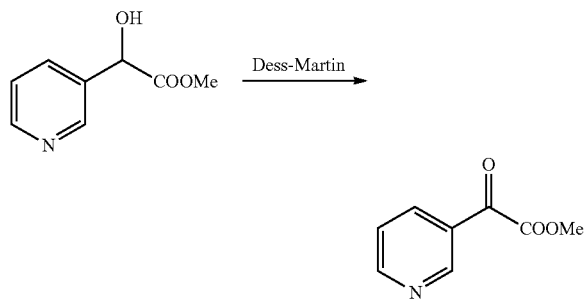

To the above product (6.14 g, 36.8 mmol) in DCM (350 mL) was added NaHCO$_3$(9.4 g, 112 mmol) followed by Dess-Martin periodinane reagent (20.2 g, 47.3 mmol). The reaction mixture was stirred at RT for 45 min, then quenched with aqueous NaHCO$_3$ and Na$_2$S$_2$O$_3$, stirred for 15 min. The organic layer was separated, and the aqueous was extracted with DCM. The combined organic extracts were washed with aqueous Na$_2$S$_2$O$_3$ and NaHCO$_3$, brine, dried over Na$_2$SO$_4$, concentrated, and the crude product was purified by flash chromatography on silica gel (hexane-acetone, 1:1-1:4) to afford the product, 5.2 g. ESI-MS m/z 166 (MH)$^+$.

Step 4. Synthesis of methyl (Z)- and (E)-2-(methoxyimino)-2-(pyridin-3-yl)acetate

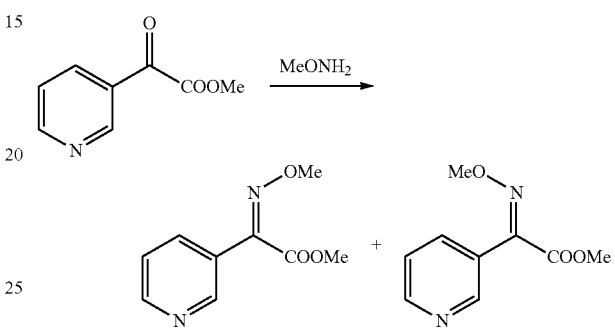

To the above product (2.35 g, 14.2 mmol) in MeOH (20 mL) was added O-methylhydroxylaminehydrochloride (1.72 g, 20.5 mmol) followed by pyridine (3.64 mL). The reaction mixture was heated at reflux overnight, concentrated in vacuo. The residue was dissolved in DCM, washed with saturated aqueous NaHCO$_3$, dried over Na$_2$SO$_4$, concentrated. The crude product was purified by flash chromatography on silica gel (hexane-acetone, 10:1-1:2) to afford two products, the Z and E isomers, 1.24 g of less polar product, and 1.2 g of more polar product. ESI-MS m/z 195 (MH)$^+$.

Step 5. Synthesis of (Z)- and (E)-2-(methoxyimino)-2-(pyridin-3-yl)acetic Acid

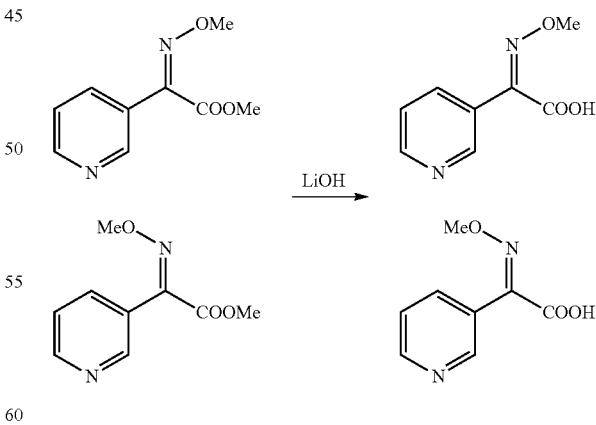

To the less polar product from step 4 (1.2 g, 6.19 mmol) in THF (25 mL) was added LiOH.H$_2$O (1.06 g, 25.2 mmol) followed by water (20 mL). The reaction mixture was stirred at RT overnight, evaporated to remove THF, acidified with 1 N HCl to pH ~4, and concentrated to dryness. The solid was washed with hot THF—CH$_3$CN (1:1) three times, and dried in vacuo to give the product as a white solid, 1.18 g, which was assigned as the Z isomer based on the literature data (*Arkivoc,* 36-47, 2004). ESI-MS m/z 181 (MH)+.

To the more polar product from Step 4 (1.2 g, 6.19 mmol) in THF (25 mL) was added LiOH.H₂O (1.06 g, 25.2 mmol) followed by water (20 mL). The reaction mixture was stirred at RT overnight, evaporated to remove THF, acidified with 1 N HCl to pH ~4, and concentrated in vacuo, white solid precipitated, and was collected by filtration, dried in vacuo to yield the E isomer as a white solid, 910 mg. ESI-MS m/z 181 (MH)+.

Step 6. Synthesis of (R,E)- and (R,Z)-2-hydroxy-3-(2-(methoxyimino)-2-(pyridin-3-yl)acetamido)-3,4-dihydro-2H-benzo[e][1,2]oxaborinine-8-carboxylic Acid

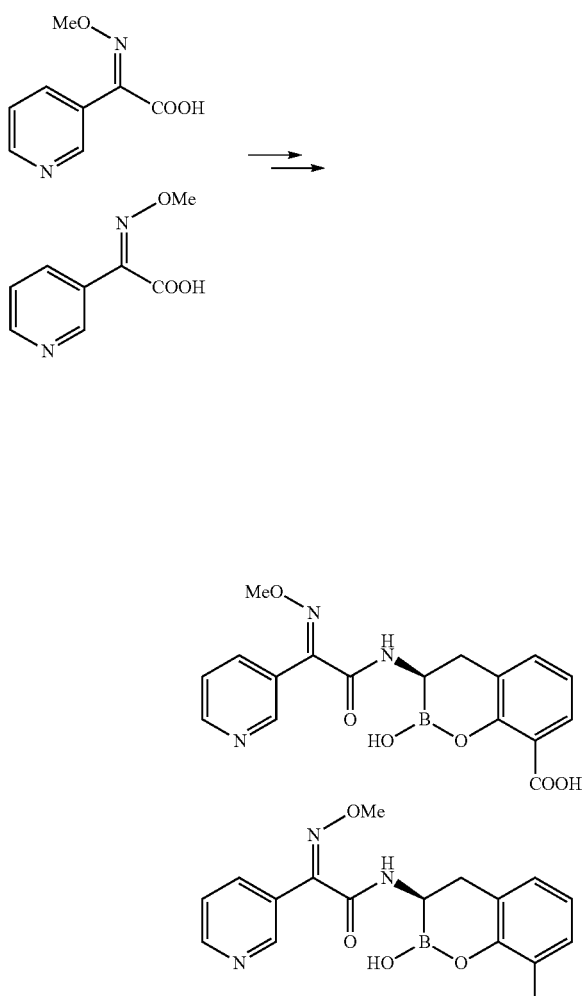

The above (E)- and (Z)-isomer acids were converted to the corresponding (R,E)- and (R,Z)-product respectively by following the same procedures as described for Example 1. ESI-MS m/z 370 (MH)+.

Example 5: (R,Z)-2-hydroxy-3-(2-(isoindolin-5-yl)-2-(methoxyimino)acetamido)-3,4-dihydro-2H-benzo[e][1,2]oxaborinine-8-carboxylic Acid

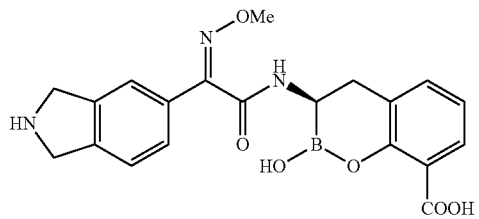

Step 1. Synthesis of tert-butyl 5-formylisoindoline-2-carboxylate

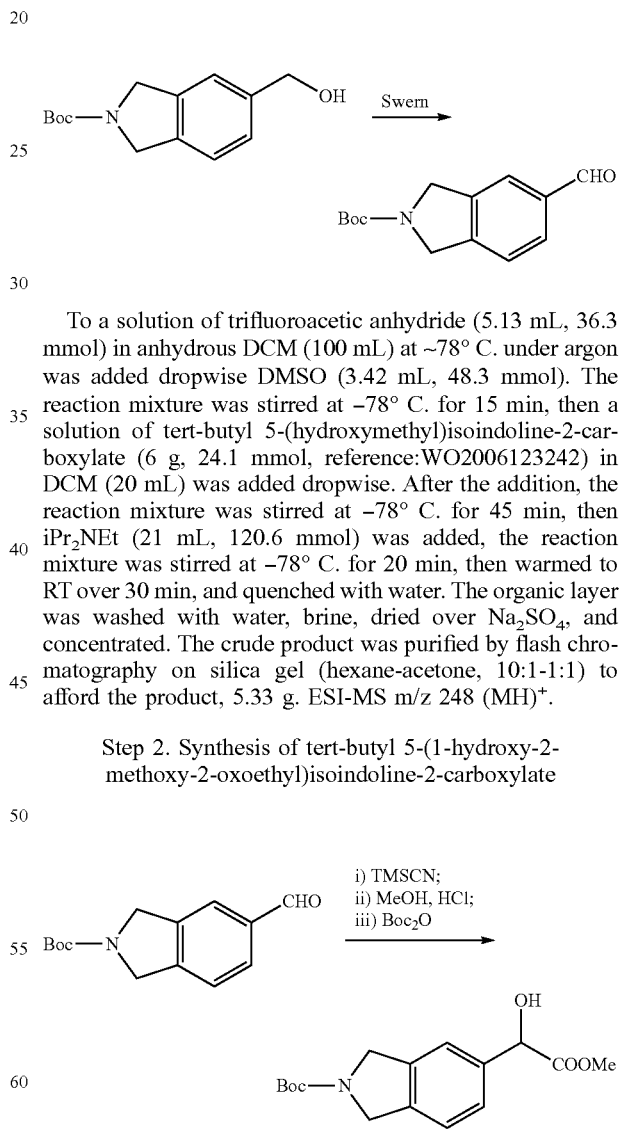

To a solution of trifluoroacetic anhydride (5.13 mL, 36.3 mmol) in anhydrous DCM (100 mL) at −78° C. under argon was added dropwise DMSO (3.42 mL, 48.3 mmol). The reaction mixture was stirred at −78° C. for 15 min, then a solution of tert-butyl 5-(hydroxymethyl)isoindoline-2-carboxylate (6 g, 24.1 mmol, reference:WO2006123242) in DCM (20 mL) was added dropwise. After the addition, the reaction mixture was stirred at −78° C. for 45 min, then iPr₂NEt (21 mL, 120.6 mmol) was added, the reaction mixture was stirred at −78° C. for 20 min, then warmed to RT over 30 min, and quenched with water. The organic layer was washed with water, brine, dried over Na₂SO₄, and concentrated. The crude product was purified by flash chromatography on silica gel (hexane-acetone, 10:1-1:1) to afford the product, 5.33 g. ESI-MS m/z 248 (MH)+.

Step 2. Synthesis of tert-butyl 5-(1-hydroxy-2-methoxy-2-oxoethyl)isoindoline-2-carboxylate To a solution of the aldehyde (3.4 g, 13.77 mmol) in CH₃CN (40 mL) was added 4-DMAP (51 mg, 0.42 mmol) followed by TMSCN (2.26 mL, 18 mmol). The reaction mixture was stirred at RT for 4.5 h, then concentrated. The residue was dissolved in 3 N methanolic HCl (70 mL), stirred at RT overnight, concentrated in vacuo. The residue was dissolved in MeOH (150 mL), added TEA (5.85 mL, 42 mmol), followed by Boc$_2$O (3.5 g, 16 mmol). The reaction mixture was stirred at RT for 2 h, concentrated, dissolved in EtOAc, washed with saturated aqueous NaHCO$_3$, dried over Na$_2$SO$_4$, concentrated in vacuo to afford the crude product, which was purified by flash chromatography on silica gel (hexane-acetone, 10:1-1:2) to afford the product, 2.4 g. ESI-MS m/z 308 (MH)$^+$.

Step 3. Synthesis of tert-butyl 5-(2-methoxy-2-oxoacetyl)isoindoline-2-carboxylate

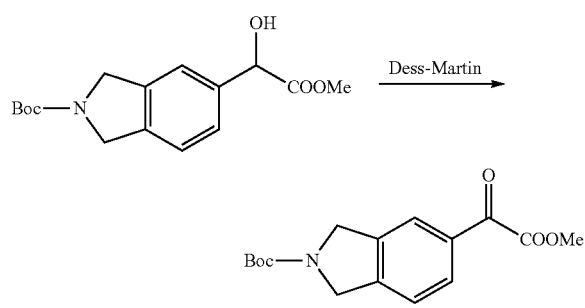

Using the same reaction condition as described in Step 3 of Example 3 and 4, the above product was oxidized to the ketoester. ESI-MS m/z 306 (MH)$^+$.

Step 4. Synthesis of 2-(2-(tert-butoxycarbonyl)isoindolin-5-yl)-2-oxoacetic Acid

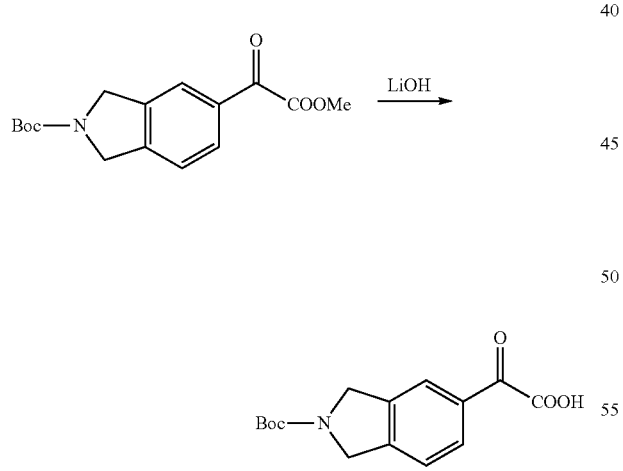

The above ketoester (2.75 g, 9 mmol) in THF (60 mL) and water (50 mL) was treated with LiOH.H$_2$O (1.52 g, 36 mmol) at RT overnight, evaporated to remove THF, and extracted with diethyl ether. The aqueous was acidified with 1 N HCl to pH ~3, extracted with DCM. The organic extracts were washed with brine, dried over Na$_2$SO$_4$, concentrated in vacuo to afford the crude product which was used directly for the next step. ESI-MS m/z 292 (MH)$^+$.

Step 5. Synthesis of tert-butyl 5-(2-((2-(3-(tert-butoxycarbonyl)-2-methoxyphenyl)-1-((3aS,4S,6R)-3a,5,5-trimethylhexahydro-4,6-methanobenzo[d][1,3,2]dioxaborol-2-yl)ethyl)amino)-2-oxoacetyl)isoindoline-2-carboxylate

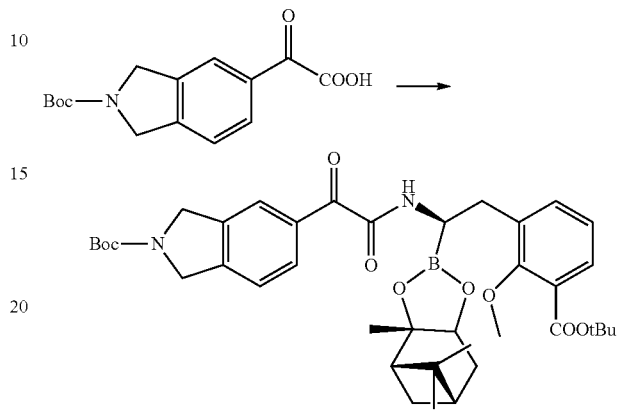

By following the same procedure as described in Step 2 of Example 1, the above acid was converted to the coupled product.

Step 6. Synthesis of tert-butyl 5-((Z)-2-((2-(3-(tert-butoxycarbonyl)-2-methoxyphenyl)-1-((3aS,4S,6R)-3a,5,5-trimethylhexahydro-4,6-methanobenzo[d][1,3,2]dioxaborol-2-yl)ethyl)amino)-1-(methoxyimino)-2-oxoethyl)isoindoline-2-carboxylate

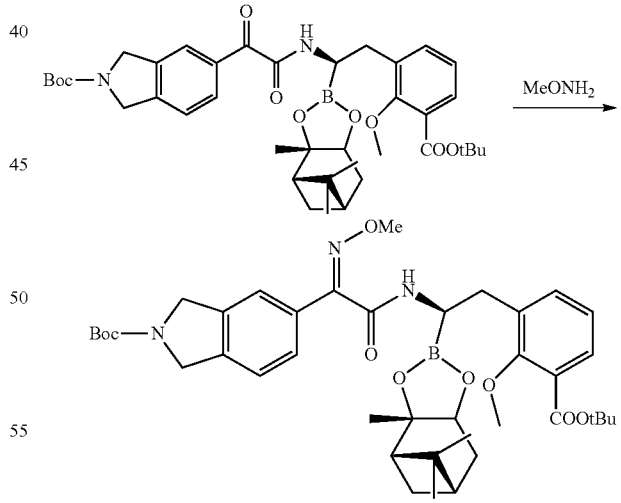

To the product from Step 5 (250 mg, 0.356 mmol) in EtOH (20 mL) was added O-methylhydroxylaminehydrochloride (120 mg, 1.43 mmol), the reaction mixture was stirred at RT overnight, concentrated in vacuo. The residue was dissolved in DCM, washed with saturated aqueous NaHCO$_3$, dried over Na$_2$SO$_4$, concentrated. The crude product was purified by flash chromatography on silica gel (hexane-EtOAc, 10:1-1:1) to afford the product, 150 mg.

Step 7. Synthesis of (R,Z)-2-hydroxy-3-(2-(isoindolin-5-yl)-2-(methoxyimino)acetamido)-3,4-dihydro-2H-benzo[e][1,2]oxaborinine-8-carboxylic Acid

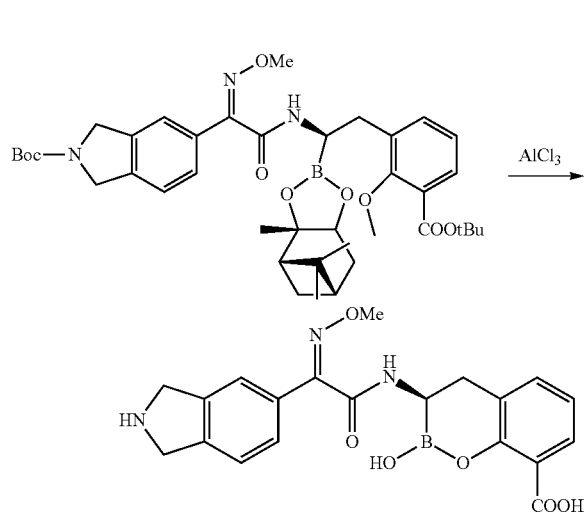

By following General Method B, the deprotected product was obtained. ESI-MS m/z 410 (MH)+.

Example 6: (R,Z)-3-(2-(2-aminothiazol-4-yl)-2-(hydroxyimino)acetamido)-2-hydroxy-3,4-dihydro-2H-benzo[e][1,2]oxaborinine-8-carboxylic Acid

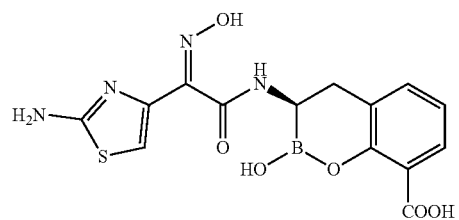 [SMILES: Nc1nc(/C(=N/O)C(=O)N[C@H]2Cc3cccc(C(=O)O)c3OB2O)cs1]

Step 1. Synthesis of ethyl 2-(2-((tert-butoxycarbonyl)amino)thiazol-4-yl)-2-oxoacetate

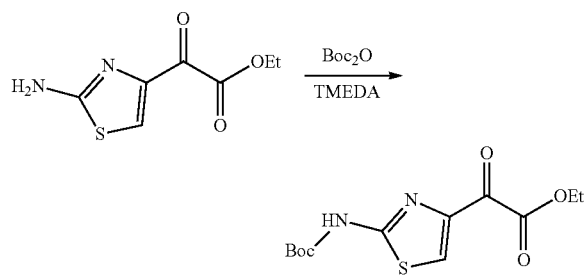

To ethyl 2-(2-amino-4-thiazolyl)-2-oxoacetate (11.2 g, 56 mmol) in CH$_3$CN (300 mL) was added TMEDA (26 mL, 175 mmol) followed by Boc$_2$O (13.4 g, 61.4 mmol). The reaction mixture was stirred at RT overnight, then concentrated, and purified by flash chromatography on silica gel (hexane-EtOAc, 10:1-2:1) to afford the product, 11 g. ESI-MS m/z 301 (MH)+.

Step 2. Synthesis of ethyl 2-((benzyloxy)imino)-2-(2-((tert-butoxycarbonyl)amino)thiazol-4-yl)acetate

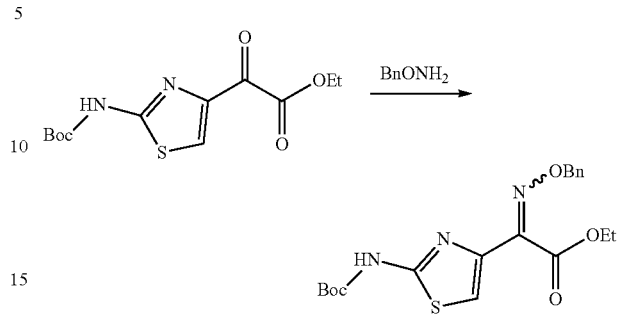

To the above product (11 g, 36.7 mmol) in EtOH (500 mL) was added O-benzylhydroxylaminehydrochloride (10 g, 62.5 mmol), the reaction mixture was stirred at RT overnight, concentrated in vacuo. The residue was dissolved in DCM, washed with saturated aqueous NaHCO$_3$, dried over Na$_2$SO$_4$, concentrated. The crude product was purified by flash chromatography on silica gel (hexane-EtOAc, 20:1-2:1) to afford the product as an inseparable mixture of Z and E isomers, 14.68 g. ESI-MS m/z 406 (MH)+.

Step 3. Synthesis of (Z)- and (E)-2-((benzyloxy)imino)-2-(2-((tert-butoxycarbonyl)amino)thiazol-4-yl)acetic Acid

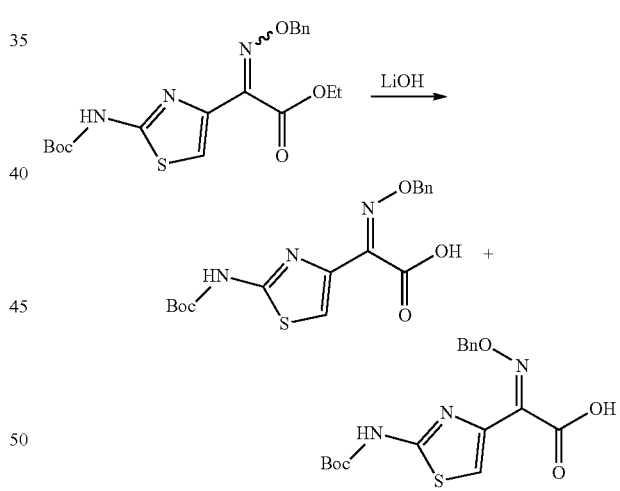

To the above product (14.68 g, 36.3 mmol) in THF (200 mL) and water (200 mL) was added LiOH.H$_2$O (840 mg, 20 mmol), the reaction mixture was stirred at RT for 2 h, then added more LiOH.H$_2$O (2.2 g, 52.4 mmol), and stirred for 1 h. LC/MS showed the minor, E isomer was completely hydrolyzed (the E isomer was less hindered and hydrolyzed much faster than Z isomer). The reaction mixture was extracted with diethyl ether. The aqueous was acidified with 1 N HCl to pH ~3, extracted with DCM. The organic extracts were washed with brine, dried over Na$_2$SO$_4$, concentrated in vacuo to afford the E-oxime acid, 3.47 g. ESI-MS m/z 378 (MH)+.

The ether extracts were combined and concentrated. The residue was dissolved in THF (150 mL), MeOH (150 mL)

and water (150 mL), and treated with LiOH.H₂O (4.41 g, 105 mmol) at RT for 2 days, then concentrated, acidified with 1 N HCl to pH ~3, the precipitated solid was collected by filtration, washed with water, and dried in vacuo to yield the pure Z-oxime acid, 9.3 g. ESI-MS m/z 378 (MH)⁺.

Step 4. Synthesis of tert-butyl 3-(2-((Z)-2-((benzyloxy)imino)-2-(2-(((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate

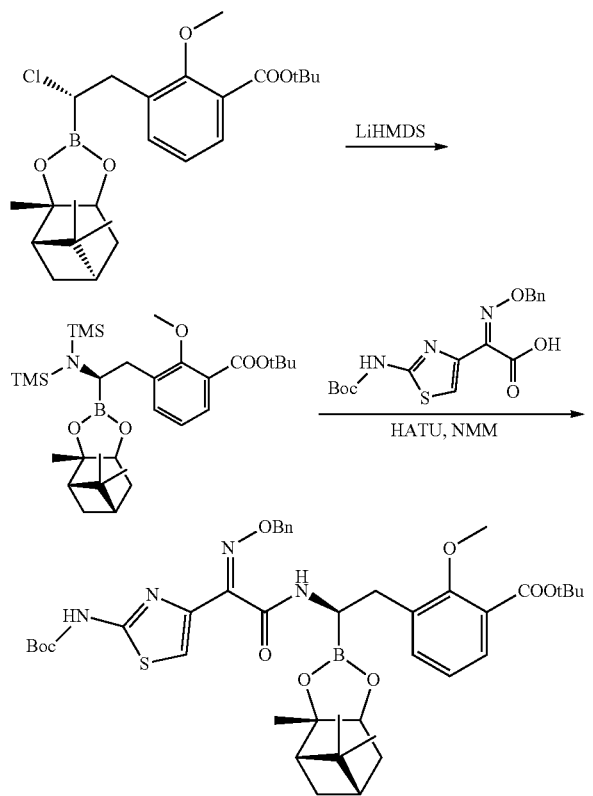

By following General Method C, the chloride (prepared as previous reported, WO2014089365) was treated with LiHMDS, and then coupled with the (Z)-oxime acid from above reaction in the presence of HATU and NMM, yielding the title compound. ESI-MS m/z 789 (MH)⁺.

Step 5. Synthesis of (R,Z)-3-(2-(2-aminothiazol-4-yl)-2-(hydroxyimino)acetamido)-2-hydroxy-3,4-dihydro-2H-benzo[e][1,2]oxaborinine-8-carboxylic Acid

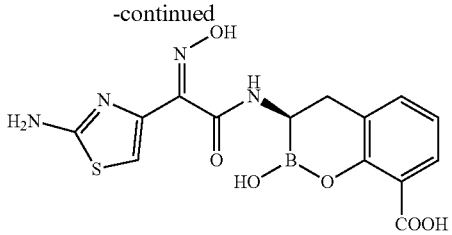

The title compound was prepared by treatment of the above product with either BCl₃ or BBr₃ by following General Method A. ESI-MS m/z 377 (MH)⁺.

Example 7: (R,E)-3-(2-(2-aminothiazol-4-yl)-2-(hydroxyimino)acetamido)-2-hydroxy-3,4-dihydro-2H-benzo[e][1,2]oxaborinine-8-carboxylic Acid

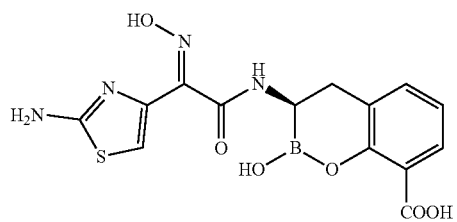 [SMILES: Nc1nc(/C(=N\O)C(=O)N[C@H]2Cc3cccc(C(=O)O)c3OB2O)cs1]

In a similar manner to the synthesis of Example 6, the target compound was prepared using the (E)-oxime acid from Step 3 of Example 6 described above. ESI-MS m/z 377 (MH)⁺.

Example 8: (R,Z)-2-hydroxy-3-(2-(hydroxyimino)-2-(isoindolin-5-yl)acetamido)-3,4-dihydro-2H-benzo[e][1,2]oxaborinine-8-carboxylic Acid

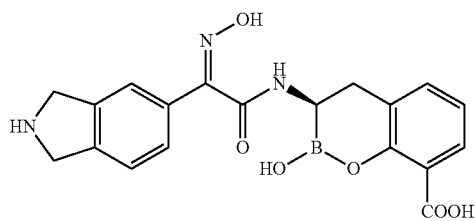

Step 1. Synthesis of tert-butyl 5-((Z)-1-((benzyloxy)imino)-2-((2-(3-(tert-butoxycarbonyl)-2-methoxyphenyl)-1-((3aS,4S,6R)-3a,5,5-trimethylhexahydro-4,6-methanobenzo[d][1,3,2]dioxaborol-2-yl)ethyl)amino)-2-oxoethyl)isoindoline-2-carboxylate

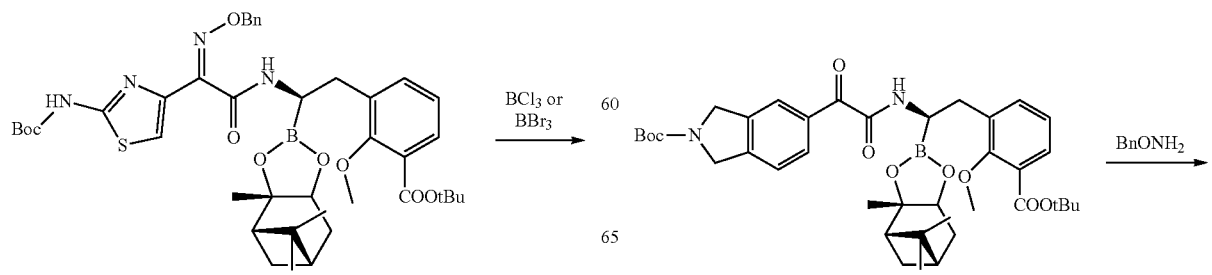

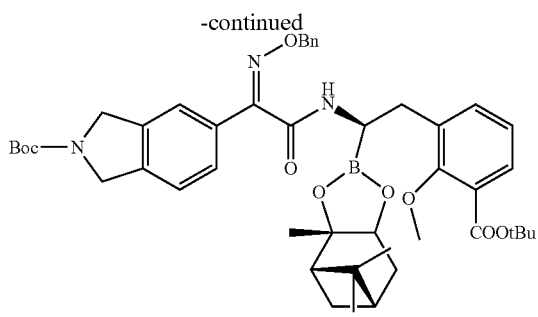

The product of Step 5 in the synthesis of Example 5 was converted to the title compound by using the same reaction condition as described in the step 2 of Example 6. ESI-MS m/z 808 (MH)+.

Step 2. Synthesis of (R,Z)-2-hydroxy-3-(2-(hydroxyimino)-2-(isoindolin-5-yl)acetamido)-3,4-dihydro-2H-benzo[e][1,2]oxaborinine-8-carboxylic Acid

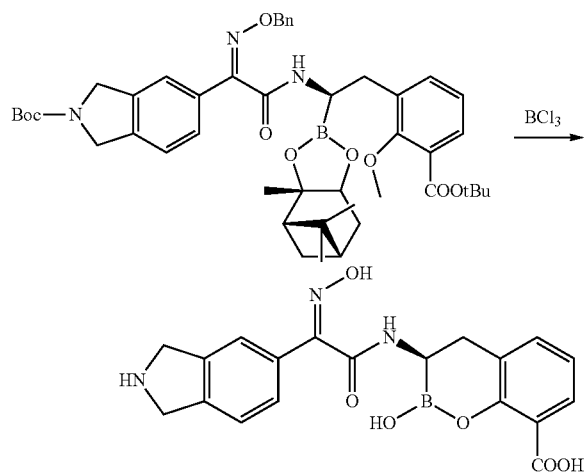

By following General Method A, the above product was treated with BCl₃ to give the title compound. ESI-MS m/z 396 (MH)+.

Example 9: (S,Z)-3-(2-(2-aminothiazol-4-yl)-2-(hydroxyimino)acetamido)-2-hydroxy3,4-dihydro-2H-benzo[e][1,2]oxaborinine-8-carboxylic Acid

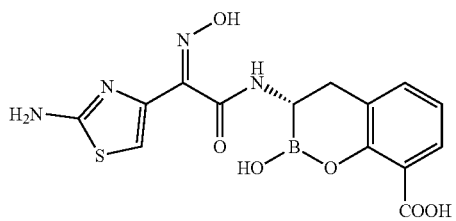 [SMILES: Nc1nc(/C(=N/O)C(=O)N[C@@H]2Cc3cccc(C(=O)O)c3OB2O)cs1]

In a similar manner to the synthesis of Example 6, the S-enantiomer of Example 6 was prepared using the R-chloride intermediate, which was prepared as previous reported (WO2014089365). ESI-MS m/z 377 (MH)+.

Example 10: (R,Z)-3-(2-(2-((2-aminoethyl)amino)thiazol-4-yl)-2-(hydroxyimino)acetamido)-2-hydroxy-3,4-dihydro-2H-benzo[e][1,2]oxaborinine-8-carboxylic Acid

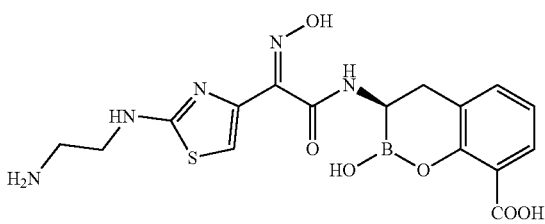 [SMILES: NCCNc1nc(/C(=N/O)C(=O)N[C@H]2Cc3cccc(C(=O)O)c3OB2O)cs1]

Step 1. Synthesis of ethyl (Z)-2-(2-aminothiazol-4-yl)-2-((benzyloxy)imino)acetate

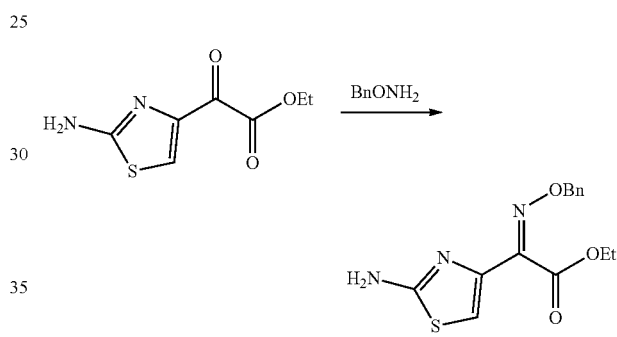

By using the same reaction procedure as described in Step 2 of Example 6, ethyl 2-(2-amino-4-thiazolyl)-2-oxoacetate was reacted with O-benzylhydroxylaminehydrochloride to give the oxime product after column chromatography, which was washed with hexane to afford the pure Z isomer. ESI-MS m/z 306 (MH)+.

Step 2. Synthesis of ethyl (Z)-2-((benzyloxy)imino)-2-(2-((2-(bis(tert-butoxycarbonyl)amino)ethyl)(tert-butoxycarbonyl)amino)thiazol-4-yl)acetate

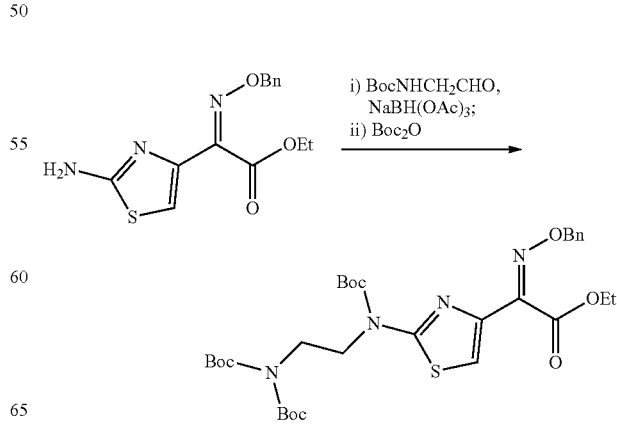

To the above product (1.22 g, 4 mmol) in DCE (40 mL) was added Boc-aminoacetaldehyde (1.27 g, 8 mmol), followed by HOAc (1.38 mL, 24 mmol) and NaBH(OAc)₃ (2.38 g, 11.2 mmol). The reaction mixture was stirred at RT for 3 days, then added more aldehyde (1.27 g, 8 mmol) and NaBH(OAc)₃ (1.2 g), the reaction mixture was stirred for another 2 days, quenched with aqueous NaHCO₃, the organic layer was dried over Na₂SO₄, concentrated, purified by flash chromatography on silica gel (hexane-EtOAc, 10:1-1:1) to afford the product, 1.58 g, which was not pure. This product was dissolved in CH₃CN (40 mL), added TEA (0.74 mL, 5.3 mmol), Boc₂O (2.4 g, 11 mmol) and 4-DMAP (49 mg, 0.4 mmol). The reaction mixture was stirred at RT for 2 days, then concentrated and purified by flash chromatography on silica gel (hexane-EtOAc, 40:1-4:1) to afford the title compound, 1.14 g. ESI-MS m/z 649 (MH)⁺.

Step 3. Synthesis of (R,Z)-3-(2-(2-((2-aminoethyl)amino)thiazol-4-yl)-2-(hydroxyimino)acetamido)-2-hydroxy-3,4-dihydro-2H-benzo[e][1,2]oxaborinine-8-carboxylic Acid

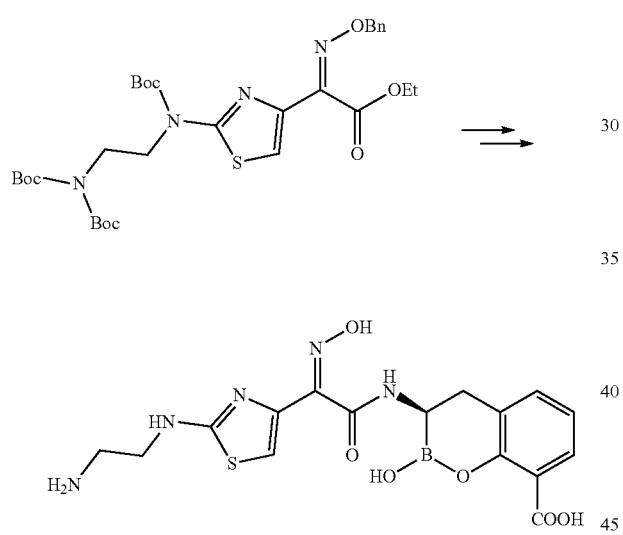

By following the same procedures as described in Step 3, Step 4 and Step 5 of Example 6, the title compound was prepared from the above product. ESI-MS m/z 420 (MH)⁺.

Example 11: (R,Z)-3-(2-(2-guanidinothiazol-4-yl)-2-(hydroxyimino)acetamido)-2-hydroxy-3,4-dihydro-2H-benzo[e][1,2]oxaborinine-8-carboxylic Acid

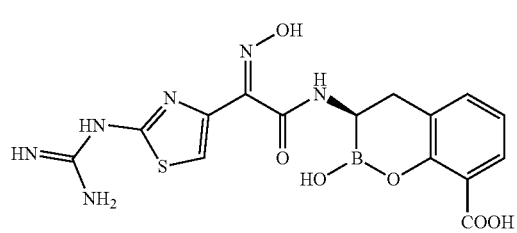

Step 1. Synthesis of ethyl (Z)-2-((benzyloxy)imino)-2-(2-((E)-2,3-bis(tert-butoxycarbonyl)guanidino)thiazol-4-yl)acetate

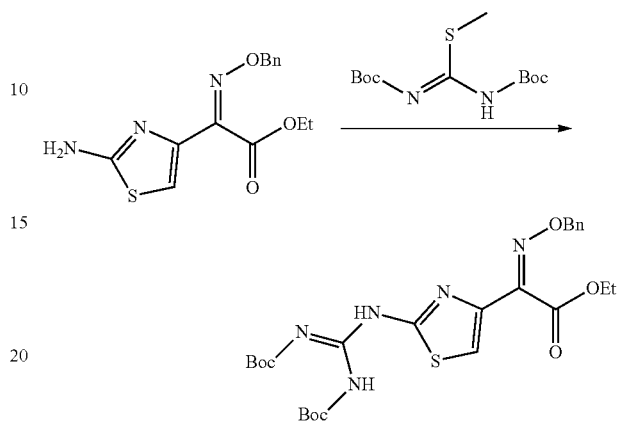

To the product of Step 1 of Example 10 (915 mg, 3 mmol) in DCM (50 mL) was added 1,3-bis(tert-butoxycarbonyl)-2-methyl-2-thiopseudourea (970 mg, 3.33 mmol), TEA (1.25 mL, 9 mmol) and HgCl₂ (905 mg, 3.33 mmol). The reaction mixture was stirred at RT overnight, added more 1,3-bis(tert-butoxycarbonyl)-2-methyl-2-thiopseudourea (194 mg, 0.66 mmol), HgCl₂ (181 mg, 0.66 mmol) and TEA (0.42 mL, 3 mmol), the reaction mixture was stirred at RT for another 24 h, then filtered, washed with aqueous NH₄Cl, water and brine, dried over Na₂SO₄, concentrated, purified by flash chromatography on silica gel (hexane-EtOAc, 40:1-4:1) to afford the product, 890 mg. ESI-MS m/z 548 (MH)⁺.

Step 2. Synthesis of (R,Z)-3-(2-(2-guanidinothiazol-4-yl)-2-(hydroxyimino)acetamido)-2-hydroxy-3,4-dihydro-2H-benzo[e][1,2]oxaborinine-8-carboxylic Acid

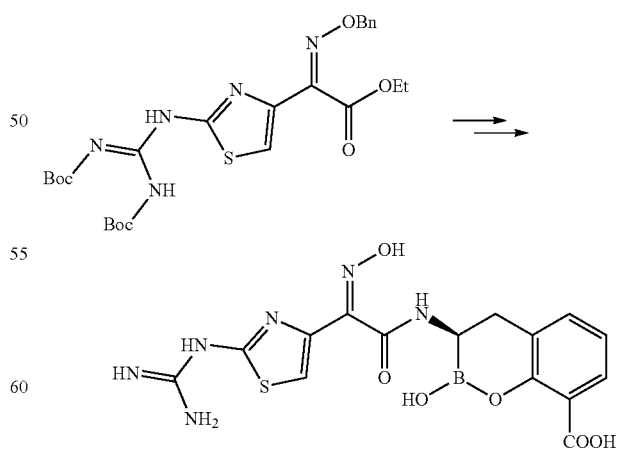

By following the same procedures as described in Step 3, Step 4 and Step 5 of Example 6, the title compound was prepared from the above product. ESI-MS m/z 419 (MH)⁺.

Example 12: (R,Z)-3-(2-(4-(aminomethyl)phenyl)-2-(hydroxyimino)acetamido)-2-hydroxy-3,4-dihydro-2H-benzo[e][1,2]oxaborinine-8-carboxylic Acid

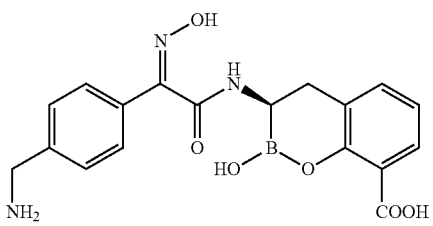

Step 1. Synthesis of ethyl 2-(4-(((tert-butoxycarbonyl)amino)methyl)phenyl)-2-oxoacetate

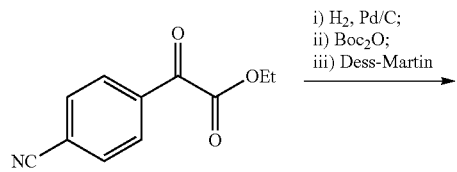

Ethyl 4-cyanobenzoylformate (3.05 g, 15 mmol) in ethanol (100 mL) was hydrogenated in the presence of 10% Pd/C (600 mg) and concentrated HCl (2.5 mL) at 60 psi for 2 days, filtered, and the filtrate was concentrated in vacuo. To this crude product was added DCM (120 mL), TEA (4.6 mL, 32 mmol), followed by Boc$_2$O (3.49 g, 16 mmol). The reaction mixture was stirred at RT overnight, washed with saturated aqueous NaHCO$_3$, dried over Na$_2$SO$_4$, concentrated. The crude product was purified by flash chromatography on silica gel (hexane-EtOAc, 5:1-1:1) to afford the title ketoester as a minor product, 380 mg, and the ketone reduced product as the major product (3.76 g). The major product was oxidized to the title compound (3.1 g) with Dess-Martin periodinane reagent by using the same reaction condition as described in Step 3 of Example 3 and 4. ESI-MS m/z 308 (MH)$^+$.

Step 2. Synthesis of (R,Z)-3-(2-(4-(aminomethyl)phenyl)-2-(hydroxyimino)acetamido)-2-hydroxy-3,4-dihydro-2H-benzo[e][1,2]oxaborinine-8-carboxylic Acid

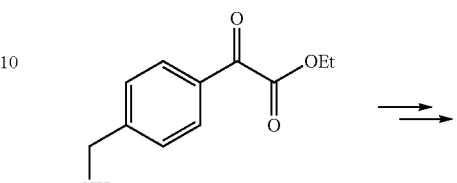

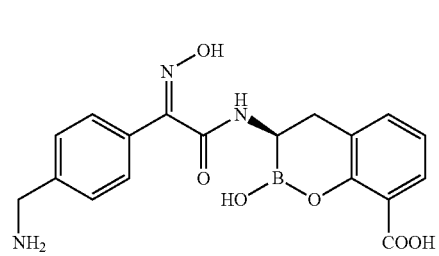 [SMILES: NCc1ccc(/C(=N/O)C(=O)N[C@H]2Cc3cccc(C(=O)O)c3OB2O)cc1]

The title compound was prepared from the above product in a similar manner to the synthesis of Example 6. ESI-MS m/z 384 (MH)+.

Example 13: (R,Z)-3-(2-(2-aminothiazol-4-yl)-2-((2-hydroxyethoxy)imino)acetamido)-2-hydroxy-3,4-dihydro-2H-benzo[e][1,2]oxaborinine-8-carboxylic Acid

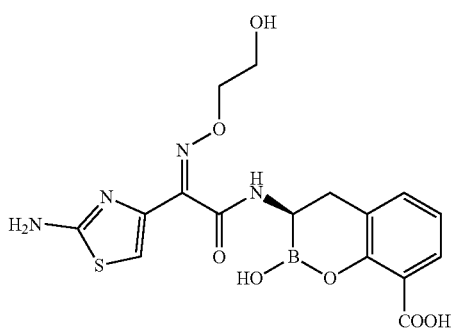 [SMILES: Nc1nc(/C(=N/OCCO)C(=O)N[C@H]2Cc3cccc(C(=O)O)c3OB2O)cs1]

Step 1. Synthesis of ethyl 2-(2-((tert-butoxycarbonyl)amino)thiazol-4-yl)-2-((2-hydroxyethoxy)imino)acetate

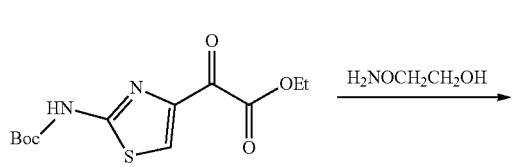

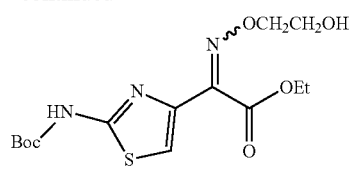

By using the same reaction procedure as described in Step 2 of Example 6, and replaced O-benzylhydroxylaminehydrochloride with 2-aminooxyethanol, the title compound was prepared. ESI-MS m/z 360 (MH)$^+$.

Step 2. Synthesis of ethyl ethyl 2-(2-((tert-butoxycarbonyl)amino)thiazol-4-yl)-2-((2-((tetrahydro-2H-pyran-2-yl)oxy)ethoxy)imino)acetate

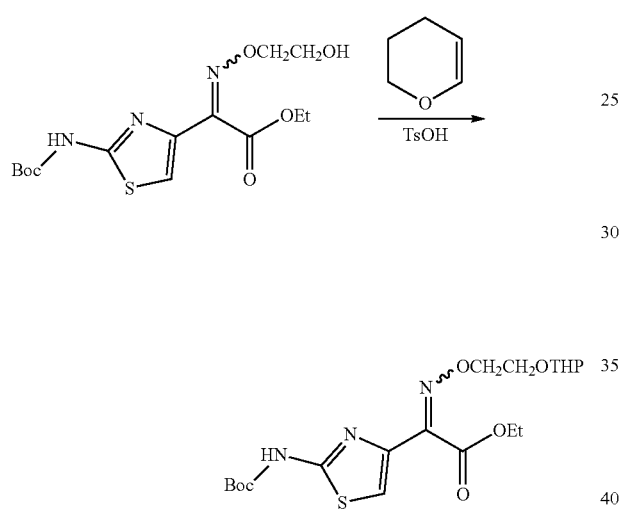

To the above product (3.58 g, 10 mmol) in DCM (150 mL) was added 3,4-dihydro-2H-pyran (1.83 mL, 20 mmol) at 0° C. followed by TsOH.H$_2$O (114 mg, 0.6 mmol). The reaction mixture was stirred at RT for 1 h, added more TsOH.H$_2$O (228 mg, 1.2 mmol), and the reaction was stirred for 6 h, washed with saturated aqueous NaHCO$_3$, dried over Na$_2$SO$_4$, concentrated in vacuo to give the title compound. ESI-MS m/z 444 (MH)$^+$.

Step 3. Synthesis of (R,Z)-3-(2-(2-aminothiazol-4-yl)-2-((2-hydroxyethoxy)imino)acetamido)-2-hydroxy-3,4-dihydro-2H-benzo[e][1,2]oxaborinine-8-carboxylic Acid

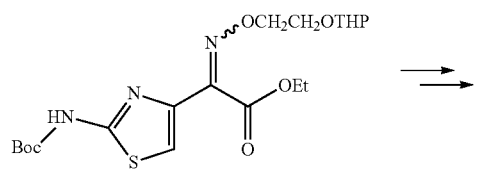

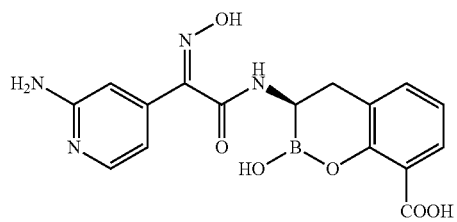 [SMILES: Nc1cc(/C(=N/O)C(=O)N[C@H]2Cc3cccc(C(=O)O)c3OB2O)ccn1]

By following the same reaction procedures as described in Step 3, Step 4 and Step 5 of Example 6, the above product was converted to the title compound. ESI-MS m/z 421 (MH)$^+$.

Example 14: (R,Z)-3-(2-(2-aminopyridin-4-yl)-2-(hydroxyimino)acetamido)-2-hydroxy-3,4-dihydro-2H-benzo[e][1,2]oxaborinine-8-carboxylic Acid

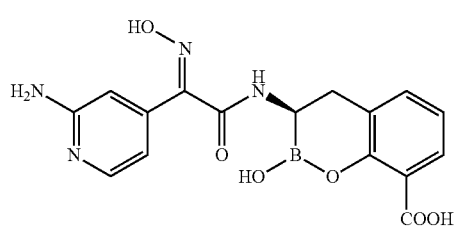 [SMILES: Nc1cc(/C(=N\O)C(=O)N[C@H]2Cc3cccc(C(=O)O)c3OB2O)ccn1]

Example 15: (R,E)-3-(2-(2-aminopyridin-4-yl)-2-(hydroxyimino)acetamido)-2-hydroxy-3,4-dihydro-2H-benzo[e][1,2]oxaborinine-8-carboxylic Acid

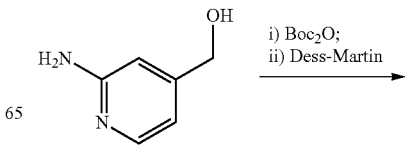

Step 1. Synthesis of tert-butyl (4-formylpyridin-2-yl)carbamate

-continued

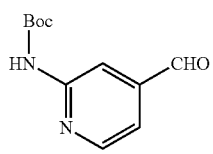

(2-Amino-4-pyridinyl)methanol (3.72 g, 30 mmol) in tBuOH (150 mL) was reacted with Boc₂O (8.72 g, 40 mmol) at RT overnight, then concentrated in vacuo, and purified by flash chromatography on silica gel (hexane-acetone, 4:1-1:1) to afford the Boc-protected product, 6.15 g, which was oxidized to the title compound with Dess-Martin reagent by using the same reaction condition as described in Step 3 of Example 3 and 4. ESI-MS m/z 223 (MH)⁺.

Step 2. Synthesis of methyl 2-(2-((tert-butoxycarbonyl)amino)pyridin-4-yl)-2-oxoacetate

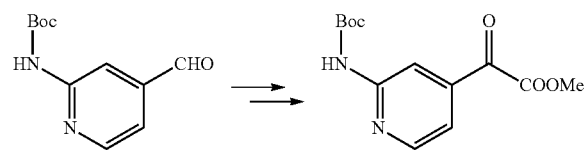 [SMILES: CC(C)(C)OC(=O)Nc1cc(C=O)ccn1 ; COC(=O)C(=O)c1ccnc(NC(=O)OC(C)(C)C)c1]

The above aldehyde was converted to the title compound by following the same procedures as described in Step 2 and Step 3 of Example 5. ESI-MS m/z 281 (MH)⁺.

Step 3. Synthesis of (Z) and (E)-2-((benzyloxy)imino)-2-(2-((tert-butoxycarbonyl)amino)pyridin-4-yl)acetic Acid

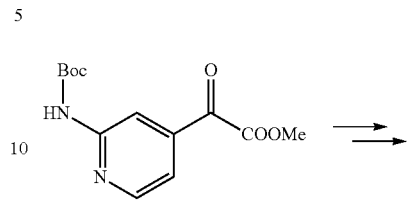

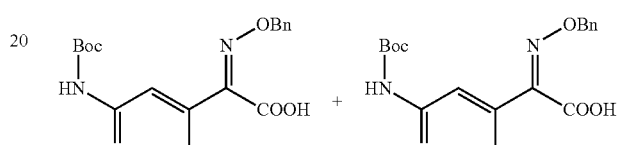

By following the same procedures as described in Step 2 and Step 3 of Example 6, the (Z)-oxime acid and (E)-oxime acid were prepared from above ketoester. ESI-MS m/z 372 (MH)⁺.

Step 4. Synthesis of (R,Z)- and (R,E)-3-(2-(2-aminopyridin-4-yl)-2-(hydroxyimino)acetamido)-2-hydroxy-3,4-dihydro-2H-benzo[e][1,2]oxaborinine-8-carboxylic Acid

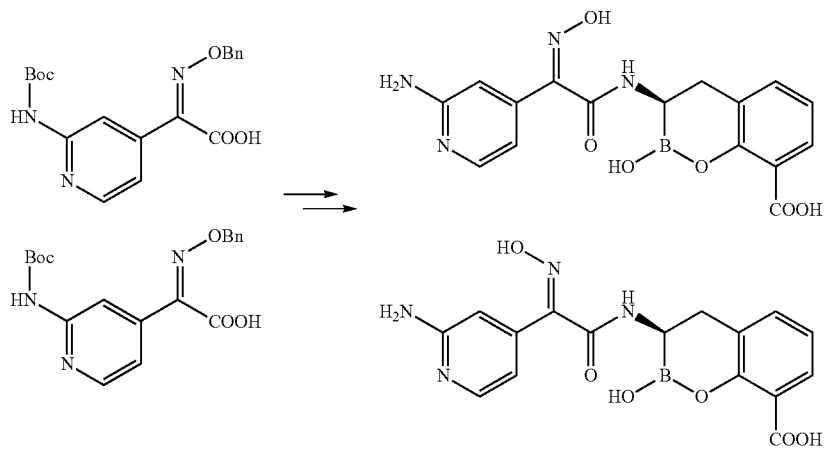 [SMILES: CC(C)(C)OC(=O)Nc1cc(/C(=N/OCc2ccccc2)C(=O)O)ccn1 ; Nc1cc(/C(=N/O)C(=O)N[C@H]2Cc3cccc(C(=O)O)c3OB2O)ccn1 ; CC(C)(C)OC(=O)Nc1cc(/C(=N/OCc2ccccc2)C(=O)O)ccn1 ; Nc1cc(/C(=N\O)C(=O)N[C@H]2Cc3cccc(C(=O)O)c3OB2O)ccn1]

By following the same procedures as described in Step 2 and Step 3 of Example 1, the above acids were converted to the title compounds. ESI-MS m/z 371 (MH)⁺.

Example 16: (R,Z)-3-(2-(6-aminopyridin-2-yl)-2-(hydroxyimino)acetamido)-2-hydroxy-3,4-dihydro-2H-benzo[e][1,2]oxaborinine-8-carboxylic Acid

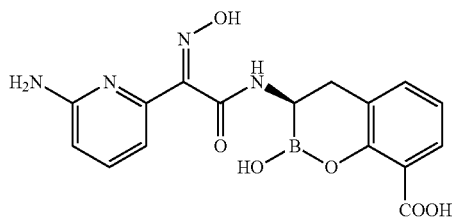

Step 1. Synthesis of tert-butyl (6-formylpyridin-2-yl)carbamate

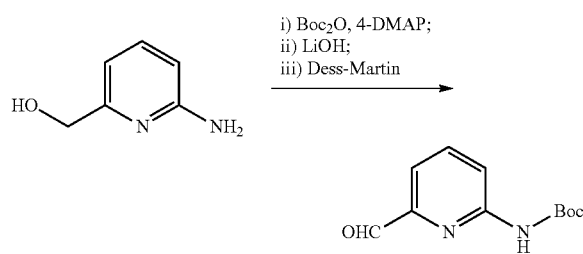

i) Boc₂O, 4-DMAP;
ii) LiOH;
iii) Dess-Martin

To 6-amino-2-pyridinemethanol (3.72 g, 30 mmol) in tBuOH (150 mL) was added Boc₂O (8.72 g, 40 mmol) followed by 4-DMAP (366 mg, 3 mmol). After 1 h, added more Boc₂O (8.72 g, 40 mmol), and the reaction mixture was stirred for an additional 2 h, concentrated in vacuo, and purified by flash chromatography on silica gel (hexane-EtOAc, 40:1-4:1) to afford the bis-Boc-protected product (N and O-Boc), 6.09 g. ESI-MS m/z 325 (MH)⁺.

The above product (5.34 g, 16.5 mmol) was dissolved in MeOH (150 mL), water (50 mL), treated with LiOH.H₂O (3.49 g, 83 mmol) at RT for 1.5 h, evaporated, extracted with DCM. The organic extracts were dried over Na₂SO₄, and concentrated to give the alcohol product, 3.69 g. ESI-MS m/z 225 (MH)⁺.

The above product was oxidized to the title compound with Dess-Martin periodinane reagent by using the same reaction condition as described in Step 3 of Example 3 and 4. ESI-MS m/z 241 (MH+H₂O)⁺.

Step 2. Synthesis of (R,Z)-3-(2-(6-aminopyridin-2-yl)-2-(hydroxyimino)acetamido)-2-hydroxy-3,4-dihydro-2H-benzo[e][1,2]oxaborinine-8-carboxylic Acid

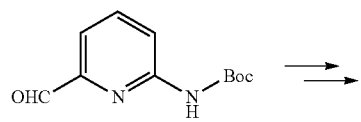

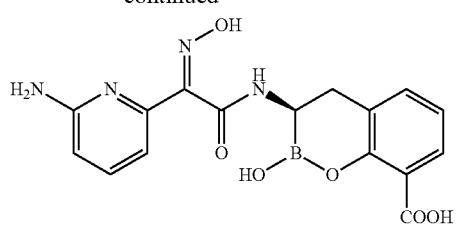

In a similar manner to the synthesis of Example 14, the title compound was prepared from the above aldehyde. ESI-MS m/z 371 (MH)⁺.

Example 17: (R,Z)-3-(2-(2-amino-5-chlorothiazol-4-yl)-2-(hydroxyimino)acetamido)-2-hydroxy-3,4-dihydro-2H-benzo[e][1,2]oxaborinine-8-carboxylic Acid

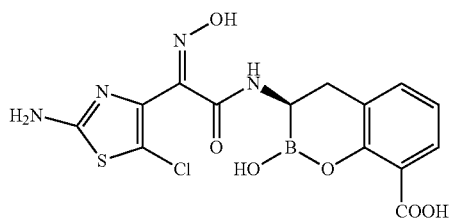 [SMILES: Nc1nc(/C(=N/O)C(=O)N[C@H]2Cc3cccc(C(=O)O)c3OB2O)c(Cl)s1]

Step 1. Synthesis of ethyl 2-(2-((tert-butoxycarbonyl)amino)-5-chlorothiazol-4-yl)-2-oxoacetate

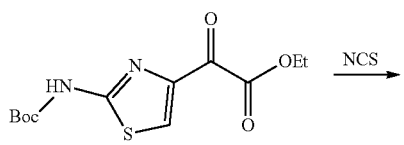

NCS

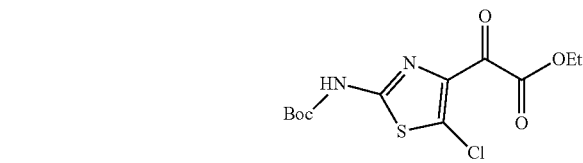

To a solution of ethyl 2-(2-((tert-butoxycarbonyl)amino) thiazol-4-yl)-2-oxoacetate (4.5 g, 15 mmol) in DMF (20 mL) was added NCS (2.16 g, 16.2 mmol), the reaction mixture was stirred at RT overnight, poured into 200 mL of water, extracted with diethyl ether. The ether extracts were washed with water, brine, dried over Na₂SO₄, concentrated and purified by flash chromatography on silica gel (hexane-EtOAc, 10:1-2:1) to afford the product, 4.95 g. ESI-MS m/z 335 (MH)⁺.

Step 2. Synthesis of (R,Z)-3-(2-(2-amino-5-chloro-thiazol-4-yl)-2-(hydroxyimino)acetamido)-2-hydroxy-3,4-dihydro-2H-benzo[e][1,2]oxaborinine-8-carboxylic acid

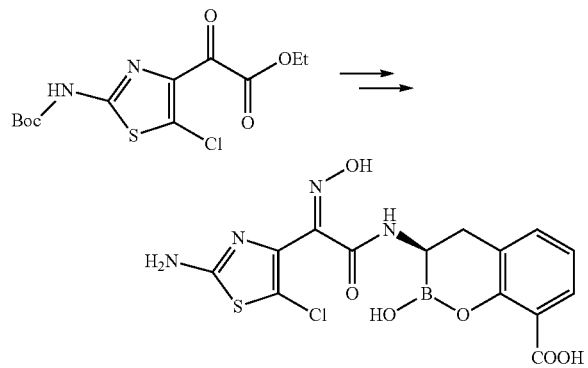

In a similar manner to the synthesis of Example 6, the above product was converted to the title compound. ESI-MS m/z 411 (MH)$^+$.

Example 18: (R,Z)-3-(2-(2-aminothiazol-4-yl)-2-((carboxymethoxy)imino)acetamido)-2-hydroxy-3,4-dihydro-2H-benzo[e][1,2]oxaborinine-8-carboxylic Acid

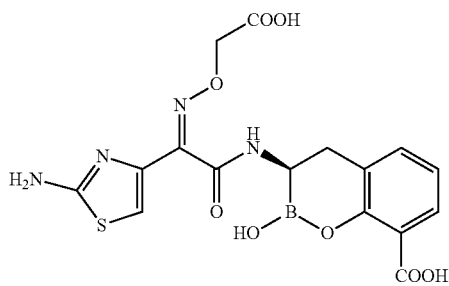 [SMILES: Nc1nc(/C(=N/OCC(=O)O)C(=O)N[C@H]2Cc3cccc(C(=O)O)c3OB2O)cs1]

Step 1. Synthesis of 2-(2-((tert-butoxycarbonyl)amino)thiazol-4-yl)-2-oxoacetic Acid

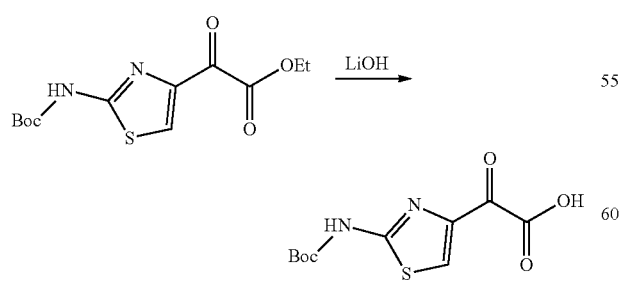

Ethyl 2-(2-((tert-butoxycarbonyl)amino)thiazol-4-yl)-2-oxoacetate (3 g, 10 mmol) was dissolved in THF (50 mL) and water (50 mL), treated with LiOH·H$_2$O (1.68 g, 40 mmol) at RT for 45 min, evaporated, acidified with 1 N HCl to pH ~3, the solid was collected, dried in vacuo, 2.7 g. ESI-MS m/z 273 (MH)$^+$.

Step 2. Synthesis of (Z)-2-((2-(tert-butoxy)-2-oxoethoxy)imino)-2-(2-((tert-butoxycarbonyl)amino)thiazol-4-yl)acetic Acid

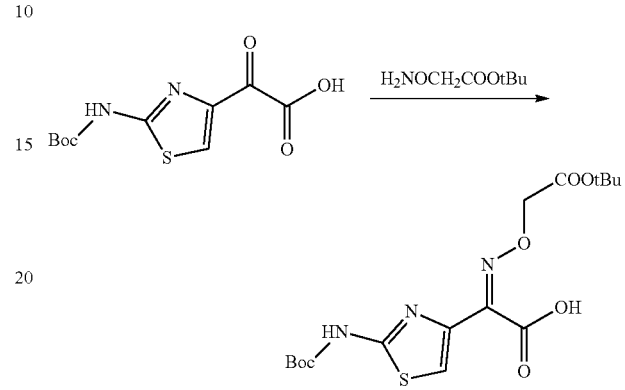

The above acid (2.7 g, 9.93 mmol) was dissolved in EtOH (120 mL), to this solution was added tert-butyl-2-(aminooxy)acetate (2.2 g, 15 mmol) followed by 4 N HCl in dioxane (3.75 mL, 15 mmol). The reaction mixture was stirred at RT for 2 h, concentrated. To the residue was added DCM and brine, the pH was adjusted to ~3-4, the organic layer was separated, concentrated, and hexane was added. The solid was collected by filtration, dried in vacuo to give the title compound as pure Z isomer, 1.4 g (ref. WO2010050468). ESI-MS m/z 402 (MH)$^+$. The filtrate was concentrated to afford more solid product, 1.9 g as a mixture of two isomers.

Step 3. (R,Z)-3-(2-(2-aminothiazol-4-yl)-2-((carboxymethoxy)imino)acetamido)-2-hydroxy-3,4-dihydro-2H-benzo[e][1,2]oxaborinine-8-carboxylic Acid

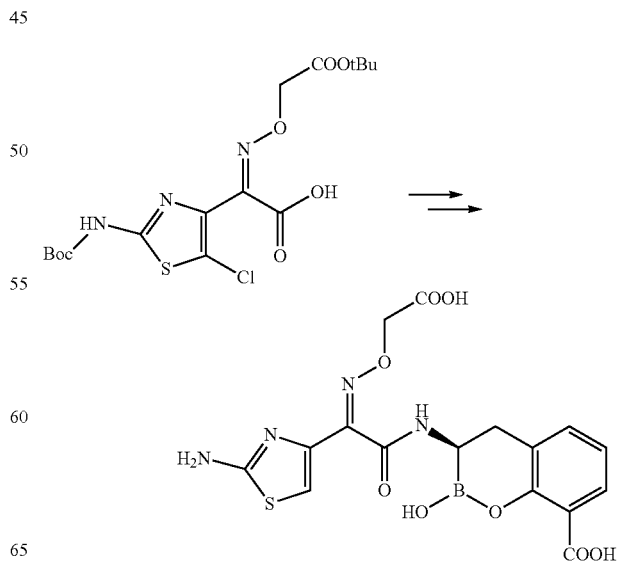

The title compound was prepared from the above acid by following the same procedures as described in Step 4 and Step 5 of Example 6. MS m/z 435 (MH)+.

Example 19: (R,Z)-3-(2-(5-amino-1,2,4-thiadiazol-3-yl)-2-(hydroxyimino)acetamido)-2-hydroxy-3,4-dihydro-2H-benzo[e][1,2]oxaborinine-8-carboxylic Acid

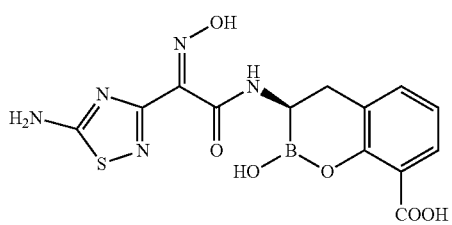 [SMILES: Nc1nc(/C(=N/O)C(=O)N[C@H]2Cc3cccc(C(=O)O)c3OB2O)ns1]

Step 1. Synthesis of methyl (Z)-2-(5-amino-1,2,4-thiadiazol-3-yl)-2-((trityloxy)imino)acetate

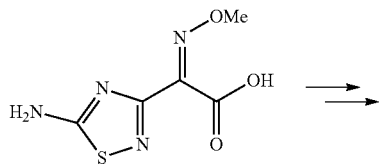

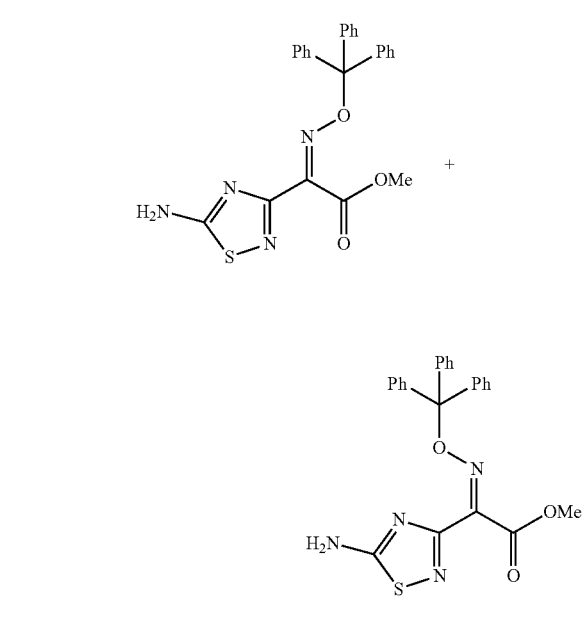

According to the reported procedure (WO2010030810), the product with Z configuration of the oxime was prepared from the commercially available (Z)-2-(5-amino-1,2,4-thiadiazol-3-yl)-2-(methoxyimino)acetic acid. Also pure E isomer was isolated as a minor product. ESI-MS m/z 445 (MH)+.

Step 2. Synthesis of (R,Z)-3-(2-(5-amino-1,2,4-thiadiazol-3-yl)-2-(hydroxyimino)acetamido)-2-hydroxy-3,4-dihydro-2H-benzo[e][1,2]oxaborinine-8-carboxylic Acid

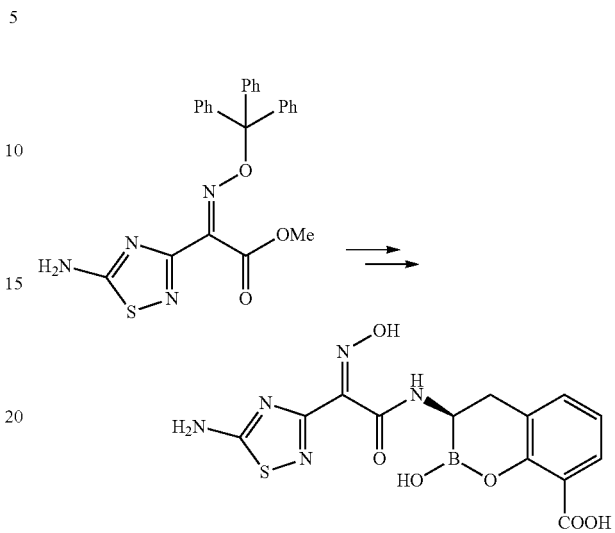

The above product was converted to the target compound by following the same procedures as described in the synthesis of Example 6. ESI-MS m/z 378 (MH)+.

Example 20: (S,Z)-3-(2-(5-amino-1,2,4-thiadiazol-3-yl)-2-(hydroxyimino)acetamido)-2-hydroxy-3,4-dihydro-2H-benzo[e][1,2]oxaborinine-8-carboxylic Acid

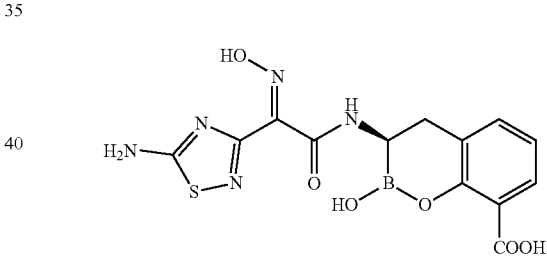

In a similar manner to the synthesis of Example 19, Step 1, the title compound was prepared from the minor product with (E)-oxime isomer described in the synthesis of Example 19. ESI-MS m/z 378 (MH)+.

Example 21: (R,Z)-3-(2-(2-aminothiazol-4-yl)-2-(hydroxyimino)acetamido)-2,7-dihydroxy-3,4-dihydro-2H-benzo[e][1,2]oxaborinine-8-carboxylic Acid

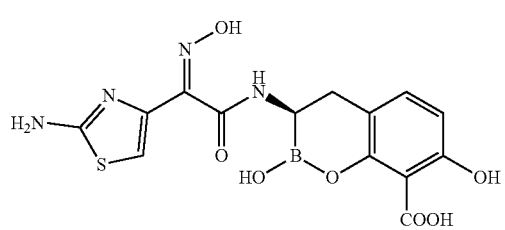 [SMILES: Nc1nc(/C(=N/O)C(=O)N[C@H]2Cc3ccc(O)c(C(=O)O)c3OB2O)cs1]

Step 1. Synthesis of tert-butyl 3-bromo-2,6-dimethoxybenzoate

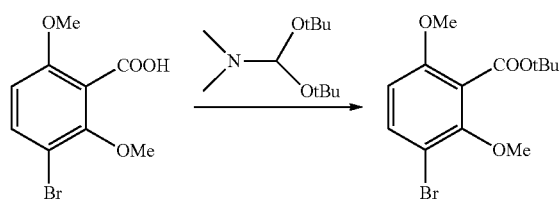

To a reflux solution of 3-bromo-2,6-dimethoxy-benzoic acid (13.00 g, 49.9 mmol) in THF (83 mL) was added N,N-dimethylformamide di-tert-butyl acetal (total 35.8 mL, 149 mmol) in three periods. In each period ⅓ of the total amount was added over 15 min followed by 15 min stirring after each addition. After the third addition was completed, the mixture remained refluxed for 2.5 h, cooled to RT, dissolved in DCM, and washed with H₂O. Aqueous layer was extracted with DCM. The Organic layers were combined, washed with H₂O and brine, dried over Na₂SO₄, concentrated, and purified by flash chromatography on silica gel (hexane-DCM, 9:1-1:1) to give the title compound as a colorless oil, 13.78 g. ESI-MS m/z 340 (MH+Na)⁺.

Step 2. Synthesis of (3-(tert-butoxycarbonyl)-2,4-dimethoxyphenyl)boronic Acid

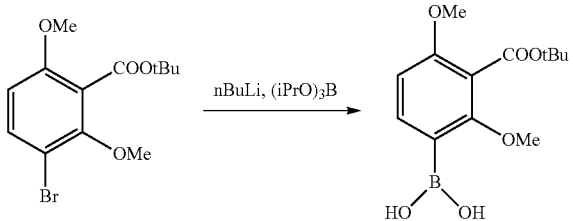

To a solution of the above product (5.08 g, 16 mmol) in THF (32 mL) at −78° C. was added triisopropyl borate (11 mL, 48 mmol) in one portion, followed by dropwise addition of n-BuLi (2.5 M in hexane, 8.33 mL, 20.8 mmol) over 30 min. The resulting pale yellow solution was stirred for 2.5 h, allowed to warm up to RT, and continued to stir for 16 h. The reaction was quenched with saturated aqueous NH₄Cl, extracted with EtOAc. The organic extracts were combined, dried over Na₂SO₄, concentrated, and triturated with hexane (3 times) to give the title compound as a white solid, 2.76 g. The hexane filtrates were combined, concentrated, and triturated with hexane to obtain more of the title compound, 0.43 g. ESI-MS m/z 305 (M+Na)⁺.

Step 3. Synthesis of tert-butyl 2,6-dimethoxy-3-((3aS,4S,6R)-3a,5,5-trimethylhexahydro-4,6-methanobenzo[d][1,3,2]dioxaborol-2-yl)benzoate

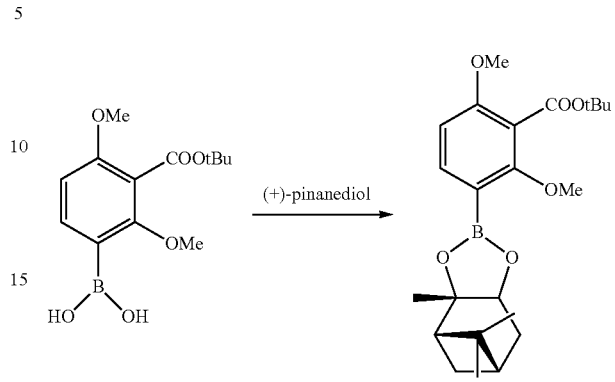

To a flask charged with the above product (3.6 g, 12.8 mmol) and of (1S,2S, 3R, 5S)-(+)-2,3-pinanediol (2.17 g, 12.8 mmol) was added THF (20 mL). The resulting mixture was stirred at RT for 2 days, then concentrated to dryness, dissolved in toluene (10 mL), concentrated, and dried in vacuo overnight to give the title compound as a yellow oil, 5.32 g. ESI-MS m/z 439 (M+Na)⁺.

Step 4. Synthesis of tert-butyl 2,6-dimethoxy-3-(((3aS,4S,6R)-3a,5,5-trimethylhexahydro-4,6-methanobenzo[d][1,3,2]dioxaborol-2-yl)methyl)benzoate

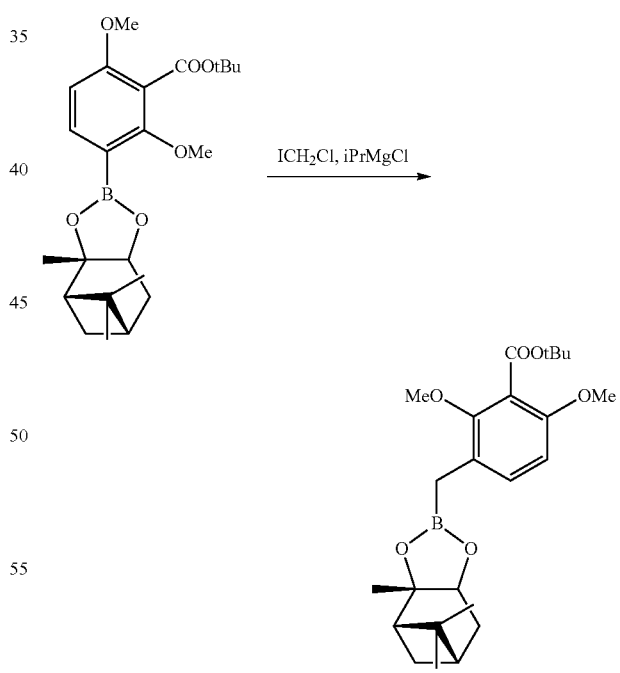

To a solution of chloroiodomethane (5.6 mL, 76.8 mmol) in THF (36 mL) at −78° C.) was added dropwise isopropyl magnesium chloride lithium chloride complex solution (1.3 M in THF, 29.5 mL, 38.4 mmol) over 30 min. The resulting solution was stirred at −78° C. for 45 min, then a solution of the above product (5.32 g, 12.8 mmol) in THF (9 mL) was added slowly over 30 min. After the addition was completed, the mixture was stirred for 2.5 h. To this solution was added ZnCl₂ solution (1.0 M in ether, 24.8 mL, 24.8 mmol) dropwise over 30 min, and stirring continued for 15 min after the addition was completed. The cold bath was removed, the mixture was stirred at RT for 16 h, diluted with diethyl ether, washed with water and brine, dried over Na₂SO₄, and concentrated to give an off-white solid. The solid was triturated with hexane followed by flash chromatography on a silica gel (DCM-hexane, 4:1-100:0, then EtOAc-hexane, 1:15) to give the title compound as a white solid, 3.91 g. ESI-MS m/z 453 (M+Na)⁺.

Step 5. Synthesis of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2,6-dimethoxybenzoate

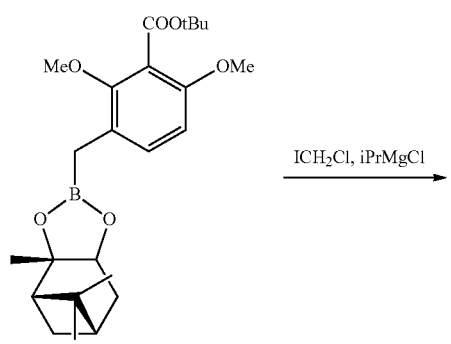

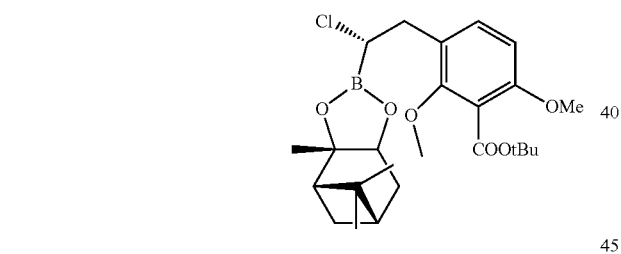

To a cooled (−100° C. MeOH/N₂) solution of DCM (0.373 mL, 5.82 mmol) in THF (5 mL) was added dropwise, down the side of the flask nBuLi (2.5 M in hexane, 1.48 mL, 3.70 mmol) over 25 min. The resulting mixture was stirred for 40 min, then a solution of the above product (861 mg, 2 mmol) in THF (3 mL) was added slowly down the side of the flask over 30 min period, and stirring continued for 2 h after the addition was completed. To the resulting mixture was added dropwise a solution of ZnCl₂ (1.0 M in ether, 3.52 mL, 3.52 mmol) over 20 min. The methanol/N₂ bath was replaced with a dry ice/acetone bath (−10° C.), and stirring continued for 80 min. The reaction mixture was diluted with diethyl ether and washed with aqueous NH₄Cl, the aqueous was separated and extracted with diethyl ether. The organic layers were combined, washed with water and brine, dried over Na₂SO₄, and concentrated. The crude product was purified by flash chromatography on silica gel (DCM-hexane, 2:1-20:1) to afford the product as a colorless oil, 667 mg. ESI-MS m/z 501 (M+Na)+.

Step 6. Synthesis of (R,Z)-3-(2-(2-aminothiazol-4-yl)-2-(hydroxyimino)acetamido)-2,7-dihydroxy-3,4-dihydro-2H-benzo[e][1,2]oxaborinine-8-carboxylic Acid

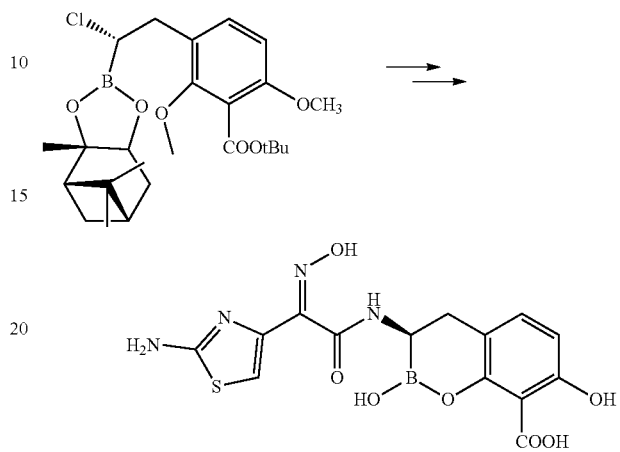

By following General Method C and General Method A, the above chloride intermediate was converted to the title compound. ESI-MS m/z 393 (MH)⁺.

Example 22: (R,Z)-2-hydroxy-3-(2-(hydroxyimino)-N-methyl-2-(2-(methylamino)thiazol-4-yl)acetamido)-3,4-dihydro-2H-benzo[e][1,2]oxaborinine-8-carboxylic Acid

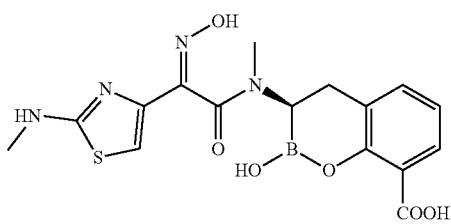 [SMILES: CNc1nc(/C(=N/O)C(=O)N(C)[C@H]2Cc3cccc(C(=O)O)c3OB2O)cs1]

Example 23: (R,Z)-3-(2-((benzyloxy)imino)-N-methyl-2-(2-(methylamino)thiazol-4-yl)acetamido)-2-hydroxy-3,4-dihydro-2H-benzo[e][1,2]oxaborinine-8-carboxylic Acid

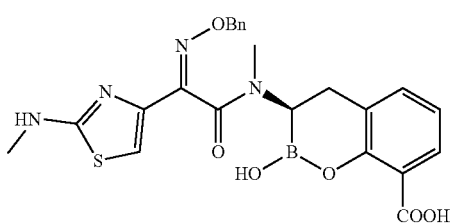 [SMILES: CNc1nc(/C(=N/OCc2ccccc2)C(=O)N(C)[C@H]2Cc3cccc(C(=O)O)c3OB2O)cs1]

Step 1. Synthesis of tert-butyl 3-((2R)-2-((Z)-2-((benzyloxy)imino)-2-(2-((tert-butoxycarbonyl)(methyl)amino)thiazol-4-yl)-N-methylacetamido)-2-((3aS,4S,6R)-3a,5,5-trimethylhexahydro-4,6-methanobenzo[d][1,3,2]dioxaborol-2-yl)ethyl)-2-methoxybenzoate

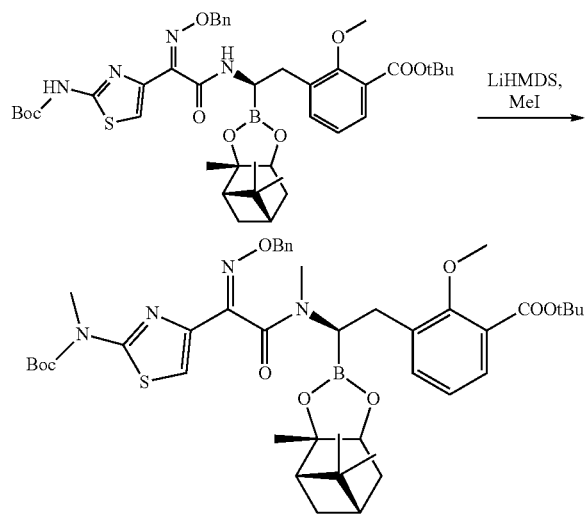

To a solution of the product from Step 4 of Example 6 (197 mg, 0.25 mmol) in anhydrous THF (6 mL) at −30° C. under argon was added dropwise LiHMDS (1.0 M in THF, 0.625 mL, 0.625 mmol). The reaction mixture was stirred between −30-0° C. for 1 h, then MeI (0.12 mL, 1.92 mmol) was added to the reaction mixture, and the reaction was stirred at RT overnight, then diluted with EtOAc, washed with water, brine, dried over Na$_2$SO$_4$, and concentrated. The crude product was purified by flash chromatography on silica gel (hexane-DCM-EtOAc, 15:15:1-4:1:1) to afford the product, 80 mg. ESI-MS m/z 817 (MH)$^+$.

Step 2. Synthesis of (R,Z)-2-hydroxy-3-(2-(hydroxyimino)-N-methyl-2-(2-(methylamino)thiazol-4-yl)acetamido)-3,4-dihydro-2H-benzo[e][1,2]oxaborinine-8-carboxylic acid and (R,Z)-3-(2-((benzyloxy)imino)-N-methyl-2-(2-(methylamino)thiazol-4-yl)acetamido)-2-hydroxy-3,4-dihydro-2H-benzo[e][1,2]oxaborinine-8-carboxylic Acid

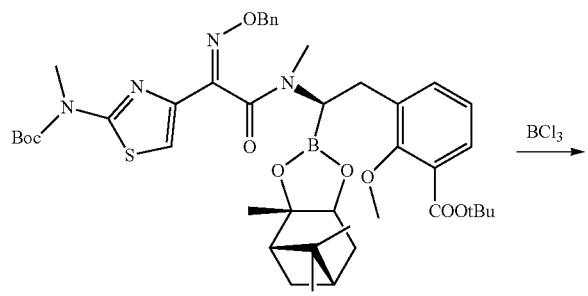

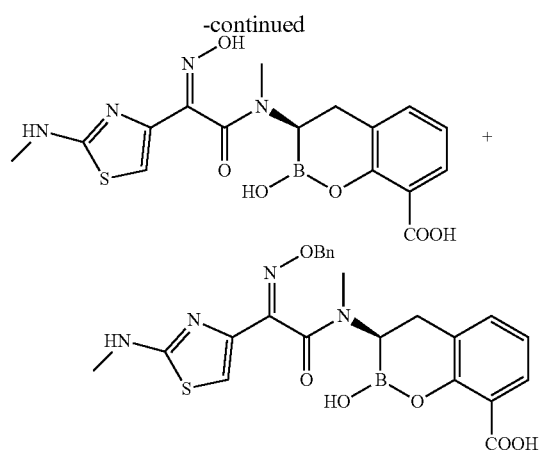

By following General Method A, the above product was treated with BCl$_3$ (6 equiv) to afford the two title compounds after HPLC purification. ESI-MS m/z 406 (MH)$^+$, and ESI-MS m/z 496 (MH)$^+$.

Example 24: (R,Z)-3-(2-(2-aminothiazol-4-yl)-2-(hydroxyimino)acetamido)-7-formyl-2-hydroxy-3,4-dihydro-2H-benzo[e][1,2]oxaborinine-8-carboxylic Acid

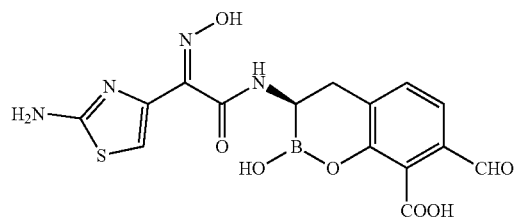 [SMILES: Nc1nc(/C(=N/O)C(=O)N[C@H]2Cc3ccc(C=O)c(C(=O)O)c3OB2O)cs1]

Step 1. Synthesis of tert-butyl 3-((tert-butyldimethylsilyl)oxy)-6-(1,3-dioxan-2-yl)-2-methoxybenzoate

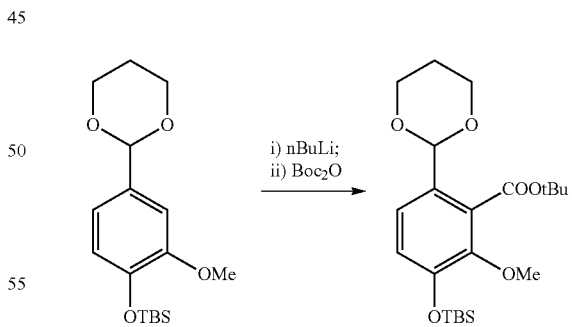

To a solution of (4-(1,3-dioxan-2-yl)-2-methoxyphenoxy)(tert-butyl)dimethylsilane (15 g, 46.3 mmol) (which was prepared according to the reported procedures (Synlett, 2004, 2736-2738) in anhydrous cyclohexane (240 mL) was added nBuLi (2.5 M, 27 mL, 67.5 mmol) dropwise at 0° C. under argon. The reaction mixture was stirred at RT for 3 h, then recooled to 0° C., Boc$_2$O (36.7 g, 168 mmol) was added. The reaction mixture was stirred at RT overnight, quenched with aqueous Na$_2$CO$_3$, extracted with diethyl ether. The ether extracts were washed with brine, dried over Na₂SO₄, and concentrated. The crude product was purified by flash chromatography on silica gel (hexane-EtOAc, 60:1-6:1) to afford the title compound, 13 g. ESI-MS m/z 871 (2M+Na)⁺.

Step 2. Synthesis of tert-butyl 6-(1,3-dioxan-2-yl)-3-hydroxy-2-methoxybenzoate centrated. The crude product was purified by flash chromatography on silica gel (hexane-DCM-diethyl ether, 20:1:1-4:1:1) to afford the title compound, 11.8 g. ESI-MS m/z 465 (M+Na)⁺.

Step 4. Synthesis of tert-butyl 6-(1,3-dioxan-2-yl)-2-methoxy-3-(((trifluoromethyl)sulfonyl)oxy)benzoate

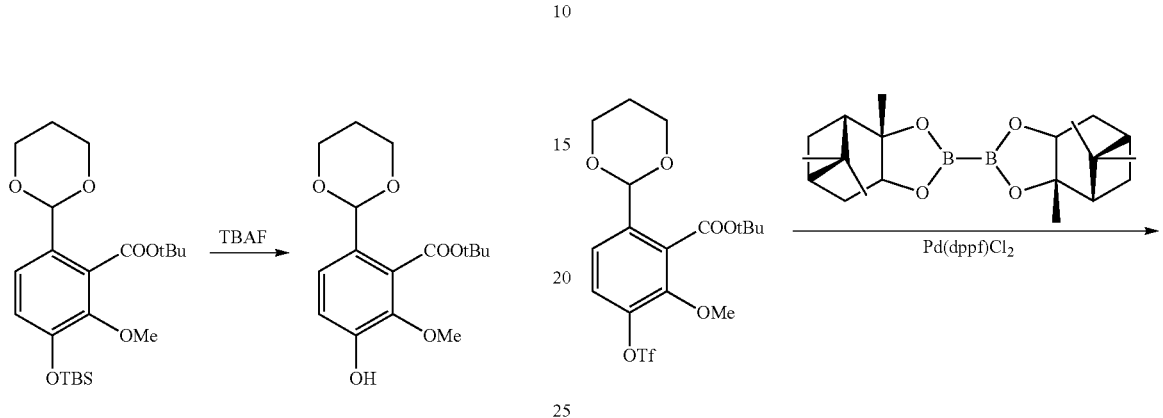

To a solution of the above product (13 g, 30.7 mmol) in THF (200 mL) was added TBAF (1.0 M, 68 mL, 68 mmol), the reaction was stirred at RT for 1 h, diluted with EtOAc, washed with saturated aqueous NaHCO₃, brine, dried over Na₂SO₄, and concentrated. The crude product was purified by flash chromatography on silica gel (hexane-EtOAc, 10:1-1:1) to afford the title compound, 8.35 g. ESI-MS m/z 643 (2M+Na)⁺.

Step 3. Synthesis of tert-butyl 6-(1,3-dioxan-2-yl)-2-methoxy-3-(((trifluoromethyl)sulfonyl)oxy)benzoate

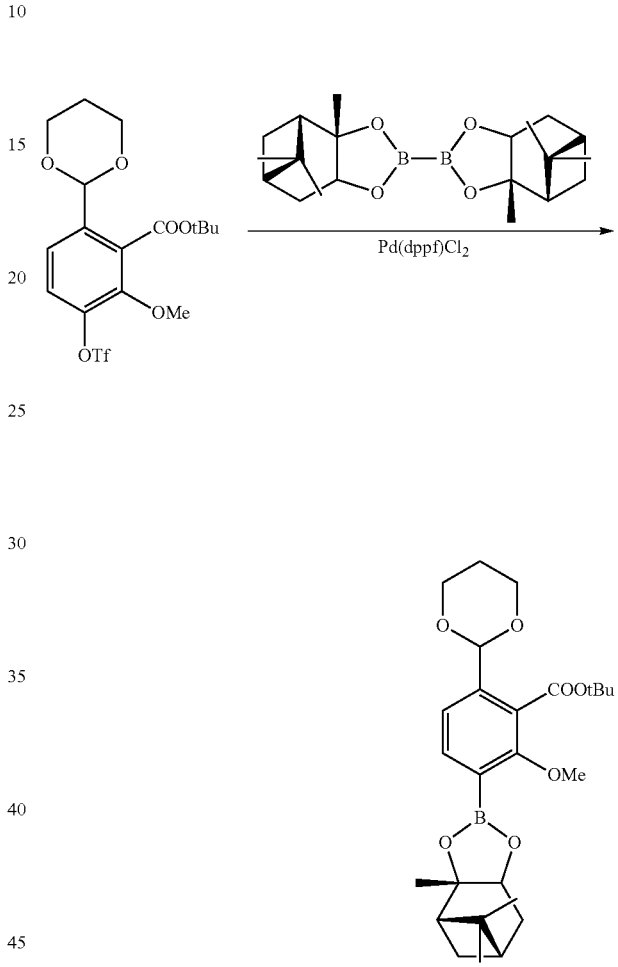

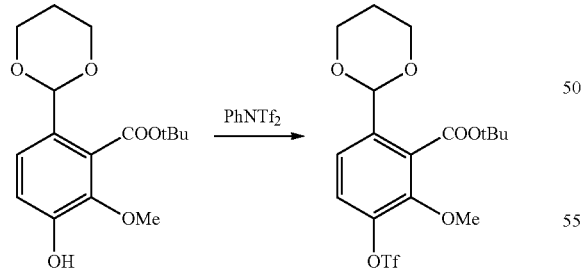

To a solution of the above product (8.34 g, 26.9 mmol) in DCM (250 mL) was added PhNTf₂ (12.5 g, 35 mmol), TEA (9.8 mL, 70 mmol) and 4-DMAP (330 mg, 2.7 mmol). The reaction mixture was stirred at RT overnight, washed with saturated aqueous NaHCO₃, dried over Na₂SO₄, and con- To the above product (11.8 g, 26.7 mmol) in dry DMF (100 mL) was added bis[(+)-pinanediolato]diboron (15 g, 41.9 mmol), KOAc (8.2 g, 83.7 mmol) and Pd(dppf)Cl₂·DCM (1.1 g, 1.35 mmol). The reaction mixture was stirred at 90-100° C. overnight, added water, and extracted with diethyl ether. The ether extracts were washed with water, brine, dried over Na₂SO₄, and concentrated. The crude product was purified by flash chromatography on silica gel (hexane-DCM-diethyl ether, 20:1:1-4:1:1) to afford the title compound, 10.2 g. ESI-MS m/z 967 (2M+Na).

Step 5. Synthesis of tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-(1,3-dioxan-2-yl)-2-methoxybenzoate

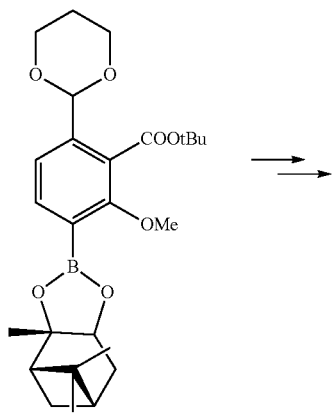

The above product was converted to the title compound via two Matteson reactions by following the same procedures as described in Step 4 and Step 5 of Example 21. ESI-MS m/z 537 (M+Na)⁺.

Step 6. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-6-(1,3-dioxan-2-yl)-2-methoxybenzoate

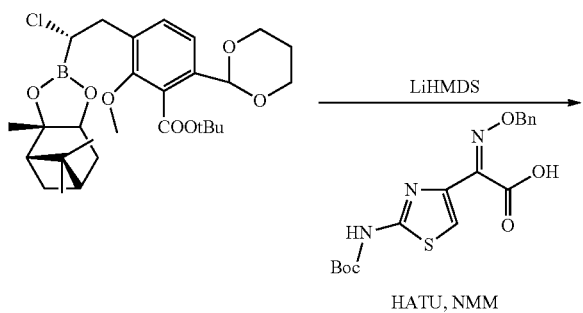

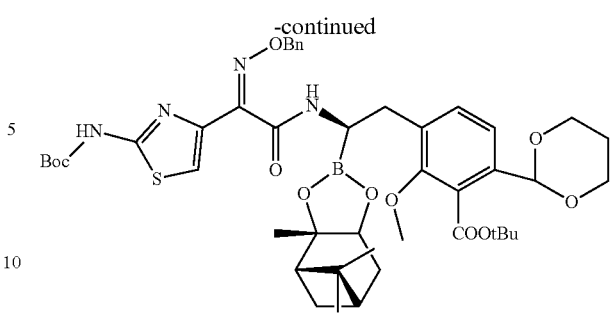

By following General Method C, the above chloride intermediate was treated with LiHMDS, and then coupled with the Z-oxime acid from Step 3 of Example 6 in the presence of HATU and NMM, yielding the title compound. ESI-MS m/z 875 (MH)⁺.

Step 7. Synthesis of (R,Z)-3-(2-(2-aminothiazol-4-yl)-2-(hydroxyimino)acetamido)-7-formyl-2-hydroxy-3,4-dihydro-2H-benzo[e][1,2]oxaborinine-8-carboxylic Acid

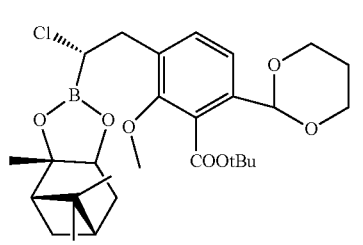

By following General Method A, the above product was treated with BCl₃ to afford the title compound. ESI-MS m/z 405 (MH)⁺.

Example 25: (R,Z)-3-(2-(2-aminothiazol-4-yl)-2-(hydroxyimino)acetamido)-2-hydroxy-7-(pyrrolidin-1-ylmethyl)-3,4-dihydro-2H-benzo[e][1,2]oxaborinine-8-carboxylic Acid

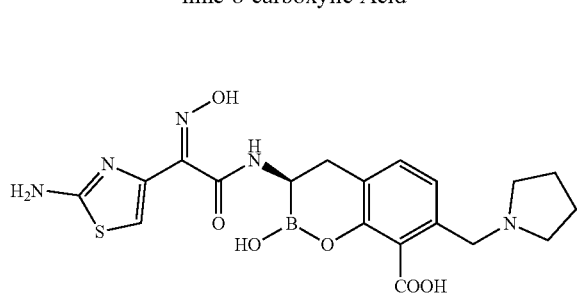

Step 1. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-6-formyl-2-methoxybenzoate

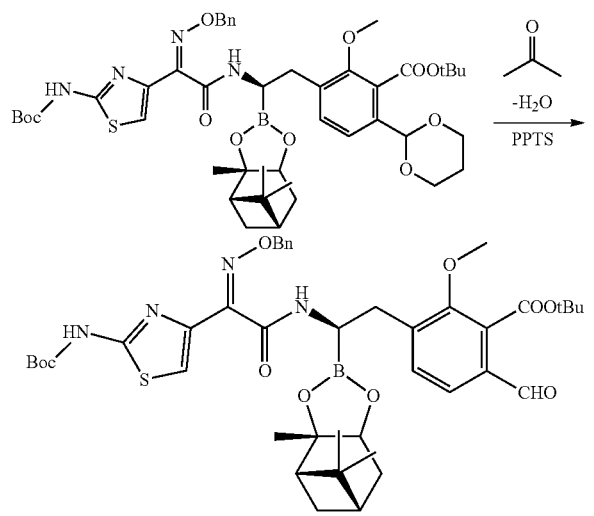

The product from Step 6 of Example 24 (2.1 g, 2.4 mmol) was dissolved in acetone (80 mL) and water (4 mL), heated at reflux in the presence of PPTS (130 mg, 0.52 mmol) for 2 days, then concentrated. The residue was dissolved in DCM, washed with brine, dried over $Na_2SO_4$, and concentrated. The crude product was purified by flash chromatography on silica gel (hexane-EtOAc, 4:1-1:1) to afford the title compound, 1.12 g. ESI-MS m/z 817 (MH)+.

Step 2. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxy-6-(pyrrolidin-1-ylmethyl)benzoate

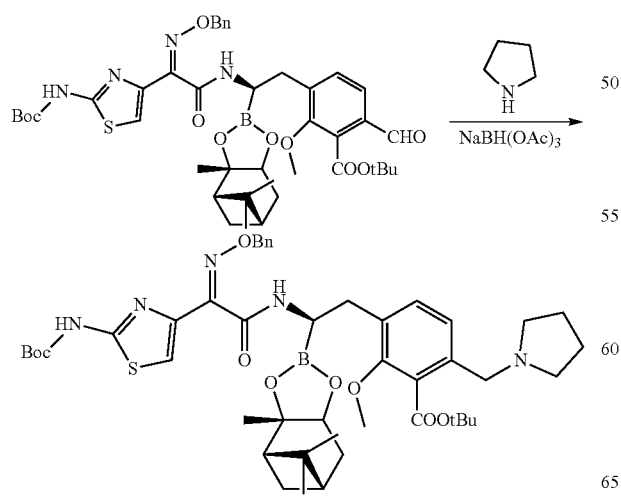

To the above aldehyde (327 mg, 0.4 mmol) in DCE (12 mL) was added pyrrolidine (43 mg, 0.6 mmol) followed by $NaBH(OAc)_3$ (136 mg, 0.64 mmol). The reaction mixture was stirred at RT for 2.5 h, diluted with DCM, washed with saturated aqueous $NaHCO_3$, dried over $Na_2SO_4$, and concentrated to give the crude product, which was used for the next step without further purification. ESI-MS m/z 872 (MH)+.

Step 3. Synthesis of (R,Z)-3-(2-(2-aminothiazol-4-yl)-2-(hydroxyimino)acetamido)-2-hydroxy-7-(pyrrolidin-1-ylmethyl)-3,4-dihydro-2H-benzo[e][1,2]oxaborinine-8-carboxylic Acid

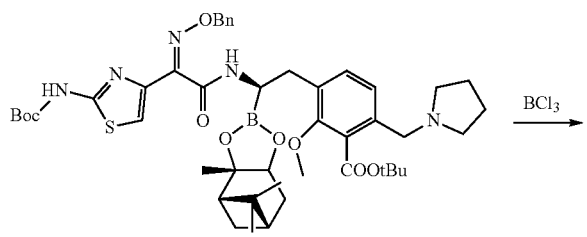

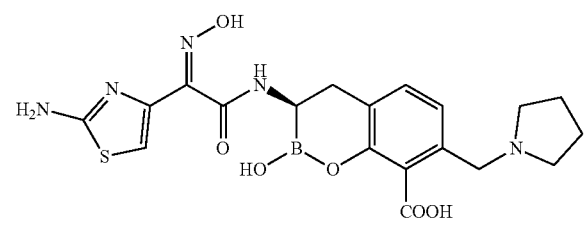 [SMILES: Nc1nc(/C(=N/O)C(=O)N[C@H]2Cc3ccc(CN4CCCC4)c(C(=O)O)c3OB2O)cs1]

By following General Method A, the above product was treated with $BCl_3$ to afford the title compound. ESI-MS m/z 460 (MH)+.

Example 26: (R,Z)-3-(2-(2-aminothiazol-4-yl)-2-(hydroxyimino)acetamido)-2-hydroxy-7-((1-methylpyrrolidin-1-ium-1-yl)methyl)-3,4-dihydro-2H-benzo[e][1,2]oxaborinine-8-carboxylate

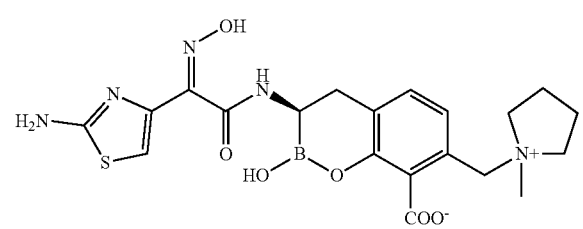

Step 1. Synthesis of 1-(4-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-(tert-butoxycarbonyl)-3-methoxybenzyl)-1-methylpyrrolidin-1-ium iodide

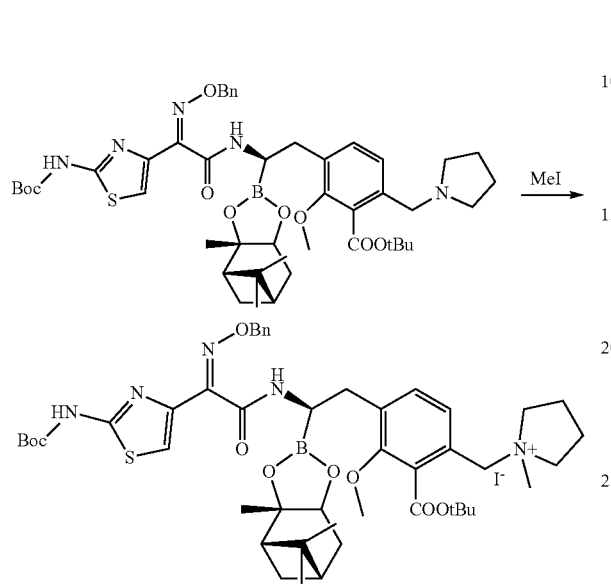

The crude product from Step 2 of Example 25 (174 mg, 0.2 mmol) was reacted with excess MeI (0.15 mL, 2.4 mmol) in acetone (5 mL) at RT overnight, then concentrated to give the crude product, which was used for the next step without further purification.

Step 2. Synthesis of (R,Z)-3-(2-(2-aminothiazol-4-yl)-2-(hydroxyimino)acetamido)-2-hydroxy-7-((1-methylpyrrolidin-1-ium-1-yl)methyl)-3,4-dihydro-2H-benzo[e][1,2]oxaborinine-8-carboxylate

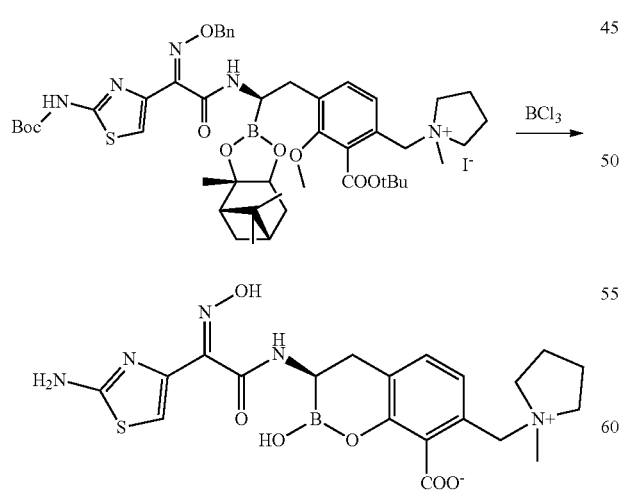

By following General Method A, the above product was treated with BCl₃ to afford the title compound. ESI-MS m/z 474 (MH)⁺.

Example 27: (R)-3-((Z)-2-(2-aminothiazol-4-yl)-2-(hydroxyimino)acetamido)-7-((E)-2-carboxyvinyl)-2-hydroxy-3,4-dihydro-2H-benzo[e][1,2]oxaborinine-8-carboxylic Acid Step 1. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-6-((E)-3-(tert-butoxy)-3-oxoprop-1-en-1-yl)-2-methoxybenzoate

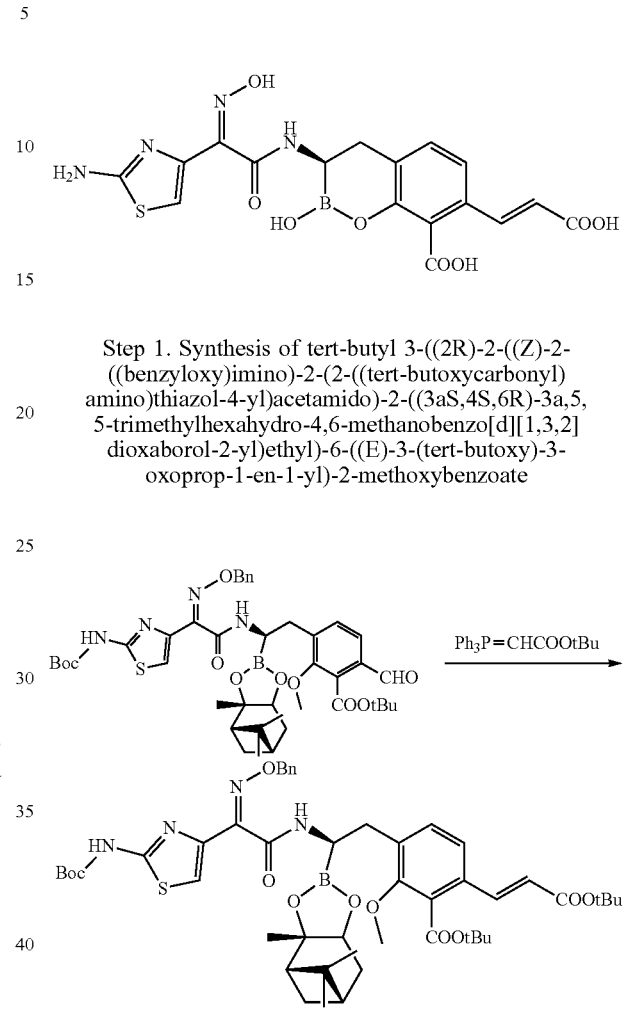

The aldehyde intermediate from Step 1 of Example 25 (327 mg, 0.4 mmol) in DCM (12 mL) was reacted with the Wittig reagent, (tert-Butoxycarbonylmethylene)triphenylphosphorane (189 mg, 0.5 mmol) at RT overnight, evaporated, and purified by flash chromatography on silica gel (hexane-EtOAc, 4:1-1:1) to afford the title compound, 230 mg. ESI-MS m/z 915 (MH)⁺.

Step 2. Synthesis of (R)-3-((Z)-2-(2-aminothiazol-4-yl)-2-(hydroxyimino)acetamido)-7-((E)-2-carboxyvinyl)-2-hydroxy-3,4-dihydro-2H-benzo[e][1,2]oxaborinine-8-carboxylic Acid

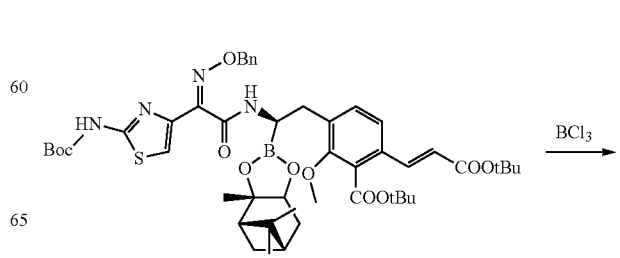

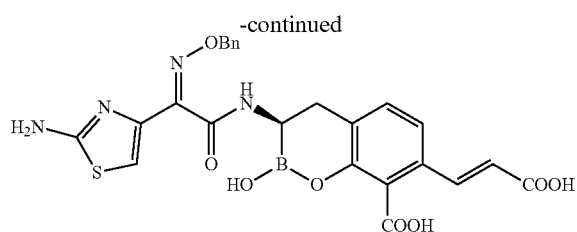

By following General Method A, the above product was treated with $BCl_3$ to afford the title compound. ESI-MS m/z 447 (MH)+.

Example 28: (R,Z)-3-(2-(2-aminothiazol-4-yl)-2-(hydroxyimino)acetamido)-7-(2-carboxyethyl)-2-hydroxy-3,4-dihydro-2H-benzo[e][1,2]oxaborinine-8-carboxylic Acid

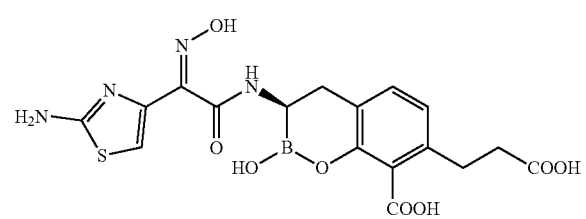 [SMILES: Nc1nc(/C(=N/O)C(=O)N[C@H]2Cc3ccc(CCC(=O)O)c(C(=O)O)c3OB2O)cs1]

Step 1. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-6-(3-(tert-butoxy)-3-oxopropyl)-2-methoxybenzoate

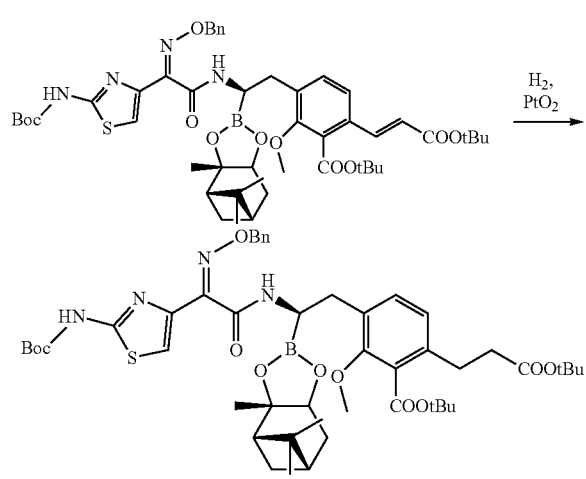

The product from Step 1 of Example 27 (290 mg, 0.32 mmol) in HOAc (4 mL) was hydrogenated in the presence of $PtO_2$ (50 mg) at RT for 24 h, added more $PtO_2$ (30 mg) each 24 h for three times, overall hydrogenated for 4 days. The reaction mixture was filtered through a pad of Celite, the filtrate was concentrated, and purified by flash chromatography on silica gel (hexane-EtOAc, 4:1-1:1) to afford the title compound, 200 mg. ESI-MS m/z 917 (MH)+.

Step 2. Synthesis of (R,Z)-3-(2-(2-aminothiazol-4-yl)-2-(hydroxyimino)acetamido)-7-(2-carboxyethyl)-2-hydroxy-3,4-dihydro-2H-benzo[e][1,2]oxaborinine-8-carboxylic acid

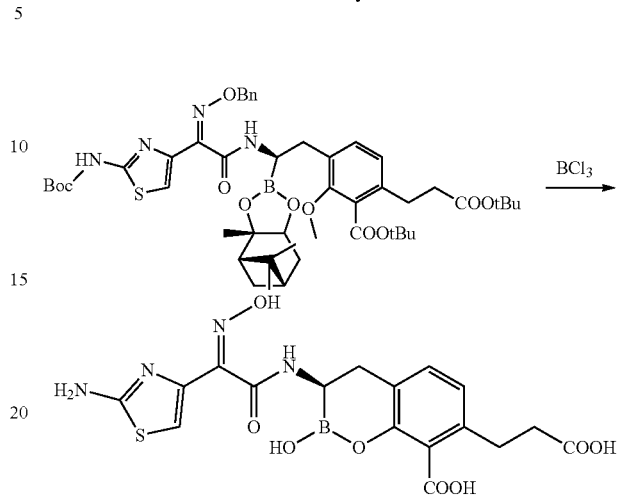

By following General Method A, the above product was treated with $BCl_3$ to afford the title compound. ESI-MS m/z 449 (MH)+.

Example 29: (R,Z)-3-(2-(2-aminothiazol-4-yl)-2-(hydroxyimino)acetamido)-2-hydroxy-7-((4-(hydroxymethyl)piperidin-1-yl)methyl)-3,4-dihydro-2H-benzo[e][1,2]oxaborinine-8-carboxylic Acid

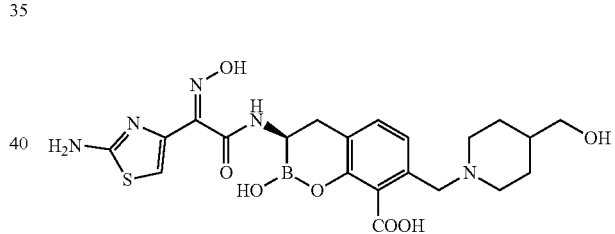

In a similar manner to the synthesis of Example 25, the title compound was prepared. ESI-MS m/z 504 (MH)+.

Example 30: (R,Z)-3-(2-(2-aminothiazol-4-yl)-2-(hydroxyimino)acetamido)-2-hydroxy-7-((4-(hydroxymethyl)-1-methylpiperidin-1-ium-1-yl)methyl)-3,4-dihydro-2H-benzo[e][1,2]oxaborinine-8-carboxylate

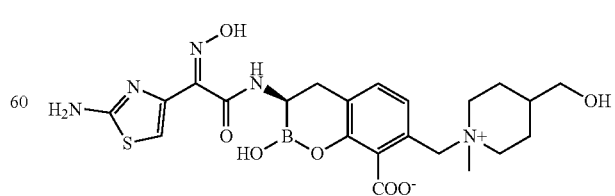

In a similar manner to the synthesis of Example 26, the title compound was prepared. ESI-MS m/z 518 (MH)+.

Example 31: (R,Z)-3-(2-(2-aminothiazol-4-yl)-2-(hydroxyimino)acetamido)-7-(((carboxymethyl)(methyl)amino)methyl)-2-hydroxy-3,4-dihydro-2H-benzo[e][1,2]oxaborinine-8-carboxylic Acid

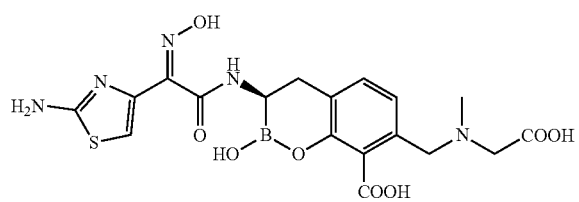 [SMILES: CN(CC(=O)O)Cc1ccc2c(c1C(=O)O)OB(O)[C@@H](NC(=O)/C(=N\O)c1csc(N)n1)C2]

In a similar manner to the synthesis of Example 25, the title compound was prepared. ESI-MS m/z 478 (MH)+.

Example 32: (R,Z)-3-(2-(2-aminothiazol-4-yl)-2-(hydroxyimino)acetamido)-6-fluoro-2-hydroxy-3,4-dihydro-2H-benzo[e][1,2]oxaborinine-8-carboxylic Acid

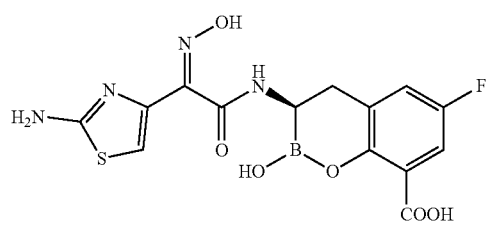

Step 1. Synthesis of tert-butyl 5-fluoro-2-hydroxybenzoate

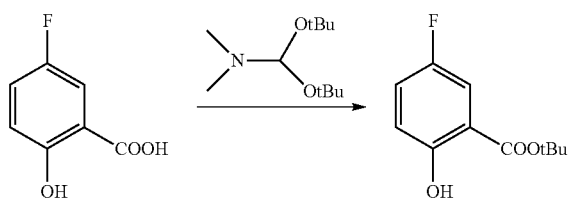

By following the same procedure as described in Step 1 of Example 21, 5-fluorosalicylic acid (5.31 g, 34 mmol) was converted to the tert-butyl ester product, 5.8 g. ESI-MS m/z 213 (MH)+.

Step 2. Synthesis of tert-butyl 5-fluoro-2-hydroxy-3-iodobenzoate

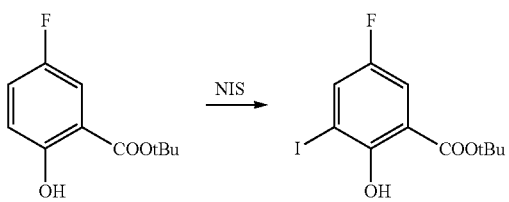

The above product (5.8 g, 27.4 mmol) in DMF (50 mL) was reacted with NIS (7.66 g, 34 mmol) at RT for 2 days, poured into water, and extracted with diethyl ether. The ether extracts were washed with water, brine, dried over Na$_2$SO$_4$, and concentrated. The crude product was purified by flash chromatography on silica gel (hexane-DCM, 20:1-1:2) to afford the title compound, 5.76 g. ESI-MS m/z 339 (MH)+.

Step 3. Synthesis of tert-butyl 5-fluoro-3-iodo-2-methoxybenzoate

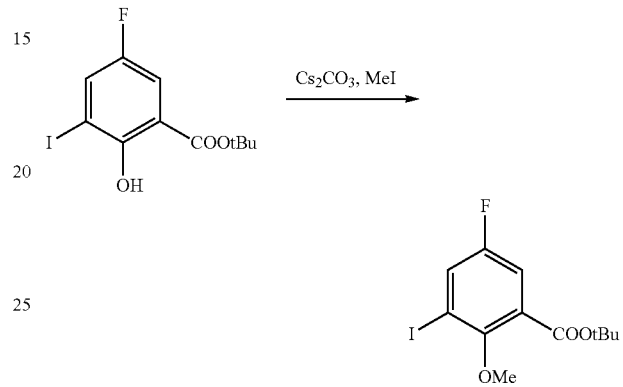

To the above product (5.76 g, 17 mmol) in DMF (50 mL) was added Cs$_2$CO$_3$ (14.8 g, 45.4 mmol), and stirred for 10 min, then added MeI (3.08 mL, 49.5 mmol). The reaction mixture was stirred at RT overnight, poured into water, and extracted with diethyl ether. The ether extracts were washed with water, brine, dried over Na$_2$SO$_4$, and concentrated. The crude product was purified by flash chromatography on silica gel (hexane-DCM, 2:1-1:3) to afford the title compound, 5.03 g. ESI-MS m/z 375 (M+Na)+.

Step 4. Synthesis of tert-butyl 5-fluoro-2-methoxy-3-((3aS,4S,6R)-3a,5,5-trimethylhexahydro-4,6-methanobenzo[d][1,3,2]dioxaborol-2-yl)benzoate

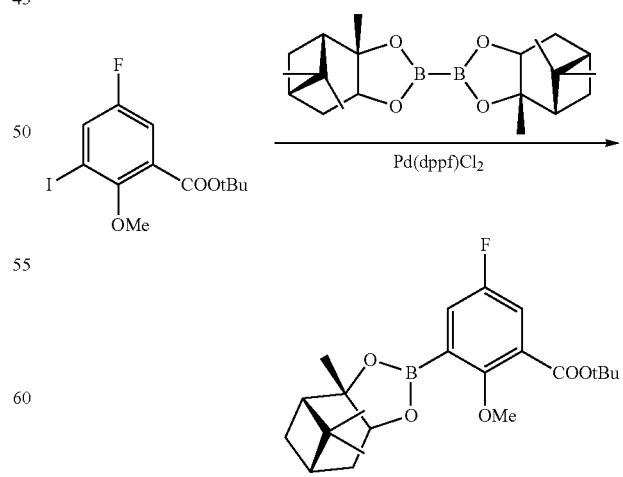

By following the same reaction condition as described in Step 4 of Example 24, the above product was converted to the title compound. ESI-MS m/z 831 (2M+Na)+.

Step 5. Synthesis of (R,Z)-3-(2-(2-aminothiazol-4-yl)-2-(hydroxyimino)acetamido)-6-fluoro-2-hydroxy-3,4-dihydro-2H-benzo[e][1,2]oxaborinine-8-carboxylic Acid

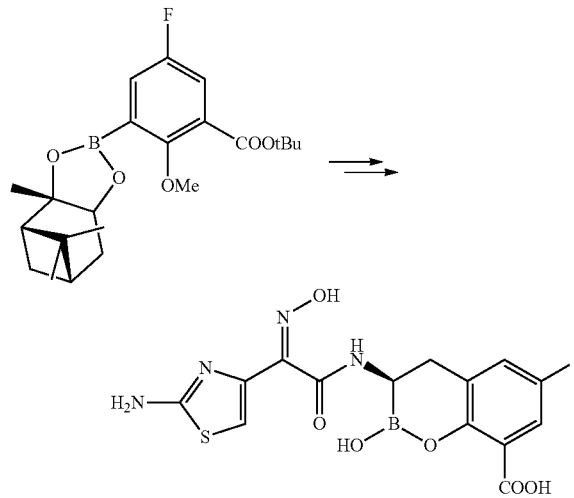

In a similar manner to the synthesis of Example 21, the title compound was prepared from above product. ESI-MS m/z 395 (MH)⁺.

Example 33: (R,Z)-3-(2-(2-aminothiazol-4-yl)-2-(hydroxyimino)acetamido)-2-hydroxy-6-(pyrrolidin-1-ylmethyl)-3,4-dihydro-2H-benzo[e][1,2]oxaborinine-8-carboxylic Acid

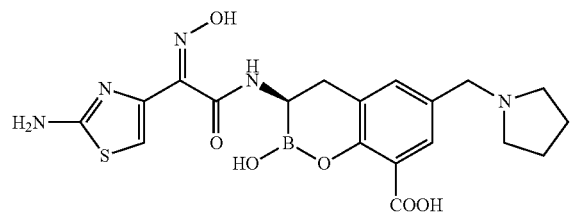 [SMILES: Nc1nc(/C(=N/O)C(=O)N[C@H]2Cc3cc(CN4CCCC4)cc(C(=O)O)c3OB2O)cs1]

Step 1. Synthesis of tert-butyl 5-formyl-3-iodo-2-methoxybenzoate

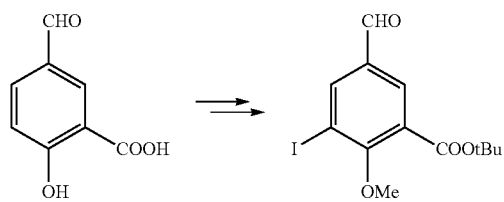

By following the same reaction procedures as described in Step 1 through Step 3 of Example 32, 5-formylsalicylic acid was converted to the title compound. ESI-MS m/z 363 (MH)⁺.

Step 2. Synthesis of tert-butyl 5-(1,3-dioxan-2-yl)-3-iodo-2-methoxybenzoate

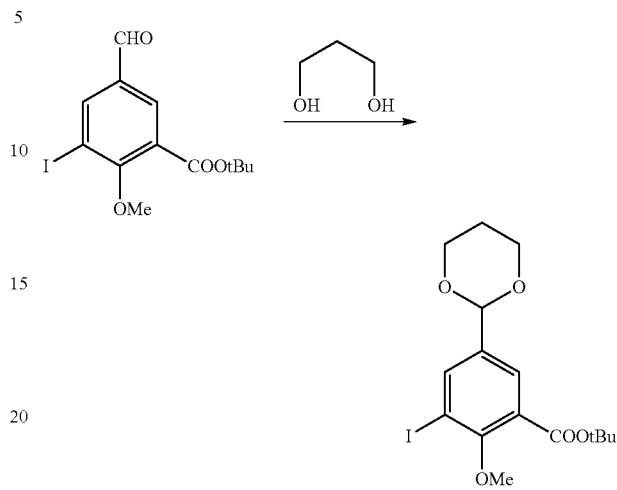

To above aldehyde (6.8 g, 18.8 mmol) in DCM (100 mL) was added 1,3-propanediol (15 mL), HC(OEt)$_3$ (15 mL) and tetrabutylammonium tribromide (386 mg, 0.8 mmol). The reaction mixture was stirred at RT for 3 h, washed with aqueous Na$_2$CO$_3$, water, brine, dried over Na$_2$SO$_4$, and concentrated. The crude product was purified by flash chromatography on silica gel (hexane-EtOAc, 30:1-5:1) to afford the title compound, 7.55 g. ESI-MS m/z 421(MH)⁺.

Step 3. Synthesis of tert-butyl 5-(1,3-dioxan-2-yl)-2-methoxy-3-((3aS,4S,6R)-3a,5,5-trimethylhexahydro-4,6-methanobenzo[d][1,3,2]dioxaborol-2-yl)benzoate

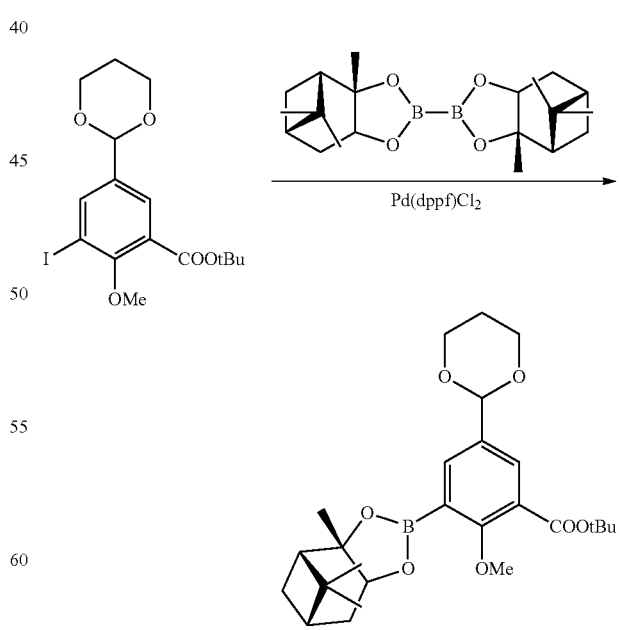

By following the same reaction condition as described in Step 4 of Example 24, the above product was converted to the title compound. ESI-MS m/z 967 (2M+Na)⁺.

Step 4. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-5-formyl-2-methoxybenzoate

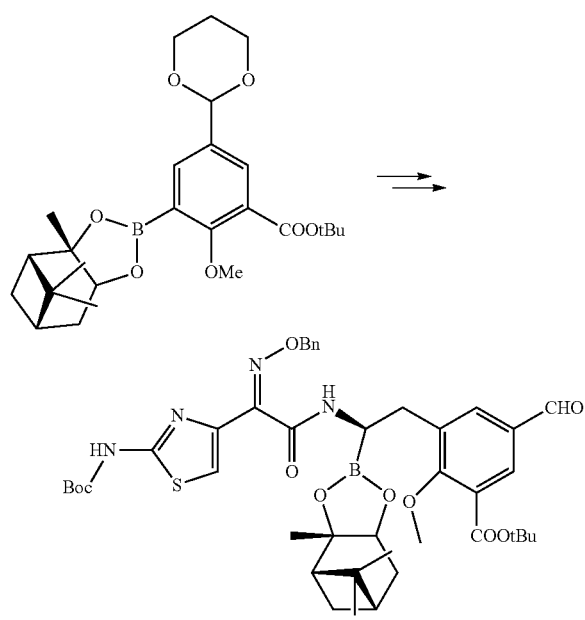

By following the same reaction procedures as described in Step 5 and Step 6 of Example 24, and Step 1 of Example 25, the above product was converted to the title compound. ESI-MS m/z 817 (MH)$^+$.

Step 5. Synthesis of (R,Z)-3-(2-(2-aminothiazol-4-yl)-2-(hydroxyimino)acetamido)-2-hydroxy-6-(pyrrolidin-1-ylmethyl)-3,4-dihydro-2H-benzo[e][1,2]oxaborinine-8-carboxylic Acid

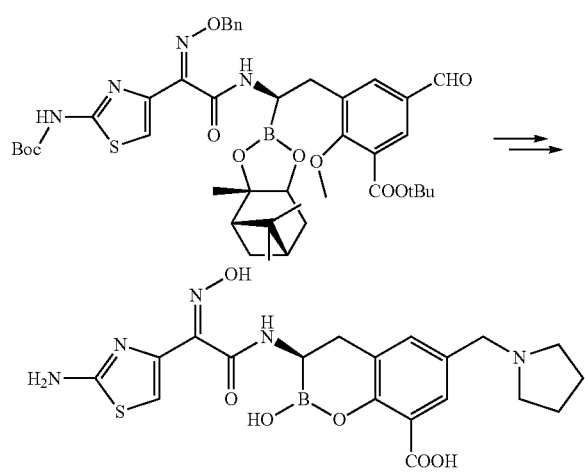

In a similar manner to the synthesis of Example 25, the title compound was prepared from the above aldehyde. ESI-MS m/z 460 (MH)$^+$.

Example 34: (R,Z)-3-(2-(2-aminothiazol-4-yl)-2-(hydroxyimino)acetamido)-2-hydroxy-6-((1-methylpyrrolidin-1-ium-1-yl)methyl)-3,4-dihydro-2H-benzo[e][1,2]oxaborinine-8-carboxylate

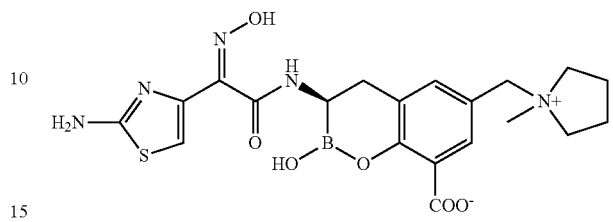

In a similar manner to the synthesis of Example 26, the title compound was prepared. ESI-MS m/z 474 (MH)$^+$.

Example 35: (R,Z)-3-(2-(2-aminothiazol-4-yl)-2-(hydroxyimino)acetamido)-2-hydroxy-6-(hydroxymethyl)-3,4-dihydro-2H-benzo[e][1,2]oxaborinine-8-carboxylic Acid

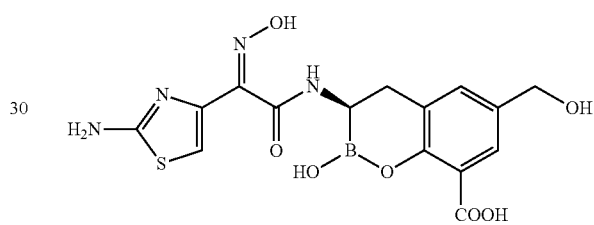

Step 1. Synthesis of tert-butyl 3-((2R)-2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-5-(hydroxymethyl)-2-methoxybenzoate

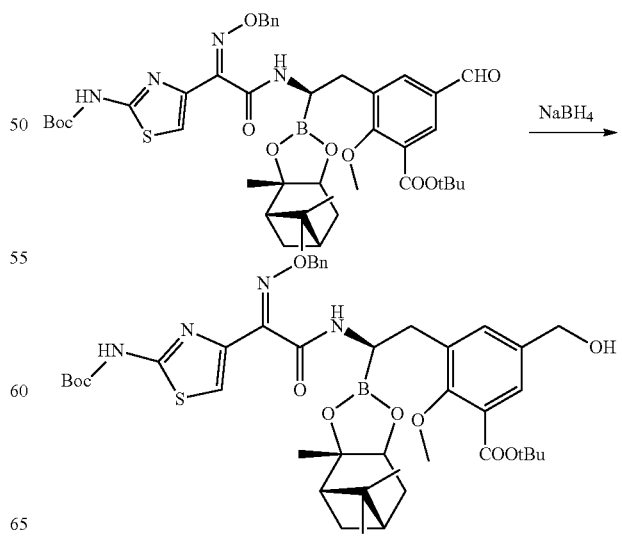

To the aldehyde from Step 4 of Example 33 (120 mg, 0.147 mmol) in THF (5 mL) and MeOH (0.5 mL) was added NaBH₄ (9 mg, 0.237 mmol) at RT, after 15 min, the reaction was quenched with water, extracted with DCM. The organic extracts were dried over Na₂SO₄, and concentrated to afford the alcohol, which was used for the next step without further purification. ESI-MS m/z 819 (MH)⁺.

Step 2. Synthesis of (R,Z)-3-(2-(2-aminothiazol-4-yl)-2-(hydroxyimino)acetamido)-2-hydroxy-6-(hydroxymethyl)-3,4-dihydro-2H-benzo[e][1,2]oxaborinine-8-carboxylic Acid

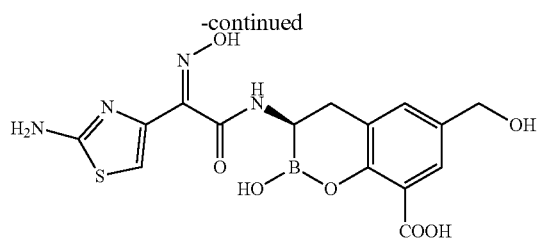

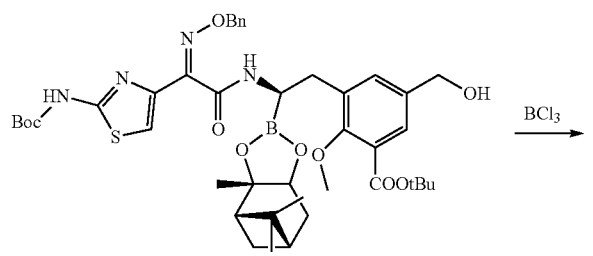

By following General Method A, the above product was treated with BCl₃ to afford the title compound. ESI-MS m/z 407 (MH)⁺.

Example 36: (R,Z)-3-(2-(2-aminothiazol-4-yl)-2-(hydroxyimino)acetamido)-2-hydroxy-6-(3-methoxy-3-oxopropyl)-3,4-dihydro-2H-benzo[e][1,2]oxaborinine-8-carboxylic Acid

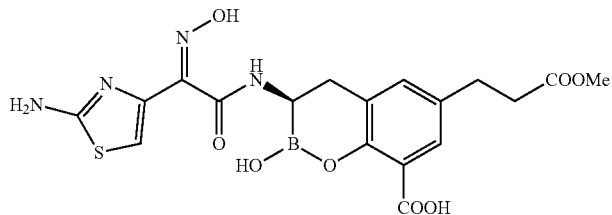

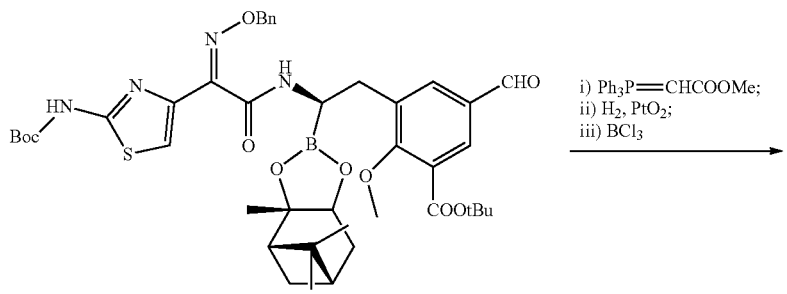

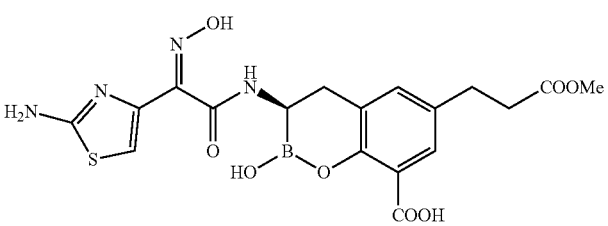

In a similar manner to the synthesis of Example 28, the aldehyde from Step 4 of Example 33 was converted to the title compound. ESI-MS m/z 463 (MH)+.

Example 37: (R,Z)-3-(2-(2-aminothiazol-4-yl)-2-(hydroxyimino)acetamido)-6-(2-carboxyethyl)-2-hydroxy-3,4-dihydro-2H-benzo[e][1,2]oxaborinine-8-carboxylic Acid

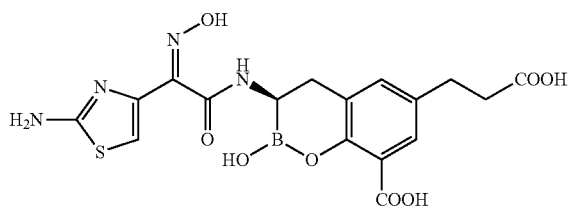 [SMILES: Nc1nc(/C(=N/O)C(=O)N[C@H]2Cc3cc(CCC(=O)O)cc(C(=O)O)c3OB2O)cs1]

In a similar manner to the synthesis of Example 28, the aldehyde from Step 4 of Example 33 was converted to the title compound. ESI-MS m/z 449 (MH)+.

Example 38: (R,Z)-3-(2-(2-aminothiazol-4-yl)-2-(hydroxyimino)acetamido)-2-hydroxy-3,4-dihydro-2H-benzo[e][1,2]oxaborinine-6,8-dicarboxylic Acid

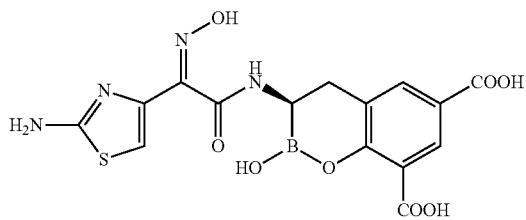 [SMILES: Nc1nc(/C(=N/O)C(=O)N[C@H]2Cc3cc(C(=O)O)cc(C(=O)O)c3OB2O)cs1]

The title compound was prepared in a similar manner to the synthesis of Example 32 by using 4-hydroxyisophthalic acid as the starting material. ESI-MS m/z 421 (MH)+.

Example 39: (R,Z)-3-(2-(2-aminothiazol-4-yl)-2-(hydroxyimino)acetamido)-7-fluoro-2-hydroxy-3,4-dihydro-2H-benzo[e][1,2]oxaborinine-8-carboxylic Acid

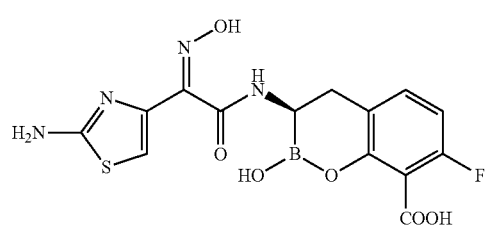 [SMILES: Nc1nc(/C(=N/O)C(=O)N[C@H]2Cc3ccc(F)c(C(=O)O)c3OB2O)cs1]

Step 1. Synthesis of tert-butyl(4-fluoro-2-methoxyphenoxy)dimethylsilane

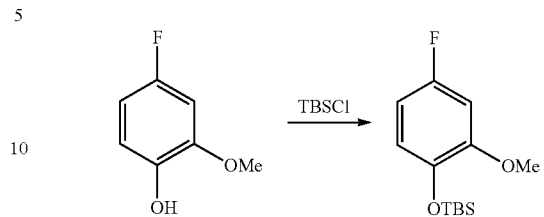

To 4-fluoro-2-methoxyphenol (5.68 g, 40 mmol) in DCM (100 mL) was added TEA (11.2 mL, 80 mmol), 4-DMAP (488 mg, 4 mmol) followed by TBSCl (7.5 g, 50 mmol), the reaction mixture was stirred at RT overnight, washed with saturated aqueous NaHCO$_3$, dried over Na$_2$SO$_4$, and concentrated. The crude product was purified by flash chromatography on silica gel (hexane-EtOAc, 50:1-10:1) to afford the title compound, 10 g. ESI-MS m/z 257 (MH)+.

Step 2. Synthesis of (R,Z)-3-(2-(2-aminothiazol-4-yl)-2-(hydroxyimino)acetamido)-7-fluoro-2-hydroxy-3,4-dihydro-2H-benzo[e][1,2]oxaborinine-8-carboxylic Acid The product from Step 1 was converted to the title compound in a similar manner to the synthesis of Example 24. ESI-MS m/z 395 (MH)+.

Example 40: (R,Z)-3-(2-(2-aminothiazol-4-yl)-2-(hydroxyimino)acetamido)-5,6-difluoro-2-hydroxy-3,4-dihydro-2H-benzo[e][1,2]oxaborinine-8-carboxylic Acid

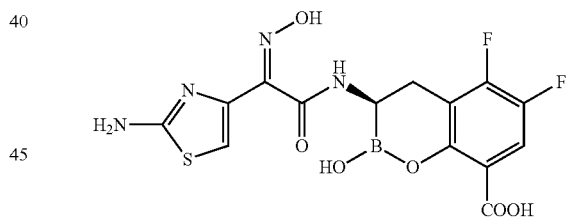

Step 1. Synthesis of 4,5-difluoro-2-hydroxybenzoic Acid

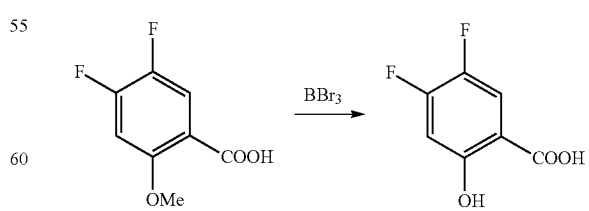

To 4,5-difluoro-2-methoxybenzoic acid (5 g, 26.6 mmol) in DCM (50 mL) at 0° C. under argon was added dropwise BBr$_3$ (1.0 M, 40 mL, 40 mmol). The reaction mixture was stirred at 0° C. for 2 h, and at RT for an additional 1 h, quenched with water and 1 N HCl, extracted with EtOAc. The organic extracts were combined, washed with brine, dried over Na₂SO₄, and concentrated to give the product, 4.62 g. ESI-MS m/z 175 (MH)⁺.

Step 2. Synthesis of tert-butyl 4,5-difluoro-3-iodo-2-methoxybenzoate

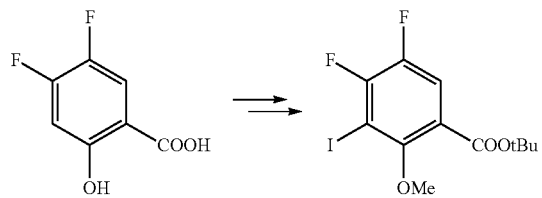

The title compound was prepared from the above product by following the same procedures as described in Steps 1-3 of Example 32. ESI-MS m/z 393 (M+Na)⁺.

Step 3. Synthesis of tert-butyl 2,3-difluoro-5,6-dimethoxy-4-(((3aS,4S,6R)-3a,5,5-trimethylhexahydro-4,6-methanobenzo[d][1,3,2]dioxaborol-2-yl)methyl)benzoate

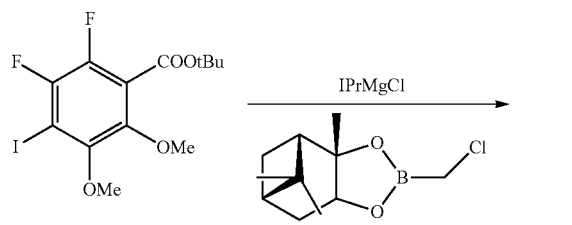

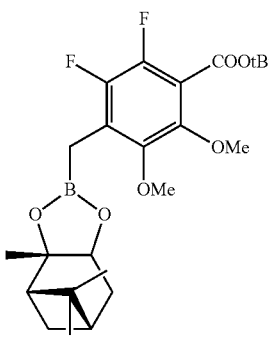

To a solution of the product from Step 2 (4.36 g, 11.8 mmol) in THF (45 mL) at −45° C. under argon was added dropwise isopropylmagnesium chloride-lithium chloride complex solution (1.3 M in THF, 9.6 mL, 12.48 mmol) over 15 min, then stirred for an additional 45 min. To this reaction mixture was added a THF (20 mL) solution of (1S,2S,3R,5S)-pinanediol chloromethyl borate (3.06 g, 13.4 mmol) (prepared according to the reported procedure, WO2009046098) over 8 min, then stirred for another 45 min. To this reaction mixture was added ZnCl₂ (1.0 M in ether, 13.2 mL, 13.2 mmol) dropwise over 5 min, then the cold bath was removed, and the reaction was stirred at RT for 2 h. The reaction mixture was diluted with diethyl ether, washed with aqueous NH₄Cl, water, brine, dried over Na₂SO₄, and concentrated. The crude product was purified by flash chromatography on silica gel (hexane-EtOAc, 40:1-8:1) to afford the title compound, 2 g. ESI-MS m/z 459 (M+Na)⁺.

Step 4. Synthesis of (R,Z)-3-(2-(2-aminothiazol-4-yl)-2-(hydroxyimino)acetamido)-5,6-difluoro-2-hydroxy-3,4-dihydro-2H-benzo[e][1,2]oxaborinine-8-carboxylic Acid

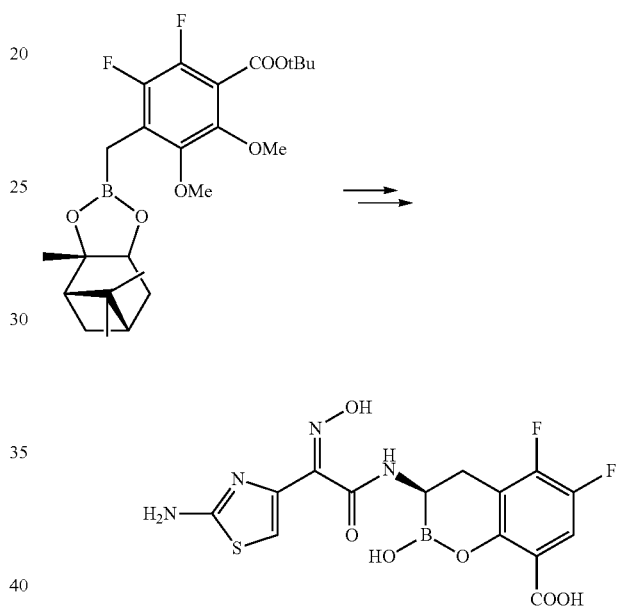

In a similar manner to the synthesis of Example 21, the title compound was prepared from above product. ESI-MS m/z 413 (MH)⁺.

Example 41: (R,Z)-3-(2-(2-aminothiazol-4-yl)-2-(hydroxyimino)acetamido)-6,7-difluoro-2-hydroxy-3,4-dihydro-2H-benzo[e][1,2]oxaborinine-8-carboxylic Acid

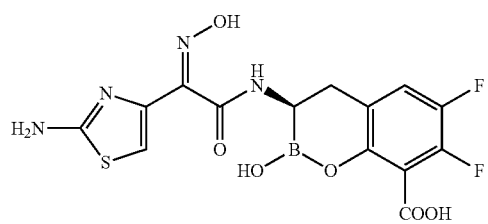 [SMILES: Nc1nc(/C(=N/O)C(=O)N[C@H]2Cc3cc(F)c(F)c(C(=O)O)c3OB2O)cs1]

The title compound was prepared from 5,6-difluorosalicylic acid in a similar manner to the synthesis of Example 40. ESI-MS m/z 413 (MH)⁺.

Example 42: (R,Z)-3-(2-(2-aminothiazol-4-yl)-2-(hydroxyimino)acetamido)-2-hydroxy-6-methoxy-3,4-dihydro-2H-benzo[e][1,2]oxaborinine-8-carboxylic Acid

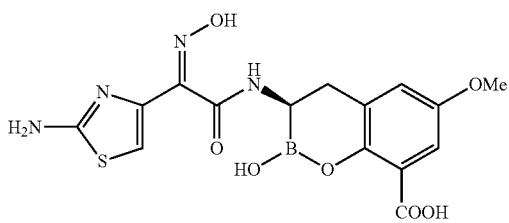

Step 1. Synthesis of tert-butyl 3-bromo-2,5-dimethoxybenzoate

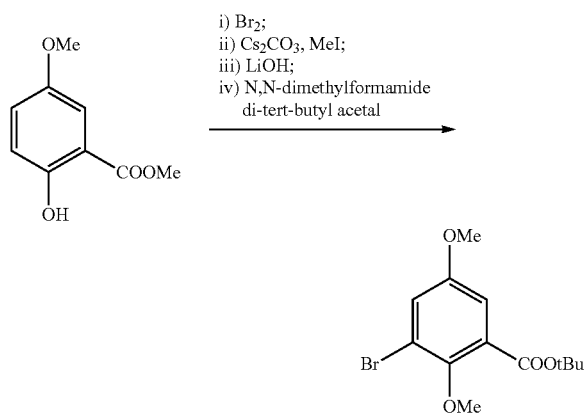

Step 1a. Bromination.

To methyl 5-methoxysalicylate (5.46 g, 30 mmol) in chloroform (80 mL) at RT was added bromine (1.73 mL, 33.6 mmol), the reaction mixture was stirred at RT overnight, then concentrated in vacuo to give the brominated product, which was used for the next step without further purification. ESI-MS m/z 261/263 (MH/MH+2)$^+$.

Step 1b. Methyl Ether Preparation.

The above crude product was converted to the methyl ether by following the same procedure as described in Step 3 of Example 32. The crude product was used for the next step without further purification. ESI-MS m/z 275/277 (MH/MH+2)$^+$.

Step 1c. Hydrolysis of Methyl Ester.

The above crude product was dissolved in THF (150 mL) and water (150 mL), treated with LiOH·H$_2$O (3.78 g, 90 mmol) at RT for 80 min, evaporated, acidified with 1 N HCl to pH ~1-2, extracted with DCM. The organic extracts were dried over Na$_2$SO$_4$, and concentrated to give the acid, which was used for the next step without further purification. ESI-MS m/z 261/263 (MH/MH+2)$^+$. MS m/z 275/277 (MH/MH+2)$^+$.

Step 1d. Synthesis of Tert-Butyl Ester.

The above crude product was converted to the tert-butyl ester by following the same procedure as described in Step 1 of Example 32, 7.21 g of pure product was obtained after column chromatography (hexane-EtOAc, 40:1-8:1). ESI-MS m/z 339/341 (M+Na/M+Na+2)$^+$.

Step 2. Synthesis of (R,Z)-3-(2-(2-aminothiazol-4-yl)-2-(hydroxyimino)acetamido)-2-hydroxy-6-methoxy-3,4-dihydro-2H-benzo[e][1,2]oxaborinine-8-carboxylic Acid

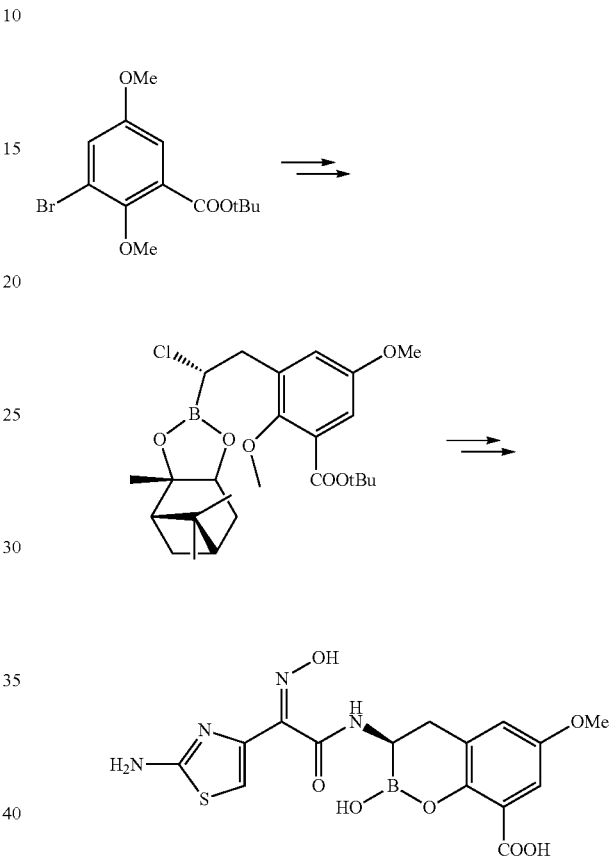

The title compound was prepared from above product by following the same procedures as described in Steps 4-7 of Example 24. ESI-MS m/z 407 (MH)$^+$.

Example 43: (R,Z)-3-(2-(2-aminothiazol-4-yl)-2-(hydroxyimino)acetamido)-2,6-dihydroxy-3,4-dihydro-2H-benzo[e][1,2]oxaborinine-8-carboxylic Acid

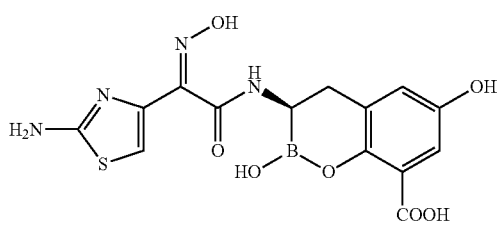 [SMILES: Nc1nc(/C(=N/O)C(=O)N[C@H]2Cc3cc(O)cc(C(=O)O)c3OB2O)cs1]

The title compound was prepared by using BBr$_3$ instead of BCl$_3$ in the last deprotection step of the synthesis of Example 42. ESI-MS m/z 393 (MH)$^+$.

Example 44: (R,Z)-3-(2-(2-aminothiazol-4-yl)-2-(hydroxyimino)acetamido)-6-chloro-2-hydroxy-3,4-dihydro-2H-benzo[e][1,2]oxaborinine-8-carboxylic Acid

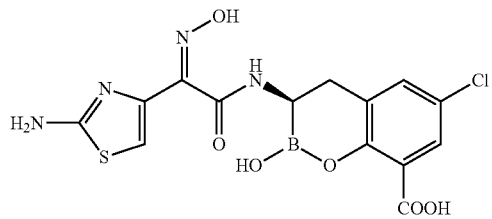 [SMILES: Nc1nc(/C(=N/O)C(=O)N[C@H]2Cc3cc(Cl)cc(C(=O)O)c3OB2O)cs1]

The title compound was prepared from methyl 5-chloro-2-hydroxybenzoate in a similar manner to the synthesis of Example 42 except in the last step using AlCl$_3$ instead of BCl$_3$ for deprotection. ESI-MS m/z 411 (MH)$^+$.

Example 45: (R,Z)-3-(2-(2-aminothiazol-4-yl)-2-(hydroxyimino)acetamido)-2-hydroxy-6-(trifluoromethoxy)-3,4-dihydro-2H-benzo[e][1,2]oxaborinine-8-carboxylic Acid

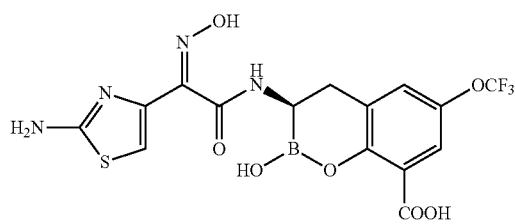 [SMILES: Nc1nc(/C(=N/O)C(=O)N[C@H]2Cc3cc(OC(F)(F)F)cc(C(=O)O)c3OB2O)cs1]

The title compound was prepared from 2-hydroxy-4-(trifluoromethoxy)benzoic acid in a similar manner to the synthesis of Example 32 except in Step 2 using NBS instead of NIS. ESI-MS m/z 461 (MH)$^+$.

Example 46: (R,Z)-3-(2-(2-aminothiazol-4-yl)-2-((2-(4-cyanophenoxy)ethoxy)imino)acetamido)-2-hydroxy-3,4-dihydro-2H-benzo[e][1,2]oxaborinine-8-carboxylic Acid

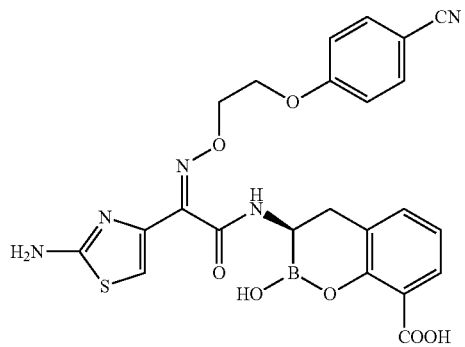 [SMILES: N#Cc1ccc(OCCO/N=C(\C(=O)N[C@H]2Cc3cccc(C(=O)O)c3OB2O)c2csc(N)n2)cc1]

Step 1. Synthesis of (2-tert-Butoxycarbonylamino-thiazol-4-yl)-[2-(4-cyano-phenoxy)-ethoxyimino]-acetic Acid

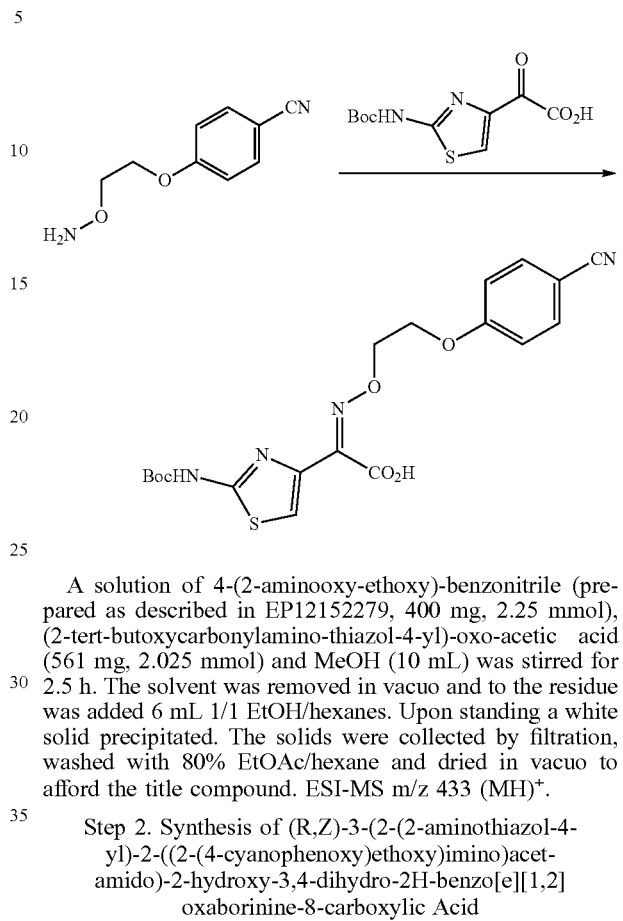

A solution of 4-(2-aminooxy-ethoxy)-benzonitrile (prepared as described in EP12152279, 400 mg, 2.25 mmol), (2-tert-butoxycarbonylamino-thiazol-4-yl)-oxo-acetic acid (561 mg, 2.025 mmol) and MeOH (10 mL) was stirred for 2.5 h. The solvent was removed in vacuo and to the residue was added 6 mL 1/1 EtOH/hexanes. Upon standing a white solid precipitated. The solids were collected by filtration, washed with 80% EtOAc/hexane and dried in vacuo to afford the title compound. ESI-MS m/z 433 (MH)$^+$.

Step 2. Synthesis of (R,Z)-3-(2-(2-aminothiazol-4-yl)-2-((2-(4-cyanophenoxy)ethoxy)imino)acetamido)-2-hydroxy-3,4-dihydro-2H-benzo[e][1,2]oxaborinine-8-carboxylic Acid

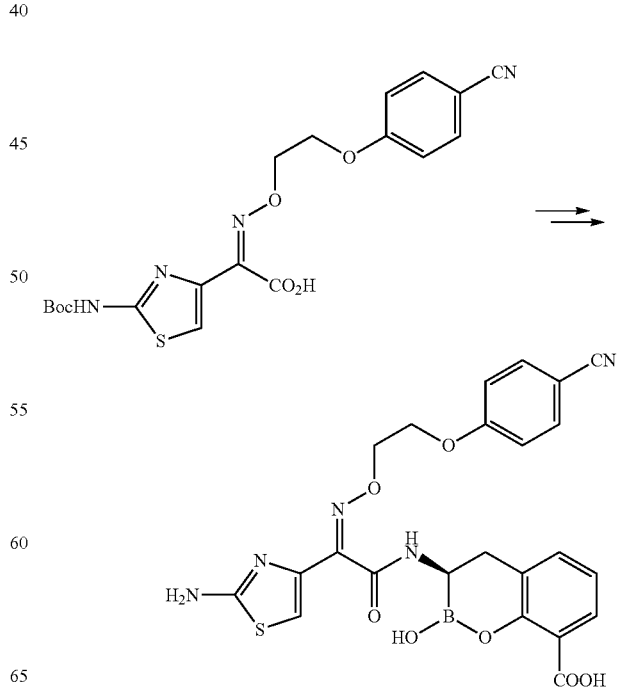

The title compound was prepared from (2-tert-butoxycarbonylamino-thiazol-4-yl)-[2-(4-cyano-phenoxy)-ethoxyimino]-acetic acid following the same procedures as described in Step 4 and Step 5 of Example 6 except that the crude product was purified by flash column chromatography on $C_{18}$-reverse phase silica gel. ESI-MS m/z 522 $(MH)^+$.

Example 47: (R,Z)-3-(2-(2-aminothiazol-4-yl)-2-((2-(4-(N-(piperidin-4-yl)carbamimidoyl)phenoxy)ethoxy)imino)acetamido)-2-hydroxy-3,4-dihydro-2H-benzo[e][1,2]oxaborinine-8-carboxylic Acid

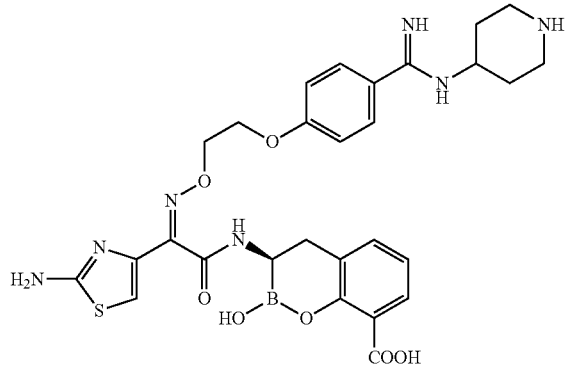 [SMILES: N=C(NC1CCNCC1)c1ccc(OCCO/N=C(\C(=O)N[C@H]2Cc3cccc(C(=O)O)c3OB2O)c2csc(N)n2)cc1]

The title compound was prepared from 4-{tert-butoxycarbonyl-[(4-{2-[(2-tert-butoxycarbonylamino-thiazol-4-yl)-carboxy-methyleneaminooxy]-ethoxy}-phenyl)-iminomethyl]-amino}-piperidine-1-carboxylic acid tert-butyl ester (prepared as described in EP12152279) in a similar manner to Example 46. ESI-MS m/z 622 $(MH)^+$.

Example 48: (R,Z)-3-(2-(2-aminothiazol-4-yl)-2-(ethoxyimino)acetamido)-2-hydroxy-3,4-dihydro-2H-benzo[e][1,2]oxaborinine-8-carboxylic Acid

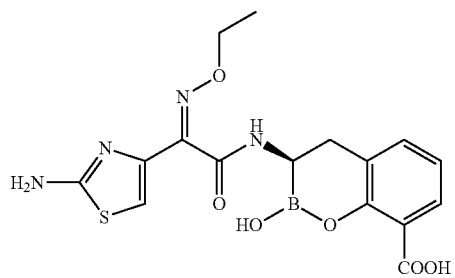 [SMILES: CCO/N=C(\C(=O)N[C@H]1Cc2cccc(C(=O)O)c2OB1O)c1csc(N)n1]

Step 1. Synthesis of (2-tert-Butoxycarbonylamino-thiazol-4-yl)-ethoxyimino-acetic Acid

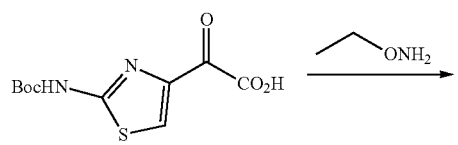

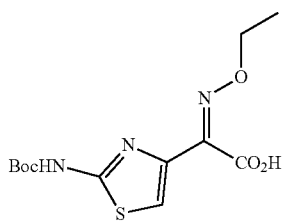

To a solution of (2-tert-butoxycarbonylamino-thiazol-4-yl)-oxo-acetic acid (800 mg, 2.94 mmol) in ethanol (14 mL) was added O-ethylhydroxylamine hydrochloride (312 mg, 3.2 mmol) followed by sodium acetate (285 mg, 3.5 mmol). After 2 h the solution was filtered and the filtrate was concentrated to a thick slurry. Methanol was added to dissolve the solids and water was added to afford a white precipitate. The solution was allowed to stand for 1 h and the solids collected by filtration, washed with water and dried to afford 635 mg (69%) of (2-tert-Butoxycarbonylamino-thiazol-4-yl)-ethoxyimino-acetic acid. ESI-MS m/z 316 $(MH)^+$.

Step 2. Synthesis of (R,Z)-3-(2-(2-aminothiazol-4-yl)-2-(ethoxyimino)acetamido)-2-hydroxy-3,4-dihydro-2H-benzo[e][1,2]oxaborinine-8-carboxylic Acid

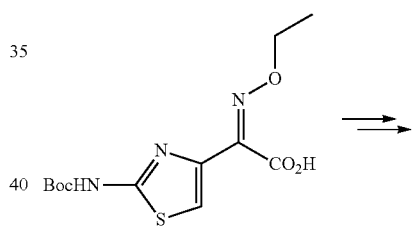

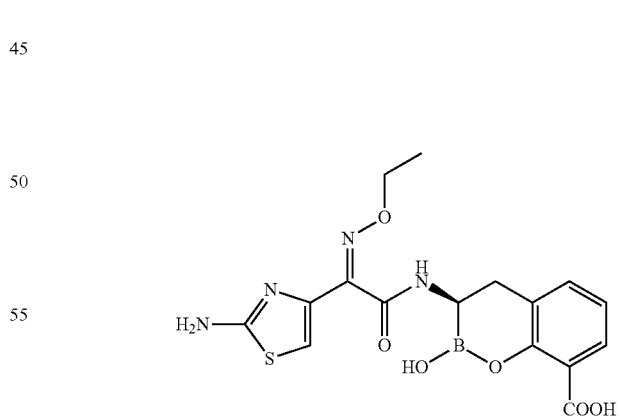

By following the same procedures as described in Step 4 and Step 5 of Example 6, the title compound was prepared from the above product. ESI-MS m/z 405 $(MH)^+$.

Example 49: (R,Z)-3-(2-(2-aminothiazol-4-yl)-2-((2-(4-(N-isopropylcarbamimidoyl)phenoxy)ethoxy)imino)acetamido)-2-hydroxy-3,4-dihydro-2H-benzo[e][1,2]oxaborinine-8-carboxylic Acid

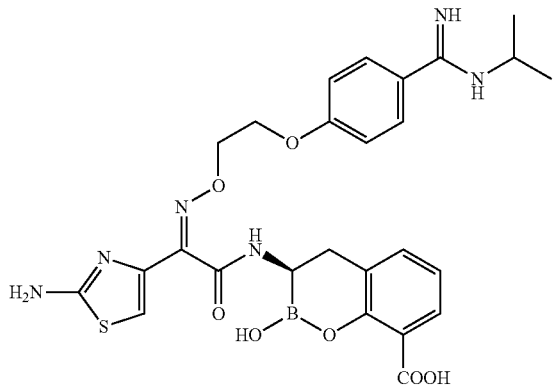 [SMILES: CC(C)NC(=N)c1ccc(OCCO/N=C(\C(=O)N[C@H]2Cc3cccc(C(=O)O)c3OB2O)c2csc(N)n2)cc1]

The title compound was prepared from (2-tert-butoxycarbonylamino-thiazol-4-yl)-(2-{4-[(tert-butoxycarbonyl-isopropyl-amino)-imino-methyl]-phenoxy}-ethoxyimino)-acetic acid (prepared as described in EP12152279) following the same procedures as described in Step 4 and Step 5 of Example 6. ESI-MS m/z 581 (MH)+.

Example 50: (R,Z)-3-(2-(2-aminothiazol-4-yl)-2-((2-phenoxyethoxy)imino)acetamido)-2-hydroxy-3,4-dihydro-2H-benzo[e][1,2]oxaborinine-8-carboxylic Acid

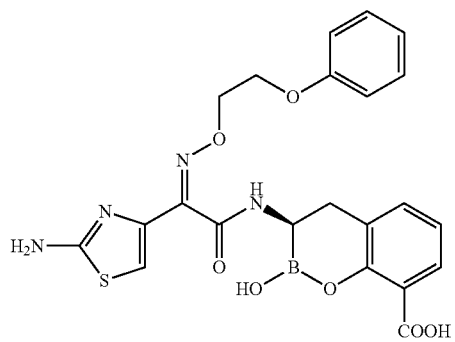 [SMILES: Nc1nc(/C(=N/OCCOc2ccccc2)C(=O)N[C@H]2Cc3cccc(C(=O)O)c3OB2O)cs1]

The title compound was prepared from O-(2-Phenoxyethyl)-hydroxylamine hydrochloride following the same procedures as described in Example 48. ESI-MS m/z 497 (MH)+.

Example 51: (R,Z)-3-(2-(2-aminothiazol-4-yl)-2-(((piperidin-4-yloxy)imino)acetamido)-2-hydroxy-3,4-dihydro-2H-benzo[e][1,2]oxaborinine-8-carboxylic Acid

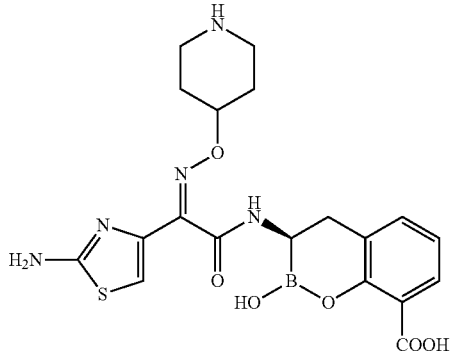 [SMILES: Nc1nc(/C(=N/OC2CCNCC2)C(=O)N[C@H]2Cc3cccc(C(=O)O)c3OB2O)cs1]

Step 1. Synthesis of 4-(1,3-Dioxo-1,3-dihydro-isoindol-2-yloxy)-piperidine-1-carboxylic acid tert-butyl Ester

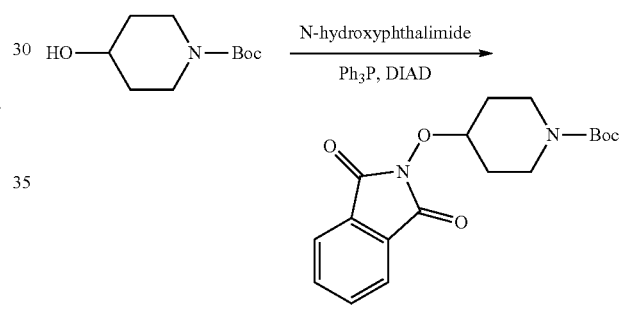

To a solution of N-tert-butoxycarbonyl)-4-hydroxypiperidine (2.5 g, 12.44 mmol) in THF (62 mL) was added triphenylphosphine (4.9 g, 18.7 mmol), N-hydroxyphalimide (3.0 g, 18.4 mmol) and diisopropylazodicarboxylate (DIAD, 3.7 mL, 18.9 mmol). After 2 h the reaction mass was concentrated, EtOAC added, and the solution washed with 5% NaHCO$_3$, H$_2$O, dried (Na$_2$SO$_4$) and concentrated. The crude material was passed through a silica gel column eluting with a gradient of 10% to 40% EtOAC/hexanes to afford an impure product which was used directly in the next step. ESI MS m/z 347 (MH)+.

Step 2. Synthesis of 4-Aminooxy-piperidine-1-carboxylic acid tert-butyl Ester

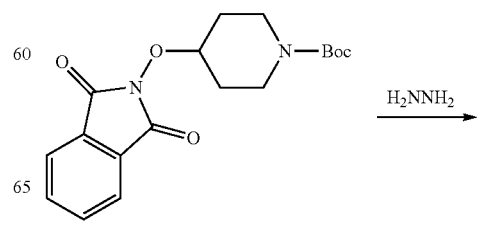

-continued

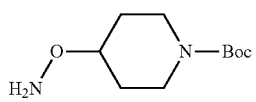

To a slurry of the product from the above reaction in EtOH (60 mL) was added hydrazine hydrate (2.7 mL). After 3.5 h the reaction was filtered, the solids washed with EtOAC and the filtrate concentrated. To the residue was added a 1/1 mixture of EtOAc/Et$_2$O. The slurry was filtered and the filtrate concentrated to afford a slightly hazy oil which was used without further purification.

Step 3. Synthesis of 4-[(2-tert-Butoxycarbonylamino-thiazol-4-yl)-carboxy-methyleneaminooxy]-piperidine-1-carboxylic acid tert-butyl Ester

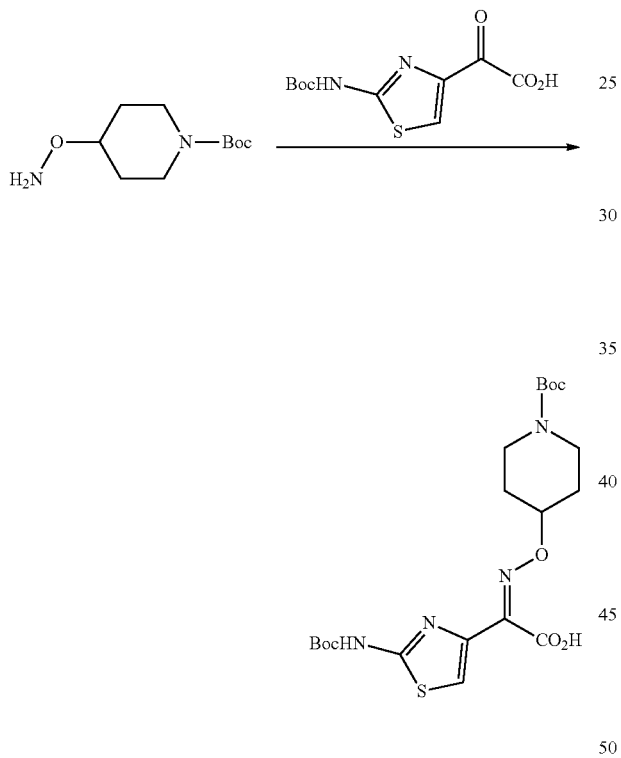

To a solution of 380 mg of the above compound in 6 mL EtOH was added (2-tert-butoxycarbonylamino-thiazol-4-yl)-oxo-acetic acid (360 mg, 1.32 mmol). After 1 h an additional aliquot of the alkoxyamine was added and the reaction stirred overnight. Water was added followed by 0.5 mL acetic acid resulting in the formation of a precipitate. The solids were collected by filtration and washed sequentially with aqueous acetic acid and water. The wet solids were dissolved in MeOH and the solution concentrated to afford the title compound as a pale yellow foam. ESI MS m/z 471 (MH)$^+$.

Step 4. Synthesis of (R,Z)-3-(2-(2-aminothiazol-4-yl)-2-((piperidin-4-yloxy)imino)acetamido)-2-hydroxy-3,4-dihydro-2H-benzo[e][1,2]oxaborinine-8-carboxylic Acid

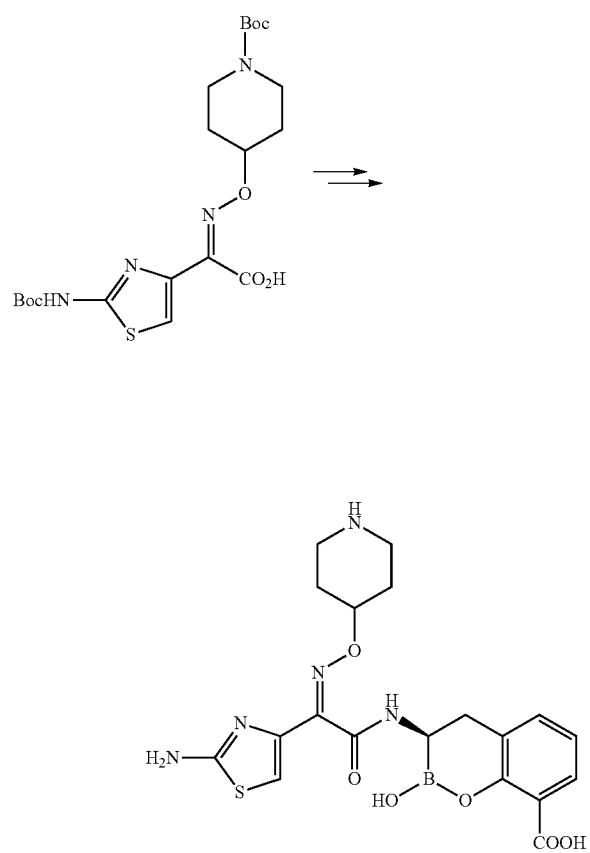

By following the same procedures as described in Step 4 and Step 5 of Example 6, the title compound was prepared from the above product. ESI-MS m/z 460 (MH)+.

Example 52: (R,Z)-3-(2-(2-aminothiazol-4-yl)-2-((piperidin-4-ylmethoxy)imino)acetamido)-2-hydroxy-3,4-dihydro-2H-benzo[e][1,2]oxaborinine-8-carboxylic Acid

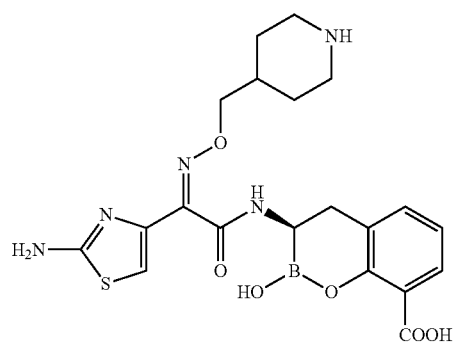 [SMILES: Nc1nc(/C(=N/OCC2CCNCC2)C(=O)N[C@H]2Cc3cccc(C(=O)O)c3OB2O)cs1]

Step 1. Synthesis of 4-Aminooxymethyl-piperidine-1-carboxylic Acid tert-butyl Ester

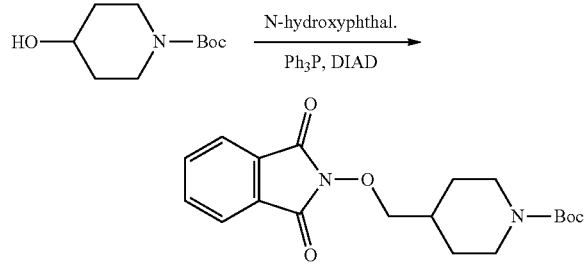

The title compound was prepared from 4-hydroxymethyl-piperidine-1-carboxylic acid tert-butyl ester following the procedure described in Step 1 and Step 2 of Example 51.

Step 2. Synthesis of 4-[(2-tert-Butoxycarbonylamino-thiazol-4-yl)-ethoxycarbonyl-methyleneaminooxymethyl]-piperidine-1-carboxylic Acid tert-butyl Ester

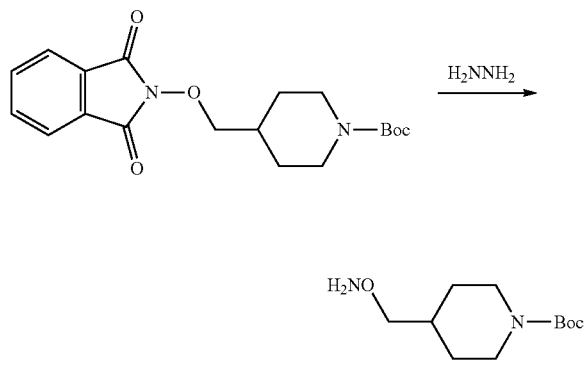

The title compound was prepared following the procedure described in Step 3 of Example 51. The crude product was purified by flash chromatography using a gradient of 15% to 30% EtOAc/hexanes. ESI-MS m/z 513 (MH)$^+$.

Step 3. Synthesis of 4-[(2-tert-Butoxycarbonylamino-thiazol-4-yl)-carboxy-methyleneaminooxymethyl]-piperidine-1-carboxylic Acid tert-butyl Ester

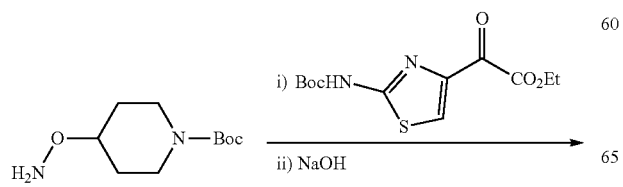

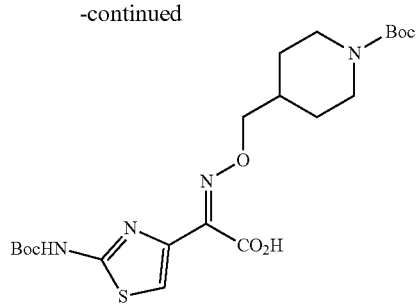

To a solution of the above compound (ca. 70% pure, 570 mg, ca. 1.7 mmol) in EtOH (12 mL) was added (2-tert-butoxycarbonylamino-thiazol-4-yl)-oxo-acetic acid ethyl ester (506 mg, 1.68 mmol). The mixture was stirred at 40° C. for 4 h, more amine was added along with acetic acid (100 uL, 1.75 mmol) and the mixture stirred overnight at 30° C. An additional aliquot of amine and acetic acid were added, the mixture stirred at 40° C. for 4 h, cooled and concentrated in vacuo. The crude product was purified by flash chromatography using a gradient of 15% to 30% EtOAc/hexanes. ESI-MS m/z 513 (MH)+.

To a solution of 4-[(2-tert-butoxycarbonylamino-thiazol-4-yl)-ethoxycarbonyl-methyleneaminooxymethyl]-piperidine-1-carboxylic acid tert-butyl ester (565 mg, 1.10 mmol) in EtOH (4 mL) was added 1 N NaOH (3.3 mL, 3.3 mmol). After 16 h and additional 1 mL of 1 N NaOH was added, the reaction stirred for an additional 5 h, diluted with water and extracted with Et2O. The aqueous layer acidified to pH 2 with 1 N HCl and extracted with EtOAc. The organic layer was washed with water, brine, dried (Na$_2$SO$_4$) and concentrated to afford a colorless foam. ESI-MS m/z 485 (MH)$^+$.

Step 4. Synthesis of (R,Z)-3-(2-(2-aminothiazol-4-yl)-2-((piperidin-4-ylmethoxy)imino)acetamido)-2-hydroxy-3,4-dihydro-2H-benzo[e][1,2]oxaborinine-8-carboxylic Acid

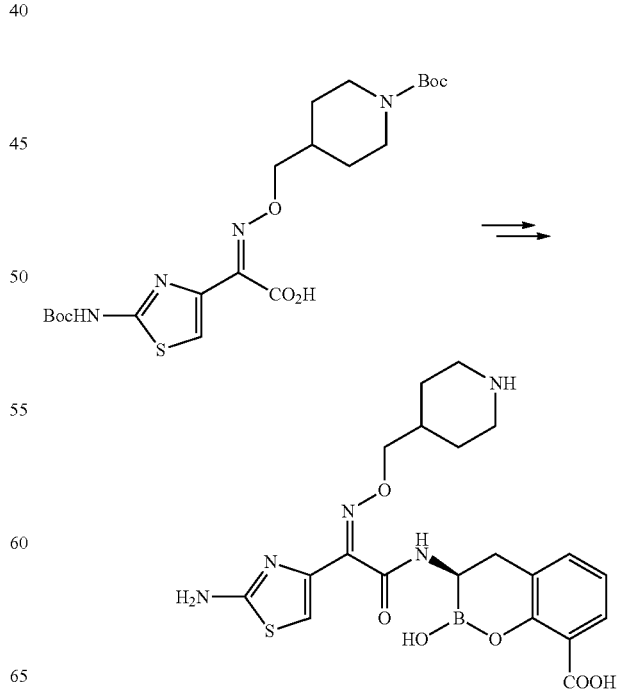

By following the same procedures as described in Step 4 and Step 5 of Example 6, with the exception that the crude product was purified by flash column chromatography on $C_{18}$-reverse phase silica gel, the title compound was prepared from the above product. ESI-MS m/z 474 (MH)⁺.

Example 53: (R,Z)-3-(2-(2-aminothiazol-4-yl)-2-((azetidin-3-yloxy)imino)acetamido)-2-hydroxy-3,4-dihydro-2H-benzo[e][1,2]oxaborinine-8-carboxylic Acid

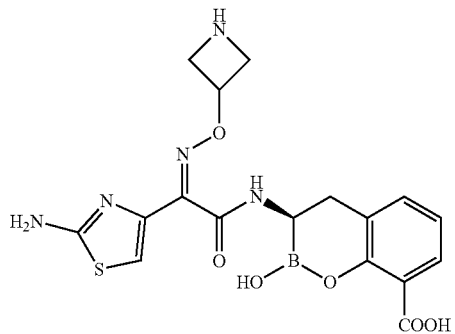 [SMILES: Nc1nc(/C(=N/OC2CNC2)C(=O)N[C@H]2Cc3cccc(C(=O)O)c3OB2O)cs1]

The title compound was prepared from 3-hydroxy-azetidine-1-carboxylic acid tert-butyl ester in a similar manner to the synthesis of Example 51. ESI-MS m/z 432 (MH)⁺.

Example 54: (R,Z)-3-(2-((2-((2-aminoethyl)amino)-2-oxoethoxy)imino)-2-(2-aminothiazol-4-yl)acetamido)-2-hydroxy-3,4-dihydro-2H-benzo[e][1,2]oxaborinine-8-carboxylic Acid

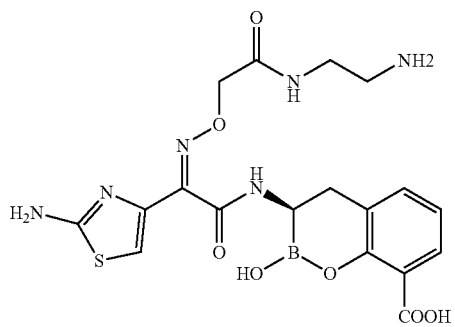 [SMILES: NCCNC(=O)CO/N=C(\C(=O)N[C@H]1Cc2cccc(C(=O)O)c2OB1O)c1csc(N)n1]

Step 1. Synthesis of [2-(2-Bocaminooxy-acetylamino)-ethyl]-carbamic Acid Benzyl Ester

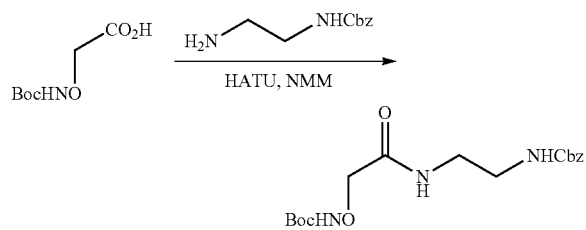

To a solution of Boc-aminooxyacetic acid (1.20 g, 7.55 mmol) in DCM (20 mL) and DMF (5 mL) was added (2-amino-ethyl)-carbamic acid benzyl ester hydrochloride (1.74 g, 7.55 mmol), NMM (2.6 mL, 23.6 mmol) and HATU (2.89 g, 7.59 mmol). After stirring for 18 h the reaction was diluted with EtOAc, washed with 0.2N HCl and 5% NaHCO₃. Hexanes was added and the solution washed with water (5×), brine, dried (Na₂SO₄) and concentrated. The crude material was purified by flash chromatography using a gradient of 50% EtOAc/hexanes to 100% EtOAc.

Step 2. Synthesis of [2-(2-Aminooxy-acetylamino)-ethyl]-carbamic Acid Benzyl Ester

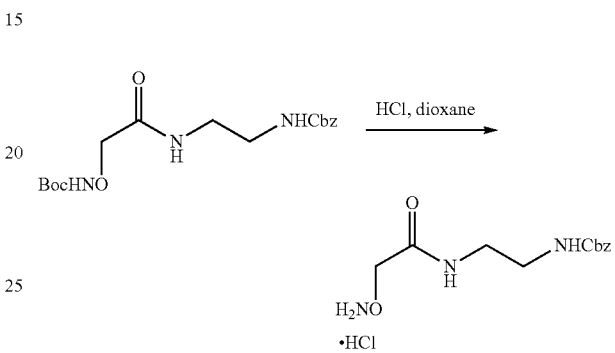

To a solution of [2-(2-Boc-aminooxy-acetylamino)-ethyl]-carbamic acid benzyl ester (1.92 g, 5.23 mmol) in Et₂O (5 mL) was added 4N HCl/dioxane (25 mL, 100 mmol). After 23 h the slurry was diluted with 1/1 EtOAc/Et₂O, filtered, and the solids washed with EtOAc/Et₂O to afford 1.46 g (92%) of the title compound.

Step 3. Synthesis of [(2-Benzyloxycarbonylamino-ethylcarbamoyl)-methoxyimino]-(2-tert-butoxycarbonylamino-thiazol-4-yl)-acetic Acid

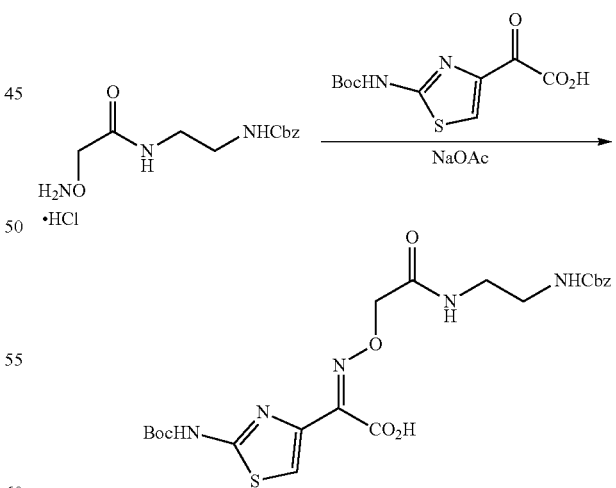

To a solution of (2-tert-butoxycarbonylamino-thiazol-4-yl)-oxo-acetic acid (313 mg, 1.15 mmol) in a mixture of EtOH (3 mL) and MeOH (3 mL) was added [2-(2-Boc-aminooxy-acetylamino)-ethyl]-carbamic acid benzyl ester (350 mg, 1.15 mmol) and sodium acetate (94 mg, 1.15 mmol). After stirring for 1 h an additional aliquot (ca. 10 mg) of ketoacid was added and the reaction stirred an additional 45 min. The slightly cloudy solution was filtered through Celite, washed with 9/1 DCM/EtOH, and the filtrate concentrated to afford a pale yellow foam which was used without purification. ESI-MS m/z 522 (MH)$^+$.

Step 4. Synthesis of (R,Z)-3-(2-((2-((2-aminoethyl)amino)-2-oxoethoxy)imino)-2-(2-aminothiazol-4-yl)acetamido)-2-hydroxy-3,4-dihydro-2H-benzo[e][1,2]oxaborinine-8-carboxylic Acid

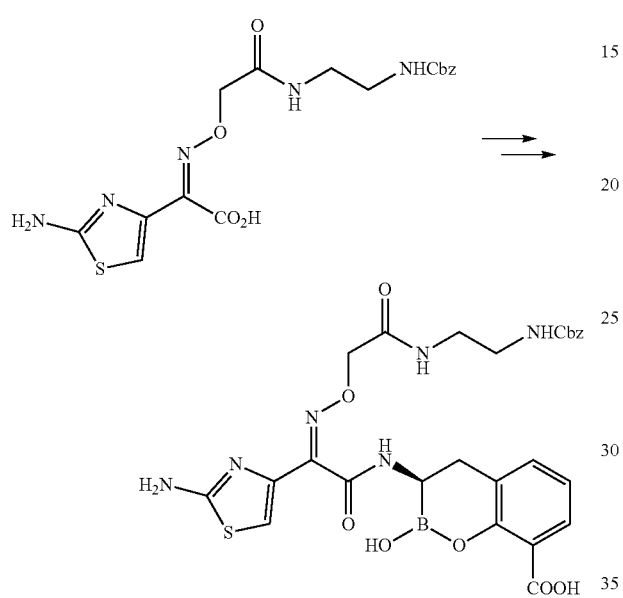

By following the same procedures as described in Step 4 and Step 5 of Example 6, with the exception that BBr$_3$ was used in the final deprotection step and the crude product was purified by flash column chromatography on C$_{18}$-reverse phase silica gel, the title compound was prepared from the above product. ESI-MS m/z 477 (MH)$^+$.

Example 55: (R,Z)-3-(2-(2-aminothiazol-4-yl)-2-((2-(4-carbamimidoylphenoxy)ethoxy)imino)acetamido)-2-hydroxy-3,4-dihydro-2H-benzo[e][1,2]oxaborinine-8-carboxylic Acid

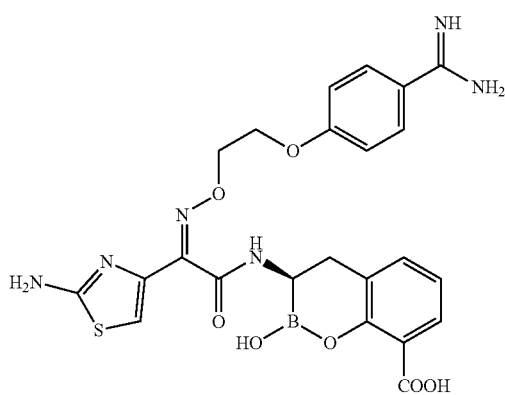 [SMILES: N=C(N)c1ccc(OCCO/N=C(\C(=O)N[C@H]2Cc3cccc(C(=O)O)c3OB2O)c2csc(N)n2)cc1]

The title compound was prepared from {2-[4-(tert-butoxycarbonylamino-imino-methyl)-phenoxy]-ethoxy-imino}-(2-tert-butoxycarbonylamino-thiazol-4-yl)-acetic acid (prepared as described in EP12152279) in a similar manner to Example 46. ESI-MS m/z 539 (MH)$^+$.

Example 56: (R,Z)-3-(2-(2-aminothiazol-4-yl)-2-((2-((4-cyanophenyl)amino)-2-oxoethoxy)imino)acetamido)-2-hydroxy-3,4-dihydro-2H-benzo[e][1,2]oxaborinine-8-carboxylic Acid

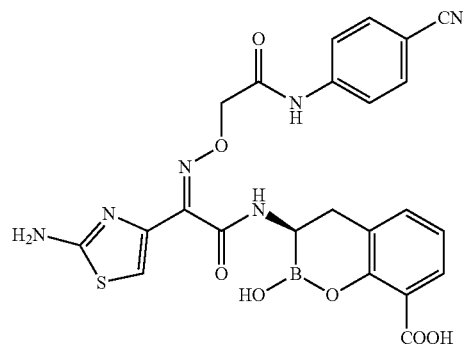 [SMILES: N#Cc1ccc(NC(=O)CO/N=C(\C(=O)N[C@H]2Cc3cccc(C(=O)O)c3OB2O)c2csc(N)n2)cc1]

Step 1. Synthesis of tert-butyl (2-((4-cyanophenyl)amino)-2-oxoethoxy)carbamate

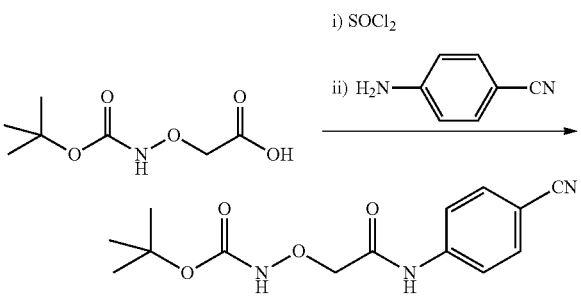

To a slurry of 2-(((tert-butoxycarbonyl)amino)oxy)acetic acid (800 mg, 4.19 mmol) in DCM (17 mL) was added oxalyl chloride (400 µL, 4.66 mmol) followed by 50 µL DMF. The reaction was stirred for 45 min, then 4-aminobenzonitrile (545 mg, 4.62 mmol) and NMM (560 µL, 5.1 mmol) were added and the solution allowed to stir for 1.5 h. The reaction was diluted with EtOAc, then washed with 1 N HCl, 5% NaHCO$_3$, water, brine, dried (Na$_2$SO$_4$) and concentrated in vacuo to afford a pale yellow solid which was used without purification.

Step 2. Synthesis of (R,Z)-3-(2-(2-aminothiazol-4-yl)-2-((2-((4-cyanophenyl)amino)-2-oxoethoxy)imino)acetamido)-2-hydroxy-3,4-dihydro-2H-benzo[e][1,2]oxaborinine-8-carboxylic Acid

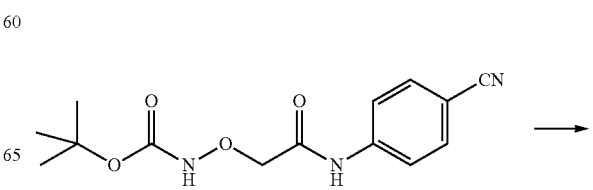

-continued

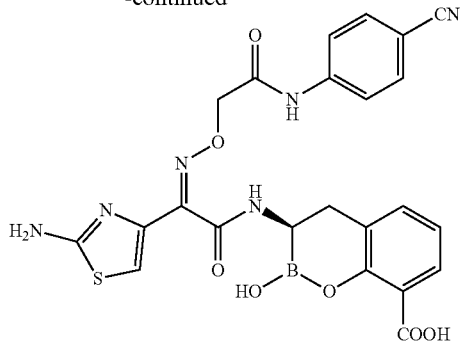

By following the same procedures as described in Step 2, Step 3 and Step 4 of Example 54, the title compound was prepared from the above product. ESI-MS m/z 535 (MH)⁺.

Example 57: (R,Z)-3-(2-(2-aminothiazol-4-yl)-2-((2-(methylamino)-2-oxoethoxy)imino)acetamido)-2-hydroxy-3,4-dihydro-2H-benzo[e][1,2]oxaborinine-8-carboxylic Acid

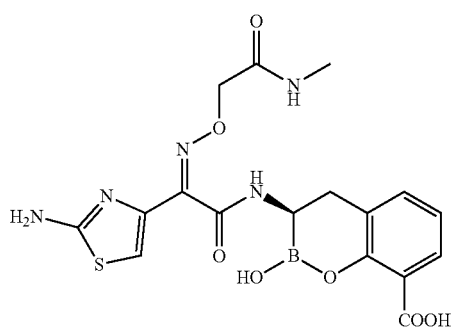 [SMILES: CNC(=O)CO/N=C(\C(=O)N[C@H]1Cc2cccc(C(=O)O)c2OB1O)c1csc(N)n1]

The title compound was prepared from methylamine (2 M solution in THF) in a similar manner to the synthesis of Example 56. ESI-MS m/z 448 (MH)⁺.

Example 58: (R,Z)-3-(2-(2-aminothiazol-4-yl)-2-((2-oxo-2-(piperazin-1-yl)ethoxy)imino)acetamido)-2-hydroxy-3,4-dihydro-2H-benzo[e][1,2]oxaborinine-8-carboxylic Acid

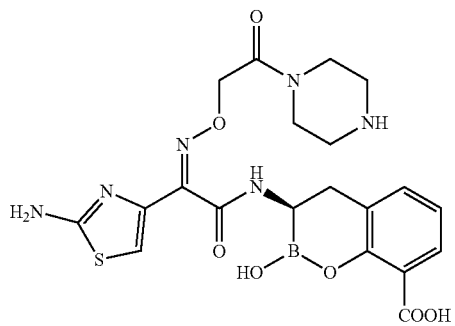 [SMILES: Nc1nc(/C(=N/OCC(=O)N2CCNCC2)C(=O)N[C@H]2Cc3cccc(C(=O)O)c3OB2O)cs1]

The title compound was prepared from piperazine-1-carboxylic acid benzyl ester in a similar manner to the synthesis of Example 56 with the exception that BBr₃ was used in the final deprotection step. ESI-MS m/z 503 (MH)⁺.

Example 59: (R,Z)-3-(2-(2-aminothiazol-4-yl)-2-((2-oxo-2-(piperidin-4-ylamino)ethoxy)imino)acetamido)-2-hydroxy-3,4-dihydro-2H-benzo[e][1,2]oxaborinine-8-carboxylic Acid

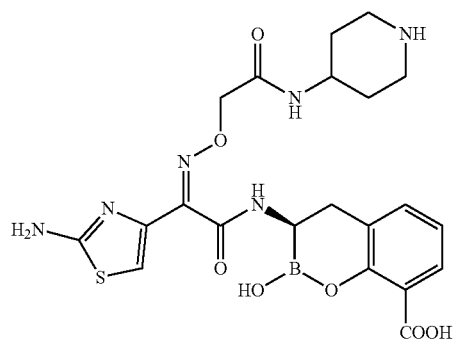 [SMILES: Nc1nc(/C(=N/OCC(=O)NC2CCNCC2)C(=O)N[C@H]2Cc3cccc(C(=O)O)c3OB2O)cs1]

The title compound was prepared from 4-amino-piperidine-1-carboxylic acid benzyl ester in a similar manner to the synthesis of Example 56 with the exception that BBr₃ was used in the final deprotection step. ESI-MS m/z 517 (MH)⁺.

Example 60: (R,Z)-3-(2-(2-aminothiazol-4-yl)-2-((2-(dimethylamino)-2-oxoethoxy)imino)acetamido)-2-hydroxy-3,4-dihydro-2H-benzo[e][1,2]oxaborinine-8-carboxylic Acid

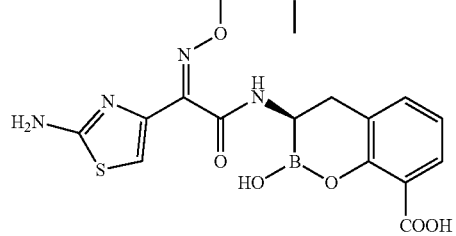

The title compound was prepared from dimethylamine (2 M solution in THF) in a similar manner to the synthesis of Example 56. ESI-MS m/z 462 (MH)⁺.

Example 61: (R,Z)-3-(2-((2-amino-2-oxoethoxy)imino)-2-(2-aminothiazol-4-yl)acetamido)-2-hydroxy-3,4-dihydro-2H-benzo[e][1,2]oxaborinine-8-carboxylic Acid

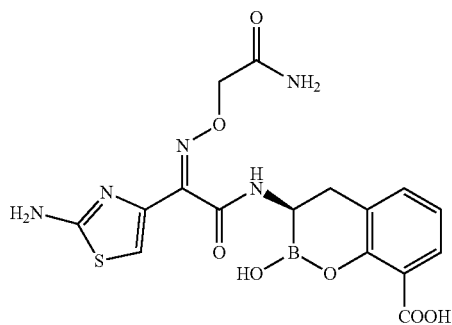 [SMILES: NC(=O)CO/N=C(\C(=O)N[C@H]1Cc2cccc(C(=O)O)c2OB1O)c1csc(N)n1]

The title compound was prepared from ammonium hydroxide in a similar manner to the synthesis of Example 56. ESI-MS m/z 434 (MH)+.

Example 63: (R)-3-((Z)-2-(2-aminothiazol-4-yl)-2-((2-(((1s,4S)-4-cyanocyclohexyl)amino)-2-oxoethoxy)imino)acetamido)-2-hydroxy-3,4-dihydro-2H-benzo[e][1,2]oxaborinine-8-carboxylic Acid

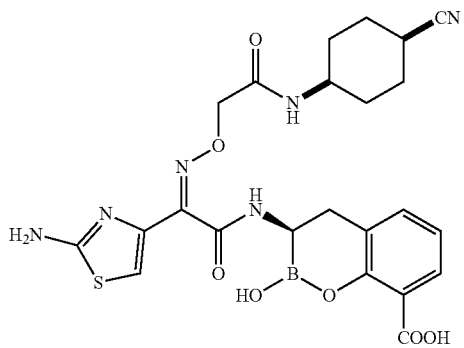

The title compound was prepared from cis-4-cyanocyclohexylamine hydrochloride in a similar manner to the synthesis of Example 56. ESI-MS m/z 541 (MH)+.

Example 62: (R)-3-((Z)-2-(2-aminothiazol-4-yl)-2-((2-(((1r,4R)-4-cyanocyclohexyl)amino)-2-oxoethoxy)imino)acetamido)-2-hydroxy-3,4-dihydro-2H-benzo[e][1,2]oxaborinine-8-carboxylic Acid

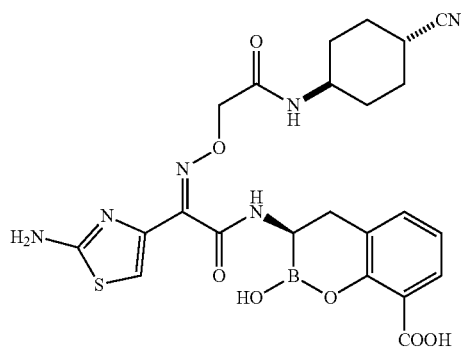

The title compound was prepared from trans-4-cyanocyclohexylamine hydrochloride in a similar manner to the synthesis of Example 56. ESI-MS m/z 541 (MH)+.

Example 64: (R,Z)-3-(2-((2-(4-(N-(2-aminoethyl)carbamimidoyl)phenoxy)ethoxy)imino)-2-(2-aminothiazol-4-yl)acetamido)-2-hydroxy-3,4-dihydro-2H-benzo[e][1,2]oxaborinine-8-carboxylic Acid

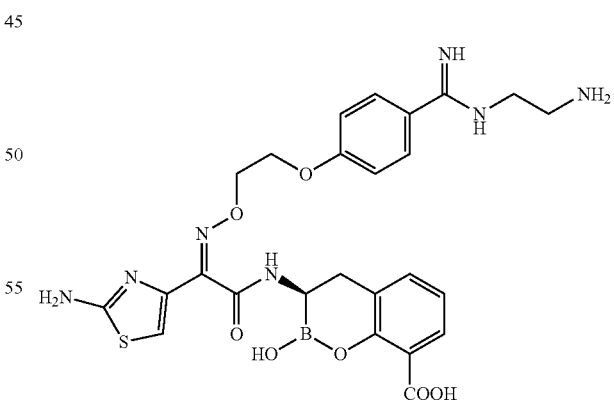

The title compound was prepared from (2-tert-butoxycarbonylamino-thiazol-4-yl)-[2-(4-{[tert-butoxycarbonyl-(2-tert-butoxycarbonylamino-ethyl)-amino]-imino-methyl}-phenoxy)-ethoxyimino]-acetic acid (prepared as described in EP12152279) in a similar manner to Example 46. ESI-MS m/z 582 (MH)+.

Example 65: (R)-3-((Z)-2-((2-(((S)-5-amino-1-carboxypentyl)amino)-2-oxoethoxy)imino)-2-(2-aminothiazol-4-yl)acetamido)-2-hydroxy-3,4-dihydro-2H-benzo[e][1,2]oxaborinine-8-carboxylic

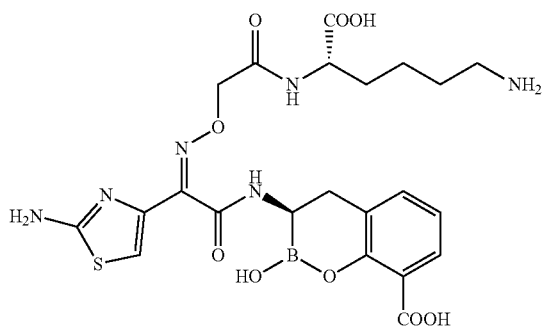 [SMILES: NCCCC[C@H](NC(=O)CO/N=C(\C(=O)N[C@H]1Cc2cccc(C(=O)O)c2OB1O)c1csc(N)n1)C(=O)O]

The title compound was prepared from (S)-2-amino-6-benzyloxycarbonylamino-hexanoic acid benzyl ester hydrochloride in a similar manner to the synthesis of Example 56 with the exception that BBr$_3$ was used in the final deprotection step. ESI-MS m/z 563 (MH)$^+$.

Example 66: (R)-3-((Z)-2-((2-(((R)-5-amino-1-carboxypentyl)amino)-2-oxoethoxy)imino)-2-(2-aminothiazol-4-yl)acetamido)-2-hydroxy-3,4-dihydro-2H-benzo[e][1,2]oxaborinine-8-carboxylic Acid

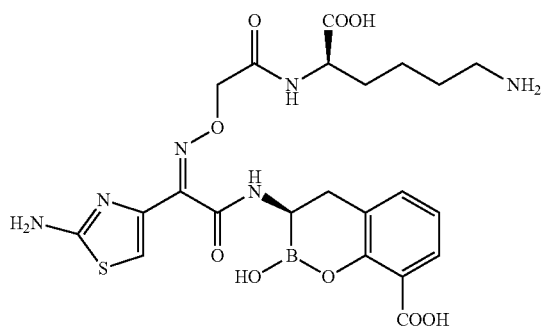 [SMILES: NCCCC[C@@H](NC(=O)CO/N=C(\C(=O)N[C@H]1Cc2cccc(C(=O)O)c2OB1O)c1csc(N)n1)C(=O)O]

The title compound was prepared from (R)-2-amino-6-benzyloxycarbonylamino-hexanoic acid benzyl ester hydrochloride in a similar manner to the synthesis of Example 56 with the exception that BBr$_3$ was used in the final deprotection step. ESI-MS m/z 563 (MH)$^+$.

Example 67: (R,Z)-3-(2-((2-(((5-aminopentyl)amino)-2-oxoethoxy)imino)-2-(2-aminothiazol-4-yl)acetamido)-2-hydroxy-3,4-dihydro-2H-benzo[e][1,2]oxaborinine-8-carboxylic Acid

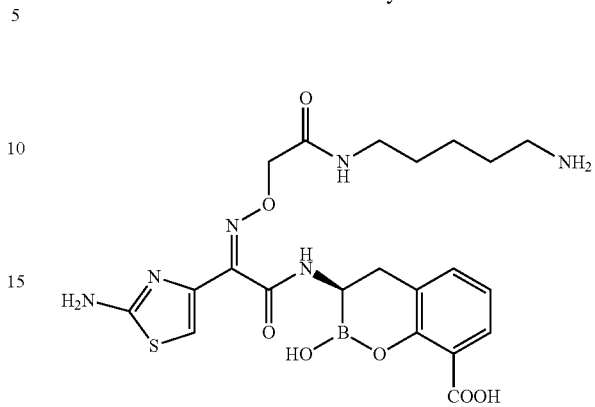

The title compound was prepared from (5-amino-pentyl)-carbamic acid benzyl ester hydrochloride in a similar manner to the synthesis of Example 56 with the exception that BBr$_3$ was used in the final deprotection step. ESI-MS m/z 519 (MH)$^+$.

Example 68: (R,Z)-3-(2-(2-aminothiazol-4-yl)-2-(((2-carboxypropan-2-yl)oxy)imino)acetamido)-2-hydroxy-3,4-dihydro-2H-benzo[e][1,2]oxaborinine-8-carboxylic Acid

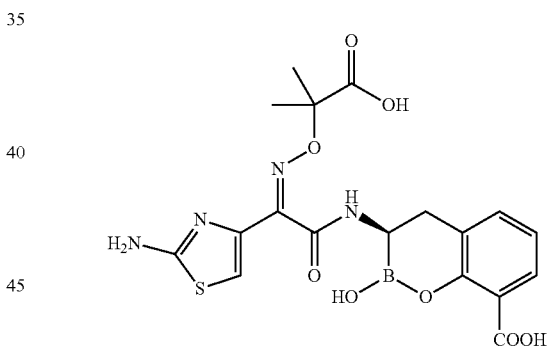

Step 1. Synthesis of 2-[(2-tert-butoxycarbonylamino-thiazol-4-yl)-carboxy-methyleneaminooxy]-2-methyl-propionic Acid tert-butyl Ester

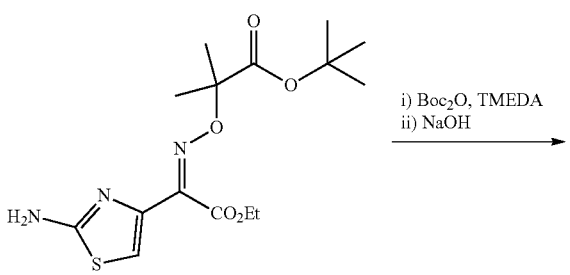

-continued

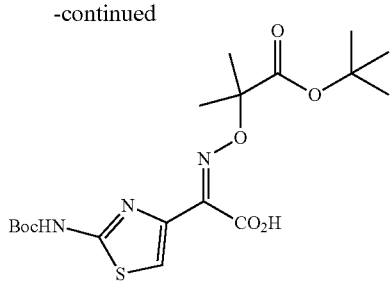

A mixture of 2-[(2-amino-thiazol-4-yl)-carboxy-methyleneaminooxy]-2-methyl-propionic acid tert-butyl ester (1.00 g, 2.80 mmol), di-tert-butyl-dicarbonate (770 uL, 3.36 mmol), TMEDA (540 uL, 3.62 mmol) in acetonitrile (14 mL) was stirred for 18 h. The solvent was removed in vacuo and the residue purified by flash chromatography using a gradient of 8% to 20% EtOAc/hexanes to afford 757 mg of 2-[(2-tert-Butoxycarbonylamino-thiazol-4-yl)-ethoxycarbonyl-methyleneaminooxy]-2-methyl-propionic acid tert-butyl ester. ESI-MS m/z 458 (MH)+. To a slurry of this ester (750 mg, 1.64 mmol) in EtOH (4.5 mL) was added 3.5 mL 1N NaOH and the reaction stirred overnight. An additional aliquot (1 mL) of 1N NaOH was added and the reaction stirred for 45 min. The mixture was diluted with water, the ethanol removed in vacuo, and the aqueous solution extracted with Et$_2$O. The aqueous layer was acidified with 1N HCl and extracted with EtOAc (3×). The combined organic layers were washed with water, brine, dried (Na$_2$SO$_4$) and concentrated in vacuo to afford the title compound which was used without purification.

Step 2. Synthesis of (2-tert-Butoxycarbonylamino-thiazol-4-yl)-(1-methyl-1-methylcarbamoyl-ethoxyimino)-acetic Acid Ethyl Ester

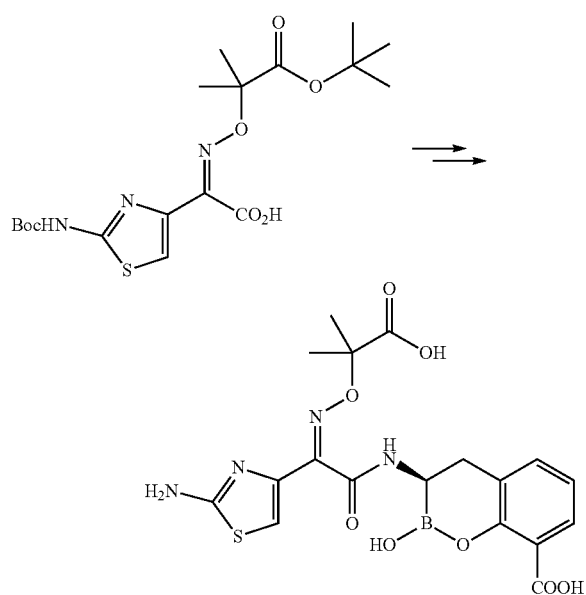

By following the same procedures as described in Step 4 and Step 5 of Example 6, with the exception that the crude product was purified by flash column chromatography on C$_{18}$-reverse phase silica gel, the title compound was prepared from the above product. ESI-MS m/z 463 (MH)+.

Example 69: (R,Z)-3-(2-(2-aminothiazol-4-yl)-2-(((2-methyl-1-(methylamino)-1-oxopropan-2-yl)oxy)imino)acetamido)-2-hydroxy-3,4-dihydro-2H-benzo[e][1,2]oxaborinine-8-carboxylic Acid

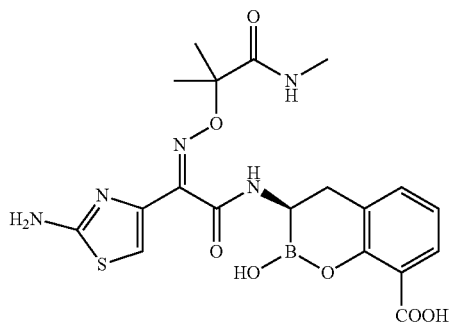 [SMILES: CNC(=O)C(C)(C)O/N=C(\C(=O)N[C@H]1Cc2cccc(C(=O)O)c2OB1O)c1csc(N)n1]

Step 1. Synthesis of 2-bromo-2,N-dimethyl-propionamide

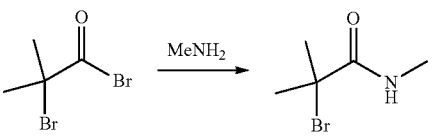

To a solution of methylamine (2 M in THF, 18 mL, 36 mmol) in DCM (36 mL) at 0° C. was added 2-bromo-2-methyl-propionyl bromide (2 mL, 16.2 mmol). The mixture was stirred at 0° C. for 5 min then at ambient temperature for 30 min. The mixture was diluted with EtOAc and washed with 1N HCl, 5% NaHCO$_3$, water, brine, dried (Na$_2$SO$_4$) and concentrated in vacuo. The residue was triturated with hexane to afford the title compound as a white solid.

Step 2. Synthesis of 2-(1,3-Dioxo-1,3-dihydro-isoindol-2-yloxy)-2,N-dimethyl-propionamide

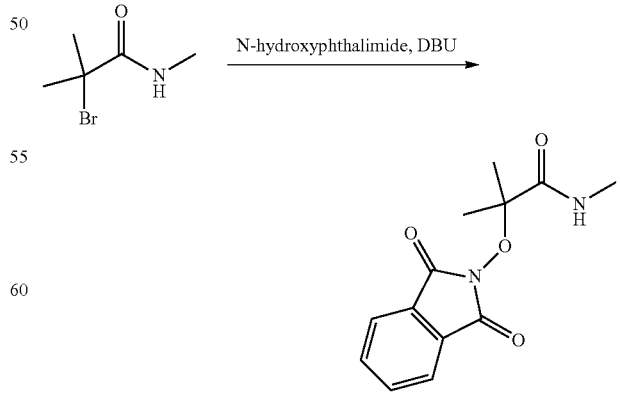

A mixture of 2-bromo-2,N-dimethyl-propionamide (1.0 g, 5.56 mmol), N-hydroxyphthalimide (1.17 g, 7.18 mmol), DBU (1.1 mL, 7.92 mmol) in acetonitrile (18 mL) and DMF (5 mL) was stirred at 50° C. for 5 h, then at ambient temperature for 24 h. The acetonitrile was removed in vacuo, the mixture diluted with EtOAc and the solution washed with 0.1N HCl, 5% Na₂CO₃, water, brine, dried (Na₂SO₄) and concentrated in vacuo to afford an off-white solid which was used without purification.

Step 3. Synthesis of 2-aminooxy-2,N-dimethyl-propionamide

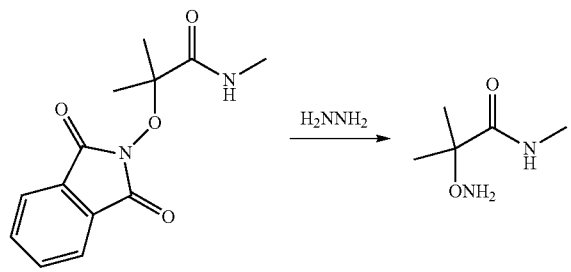

To a solution of 2-(1,3-dioxo-1,3-dihydro-isoindol-2-yloxy)-2,N-dimethyl-propionamide (390 mg, 1.49 mmol) in EtOH (7 mL) was added hydrazine hydrate (80%, 180 uL). After 5 min EtOH (7 mL) was added and the mixture allowed to stir 3.25 h. The mixture was diluted with 1/1 EtOAc/Et₂O, filtered, and the solids washed with 2/1 Et₂O/EtOAc. The filtrate was concentrated in vacuo, EtOAc was added and the solution filtered. The filtrate was concentrated in vacuo to afford a cloudy oil which was used without further purification.

Step 4. Synthesis of (2-tert-Butoxycarbonylamino-thiazol-4-yl)-(1-methyl-1-methylcarbamoyl-ethoxy-imino)-acetic Acid Ethyl Ester

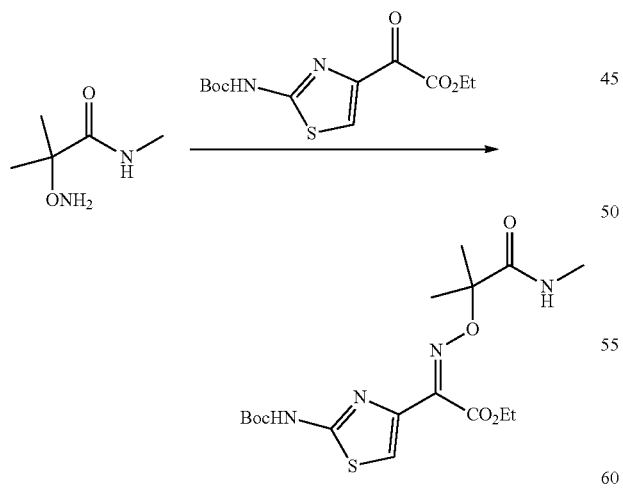

A solution of 2-aminooxy-2,N-dimethyl-propionamide (1.49 mmol), (2-tert-Butoxycarbonylamino-thiazol-4-yl)-oxo-acetic acid ethyl ester (445 mg, 1.48 mmol), acetic acid (89 uL, 1.46 mmol) and EtOH (6 mL) was heated to 60° C. until complete reaction was observed by HPLC. The solution was cooled and concentrated in vacuo. The residue was purified by flash chromatography using a gradient of 25% to 60% EtOAc/hexanes to afford the title compound.

Step 5. Synthesis of (R,Z)-3-(2-(2-aminothiazol-4-yl)-2-(((2-methyl-1-(methylamino)-1-oxopropan-2-yl)oxy)imino)acetamido)-2-hydroxy-3,4-dihydro-2H-benzo[e][1,2]oxaborinine-8-carboxylic Acid

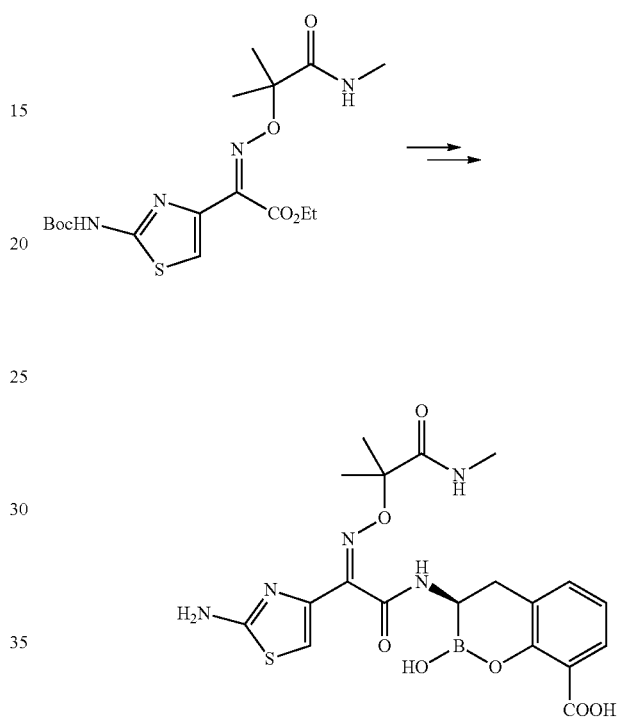

Saponification of (2-tert-butoxycarbonylamino-thiazol-4-yl)-(1-methyl-1-methylcarbamoyl-ethoxyimino)-acetic acid ethyl ester and conversion to the title compound was performed in a similar manner to Step 1 and Step 2 of Example 68. ESI-MS m/z 476 (MH)⁺

Example 70: (3R)-3-((Z)-2-(2-aminothiazol-4-yl)-2-(((1-(methylamino)-1-oxopropan-2-yl)oxy)imino)acetamido)-2-hydroxy-3,4-dihydro-2H-benzo[e][1,2]oxaborinine-8-carboxylic Acid

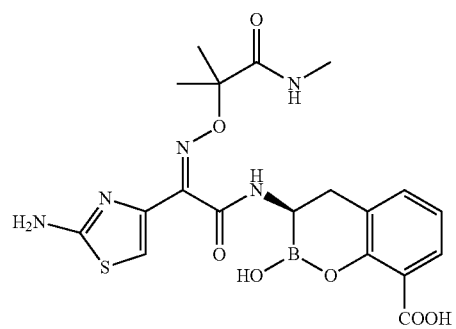 [SMILES: CNC(=O)C(C)(C)O/N=C(\C(=O)N[C@H]1Cc2cccc(C(=O)O)c2OB1O)c1csc(N)n1]

Step 1. Synthesis of 2-(1,3-dioxo-1,3-dihydro-isoindol-2-yloxy)-N-methyl-propionamide

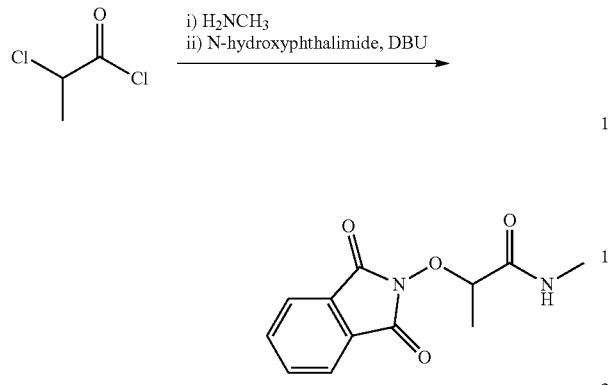

The title compound was prepared from 2-chloropropionyl chloride in a similar manner to Step 1 and Step 2 of Example 69.

Step 2. Synthesis of 2-aminooxy-N-methyl-propionamide hydrochloride

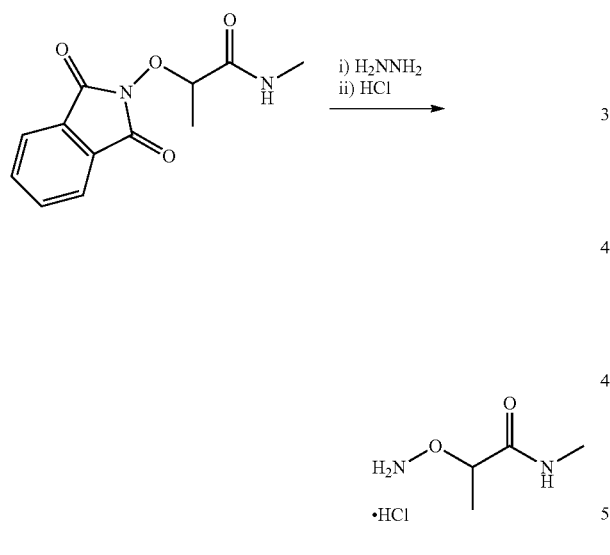

To a slurry of 2-(1,3-dioxo-1,3-dihydro-isoindol-2-yloxy)-N-methyl-propionamide (2.01 g, 8.10 mmol) in a 55 mL/5 mL/5 mL mixture of EtOH/MeOH/DCM was added hydrazine hydrate (80%, 0.97 mL). After 5 min EtOH (55 mL) was added and the solution stirred for 1 h. The mixture was filtered, the solids washed with EtOAc and the filtrate concentrated. To the residue was added 2/1 $Et_2O$/EtOAc, the mixture filtered and the solids washed with 3/1 DCM/$Et_2O$. The filtrate was diluted with EtOAc and 4 mL of 4 N HCl/dioxane was added resulting in very tacky solids. The mother liquor was decanted, and the solids triturated successively with EtOAc, $Et_2O$ and hexanes. To the still tacky material was added toluene and the solution concentrated in vacuo to afford the title compound as a slightly sticky yellow solid which was used without further purification.

Step 3. Synthesis of (2-tert-butoxycarbonylamino-thiazol-4-yl)-(1-methylcarbamoyl-ethoxyimino)-acetic Acid

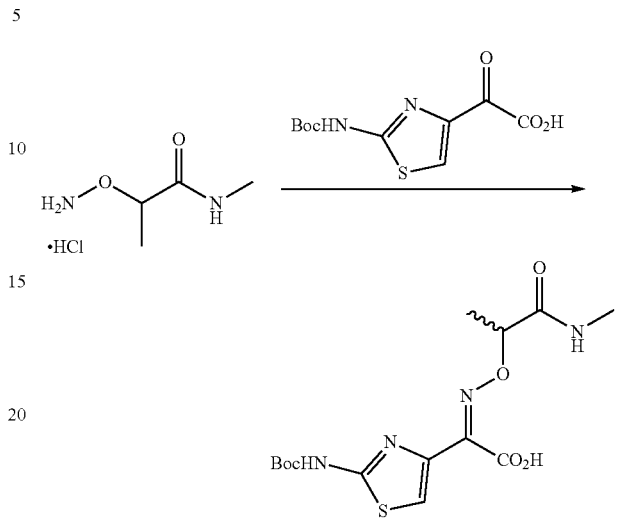

A solution containing (2-tert-butoxycarbonylamino-thiazol-4-yl)-oxo-acetic acid (386 mg, 1.42 mmol), 2-aminooxy-N-methyl-propionamide hydrochloride (221 mg, 1.43 mmol), sodium acetate (117 mg, 1.43 mmol) and MeOH (7 mL) was stirred for 2.5 h at room temperature. The mixture was concentrated in vacuo and the residue triturated successively with $Et_2O$ and hexane to afford a pale yellow solid which was used without further purification. ESI-MS m/z 373 (MH)⁺.

Step 4. Synthesis of (3R)-3-((Z)-2-(2-aminothiazol-4-yl)-2-(((1-(methylamino)-1-oxopropan-2-yl)oxy)imino)acetamido)-2-hydroxy-3,4-dihydro-2H-benzo[e][1,2]oxaborinine-8-carboxylic Acid

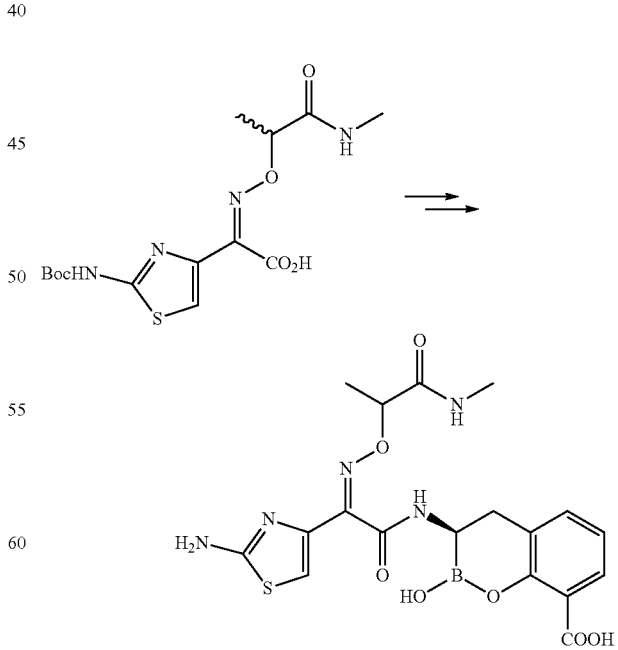

The title compound was prepared from the above compound following the same procedures as described in Step 4 and Step 5 of Example 6 with the exception that the crude product was purified by flash column chromatography on $C_{18}$-reverse phase silica gel. ESI-MS m/z 462 (MH)+.

Example 71: (3R)-3-((Z)-2-(2-aminothiazol-4-yl)-2-((1-carboxyethoxy)imino)acetamido)-2-hydroxy-3,4-dihydro-2H-benzo[e][1,2]oxaborinine-8-carboxylic Acid

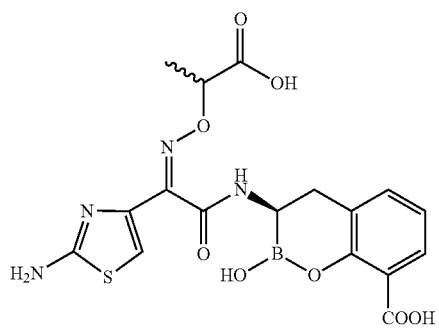 [SMILES: CC(O/N=C(\C(=O)N[C@H]1Cc2cccc(C(=O)O)c2OB1O)c1csc(N)n1)C(=O)O]

Step 1. Synthesis of 2-(1,3-dioxo-1,3-dihydro-isoindol-2-yloxy)-propionic Acid tert-butyl Ester

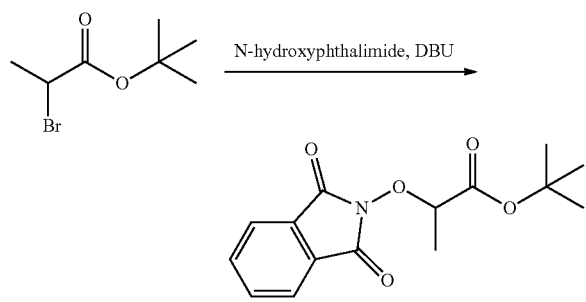

The title compound was prepared from 2-bromo-propionic acid tert-butyl ester in a manner similar to Step 2 of Example 69.

Step 2. Synthesis of 2-aminooxy-propionic Acid tert-butyl Ester

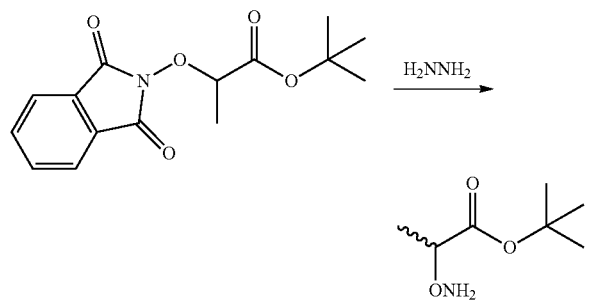

To a solution of 2-(1,3-dioxo-1,3-dihydro-isoindol-2-yloxy)-propionic acid tert-butyl ester (1.8 g, 6.19 mmol) in 40 mL EtOH/3 mL DCM was added hydrazine hydrate (80%, 750 μL). After stirring for 5 min 50 mL of EtOH was added and the reaction stirred an additional 19 h. The mixture was filtered, the solids washed with EtOAc, and the filtrate concentrated in vacuo. The residue was purified by flash chromatography using a gradient of 15% to 30% EtOAc/hexane.

Step 3. Synthesis of (2-tert-butoxycarbonylamino-thiazol-4-yl)-(1-methyl-2-oxo-butoxyimino)-acetic Acid

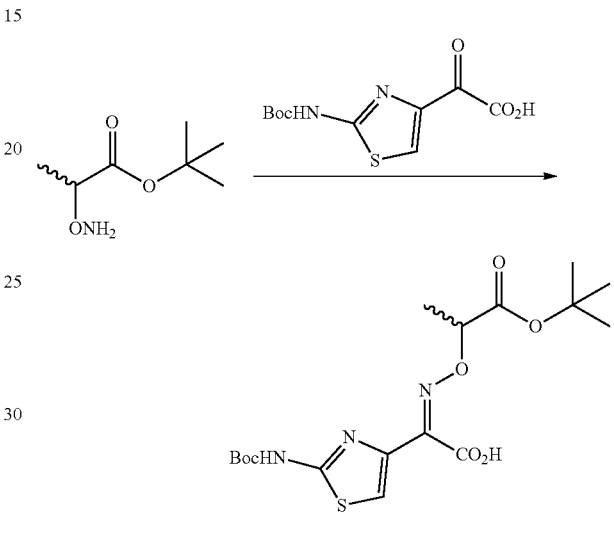

A solution containing 2-aminooxy-propionic acid tert-butyl ester (296 mg, 1.84 mmol), (2-tert-butoxycarbonylamino-thiazol-4-yl)-oxo-acetic acid (499 mg, 1.84 mmol) and MeOH (8 mL) was stirred for 2 h. An additional aliquot (10 mg) of keto acid was added and the reaction allowed to proceed an additional 10 min. The mixture was concentrated in vacuo, EtOAc was added and the solution concentrated in vacuo to afford the title compound as a colorless foam, which was used without further purification. ESI-MS m/z 416 (MH)+.

Step 4. Synthesis of (3R)-3-((Z)-2-(2-aminothiazol-4-yl)-2-(((1-(methylamino)-1-oxopropan-2-yl)oxy)imino)acetamido)-2-hydroxy-3,4-dihydro-2H-benzo[e][1,2]oxaborinine-8-carboxylic Acid

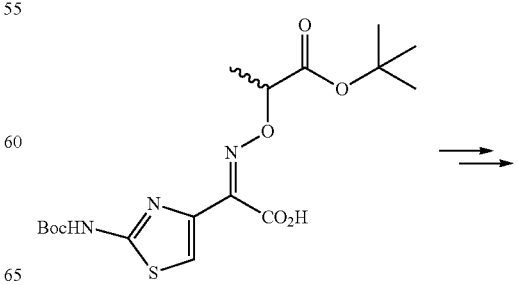

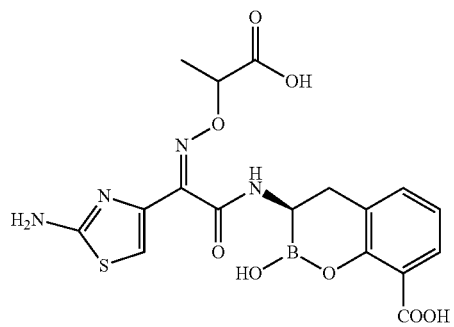

The title compound was prepared from the above compound following the same procedures as described in Step 4 and Step 5 of Example 6 with the exception that the crude product was purified by flash column chromatography on $C_{18}$-reverse phase silica gel. ESI-MS m/z 449 (MH)$^+$.

Example 72: (R,Z)-3-(2-(((1-amino-2-methyl-1-oxopropan-2-yl)oxy)imino)-2-(2-aminothiazol-4-yl)acetamido)-2-hydroxy-3,4-dihydro-2H-benzo[e][1,2]oxaborinine-8-carboxylic Acid

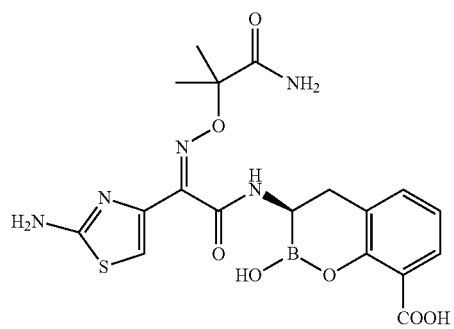

Step 1. Synthesis of 2-(1,3-dioxo-1,3-dihydro-isoindol-2-yloxy)-2-methyl-propionamide

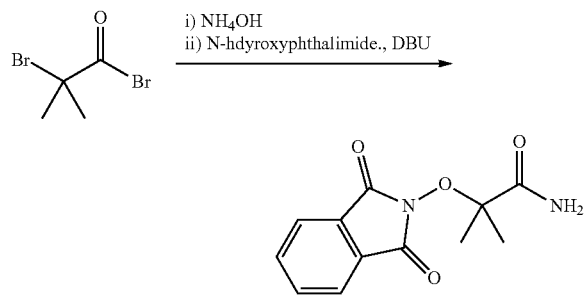

The title compound was prepared from ammonium hydroxide in a similar manner to Step 1 and Step 2 of Example 69.

Step 2. Synthesis of 2-aminooxy-2-methyl-propionamide

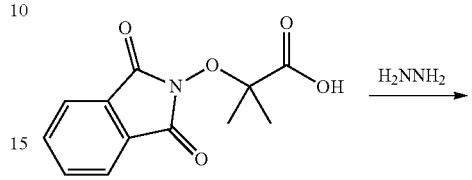

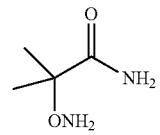

The title compound was prepared in a similar manner to Step 2 of Example 71. The crude product was purified by flash chromatography using a gradient of 20% acetonitrile/DCM to 100% acetonitrile. ESI-MS m/z 119 (MH)$^+$.

Step 3. Synthesis of (R,Z)-3-(2-(((1-amino-2-methyl-1-oxopropan-2-yl)oxy)imino)-2-(2-aminothiazol-4-yl)acetamido)-2-hydroxy-3,4-dihydro-2H-benzo[e][1,2]oxaborinine-8-carboxylic Acid

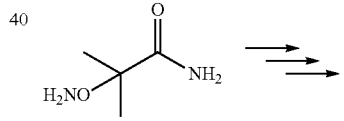

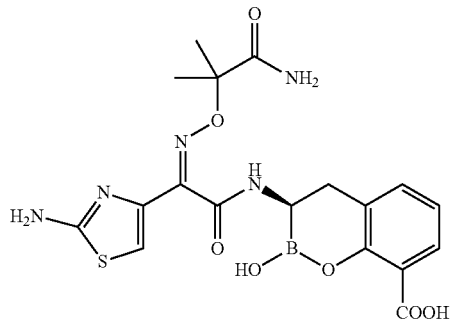 [SMILES: CC(C)(O/N=C(\C(=O)N[C@H]1Cc2cccc(C(=O)O)c2OB1O)c1csc(N)n1)C(N)=O]

The title compound was prepared from the above compound following the same procedures as described in Step 3 and Step 4 of Example 71. ESI-MS m/z 462 (MH)$^+$.

Example 73: (3R)-3-((Z)-2-(((1-amino-1-oxopropan-2-yl)oxy)imino)-2-(2-aminothiazol-4-yl)acetamido)-2-hydroxy-3,4-dihydro-2H-benzo[e][1,2]oxaborinine-8-carboxylic Acid

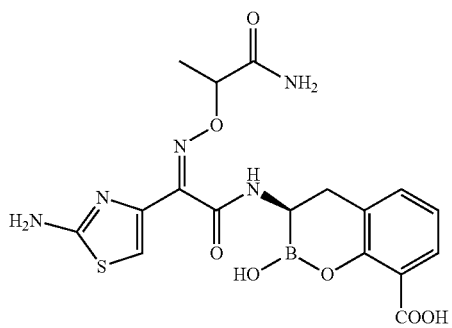 [SMILES: CC(O/N=C(\C(=O)N[C@H]1Cc2cccc(C(=O)O)c2OB1O)c1csc(N)n1)C(N)=O]

Step 1. Synthesis of 2-(1,3-dioxo-1,3-dihydro-isoindol-2-yloxy)-propionamide

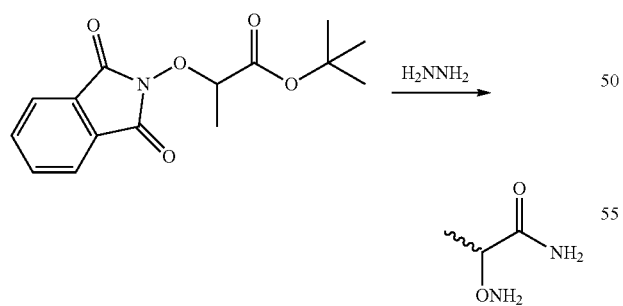

The title compound was prepared from ammonium hydroxide in a similar manner to Step 1 of Example 70.

Step 2. Synthesis of 2-aminooxy-propionamide

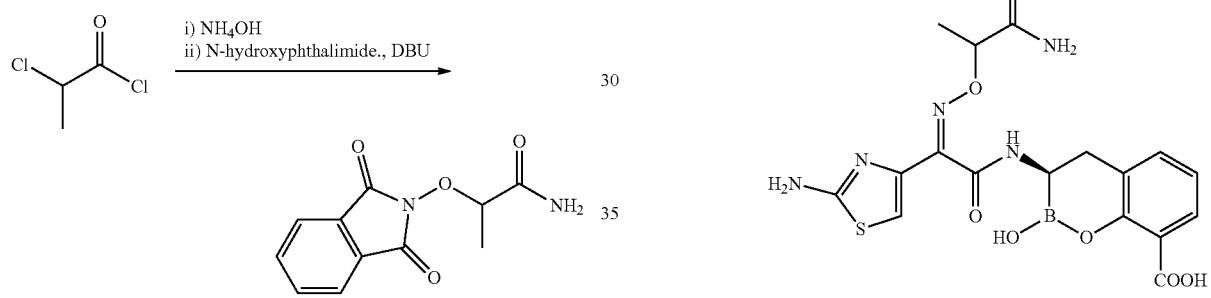

To a mixture of 2-(1,3-dioxo-1,3-dihydro-isoindol-2-yloxy)-propionamide (1.30 g. 5.55 mmol) in EtOH (35 mL) was added hydrazine hydrate (80%, 660 uL). After 5 min an additional 35 mL of EtOH was added and the reaction stirred for 3 h. The mixture was filtered, the solids washed with EtOAc and the filtrate concentrated in vacuo. To the residue was added EtOAc and the resultant solid collected by filtration, washed EtOAc then Et$_2$O and dried in vacuo to afford the title compound, which was used without purification.

Step 3. Synthesis of (R,Z)-3-(2-(((1-amino-2-methyl-1-oxopropan-2-yl)oxy)imino)-2-(2-aminothiazol-4-yl)acetamido)-2-hydroxy-3,4-dihydro-2H-benzo[e][1,2]oxaborinine-8-carboxylic Acid

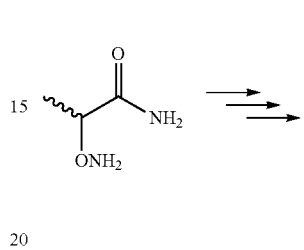

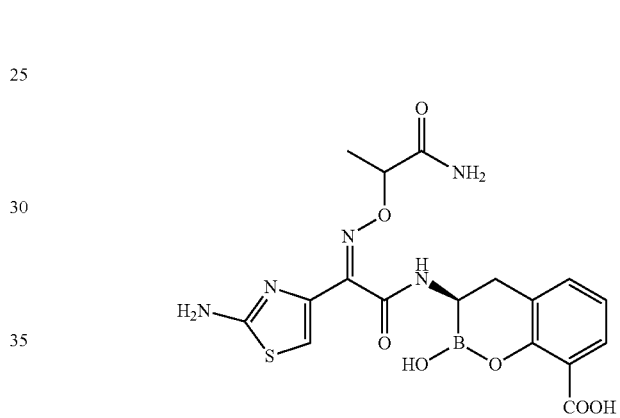

The title compound was prepared from the above compound following the same procedures as described in Step 3 and Step 4 of Example 71. ESI-MS m/z 448 (MH)$^+$.

Example 74: (R)-3-((Z)-2-(2-aminothiazol-4-yl)-2-(((1-(((S)-1-carboxy-2-hydroxyethyl)amino)-2-methyl-1-oxopropan-2-yl)oxy)imino)acetamido)-2-hydroxy-3,4-dihydro-2H-benzo[e][1,2]oxaborinine-8-carboxylic Acid

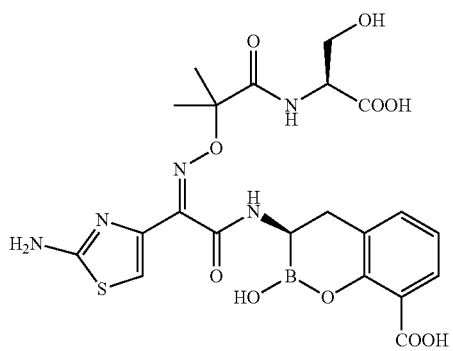 [SMILES: CC(C)(O/N=C(\C(=O)N[C@H]1Cc2cccc(C(=O)O)c2OB1O)c1csc(N)n1)C(=O)N[C@@H](CO)C(=O)O]

Step 1. Synthesis of (S)-2-(2-bromo-2-methyl-propionylamino)-3-tert-butoxy-propionic Acid tert-butyl Ester

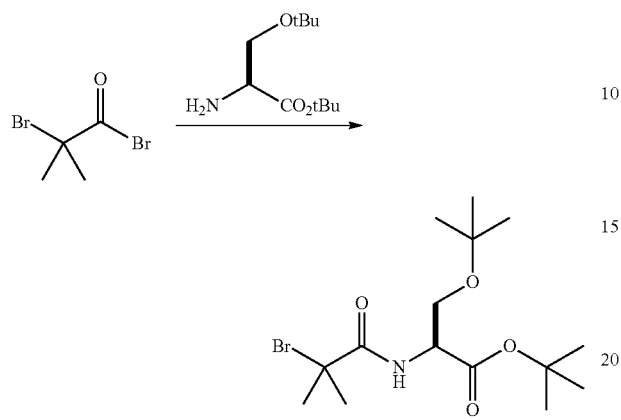

To a solution of 2-amino-3-tert-butoxy-propionic acid tert-butyl ester (3.0 g, 13.81 mmol) in DCM (55 mL) at 0° C. was added NMM (1.7 mL, 15.4 mmol) followed by 2-bromo-2-methylpropionyl bromide (1.7 mL, 13.75 mmol). The cooling bath was removed and the reaction was stirred for 1 h, quenched with 1 N HCl and extracted with EtOAc (3×). The combined organic layers were washed with 5% NaHCO$_3$, water, brine, dried (Na$_2$SO$_4$) and concentrated in vacuo to afford a slowly crystallizing solid, which was used without purification.

Step 2. Synthesis of (S)-3-tert-Butoxy-2-[2-(1,3-dioxo-1,3-dihydro-isoindol-2-yloxy)-2-methyl-propionylamino]-propionic Acid tert-butyl Ester

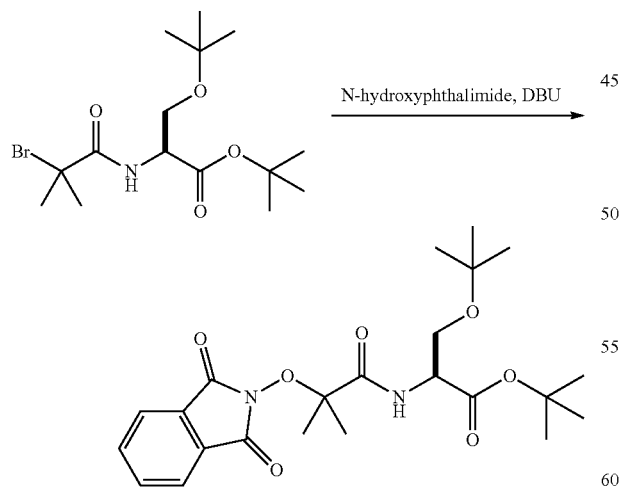

The title compound was prepared from the above compound in a manner similar to Step 2 of Example 69 with the exception that the crude product was purified by flash chromatography using a gradient of 15% to 50% EtOAc/hexanes.

Step 3. Synthesis of (R)-3-((Z)-2-(2-aminothiazol-4-yl)-2-(((1-(((S)-1-carboxy-2-hydroxyethyl)amino)-2-methyl-1-oxopropan-2-yl)oxy)imino)acetamido)-2-hydroxy-3,4-dihydro-2H-benzo[e][1,2]oxaborinine-8-carboxylic Acid

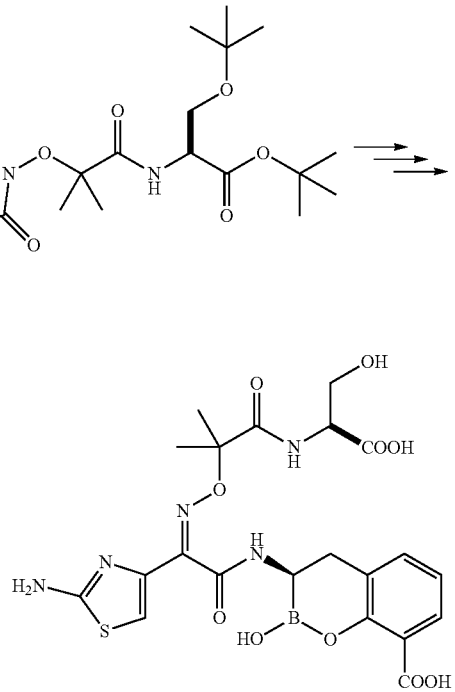

The title compound was prepared from the above compound following the same procedures as described in Step 2 and Step 3 of Example 72. ESI-MS m/z 550 (MH)$^+$.

Example 75: (R,Z)-3-(2-(2-aminothiazol-4-yl)-2-(((1-((carboxymethyl)amino)-2-methyl-1-oxopropan-2-yl)oxy)imino)acetamido)-2-hydroxy-3,4-dihydro-2H-benzo[e][1,2]oxaborinine-8-carboxylic Acid

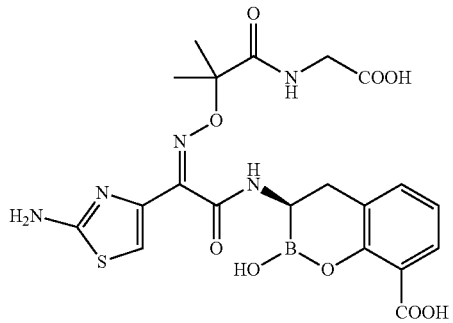 [SMILES: CC(C)(O/N=C(\C(=O)N[C@H]1Cc2cccc(C(=O)O)c2OB1O)c1csc(N)n1)C(=O)NCC(=O)O]

The title compound was prepared from glycine benzyl ester hydrochloride in a similar manner to the synthesis of Example 74 with the exception that BBr$_3$ was used in the final deprotection step. ESI-MS m/z 520 (MH)$^+$.

Example 76: (3R)-3-((Z)-2-(2-aminothiazol-4-yl)-2-((2,3-dihydroxypropoxy)imino)acetamido)-2-hydroxy-3,4-dihydro-2H-benzo[e][1,2]oxaborinine-8-carboxylic Acid

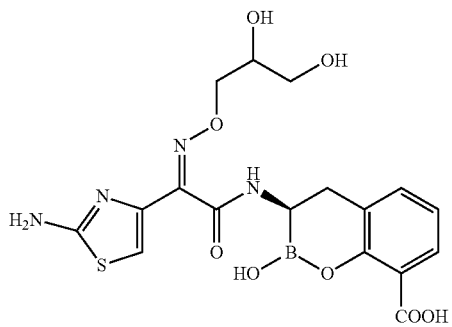 [SMILES: Nc1nc(/C(=N/OCC(O)CO)C(=O)N[C@H]2Cc3cccc(C(=O)O)c3OB2O)cs1]

Step 1. Synthesis of 2-(2,2-dimethyl-[1,3]dioxolan-4-ylmethoxy)-isoindole-1,3-dione

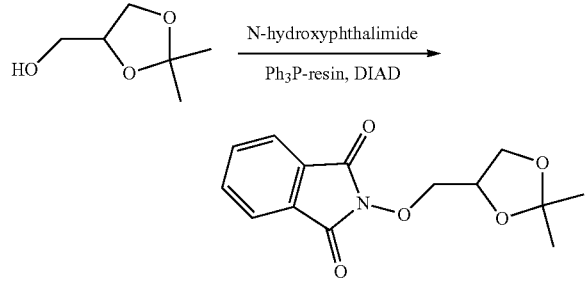

To a mixture of (2,2-dimethyl-[1,3]dioxolan-4-yl)-methanol (1.6 mL, 12.5 mmol), N-hydroxyphthalimide (2.45 g, 15 mmol), resin bound triphenylphosphine (100-200 mesh, ~3 mmol/g, 5 g, 15 mmol), and DCM (50 mL) was added DIAD (2.9 mL, 15 mmol). The reaction was stirred for 1 h, filtered through Celite®, washed with DCM and the filtrate concentrated. The crude product was purified by flash chromatography using a gradient of 15% to 35% EtOAc/hexane to afford an impure product which was used in the next step.

Step 2. Synthesis of (3R)-3-((Z)-2-(2-aminothiazol-4-yl)-2-((2,3-dihydroxypropoxy)imino)acetamido)-2-hydroxy-3,4-dihydro-2H-benzo[e][1,2]oxaborinine-8-carboxylic Acid

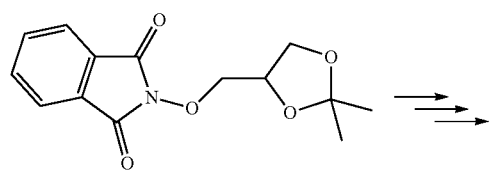

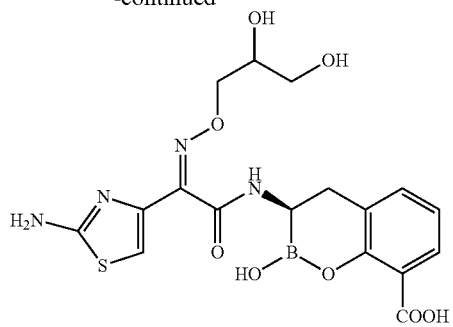

The title compound was prepared from the above compound following the same procedures as described in Step 2 and Step 3 of Example 72. ESI-MS m/z 451 (MH)+.

Example 77: (2-((((Z)-1-(2-aminothiazol-4-yl)-2-(((R)-8-carboxy-2-hydroxy-3,4-dihydro-2H-benzo[e][1,2]oxaborinin-3-yl)amino)-2-oxoethylidene)amino)oxy)-2-methylpropanoyl)-L-glutamic Acid

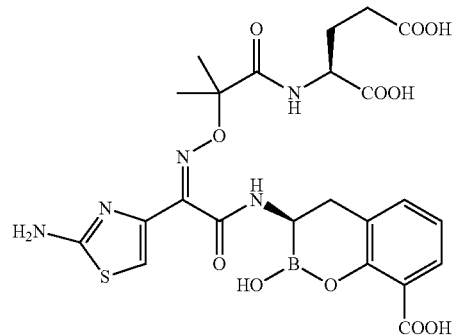 [SMILES: CC(C)(O/N=C(\C(=O)N[C@H]1Cc2cccc(C(=O)O)c2OB1O)c1csc(N)n1)C(=O)N[C@@H](CCC(=O)O)C(=O)O]

The title compound was prepared from 2-amino-pentanedioic acid di-tert-butyl ester hydrochloride in a similar manner to the synthesis of Example 74. ESI-MS m/z 592 (MH)+.

Example 78: (R,Z)-3-(2-(2-aminothiazol-4-yl)-15-bromo-6,14-dioxo-4-oxa-3,7,13-triazapentadec-2-enamido)-2-hydroxy-3,4-dihydro-2H-benzo[e][1,2]oxaborinine-8-carboxylic Acid

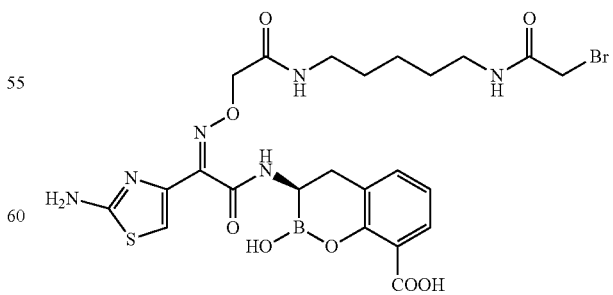

To a solution of (R,Z)-3-(2-((2-((5-aminopentyl)amino)-2-oxoethoxy)imino)-2-(2-aminothiazol-4-yl)acetamido)-2-hydroxy-3,4-dihydro-2H-benzo[e][1,2]oxaborinine-8-carboxylic acid (prepared as described in Example 67, ca. 20 mg) in 500 μL DMF containing 100 μL water was added NaHCO₃. This mixture was stirred for 5 min then 2-bromoacetic acid NHS ester (ca 10 mg) was added and the mixture stirred for 2 h. Water was added, the mixture stirred for 5 min then extracted with 3×Et₂O. The combined organic layers were washed with 90/10 water/methanol. All the aqueous layers were combined, back-extracted with EtOAc, and the product isolated by subjecting the aqueous layer to C₁₈reverse-phase silica gel chromatography, eluting with a gradient of 10% H₂O to 30% IPA/H₂O. The product was dried via lyophilization. ESI-MS m/z 639, 641 (MH, (M+2)H)⁺.

Example 79: (R,Z)-3-(2-(2-aminothiazol-4-yl)-2-(((2-carboxypropan-2-yl)oxy)imino)acetamido)-2-hydroxy-6-methoxy-3,4-dihydro-2H-benzo[e][1,2]oxaborinine-8-carboxylic Acid

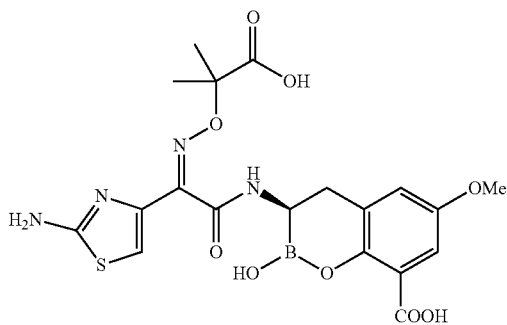

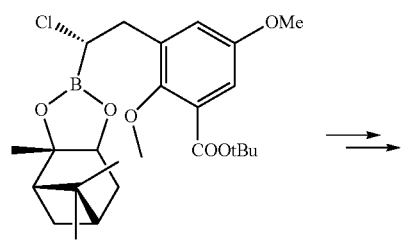

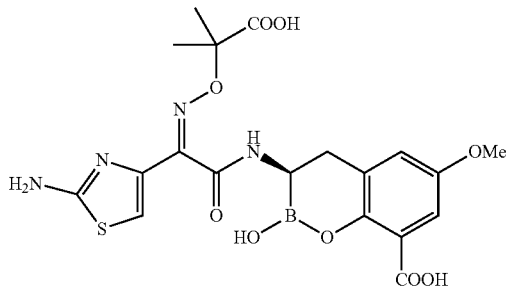

In a similar manner to the synthesis of Example 68, the title compound was prepared from the dimethoxy substituted chloride intermediate synthesized in the preparation of Example 42. ESI-MS m/z 493 (MH)⁺.

Example 80: (R,Z)-3-(2-(2-aminothiazol-4-yl)-2-(((2-carboxypropan-2-yl)oxy)imino)acetamido)-2,6-dihydroxy-3,4-dihydro-2H-benzo[e][1,2]oxaborinine-8-carboxylic Acid

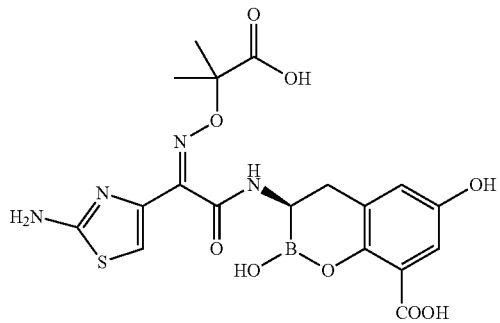 [SMILES: CC(C)(O/N=C(\C(=O)N[C@H]1Cc2cc(O)cc(C(=O)O)c2OB1O)c1csc(N)n1)C(=O)O]

In a similar manner to the synthesis of Example 79, and using BBr₃ instead of BCl₃ for the last deprotection step, the title compound was prepared. ESI-MS m/z 479 (MH)⁺.

Example 81: (R,Z)-3-(2-(((1-amino-2-methyl-1-oxopropan-2-yl)oxy)imino)-2-(2-aminothiazol-4-yl)acetamido)-2-hydroxy-6-methoxy-3,4-dihydro-2H-benzo[e][1,2]oxaborinine-8-carboxylic Acid

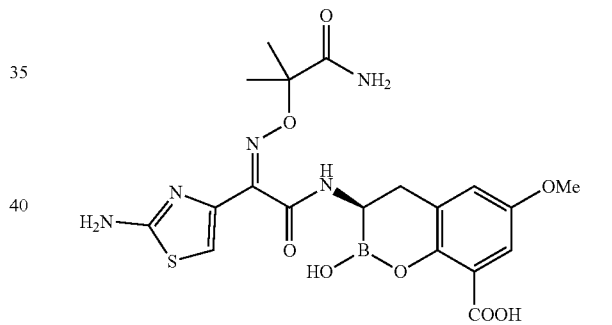

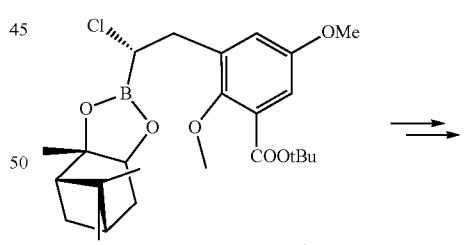

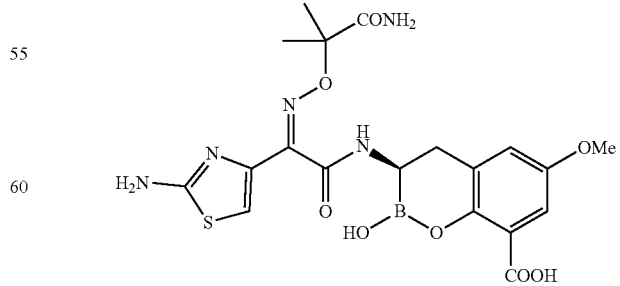

In a similar manner to the synthesis of Example 72, and using AlCl₃ for the last deprotection step, the title compound was prepared from the dimethoxy substituted chloride intermediate synthesized in the preparation of Example 42. ESI-MS m/z 492 (MH)+.

Example 82: (R,Z)-3-(2-(((1-amino-2-methyl-1-oxopropan-2-yl)oxy)imino)-2-(2-aminothiazol-4-yl)acetamido)-2,6-dihydroxy-3,4-dihydro-2H-benzo[e][1,2]oxaborinine-8-carboxylic Acid

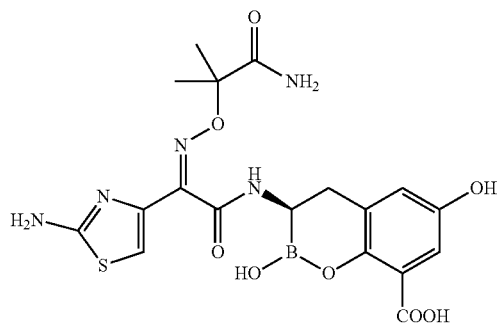

In a similar manner to the synthesis of Example 81, and using BBr₃ instead of AlCl₃ for the last deprotection step, the title compound was prepared. ESI-MS m/z 478 (MH)+.

Example 83: (R,Z)-2-hydroxy-3-(2-(hydroxyimino)-2-phenylacetamido)-3,4-dihydro-2H-benzo[e][1,2]oxaborinine-8-carboxylic Acid

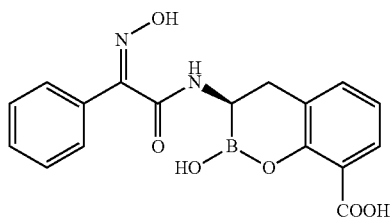

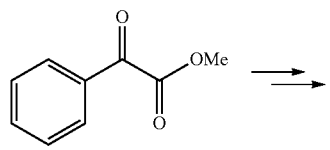

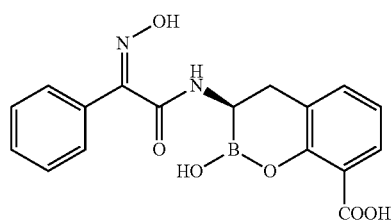

In a similar manner to the synthesis of Example 6, the title compound was prepared from methyl benzoylformate. ESI-MS m/z 355 (MH)+.

Example 84: (R)-3-(2-(2-aminothiazol-4-yl)-5-carboxypent-2-enamido)-2-hydroxy-3,4-dihydro-2H-benzo[e][1,2]oxaborinine-8-carboxylic Acid

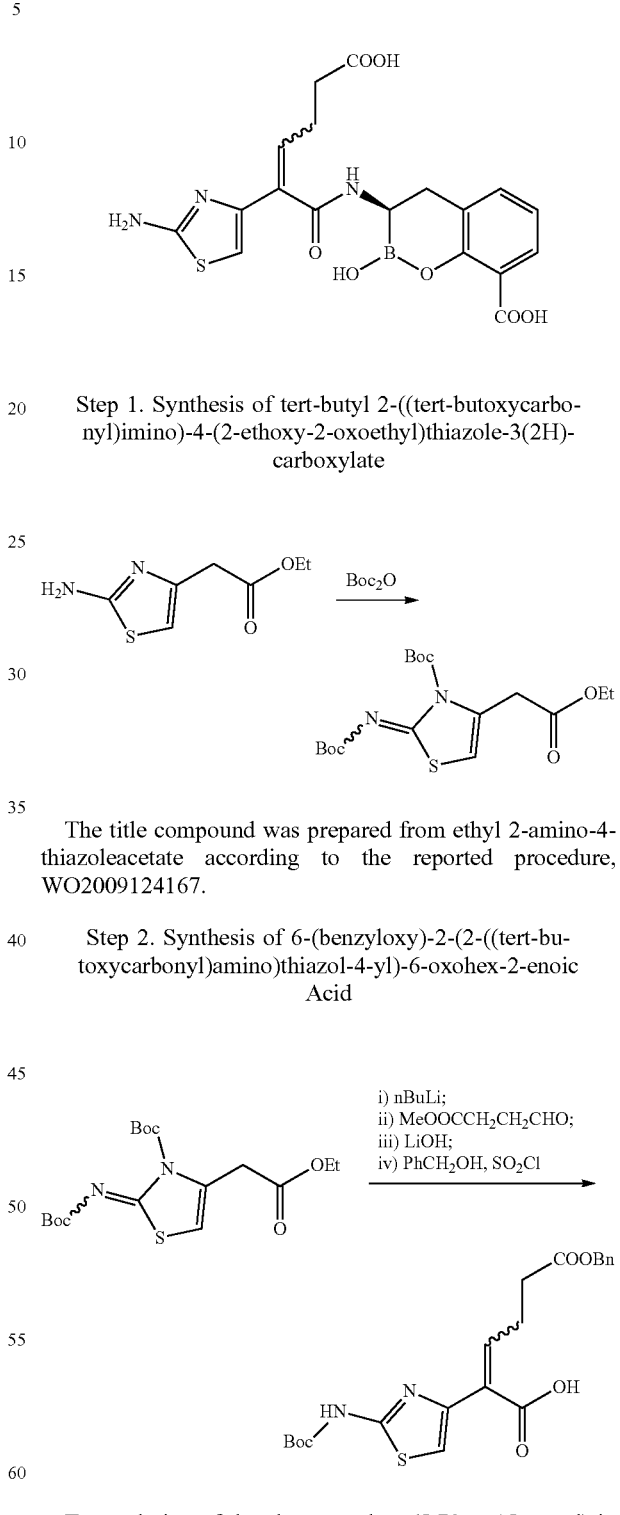

Step 1. Synthesis of tert-butyl 2-((tert-butoxycarbonyl)imino)-4-(2-ethoxy-2-oxoethyl)thiazole-3(2H)-carboxylate The title compound was prepared from ethyl 2-amino-4-thiazoleacetate according to the reported procedure, WO2009124167.

Step 2. Synthesis of 6-(benzyloxy)-2-(2-((tert-butoxycarbonyl)amino)thiazol-4-yl)-6-oxohex-2-enoic Acid To a solution of the above product (5.79 g, 15 mmol) in anhydrous THF (60 mL) was added at −65° C. under argon nBuLi (2.5 M, 6.6 mL, 16.5 mmol) dropwise (addition: 4 min, then stirred for 8 min) followed by methyl 4-oxobutanoate (2.58 g, 90% pure, 20 mmol) in THF (5 mL). The reaction mixture was stirred between −65-0° C. for 1.5 h, RT overnight. To the reaction mixture was added 10% aqueous citric acid solution (30 mL), stirred at RT for 6 h, then added brine, and extracted with EtOAc. The combined organic extract was dried over Na$_2$SO$_4$, and concentrated to give the crude product.

The above crude product was dissolved in THF (150 mL) and water (150 mL), treated with LiOH.H$_2$O (5.04 g, 120 mmol) at RT for 2 days, then acidified with 1 N HCl to pH ~3-4, extracted with DCM. The organic extracts were dried over Na$_2$SO$_4$, concentrated to give the crude diacid product, 4.62 g. ESI-MS m/z 343 (MH)$^+$.

To the above crude product (4.55 g, 13.3 mmol) in DCM (120 mL) was added benzyl alcohol (11 mL, 105.6 mmol) followed by thionyl chloride (1.2 mL, 16 mmol). The reaction mixture was stirred at RT for 2.5 h, washed with brine, dried over Na$_2$SO$_4$, and concentrated. The crude product was purified by flash chromatography on silica gel (hexane-DCM-acetone, 10:1:1-1:1:1) to afford the title compound, 2.82 g as a mixture of (Z)- and (E)-isomers. ESI-MS m/z 433 (MH)$^+$.

Step 3. Synthesis of (R)-3-(2-(2-aminothiazol-4-yl)-5-carboxypent-2-enamido)-2-hydroxy-3,4-dihydro-2H-benzo[e][1,2]oxaborinine-8-carboxylic Acid In a similar manner to the synthesis of Example 6, the title compound was prepared from the above acid. ESI-MS m/z 432 (MH)$^+$.

Example 85: (R)-3-(2-(2-aminothiazol-4-yl)-5-hydroxypent-2-enamido)-2-hydroxy-3,4-dihydro-2H-benzo[e][1,2]oxaborinine-8-carboxylic Acid

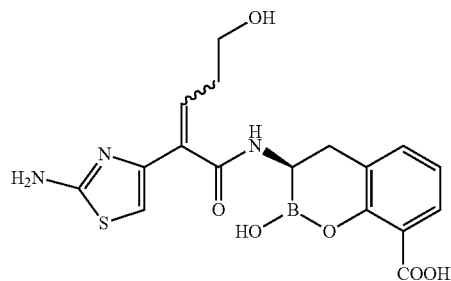 [SMILES: Nc1nc(C(=CCCO)C(=O)N[C@H]2Cc3cccc(C(=O)O)c3OB2O)cs1]

Step 1. Synthesis of tert-butyl (Z)-2-((tert-butoxycarbonyl)imino)-4-(2-ethoxy-2-oxoacetyl)thiazole-3(2H)-carboxylate

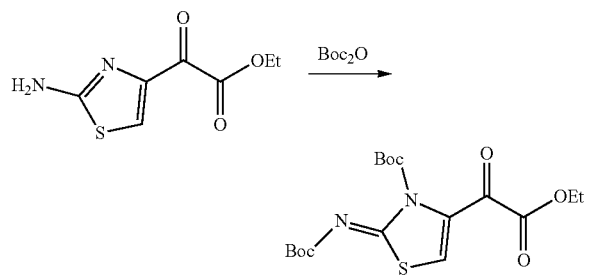

Ethyl 2-(2-amino-4-thiazolyl)-2-oxoacetate (10 g, 50 mmol) in CH$_3$CN (150 mL) was reacted with Boc$_2$O (24 g, 110 mmol) in the presence of iPr$_2$NEt (20 mL, 115 mmol) and 4-DMAP (1.9 g, 15.6 mmol) at RT overnight. The reaction mixture was concentrated, and purified by flash chromatography on silica gel (hexane-EtOAc, 40:1-4:1) to afford the title compound, 5.7 g. ESI-MS m/z 401 (MH)$^+$.

Step 2. Synthesis of tert-butyl (2Z)-4-(5-(benzyloxy)-1-ethoxy-1-oxopent-2-en-2-yl)-2-((tert-butoxycarbonyl)imino)thiazole-3(2H)-carboxylate

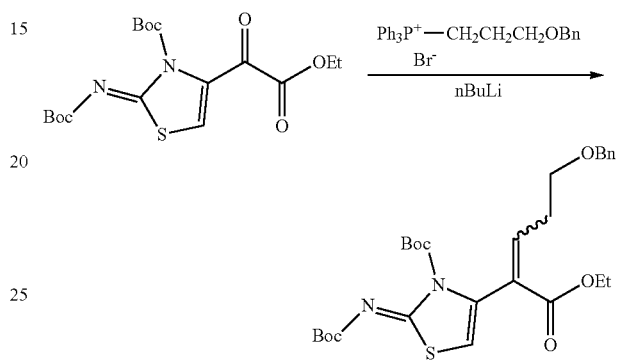

To a solution of (3-(benzyloxy)propyl)triphenylphosphonium bromide (7.4 g, 15 mmol) in THF (100 mL) at −78° C. was added nBuLi (2.5 M, 6.4 mL, 16 mmol) dropwise under argon. The reaction mixture was stirred between −78-−40° C. for 45 min, then a THF (40 mL) solution of the above product (4.9 g, 12.25 mmol) was added dropwise to the reaction mixture, and the resulting reaction mixture was slowly warmed to RT overnight, and quenched with 10% aqueous citric acid solution (20 mL), stirred at RT for 2 h, diluted with water, extracted with EtOAc. The organic extracts were dried over Na$_2$SO$_4$, and concentrated. The crude product was purified by flash chromatography on silica gel (hexane-EtOAc, 40:1-4:1) to afford the title compound, 2.2 g. ESI-MS m/z 533 (MH)$^+$.

Step 3. Synthesis of 5-(benzyloxy)-2-(2-((tert-butoxycarbonyl)amino)thiazol-4-yl)pent-2-enoic Acid

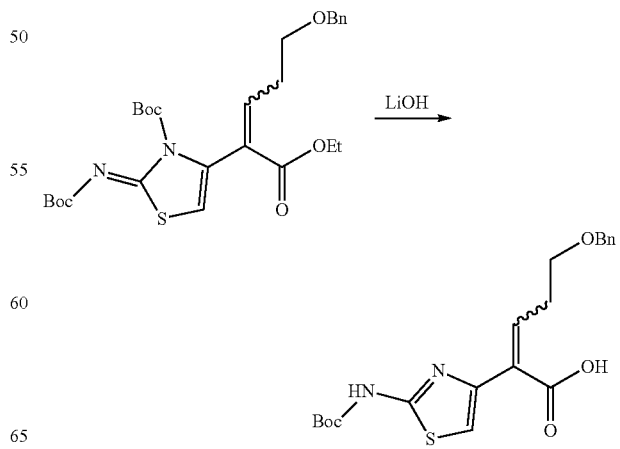

The above product (2.2 g, 4.14 mmol) was dissolved in THF (40 mL) and water (40 mL), treated with LiOH.H$_2$O (840 mg, 20 mmol) at RT for 24 h, concentrated, extracted with diethyl ether. The aqueous was acidified with 1 N HCl to pH ~3-4, extracted with DCM. The organic extracts were dried over Na$_2$SO$_4$, concentrated, purified by flash chromatography on silica gel (hexane-acetone-DCM, 10:1:1-1:1:1) to afford the title compound, 410 mg. ESI-MS m/z 405 (MH)$^+$.

Step 4. Synthesis of (R)-3-(2-(2-aminothiazol-4-yl)-5-hydroxypent-2-enamido)-2-hydroxy-3,4-dihydro-2H-benzo[e][1,2]oxaborinine-8-carboxylic Acid In a similar manner to the synthesis of Example 6, the title compound was prepared from the above acid. ESI-MS m/z 404 (MH)$^+$.

Example 86: (R,E)-3-(2-(2-aminothiazol-4-yl)-3-(pyridin-3-yl)acrylamido)-2-hydroxy-3,4-dihydro-2H-benzo[e][1,2]oxaborinine-8-carboxylic Acid

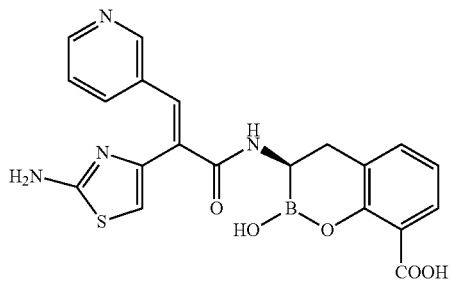 [SMILES: Nc1nc(/C(=C\c2cccnc2)C(=O)N[C@H]2Cc3cccc(C(=O)O)c3OB2O)cs1]

Example 87: (R,Z)-3-(2-(2-aminothiazol-4-yl)-3-(pyridin-3-yl)acrylamido)-2-hydroxy-3,4-dihydro-2H-benzo[e][1,2]oxaborinine-8-carboxylic Acid

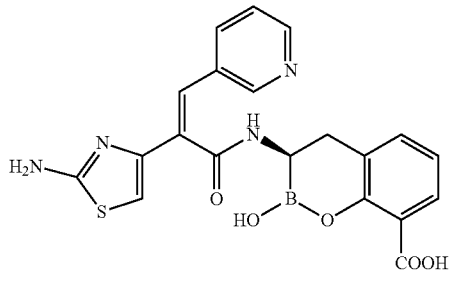 [SMILES: Nc1nc(/C(=C/c2cccnc2)C(=O)N[C@H]2Cc3cccc(C(=O)O)c3OB2O)cs1]

Step 1. Synthesis of ethyl (E)-2-(2-((tert-butoxycarbonyl)amino)thiazol-4-yl)-3-(pyridin-3-yl)acrylate and ethyl (Z)-2-(2-((tert-butoxycarbonyl)amino)thiazol-4-yl)-3-(pyridin-3-yl)acrylate

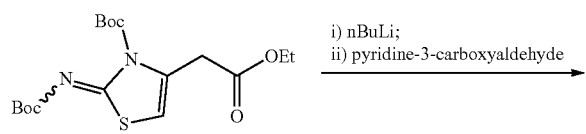

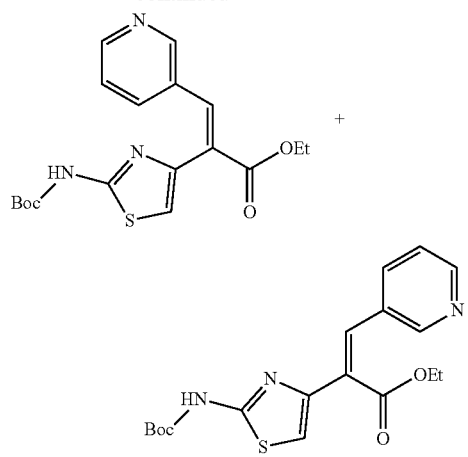

To a solution of tert-butyl 2-((tert-butoxycarbonyl)imino)-4-(2-ethoxy-2-oxoethyl)thiazole-3(2H)-carboxylate (5.79 g, 15 mmol) in anhydrous THF (60 mL) at −65° C. under argon n-BuLi (2.5 M, 6.6 mL, 16.5 mmol) was added dropwise (addition: 4 min, then stirred for 8 min) followed by pyridine-3-carboxaldehyde (1.88 mL, 20 mmol). The reaction mixture was stirred between ~65-0° C. for 1.5 h, RT overnight. To the reaction mixture was added 10% aqueous citric acid solution (18 mL), stirred at RT for 6 h, then added brine, and extracted with EtOAc. The combined organic extracts were dried over Na$_2$SO$_4$, concentrated, and purified by flash chromatography on silica gel (hexane-EtOAc, 20:1-1:1) to yield two isomers, 1.0 g of the minor product (higher spot on TLC) as a solid which was tentatively assigned as (Z)-isomer, and 2.9 g of the major product (lower spot on TLC) which was tentatively assigned as (E)-isomer. ESI-MS m/z 376 (MH)$^+$.

Step 2. Synthesis of (E)-2-(2-((tert-butoxycarbonyl)amino)thiazol-4-yl)-3-(pyridin-3-yl)acrylic Acid and (Z)-2-(2-((tert-butoxycarbonyl)amino)thiazol-4-yl)-3-(pyridin-3-yl)acrylic Acid

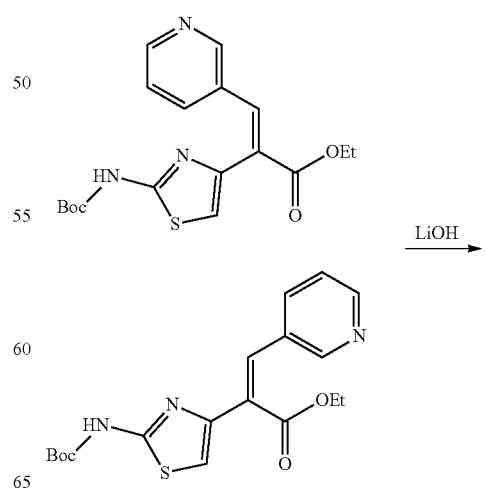

-continued

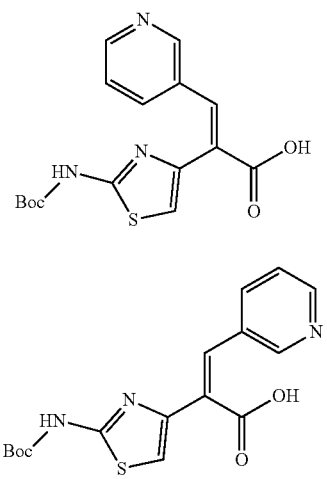

The major product from Step 1 (2.8 g, 7.47 mmol) was dissolved in THF (80 mL) and water (80 mL), hydrolyzed with excess LiOH.H$_2$O (1.6 g, 38 mmol) at RT, the reaction was complete in 1 h (which was hydrolyzed more easily and much faster than the minor product from Step 1, consistent with the E configuration of the double). Standard workup afforded the E acid, 2.4 g. ESI-MS m/z 347 (MH)$^+$.

The minor product from Step 1 (900 mg, 2.4 mmol) was hydrolyzed with excess LiOH.H$_2$O (840 mg, 20 mmol) at RT for 6 days (which was hydrolyzed much slower than the major product from step 1, consistent with the (Z)-configuration of the double bond, see J Antibiotics 1994, 47, 453-465). Standard workup afforded the (Z)-acid, 700 mg. ESI-MS m/z 347 (MH)$^+$.

Step 3. Synthesis of (R,E)-3-(2-(2-aminothiazol-4-yl)-3-(pyridin-3-yl)acrylamido)-2-hydroxy-3,4-dihydro-2H-benzo[e][1,2]oxaborinine-8-carboxylic acid and (R,Z)-3-(2-(2-aminothiazol-4-yl)-3-(pyridin-3-yl)acrylamido)-2-hydroxy-3,4-dihydro-2H-benzo[e][1,2]oxaborinine-8-carboxylic Acid In a similar manner to the synthesis of Example 6, Example 86 and Example 87 were prepared from the above (E)-acid and (Z)-acid respectively. ESI-MS m/z 437 (MH)$^+$.

Example 88: (R,E)-3-(2-(2-aminothiazol-4-yl)-3-carboxyacrylamido)-2-hydroxy-3,4-dihydro-2H-benzo[e][1,2]oxaborinine-8-carboxylic Acid

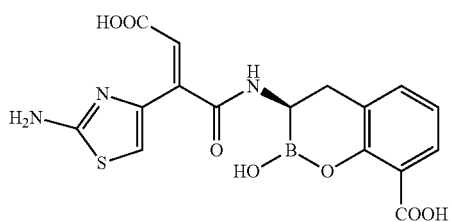 [SMILES: Nc1nc(/C(=C\C(=O)O)C(=O)N[C@H]2Cc3cccc(C(=O)O)c3OB2O)cs1]

Step 1. Synthesis of (E)-4-(tert-butoxy)-2-(2-((tert-butoxycarbonyl)amino)thiazol-4-yl)-4-oxobut-2-enoic acid and 4-(tert-butyl) 1-ethyl 2-(2-((tert-butoxycarbonyl)amino)thiazol-4-yl)maleate

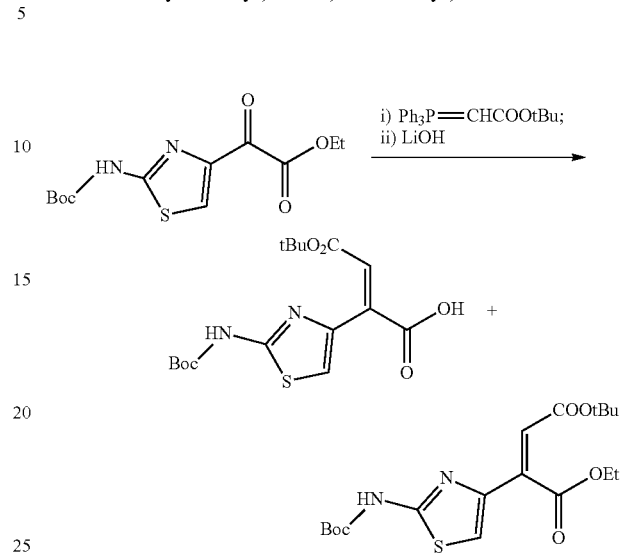

To a solution of ethyl 2-(2-((tert-butoxycarbonyl)amino)thiazol-4-yl)-2-oxoacetate (4.77 g, 15.9 mmol) in DCM (65 mL) was added the Wittig reagent, (tert-butoxycarbonylmethylene)triphenylphosphorane (7.48 g, 19.9 mmol), the reaction mixture was stirred at RT for 24 h, evaporated to dryness. The residue was triturated with diethyl ether, filtered, the solid was washed with diethyl ether. The filtrate and washings were combined, and concentrated to give the crude product as a mixture of (E)- and (E)-isomers, which was used for the next step without further purification. ESI-MS m/z 399 (MH)$^+$.

To the above crude product in THF (20 mL) was added LiOH.H$_2$O (836 mg, 19.9 mmol) in water (20 mL), the reaction mixture was stirred at RT for 4 h, refrigerated overnight, and stirred at RT for an additional 1 h, then evaporated to remove THF. This aqueous solution was extracted with diethyl ether, the ether extracts were combined, and the aqueous was acidified with 1 N HCl to pH ~3-4, extracted with a mixed solvent of EtOAc-DCM (1:4). The combined organic extracts were dried over Na$_2$SO$_4$, concentrated to afford the pure acid, 2.29 g, which was assigned as (E)-isomer (consistently, the ester with (E)-configuration of the double was hydrolyzed much faster than the (Z)-isomer). ESI-MS m/z 371 (MH)$^+$.

The above combined ether extracts were washed with brine, dried over Na$_2$SO$_4$, concentrated, and purified by flash chromatography on silica gel (DCM, then DCM-EtOAC, 30:1-5:1) to recover the unreacted (Z)-ester isomer, 2.67 g. ESI-MS m/z 399 (MH)$^+$.

Step 2. Synthesis of (R,E)-3-(2-(2-aminothiazol-4-yl)-3-carboxyacrylamido)-2-hydroxy-3,4-dihydro-2H-benzo[e][1,2]oxaborinine-8-carboxylic Acid In a similar manner to the synthesis of Example 6, the title compound was prepared from the above (E)-acid isomer. ESI-MS m/z 404 (MH)$^+$.

Example 89: (R,Z)-3-(2-(2-aminothiazol-4-yl)-3-carboxyacrylamido)-2-hydroxy-3,4-dihydro-2H-benzo[e][1,2]oxaborinine-8-carboxylic Acid

Example 90: (R,Z)-2-hydroxy-3-(2-(hydroxyimino)-2-(thiazol-4-yl)acetamido)-3,4-dihydro-2H-benzo[e][1,2]oxaborinine-8-carboxylic Acid

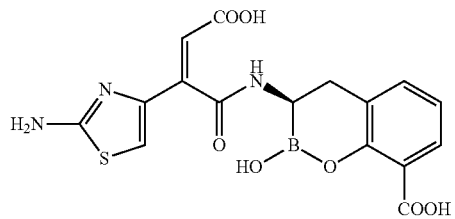 [SMILES: Nc1nc(/C(=C/C(=O)O)C(=O)N[C@H]2Cc3cccc(C(=O)O)c3OB2O)cs1]

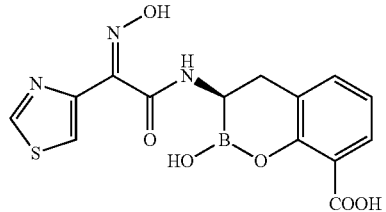 [SMILES: O=C(N[C@H]1Cc2cccc(C(=O)O)c2OB1O)/C(=N\O)c1cscn1]

Step 1. Synthesis of (Z)-4-(tert-butoxy)-2-(2-((tert-butoxycarbonyl)amino)thiazol-4-yl)-4-oxobut-2-enoic Acid

Step 1. Synthesis of ethyl 2-oxo-2-(thiazol-4-yl)acetate

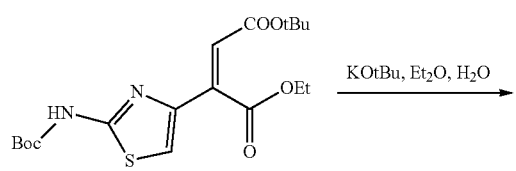

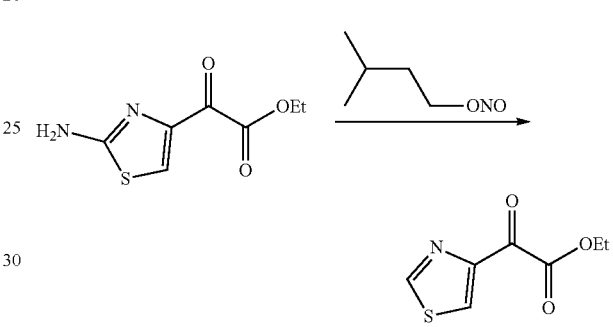

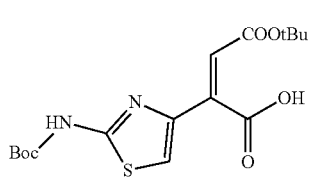

To a solution of ethyl 2-(2-amino-4-thiazolyl)-2-oxoacetate (3 g, 15 mmol) in THF (18 mL) was added isopentylnitrite (4.05 mL, 30 mmol) in THF (30 mL) dropwise. The reaction mixture was then heated at 60° C. overnight, cooled to RT, concentrated. The residue was dissolved in EtOAc, washed with saturated aqueous NaHCO$_3$ and brine, dried over Na$_2$SO$_4$, concentrated, and purified by flash chromatography on silica gel (hexane-EtOAc, 10:1-1:1) to afford the title compound, 2.2 g. ESI-MS m/z 186 (MH)$^+$.

Step 2. Synthesis of (R,Z)-2-hydroxy-3-(2-(hydroxyimino)-2-(thiazol-4-yl)acetamido)-3,4-dihydro-2H-benzo[e][1,2]oxaborinine-8-carboxylic Acid To a suspension of KOtBu (3.76 g, 33.5 mmol) in Et$_2$O (135 mL) at 0° C. was added water (0.48 mL, 26.8 mmol) dropwise. The resulting slurry mixture was stirred for 30 min, then a solution of the recovered (Z)-ester (2.67 g, 6.71 mmol) from Step 1 of Example 88 in Et$_2$O (15 mL) was added dropwise over 5 min. The reaction mixture was stirred at 0° C. for 1 h, then quenched with ice water, extracted with ether. The ether extracts were combined, washed with brine, dried over Na$_2$SO$_4$, concentrated to recover unreacted ester, 1.45 g. The aqueous layer was acidified with 1 N HCl to pH ~3, extracted with EtOAc. The organic extracts were combined, washed with brine, dried over Na$_2$SO$_4$, concentrated to yield the acid with (Z)-configuration of the double bond, 654 mg. ESI-MS m/z 371 (MH)$^+$.

In a similar manner to the synthesis of Example 6, the title compound was prepared from the above product. ESI-MS m/z 362 (MH)+.

Example 91: (R,Z)-2-hydroxy-3-(2-(hydroxyimino)-2-(2-mercaptothiazol-4-yl)acetamido)-3,4-dihydro-2H-benzo[e][1,2]oxaborinine-8-carboxylic Acid

Step 2. Synthesis of (R,Z)-3-(2-(2-aminothiazol-4-yl)-3-carboxyacrylamido)-2-hydroxy-3,4-dihydro-2H-benzo[e][1,2]oxaborinine-8-carboxylic Acid In a similar manner to the synthesis of Example 6, the title compound was prepared from the above (Z)-acid. ESI-MS m/z 404 (MH)$^+$.

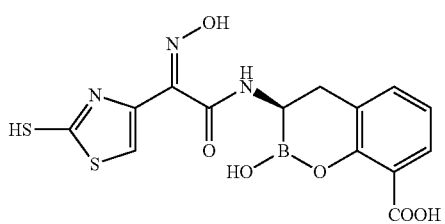 [SMILES: O=C(N[C@H]1Cc2cccc(C(=O)O)c2OB1O)/C(=N\O)c1csc(S)n1]

Example 92: (R,Z)-2-hydroxy-3-(2-(hydroxyimino)-2-(2-((4-methoxybenzyl)thio)thiazol-4-yl)acetamido)-3,4-dihydro-2H-benzo[e][1,2]oxaborinine-8-carboxylic Acid

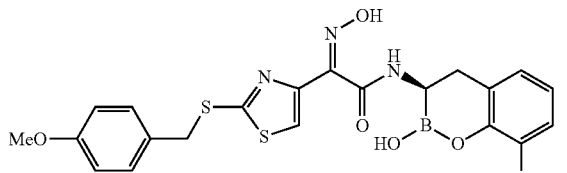

Step 1. Synthesis of ethyl 2-(2-bromothiazol-4-yl)-2-oxoacetate

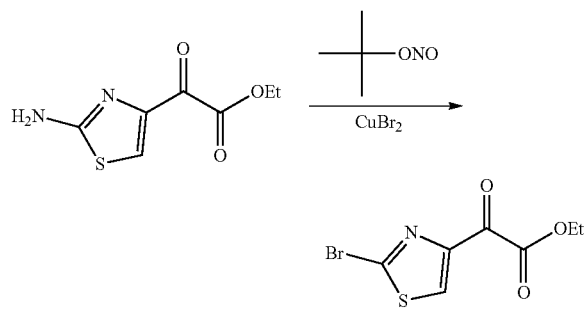

To a solution of ethyl 2-(2-amino-4-thiazolyl)-2-oxoacetate (12.5 g, 62.5 mmol) in $CH_3CN$ (100 mL) at 0° C. was added copper(II) bromide (14.8 g, 65.9 mmol), followed by slow addition of tert-butyl nitrite (10.8 g, 104.1 mmol) over 1 h. The reaction mixture was stirred at RT for 2 h, concentrated. The residue was purified by flash chromatography on silica gel (hexane-EtOAc, 10:1-1:1) to afford the title compound, 8.1 g. ESI-MS m/z 264/266 (MH/MH+2)$^+$.

Step 2. Synthesis of ethyl (Z)-2-((benzyloxy)imino)-2-(2-bromothiazol-4-yl)acetateoxoacetate

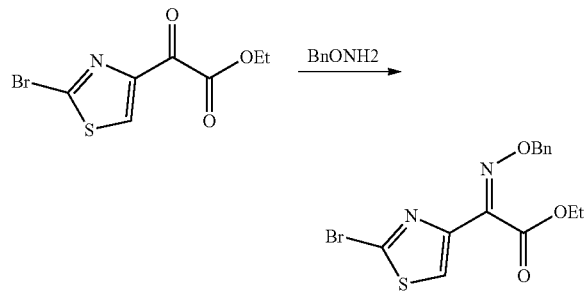

By using the same reaction procedures as described in Step 2 of Example 6, the product from Step 1 was reacted with O-benzyl hydroxylamine hydrochloride to give the oxime product. ESI-MS m/z 369/371 (MH/MH+2)$^+$.

Step 3. Synthesis of ethyl (Z)-2-((benzyloxy)imino)-2-(2-((4-methoxybenzyl)thio)thiazol-4-yl)acetate

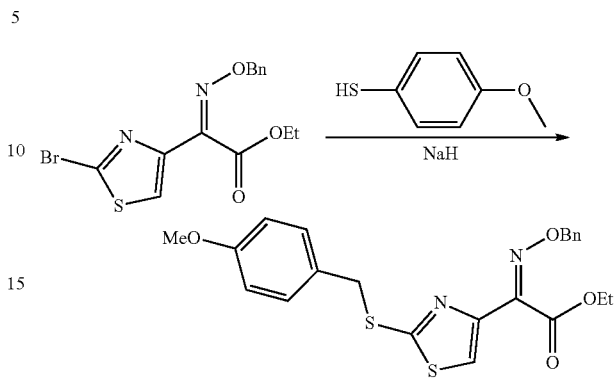

To a solution of the product from Step 2 (2.77 g, 7.5 mmol) in isopropanol (60 mL) was added 4-methoxybenzenethiol (1.6 mL, 11.5 mmol) at 0° C., followed by sodium hydride (60%, 460 mg, 11.5 mmol). The reaction mixture was stirred at RT overnight, quenched with aqueous saturated $NH_4Cl$, extracted with diethyl ether. The organic extracts were washed with brine, dried over $Na_2SO_4$, concentrated, and purified by flash chromatography on silica gel (hexane-EtOAc, 30:1-5:1) to afford the title compound as a mixture of ethyl and isopropyl ester, 2.7 g. ESI-MS m/z 443 (MH)$^+$(ethyl ester), 457 (MH)$^+$(isopropyl ester).

Step 4. Synthesis of (R,Z)-2-hydroxy-3-(2-(hydroxyimino)-2-(2-mercaptothiazol-4-yl)acetamido)-3,4-dihydro-2H-benzo[e][1,2]oxaborinine-8-carboxylic Acid &(R,Z)-2-hydroxy-3-(2-(hydroxyimino)-2-(2-((4-methoxybenzyl)thio)thiazol-4-yl)acetamido)-3,4-dihydro-2H-benzo[e][12]oxaborinine-8-carboxylic Acid

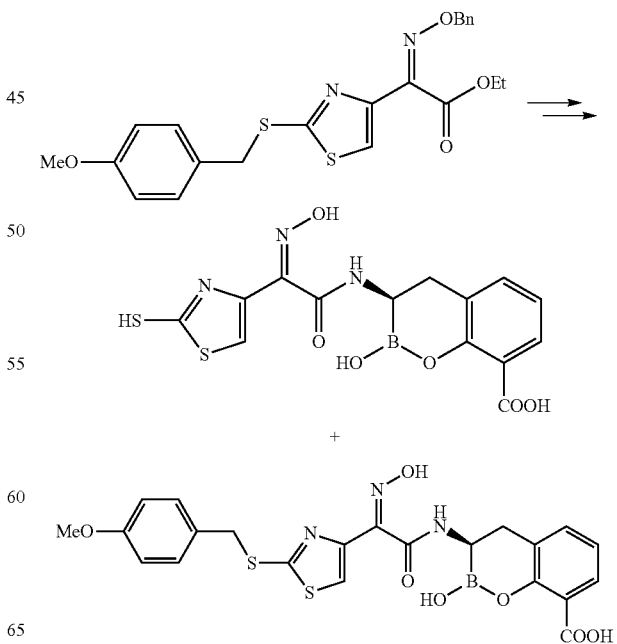

By following the same procedures as described in Step 3, Step 4 of Example 6, and General Method B, the title compounds, Example 91 and Example 92 were prepared from the above product. Example 91: ESI-MS m/z 394 (MH)⁺, Example 92: ESI-MS m/z 514 (MH)⁺.

Example 93: (R)-3-(2-(2-(1H-imidazol-1-yl)thiazol-4-yl)-2-(hydroxyimino)acetamido)-2-hydroxy-3,4-dihydro-2H-benzo[e][1,2]oxaborinine-8-carboxylic Acid

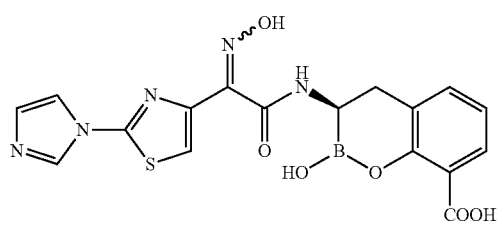 [SMILES: O=C(N[C@H]1Cc2cccc(C(=O)O)c2OB1O)C(=NO)c1csc(-n2ccnc2)n1]

Step 1. Synthesis of ethyl 2-(2-(1H-imidazol-1-yl)thiazol-4-yl)-2-((benzyloxy)imino)acetate

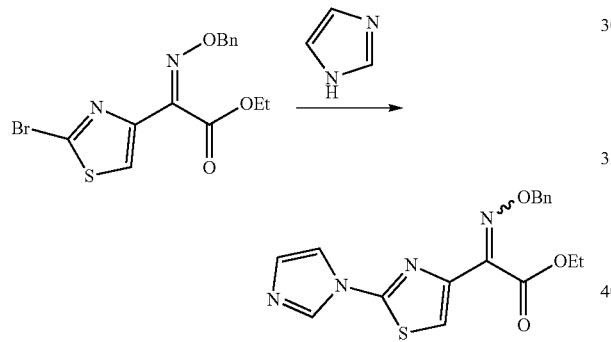

To a DMSO (50 mL) solution of ethyl (Z)-2-((benzyloxy)imino)-2-(2-bromothiazol-4-yl)acetateoxoacetate (4.42 g, 12 mmol) (the product from Step 2 of Example 91, Example 92) was added imidazole (2.04 g, 30 mmol), L-proline (560 mg, 4.86 mmol), copper (I) iodide (460 mg, 1.82 mmol), and K₂CO₃ (5.04 g, 36.5 mmol), the reaction mixture was heated at ~105° C. under Argon atmosphere for 2 days, then cooled to RT, added water, extracted with diethyl ether. The organic extracts were combined, washed with water, brine, dried over Na₂SO₄, concentrated, and purified by flash chromatography on silica gel (hexane-EtOAc, 4:1-1:10) to afford the title compound as a mixture of E- and Z-oximes, 1.63 g. ESI-MS m/z 357 (MH)⁺.

Step 2. Synthesis of (R)-3-(2-(2-(1H-imidazol-1-yl)thiazol-4-yl)-2-(hydroxyimino)acetamido)-2-hydroxy-3,4-dihydro-2H-benzo[e][1,2]oxaborinine-8-carboxylic Acid In a similar manner to the synthesis of Example 6, the title compound was prepared from the above product as an inseparable mixture of (E)- and (Z)-oximes. ESI-MS m/z 428 (MH)⁺.

Example 94: (R,Z)-3-(2-(2-(bis(2-aminoethyl)amino)thiazol-4-yl)-2-(hydroxyimino)acetamido)-2-hydroxy-3,4-dihydro-2H-benzo[e][1,2]oxaborinine-8-carboxylic Acid

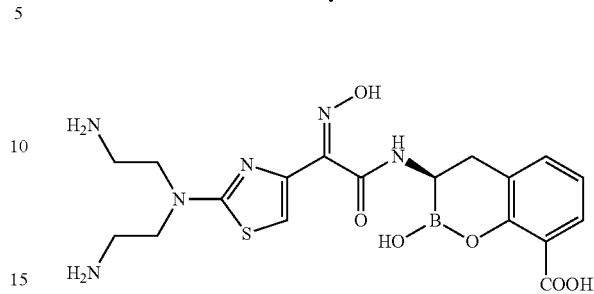

By using the same reaction procedure as described in the synthesis of Example 93, except in Step 1 using di-tert-butyl (azanediylbis(ethane-2,1-diyl))dicarbamate in place of imidazole, the title compound was prepared. ESI-MS m/z 463 (MH)⁺.

Example 95: (R,Z)-3-(2-(2-aminothiazol-5-yl)-2-(hydroxyimino)acetamido)-2-hydroxy-3,4-dihydro-2H-benzo[e][1,2]oxaborinine-8-carboxylic Acid

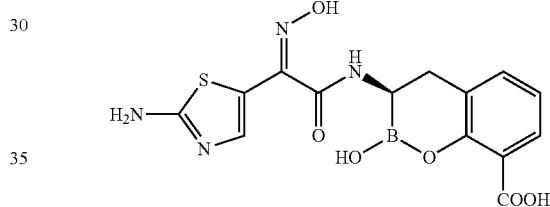

Example 96: (R,E)-3-(2-(2-aminothiazol-5-yl)-2-(hydroxyimino)acetamido)-2-hydroxy-3,4-dihydro-2H-benzo[e][1,2]oxaborinine-8-carboxylic Acid

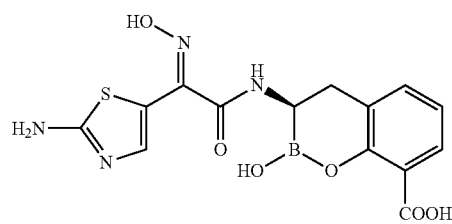 [SMILES: Nc1ncc(/C(=N\O)C(=O)N[C@H]2Cc3cccc(C(=O)O)c3OB2O)s1]

Step 1. Synthesis of tert-butyl (5-formylthiazol-2-yl)carbamate

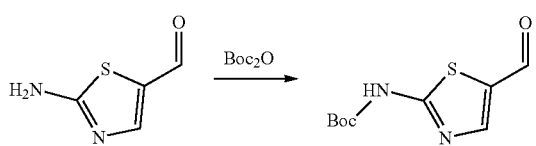 [SMILES: "Boc2O" ; Nc1ncc(C=O)s1 ; CC(C)(C)OC(=O)Nc1ncc(C=O)s1]

To a solution of 2-imino-5-formylthiazole (6 g, 46.9 mmol) in CH₃CN was added TMEDA (22 mL) followed by Boc₂O (11.7 g, 53.6 mmol). The reaction mixture was stirred at RT overnight, then concentrated in vacuo, and purified by flash chromatography on silica gel (hexane-acetone, 4:1-1:1) to afford the Boc-protected product, 7.8 g. ESI-MS m/z 229 (MH)⁺.

Step 2. Synthesis of (R,Z)-3-(2-(2-aminothiazol-5-yl)-2-(hydroxyimino)acetamido)-2-hydroxy-3,4-dihydro-2H-benzo[e][1,2]oxaborinine-8-carboxylic Acid &(R,E)-3-(2-(2-aminothiazol-5-yl)-2-(hydroxyimino)acetamido)-2-hydroxy-3,4-dihydro-2H-benzo[e][1,2]oxaborinine-8-carboxylic Acid

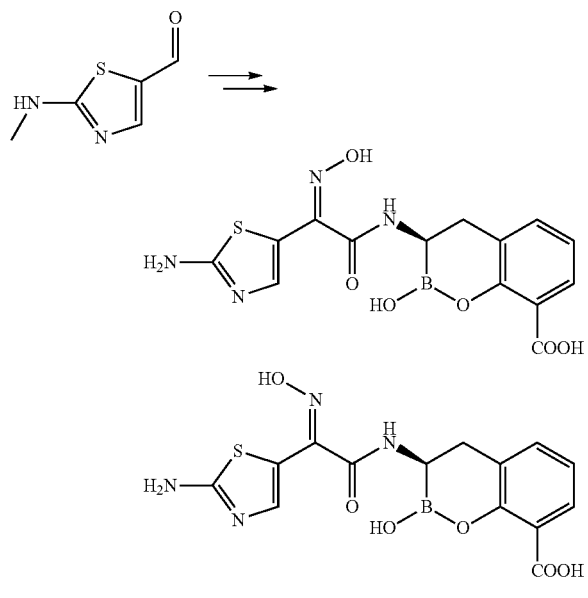

In a similar manner to the synthesis of Example 14 and Example 15, the title compounds Example 95 and Example 96 were prepared from the aldehyde from Step 1. ESI-MS m/z 377 (MH)⁺.

Example 97: (R,Z)-3-(2-(2-aminothiazol-4-yl)-2-(isopropoxyimino)acetamido)-2-hydroxy-3,4-dihydro-2H-benzo[e][1,2]oxaborinine-8-carboxylic Acid

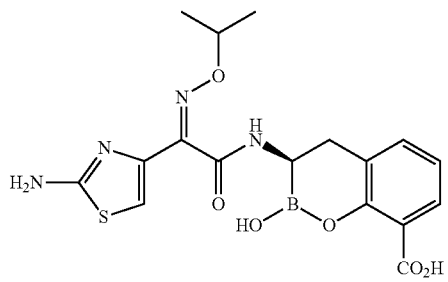 [SMILES: CC(C)O/N=C(\C(=O)N[C@H]1Cc2cccc(C(=O)O)c2OB1O)c1csc(N)n1]

The title compound was prepared according to the method of Example 6, utilizing O-2-propylhydroxylaminehydrochloride in place of O-benzylhydroxylamine hydrochloride in Step 2, obtained as a yellow powder. ESI-MS m/z 419 (MH)⁺.

Example 98: (R,Z)-3-(2-(2-aminothiazol-4-yl)-2-(propoxyimino)acetamido)-2-hydroxy-3,4-dihydro-2H-benzo[e][1,2]oxaborinine-8-carboxylic Acid

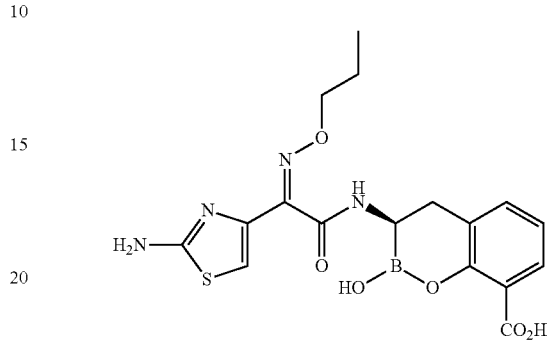

The title compound was prepared according to the method of Example 6, utilizing O-propylhydroxylamine hydrochloride in place of O-benzylhydroxylamine hydrochloride in Step 2, obtained as a yellow powder. ESI-MS m/z 419 (MH)⁺.

Example 99: (3R)-3-(2-(2-aminothiazol-4-yl)-3-carboxypropanamido)-2-hydroxy-3,4-dihydro-2H-benzo[e][1,2]oxaborinine-8-carboxylic Acid

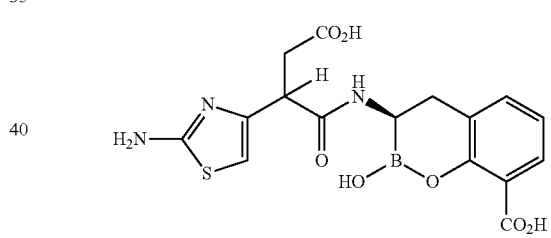

Step 1. Synthesis of 4-(tert-butyl) 1-ethyl 2-(2-((bis-(tert-butoxycarbonyl))amino)thiazol-4-yl)succinate The product from Example 84, Step 1 (820 mg, 2.12 mmol) was dissolved in THF, cooled to −78° C., and a solution of LiHMDS (2.3 mL, 1 M in hexane, 2.3 mmol) was added dropwise. The bright yellow solution was stirred at −78° C. for 30 min, then t-butyl bromoacetate (400 μL, 2.71 mmol) was added via syringe, and the resulting reaction mixture was stirred at −78° C. for 30 min, then allowed to warm to RT and stir for 1 h total. The reaction was quenched by addition of water, and the resulting mixture was extracted with EtOAc. The organic phase was washed sequentially with water and brine, dried (Na₂SO₄), and concentrated in vacuo. The crude product was filtered through a short pad of silica gel, using 15% EtOAc-hexane to elute. The eluent was concentrated in vacuo to provide the title compound as a yellow oil (0.99 g, 93% yield). ¹H NMR spectrum was consistent with title compound, bearing both Boc groups on the exocyclic amino group.

Step 2. Synthesis of 4-(tert-butoxy)-2-(2-((tert-butoxycarbonyl)amino)thiazol-4-yl)-4-oxobutanoic Acid The resulting ethyl ester from Step 1 (980 mg, 1.96 mmol) was dissolved in 8 mL ethanol, and NaOH (8 mL, 1.0 N in water) was added. The reaction was stirred at RT for 5 h, then concentrated to an aqueous suspension. The basic mixture was extracted with $Et_2O$, then the aqueous phase was acidified to pH 2 with 1 N aq. HCl. The resulting acidic phase was extracted with EtOAc, the combined EtOAc extracts were washed sequentially with water and brine, dried ($Na_2SO_4$), and concentrated to provide the title compound as a yellow foam (566 mg, 78% yield).

Step 3. Synthesis of (3R)-3-(2-(2-aminothiazol-4-yl)-3-carboxypropanamido)-2-hydroxy-3,4-dihydro-2H-benzo[e][1,2]oxaborinine-8-carboxylic Acid The procedure of General Method C, followed by General Method A, provided the title compound (1:1 mixture of diastereomers) as a white powder. ESI-MS m/z 406 (MH)+.

Example 100: (R,Z)-3-(2-(2-aminothiazol-4-yl)-2-(isobutoxyimino)acetamido)-2-hydroxy-3,4-dihydro-2H-benzo[e][1,2]oxaborinine-8-carboxylic Acid

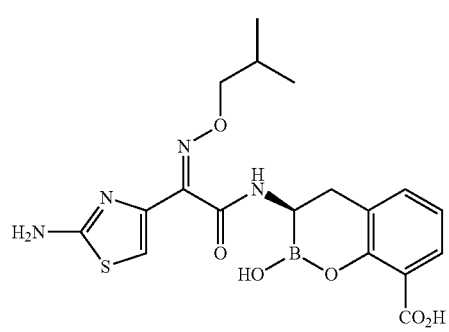 [SMILES: CC(C)CO/N=C(\C(=O)N[C@H]1Cc2cccc(C(=O)O)c2OB1O)c1csc(N)n1]

The title compound was prepared according to the method of Example 6, utilizing O-(2-methylpropyl)hydroxylamine hydrochloride in place of O-benzylhydroxylamine hydrochloride in Step 2, obtained as a yellow powder. ESI-MS m/z 433 (MH)+.

Example 101: (R,Z)-3-(2-(2-((2-fluoroethyl)amino)thiazol-4-yl)-2-(hydroxyimino)acetamido)-2-hydroxy-3,4-dihydro-2H-benzo[e][1,2]oxaborinine-8-carboxylic Acid

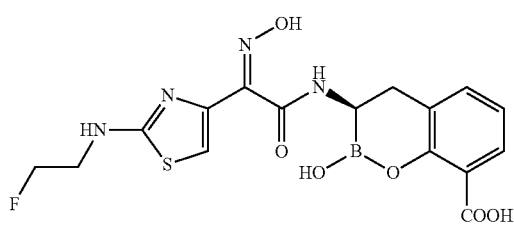 [SMILES: O=C(N[C@H]1Cc2cccc(C(=O)O)c2OB1O)/C(=N\O)c1csc(NCCF)n1]

Step 1. Synthesis of tert-butyl 3-((2R)-2-((Z)-2-(2-aminothiazol-4-yl)-2-((trityloxy)imino)acetamido)-2-((3aS,4S,6R)-3a,5,5-trimethylhexahydro-4,6-methanobenzo[d][1,3,2]dioxaborol-2-yl)ethyl)-2-methoxybenzoate

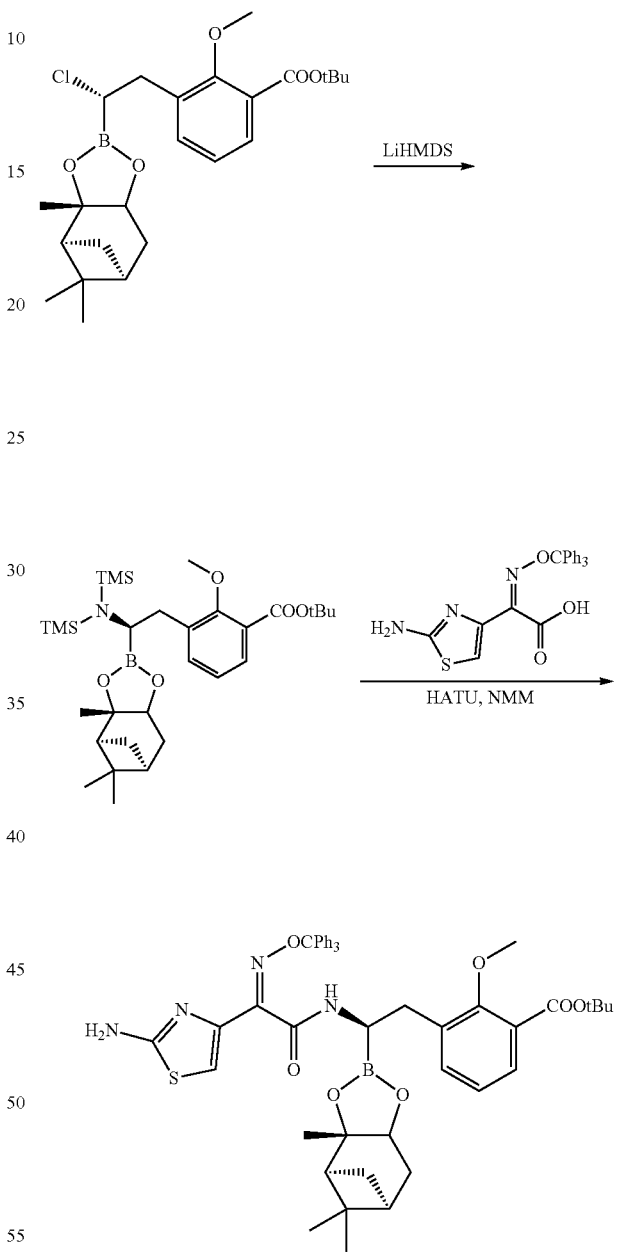

By following General Procedure C, the starting chloride (Example 1, Step 1) was treated with LiHMDS, and then coupled with the commercially available (Z)-2-(2-aminothiazol-4-yl)-2-((trityloxy)imino)acetic acid in the presence of HATU and 4-methylmorpholine, yielding the title compound. ESI-MS m/z 841 (MH)+.

Step 2. Synthesis of tert-butyl 3-((2R)-2-((Z)-2-(2-((2-fluoroethyl)amino)thiazol-4-yl)-2-((trityloxy)imino)acetamido)-2-((3aS,4S,6R)-3a,5,5-trimethylhexahydro-4,6-methanobenzo[d][1,3,2]dioxaborol-2-yl)ethyl)-2-methoxybenzoate

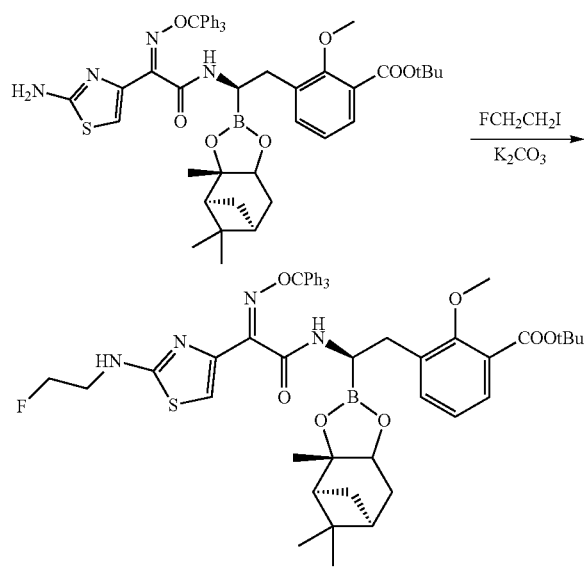

The above product (1.26 g, 1.5 mmol), 1-fluoro-2-iodoethane (940 mg, 5.4 mmol), K₂CO₃ (311 mg, 2.25 mmol) in acetone (25 mL) was refluxed for 24 h, cooled to RT, filtered. The filtrate was concentrated in vacuo, and purified by flash chromatography on silica gel (DCM-EtOAc, 20:1-3:1, then hexane-acetone, 2:1) to afford the title compound, 600 mg. ESI-MS m/z 887 (MH)⁺.

Step 3. Synthesis of (R,Z)-3-(2-(2-((2-fluoroethyl)amino)thiazol-4-yl)-2-(hydroxyimino)acetamido)-2-hydroxy-3,4-dihydro-2H-benzo[e][1,2]oxaborinine-8-carboxylic Acid

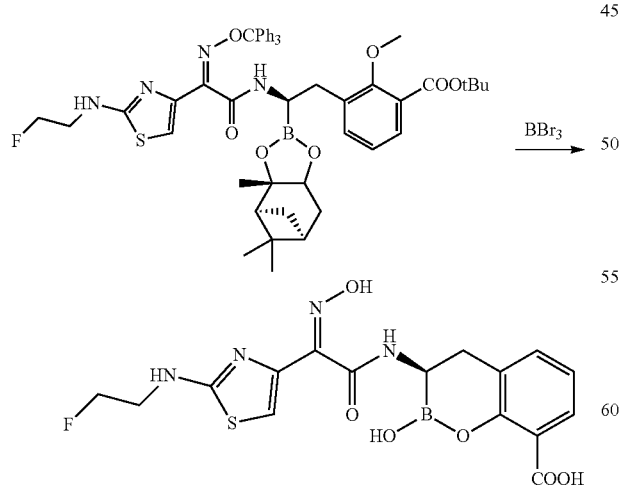

The title compound was prepared by treatment of the above product with BBr₃ by following the general procedure A. ESI-MS m/z 423 (MH)⁺.

Example 102: (R,Z)-2-hydroxy-3-(2-(2-((2-hydroxyethyl)amino)thiazol-4-yl)-2-(hydroxyimino)acetamido)-3,4-dihydro-2H-benzo[e][1,2]oxaborinine-8-carboxylic Acid

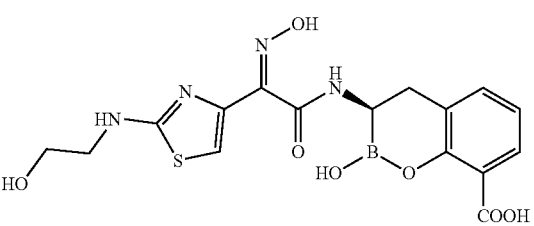 [SMILES: O=C(N[C@H]1Cc2cccc(C(=O)O)c2OB1O)/C(=N\O)c1csc(NCCO)n1]

By using the same reaction procedure as described in the synthesis of Example 101, except in Step 2 using 1-benzyloxy-2-iodoethane in place of 1-fluoro-2-iodoethane, the title compound was prepared. ESI-MS m/z 421 (MH)⁺.

Example 103: (R,E)-2-hydroxy-3-(2-(hydroxyimino)-2-(1H-tetrazol-5-yl)acetamido)-3,4-dihydro-2H-benzo[e][1,2]oxaborinine-8-carboxylic Acid

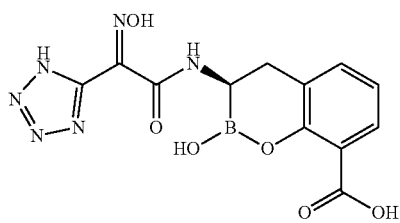

Step 1. Synthesis of tert-butyl 3-((R)-2-((Z)-2-(hydroxyimino)-2-(1H-tetrazol-5-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

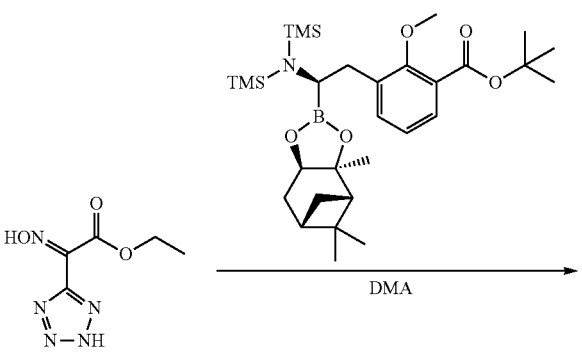

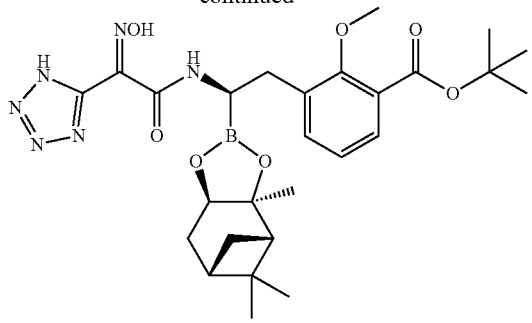

A solution of tert-butyl 3-((R)-2-(bis(trimethylsilyl)amino)-2-((3aS,4S,6S,7aR)-3a,5,5-trimethylhexahydro-4,6-methanobenzo[d][1,3,2]dioxaborol-2-yl)ethyl)-2-methoxybenzoate (0.8 mmol, Example 1, Step 2) was added to a solution of ethyl 2-(hydroxyimino)-2-(2H-tetrazol-5-yl)acetate (0.1 g, 0.7 mmol, prepared according to the procedure of Kaurs, J., et al., *J. Med. Chem.* 2009, 52(14), 4358-4369) in DMA (4 mL) at RT. The mixture was stirred at RT for 24 h, then quenched with HCl (0.2 N, 4 mL), extracted with EtOAc, concentrated and purified by column chromatography (5%-100% EtOAc in hexane) to afford the title compound. ESI-MS m/z 569 (MH)+.

Step 2. Synthesis of (R,E)-2-hydroxy-3-(2-(hydroxyimino)-2-(1H-tetrazol-5-yl)acetamido)-3,4-dihydro-2H-benzo[e][1,2]oxaborinine-8-carboxylic Acid The title compound was prepared from the resultant product of Step 1 using General Method A, and isolated as a white solid. ESI-MS m/z 347 (MH)+.

Example 104: (3R)-3-((Z)-12-amino-2-(2-aminothiazol-4-yl)-5-methyl-6-oxo-4-oxa-3,7,10-triazadodec-2-enamido)-2-hydroxy-3,4-dihydro-2H-benzo[e][1,2]oxaborinine-8-carboxylic Acid

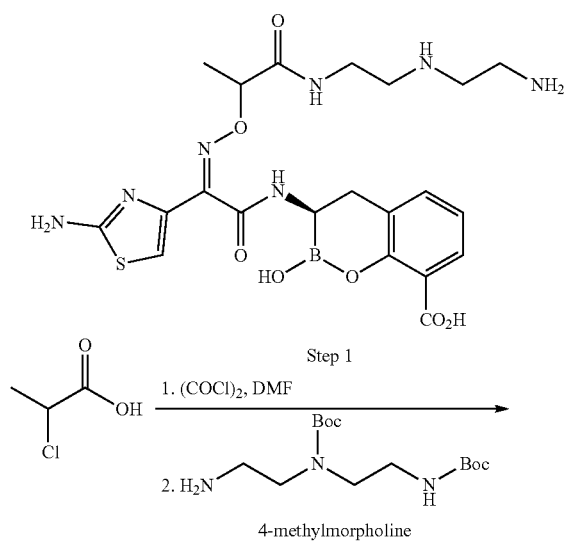

Step 2

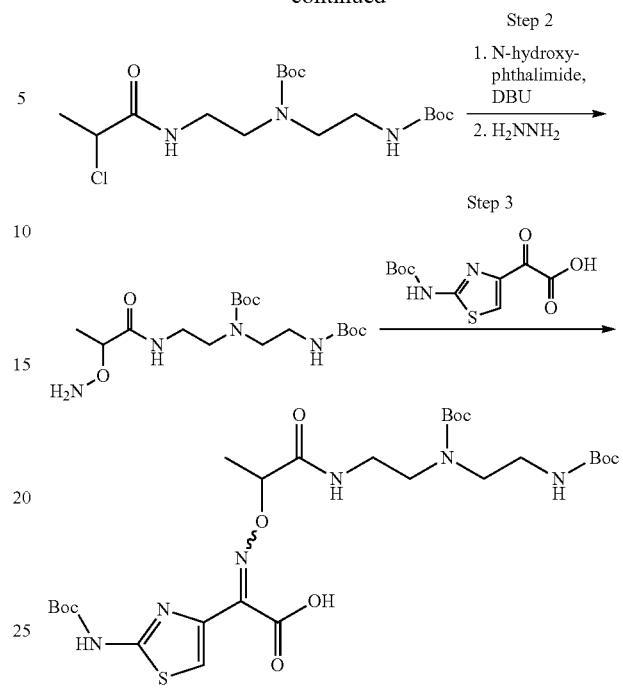

Step 1. Synthesis of tert-butyl (2-((tert-butoxycarbonyl)amino)ethyl)(2-(2-chloropropanamido)ethyl)carbamate A solution of 2-chloropropanoic acid (275 μL, 2.99 mmol) in DCM (15 mL) was treated with oxalyl chloride (250 μL, 2.96 mmol), followed by 1 drop of DMF. The resulting solution was stirred at RT for 45 min, then the solution was cooled to 0° C., and 4-methylmorpholine (350 μL, 3.18 mmol) and tert-butyl (2-aminoethyl)(2-((tert-butoxycarbonyl)amino)ethyl)carbamate (900 mg, 2.97 mmol) was added. The reaction was stirred at 0° C. for 3 minutes, then warmed to RT and stirred an additional 2 h. The reaction mixture was then partitioned between Et$_2$O and water, the organic phase was washed sequentially with 0.2 N HCl, 5% aq. NaHCO$_3$, water, and brine, then dried (Na$_2$SO$_4$), and concentrated to a colorless foam (0.71 g, 61% yield).

Step 2. Synthesis of tert-butyl (2-(2-(aminooxy)propanamido)ethyl)(2-((tert-butoxycarbonyl)amino)ethyl)carbamate A solution of tert-butyl (2-((tert-butoxycarbonyl)amino)ethyl)(2-(2-chloropropanamido)ethyl)carbamate (680 mg, 1.73 mmol), N-hydroxyphthalimide (365 mg, 2.19 mmol), and DBU (340 μL, 2.28 mmol) in 7 mL DMF was stirred at RT for 1.5 h, then the reaction was warmed to 50° C. for 16 h. The cooled reaction mixture was partitioned between water and EtOAc, the organic phase was washed sequentially with 0.1 N HCl, 5% aq. NaHCO$_3$ (three times), the organic phase was diluted with hexane and then further washed with water (5 times), then brine, then the resulting organic phase was dried (Na$_2$SO$_4$), and concentrated to a white foam (0.66 g, 73% yield).

The resulting phthalimide was dissolved in EtOH (9 mL), and treated with hydrazine hydrate (160 μL), producing a thick slurry. An additional 8 mL EtOH was added, the resulting mixture was stirred an additional 5 h. The mixture was diluted with EtOAc and filtered. The filtrate was concentrated, and purified by column chromatography (60-100% MeCN/DCM) to provide a colorless oil (347 mg, 70% yield).

Step 3. Synthesis of 10-(tert-butoxycarbonyl)-2-(2-((tert-butoxycarbonyl)amino)thiazol-4-yl)-5,16,16-trimethyl-6,14-dioxo-4,15-dioxa-3,7,10,13-tetraazaheptadec-2-enoic Acid The title compound was prepared according to the procedure of Example 54, using tert-butyl (2-(2-(aminooxy)propanamido)ethyl)(2-((tert-butoxycarbonyl)amino)ethyl)carbamate in place of (2-tert-butoxycarbonylamino-thiazol-4-yl)-oxo-acetic acid, providing a white foam.

Step 4. Synthesis of (3R)-3-((Z)-12-amino-2-(2-aminothiazol-4-yl)-5-methyl-6-oxo-4-oxa-3,7,10-triazadodec-2-enamido)-2-hydroxy-3,4-dihydro-2H-benzo[e][1,2]oxaborinine-8-carboxylic Acid The title compound was prepared from the product from Step 3, using General Method C, followed by General Method A, affording a pale yellow solid in 31% overall yield. ESI-MS m/z 534 (MH)+.

Example 105: (R,Z)-3-(2-(((2-aminoethoxy)imino)-2-(2-aminothiazol-4-yl)acetamido)-2-hydroxy-3,4-dihydro-2H-benzo[e][1,2]oxaborinine-8-carboxylic Acid

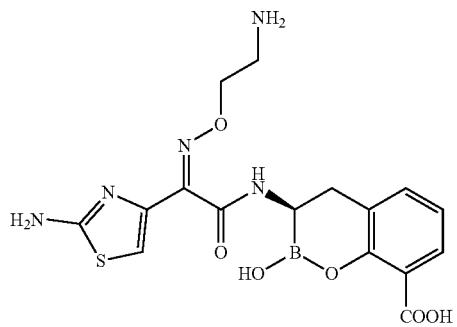

The title compound was prepared according to the method of Example 6, utilizing tert-butyl (2-(aminooxy)ethyl)carbamate in place of O-benzylhydroxylaminehydrochloride in Step 2, obtained as the hydrochloride salt as a yellow powder. ESI-MS m/z 420 (MH)+.

Example 106: (R,Z)-2-hydroxy-3-(2-(hydroxyimino)-2-(2-(methylamino)thiazol-4-yl)acetamido)-3,4-dihydro-2H-benzo[e][1,2]oxaborinine-8-carboxylic Acid

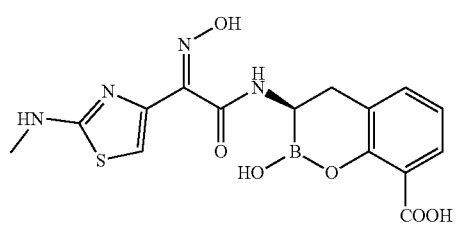 [SMILES: CNc1nc(/C(=N/O)C(=O)N[C@H]2Cc3cccc(C(=O)O)c3OB2O)cs1]

The title compound was prepared according to the method of Example 101, utilizing iodomethane in place of 1-fluoro-2-iodoethane in Step 2. ESI-MS m/z 391 (MH)+

Example 107: (R,Z)-3-(2-(2-((ethylamino)thiazol-4-yl)-2-(hydroxyimino)acetamido)-2-hydroxy-3,4-dihydro-2H-benzo[e][1,2]oxaborinine-8-carboxylic Acid

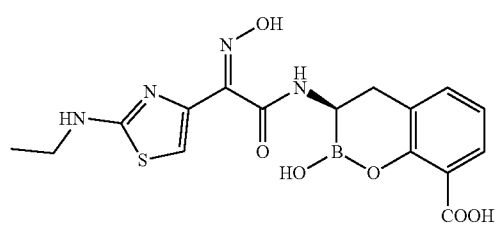 [SMILES: CCNc1nc(/C(=N/O)C(=O)N[C@H]2Cc3cccc(C(=O)O)c3OB2O)cs1]

The title compound was prepared according to the method of Example 101, utilizing iodoethane in place of 1-fluoro-2-iodoethane in Step 2. ESI-MS m/z 405 (MH)+.

Example 108: (R,Z)-3-(2-(2-((carboxymethyl)amino)thiazol-4-yl)-2-(hydroxyimino)acetamido)-2-hydroxy-3,4-dihydro-2H-benzo[e][1,2]oxaborinine-8-carboxylic Acid

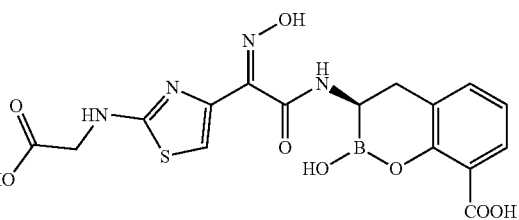

The title compound was prepared according to the method of Example 101, utilizing tert-butyl bromoacetate in place of 1-fluoro-2-iodoethane in Step 2. ESI-MS m/z 435 (MH)+.

Example 109: (R,Z)-3-(2-(2-((2-amino-2-oxoethyl)amino)thiazol-4-yl)-2-(hydroxyimino)acetamido)-2-hydroxy-3,4-dihydro-2H-benzo[e][1,2]oxaborinine-8-carboxylic Acid

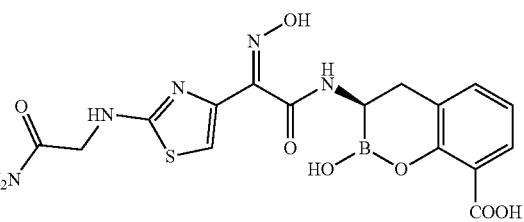

The title compound was prepared according to the method of Example 101, utilizing 2-bromoacetamide in place of 1-fluoro-2-iodoethane in Step 2. ESI-MS m/z 434 (MH)+.

Example 110: (R)-3-(2-((2-aminoethoxy)imino)-2-(1H-tetrazol-5-yl)acetamido)-2-hydroxy-3,4-dihydro-2H-benzo[e][1,2]oxaborinine-8-carboxylic Acid

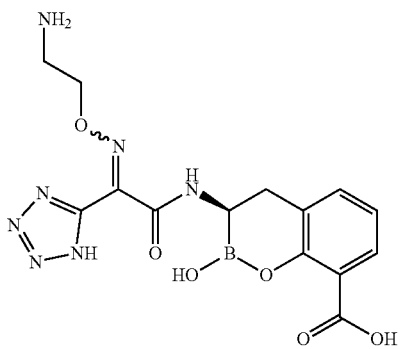 [SMILES: NCCON=C(C(=O)N[C@H]1Cc2cccc(C(=O)O)c2OB1O)c1nnn[nH]1]

Step 1. Synthesis of ethyl 10,10-dimethyl-8-oxo-2-(1H-tetrazol-5-yl)-4,9-dioxa-3,7-diazaundec-2-enoate

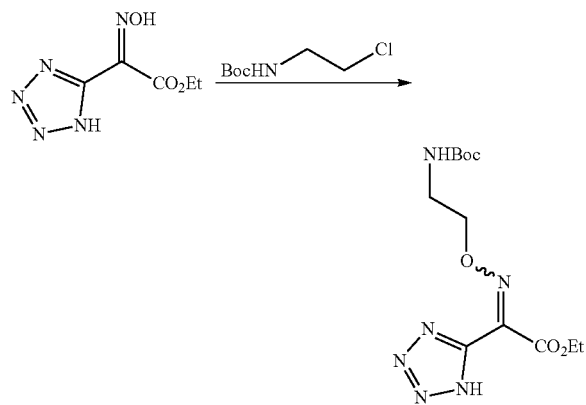

A mixture of ethyl (E)-2-(hydroxyimino)-2-(1H-tetrazol-5-yl)acetate (3 g, 16 mmol), K₂CO₃ (5 g), tert-butyl (2-chloroethyl)carbamate (2 g, 11 mmol) and KI (0.1 g) in 15 mL of DMA was stirred at 70° C. for 24 hrs. The reaction mixture was cooled to rt, then, water (40 mL) and EtOAc (100 mL) was added. and neutralized to pH ~3 with 2 N HCl at 0° C. The organic layer was washed with brine, concentrated and purified by column to give the title compound as yellow oil (0.3 g). ESI-MS m/z 329 (MH)⁺.

Step 2. Synthesis of (R)-3-(2-((2-aminoethoxy)imino)-2-(1H-tetrazol-5-yl)acetamido)-2-hydroxy-3,4-dihydro-2H-benzo[e][1,2]oxaborinine-8-carboxylic Acid The compound was prepared following the procedure in Example 103 using ethyl 10,10-dimethyl-8-oxo-2-(1H-tetrazol-5-yl)-4,9-dioxa-3,7-diazaundec-2-enoate in place of ethyl 2-(hydroxyimino)-2-(2H-tetrazol-5-yl)acetate. ESI-MS m/z 390 (MH)⁺.

Example 111: (R)-3-(2-(2-(2-aminoethyl)-2H-tetrazol-5-yl)-2-(hydroxyimino)acetamido)-2-hydroxy-3,4-dihydro-2H-benzo[e][1,2]oxaborinine-8-carboxylic Acid

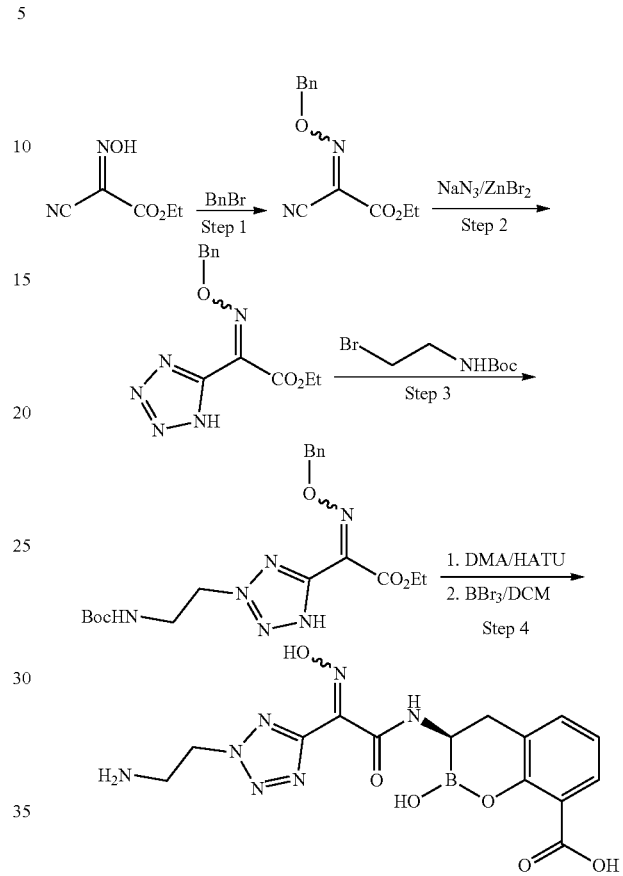

Step 1. Synthesis of ethyl 2-((benzyloxy)imino)-2-cyanoacetate

A mixture of ethyl (E)-2-cyano-2-(hydroxyimino)acetate (2 g, 15 mmol), K₂CO₃ (4 g, 29 mmol) and BnBr (3 g, 17 mmol) in 10 mL DMA was stirred at RT for 24 h. The reaction was quenched with water (30 mL), and extracted with EtOAc (100 mL). The organic layer was washed with brine, concentrated and purified by column chromatography (5%-100% EtOAc in Hexane) to afford the title compound as yellow oil (2 g). ESI-MS m/z 233 (MH)⁺.

Step 2. Synthesis of ethyl 2-((benzyloxy)imino)-2-(1H-tetrazol-5-yl)acetate

A mixture of ethyl 2-((benzyloxy)imino)-2-cyanoacetate (1 g, 4.3 mmol), NaN₃ (0.6 g, 9 mmol) and ZnBr₂ (0.6 g, 2.5 mmol) in DMA (10 mL) was stirred at 90° C. for 4 h. The reaction mixture was cooled with ice-water, then quenched with 10% citric acid (10 mL) and extracted with EtOAc. The organic layer was washed with water and brine, and purified by column to give the title compound as brown solid (0.40 g). ESI-MS m/z 276 (MH)⁺.

Step 3. Synthesis of ethyl 2-((benzyloxy)imino)-2-(2-(2-((tert-butoxycarbonyl)amino)ethyl)-2H-tetrazol-5-yl)acetate A mixture of ethyl 2-((benzyloxy)imino)-2-(1H-tetrazol-5-yl)acetate (0.4 g), tert-butyl (2-bromoethyl)carbamate (0.3 g), and K₂CO₃ (1 g) in DMA (4 mL) was stirred at 40° C. for 24 h. After cooling to RT, the reaction was quenched with water and extracted with EtOAc. The organic layer was concentrated and purified by column chromatography (5%-100% EtOAc in Hexane) to afford the title compound as brown oil (0.25 g). ESI-MS m/z 419 (MH).

Step 4. Synthesis of (R)-3-(2-(2-(2-aminoethyl)-2H-tetrazol-5-yl)-2-(hydroxyimino)acetamido)-2-hydroxy-3,4-dihydro-2H-benzo[e][1,2]oxaborinine-8-carboxylic Acid The title compound was prepared following the procedure in Example 103 using ethyl 2-((benzyloxy)imino)-2-(2-(2-((tert-butoxycarbonyl)amino)ethyl)-2H-tetrazol-5-yl)acetate in place of ethyl 2-(hydroxyimino)-2-(2H-tetrazol-5-yl)acetate. ESI-MS m/z 390 (MH)⁺.

Example 112: (R,Z)-3-(2-((carboxymethoxy)imino)-3-(1H-1,2,4-triazol-1-yl)propanamido)-2-hydroxy-3,4-dihydro-2H-benzo[e][1,2]oxaborinine-8-carboxylic Acid

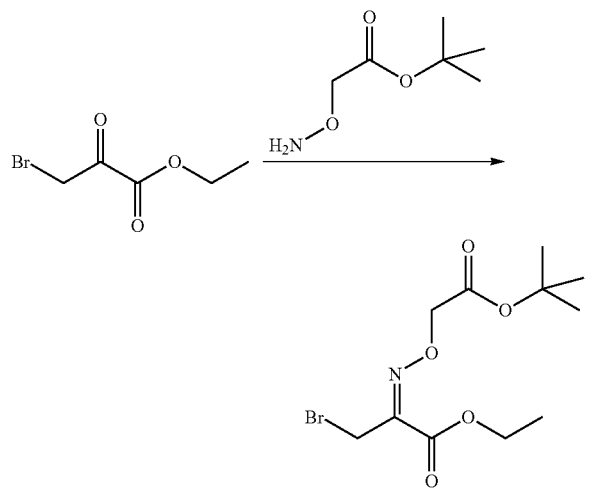

Step 1. Synthesis of tert-butyl (Z)-2-(((3-bromo-1-ethoxy-2-oxopropylidene)amino)oxy)acetate

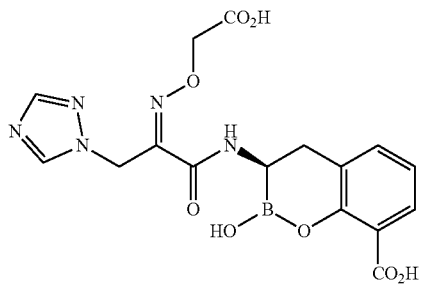 [SMILES: O=C(O)CO/N=C(/Cn1cncn1)C(=O)N[C@H]1Cc2cccc(C(=O)O)c2OB1O]

A solution of ethyl 3-bromo-2-oxopropanoate (1.0 mL, 6.8 mmol) and tert-butyl 2-(aminooxy)acetate (1.01 g, 6.86 mmol) in 30 mL MeCN was stirred at RT for 1.5 h. An additional portion of ethyl 3-bromo-2-oxopropanoate (0.5 mL, 3.4 mmol) was added, the reaction stirred an additional 45 min, at which time TLC (15% EtOAc-hexane) indicated consumption of hydroxylamine starting material. The reaction was concentration and purified by silica gel column chromatography (8-10% EtOAc-hexane) to provide the title compound as a colorless oil (1.93 g, 87% yield).

Step 2. Synthesis of tert-butyl (Z)-2-(((1-ethoxy-2-oxo-3-(1H-1,2,4-triazol-1-yl)propylidene)amino)oxy)acetate

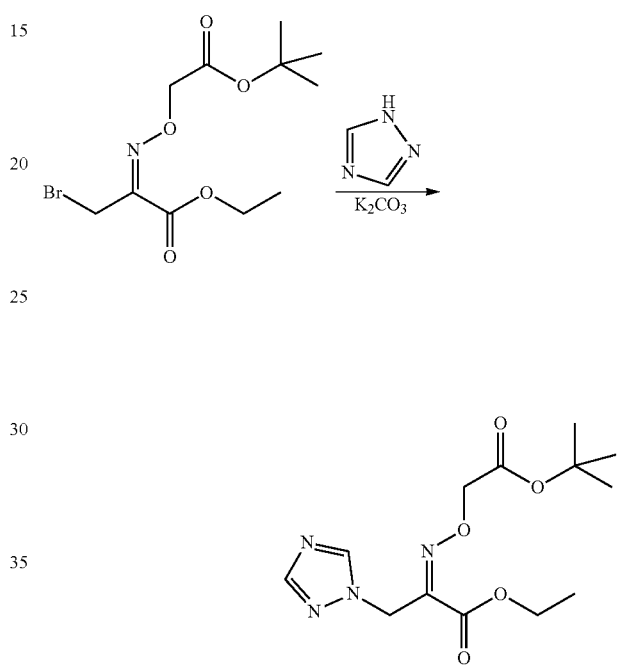

The resultant product from Step 1 (917 mg, 2.80 mmol) was combined with 1,2,4-triazole (254 mg, 3.68 mmol), potassium carbonate (585 mg, 4.20 mmol) in 20 mL MeCN and stirred at RT for 16 h. The reaction was quenched with saturated aq. NH₄Cl solution and extracted with EtOAc. The organic phase was washed sequentially with water and brine, dried (Na₂SO₄), concentrated, and the residue was purified by silica gel column chromatography (50-75% EtOAc-hexane) to provide the title compound as a colorless oil (696 mg, 79% yield).

Step 3. Synthesis of (R,Z)-3-(2-((carboxymethoxy)imino)-3-(1H-1,2,4-triazol-1-yl)propanamido)-2-hydroxy-3,4-dihydro-2H-benzo[e][1,2]oxaborinine-8-carboxylic Acid The resultant compound from Step 2 was converted to the title compound in a procedure analogous to that described in Example 99, Steps 2 and 3. ESI-MS m/z 418 (MH)⁺.

Example 113: (R,Z)-3-(2-(2-aminothiazol-4-yl)-2-((2-fluoroethoxy)imino)acetamido)-2-hydroxy-3,4-dihydro-2H-benzo[e][1,2]oxaborinine-8-carboxylic Acid

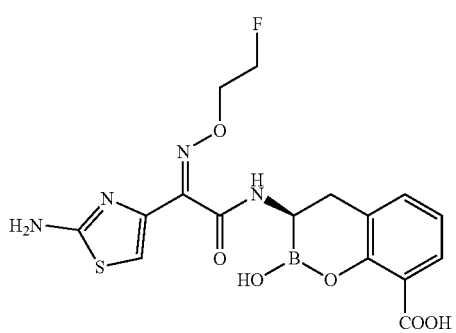 [SMILES: Nc1nc(/C(=N/OCCF)C(=O)N[C@H]2Cc3cccc(C(=O)O)c3OB2O)cs1]

Step 1. Synthesis of ethyl (Z)-2-(2-aminothiazol-4-yl)-2-((2-fluoroethoxy)imino)acetate

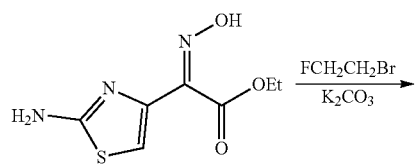

Ethyl (Z)-2-(2-aminothiazol-4-yl)-2-(hydroxyimino)acetate (8.4 g, 39 mmol), 1-fluoro-2-bromoethane (8.43 g, 66.3 mmol), $K_2CO_3$ (9 g, 65 mmol) in DMSO (80 mL) was heated at ~70° C. for 80 min, cooled to RT, diluted with EtOAc, washed with water and brine, dried over $Na_2SO_4$, concentrated, and purified by flash chromatography on silica gel (hexane-EtOAc, 10:1-1:3) to afford the title compound, 4.9 g. ESI-MS m/z 262 $(MH)^+$.

Step 2. Synthesis of ethyl (Z)-2-(2-(((benzyloxy)carbonyl)amino)thiazol-4-yl)-2-((2-fluoroethoxy)imino)acetate

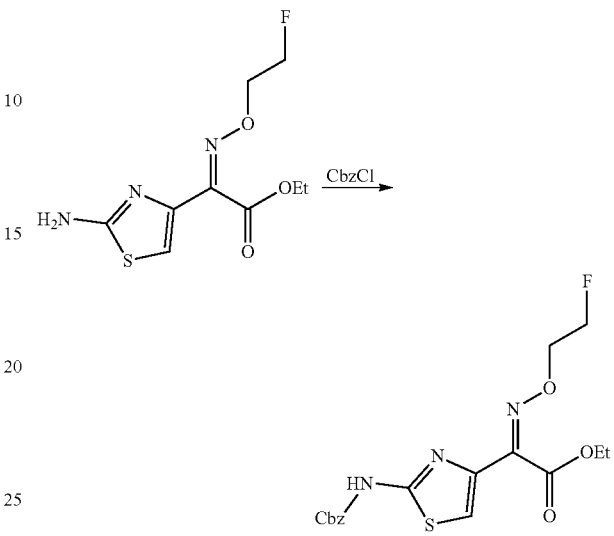

To a solution of the above product (2.3 g, 8.81 mmol) in DCM (100 mL) was added pyridine (1.5 mL, 18.5 mmol) followed by benzyl chloroformate (1.7 mL, 11.9 mL). The reaction mixture was stirred at RT overnight, washed with aqueous saturated $NaHCO_3$, dried over $Na_2SO_4$, concentrated, and purified by flash chromatography on silica gel (hexane-DCM-EtOAc, 4:1:1-2:2:1) to afford the title compound, 3 g. ESI-MS m/z 396 $(MH)^+$.

Step 3. Synthesis of (R,Z)-3-(2-(2-aminothiazol-4-yl)-2-((2-fluoroethoxy)imino)acetamido)-2-hydroxy-3,4-dihydro-2H-benzo[e][1,2]oxaborinine-8-carboxylic Acid

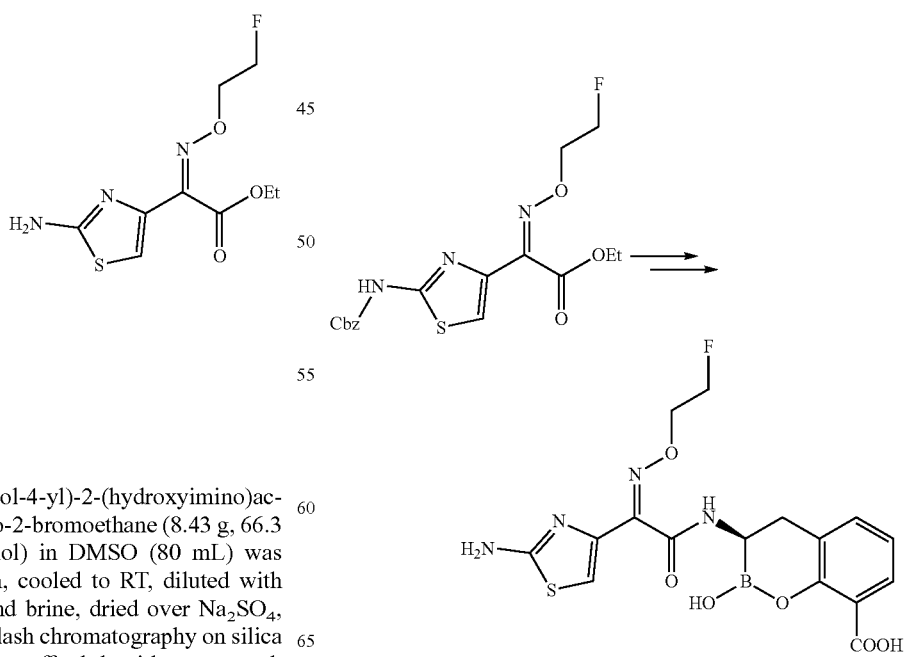

In a similar manner to the synthesis of Example 6, the title compound was prepared from the above product. ESI-MS m/z 423 (MH)+.

Example 114: (R,Z)-3-(2-(2-aminothiazol-4-yl)-2-((2,2-difluoroethoxy)imino)acetamido)-2-hydroxy-3,4-dihydro-2H-benzo[e][1,2]oxaborinine-8-carboxylic Acid

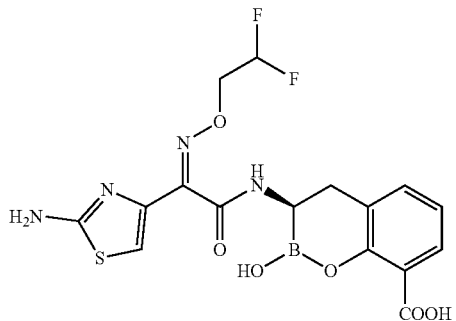 [SMILES: Nc1nc(/C(=N/OCC(F)F)C(=O)N[C@H]2Cc3cccc(C(=O)O)c3OB2O)cs1]

The title compound was prepared according to the method of Example 113, utilizing 2-bromo-1,1-difluoroethane in place of 1-fluoro-2-bromoethane in Step 1. ESI-MS m/z 441 (MH)+.

Example 115: (R,Z)-3-(2-(2-aminothiazol-4-yl)-2-((3-chloropropoxy)imino)acetamido)-2-hydroxy-3,4-dihydro-2H-benzo[e][1,2]oxaborinine-8-carboxylic Acid

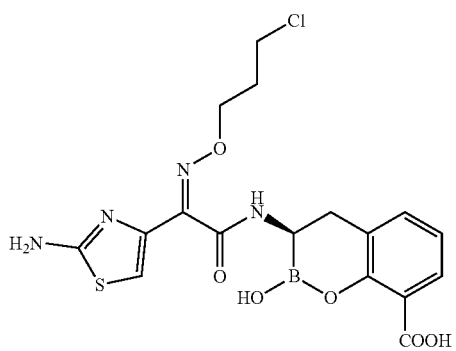

The title compound was prepared according to the method of Example 113, utilizing 1-bromo-3-fluoropropane in place of 1-fluoro-2-bromoethane in Step 1, and utilizing $BCl_3$ in the final deprotection step. ESI-MS m/z 453/455 (MH/MH+2)+.

Example 116: (R,Z)-3-(2-(2-aminothiazol-4-yl)-2-((3-bromopropoxy)imino)acetamido)-2-hydroxy-3,4-dihydro-2H-benzo[e][1,2]oxaborinine-8-carboxylic Acid

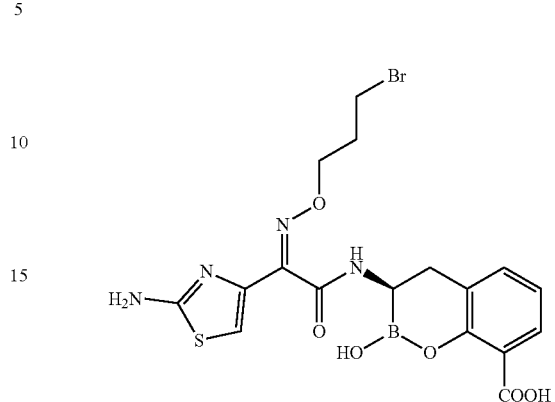

The title compound was prepared according to the method of Example 113, utilizing 1-bromo-3-fluoropropane in place of 1-fluoro-2-bromoethane in Step 1, and utilizing $BBr_3$ in the final deprotection step. ESI-MS m/z 497/499 (MH/MH+2)+.

Example 117: (R,Z)-3-(2-(2-aminothiazol-4-yl)-2-((2,2,2-trifluoroethoxy)imino)acetamido)-2-hydroxy-3,4-dihydro-2H-benzo[e][1,2]oxaborinine-8-carboxylic Acid

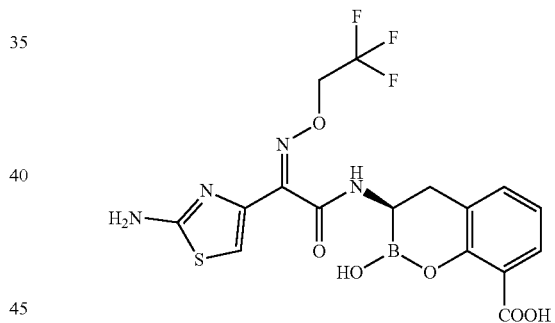

The title compound was prepared according to the method of Example 113, utilizing 2-bromo-1,1,1-trifluoroethane in place of 1-fluoro-2-bromoethane in Step 1. ESI-MS m/z 459 (MH)+.

Example 118: (R)-3-(2-(2-aminothiazol-4-yl)-2-hydrazineylideneacetamido)-2-hydroxy-3,4-dihydro-2H-benzo[e][1,2]oxaborinine-8-carboxylic Acid

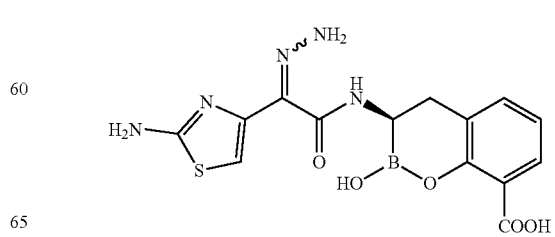

Step 1. Synthesis of tert-butyl 2-(1-(2-((tert-butoxy-carbonyl)amino)thiazol-4-yl)-2-ethoxy-2-oxoethyl-idene)hydrazine-1-carboxylate

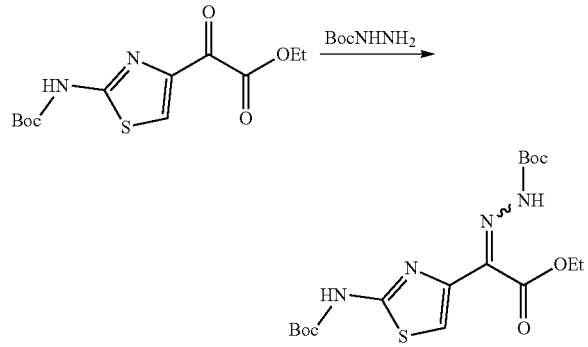

To a solution of 2-(2-((tert-butoxycarbonyl)amino)thi-azol-4-yl)-2-oxoacetate (3 g, 10 mmol) (from Step 1 of Example 6) in EtOH (50 mL) was added tert-butyl carbazate (1.58 g, 12 mmol) followed by HOAc (0.27 mL). The reaction mixture was stirred at RT for 3 h, then heated at 60° C. overnight, concentrated, and purified by flash chromatography on silica gel (hexane-EtOAc, 10:1-2:1) to afford the product, 4.1 g as a mixture of (E)- and (Z)-isomers. ESI-MS m/z 415 (MH)⁺.

Step 2. Synthesis of 2-(2-((tert-butoxycarbonyl)amino)thiazol-4-yl)-2-(2-(tert-butoxycarbonyl)hydrazono)acetic Acid

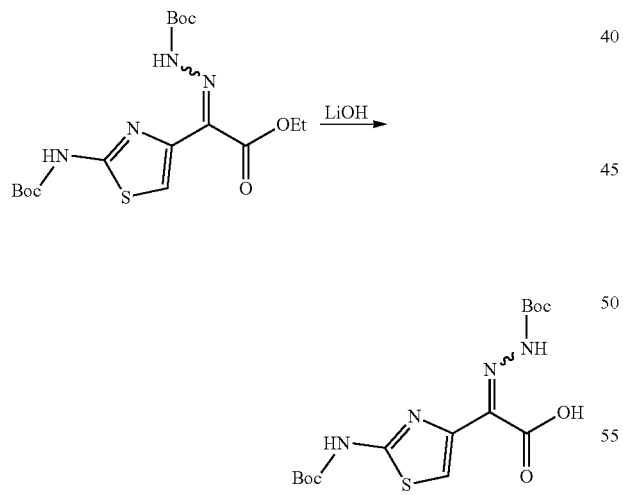

To the above product (4.1 g, 9.9 mmol) in THF (120 mL) and water (120 mL) was added LiOH.H₂O (840 mg, 20 mmol), the reaction mixture was stirred at RT for 45 min, then added more LiOH.H₂O (420 mg, 10 mmol), and stirred for 2 h, concentrated in vacuo, and acidified with 1 N HCl to pH ~3-4. The solid was collected by filtration, dried in vacuo to yield the title compound, 3.8 g, as a mixture of (E)- and (Z)-isomers. ESI-MS m/z 387 (MH)⁺.

Step 3. Synthesis of (R)-3-(2-(2-aminothiazol-4-yl)-2-hydrazonoacetamido)-2-hydroxy-3,4-dihydro-2H-benzo[e][1,2]oxaborinine-8-carboxylic Acid

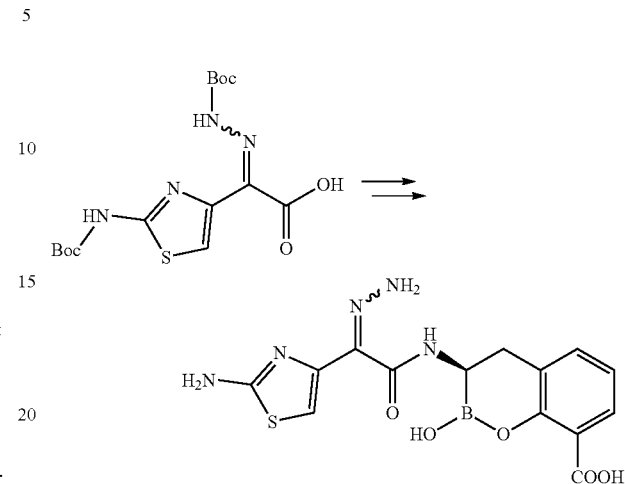

In a similar manner to the synthesis of Example 6, the target compound was prepared from the above acid. ESI-MS m/z 376 (MH)⁺.

Example 119: (R,Z)-3-(2-((2-acetamidoethoxy)imino)-2-(2-aminothiazol-4-yl)acetamido)-2-hydroxy-3,4-dihydro-2H-benzo[e][1,2]oxaborinine-8-carboxylic Acid

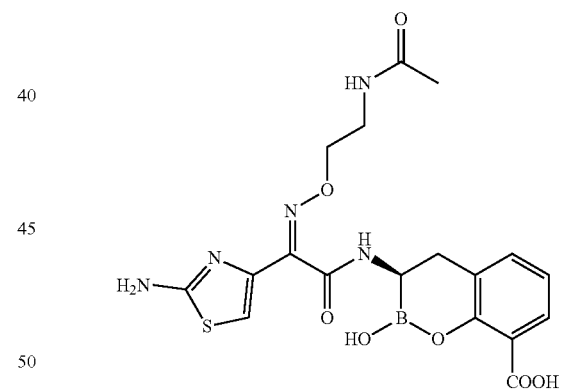

Step 1. Synthesis of ethyl (Z)-2-(2-aminothiazol-4-yl)-10,10-dimethyl-8-oxo-4,9-dioxa-3,7-diazaundec-2-enoate

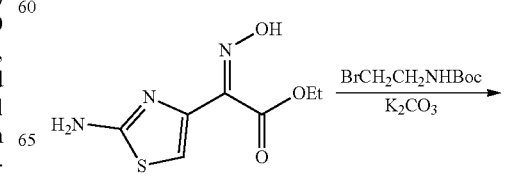

-continued

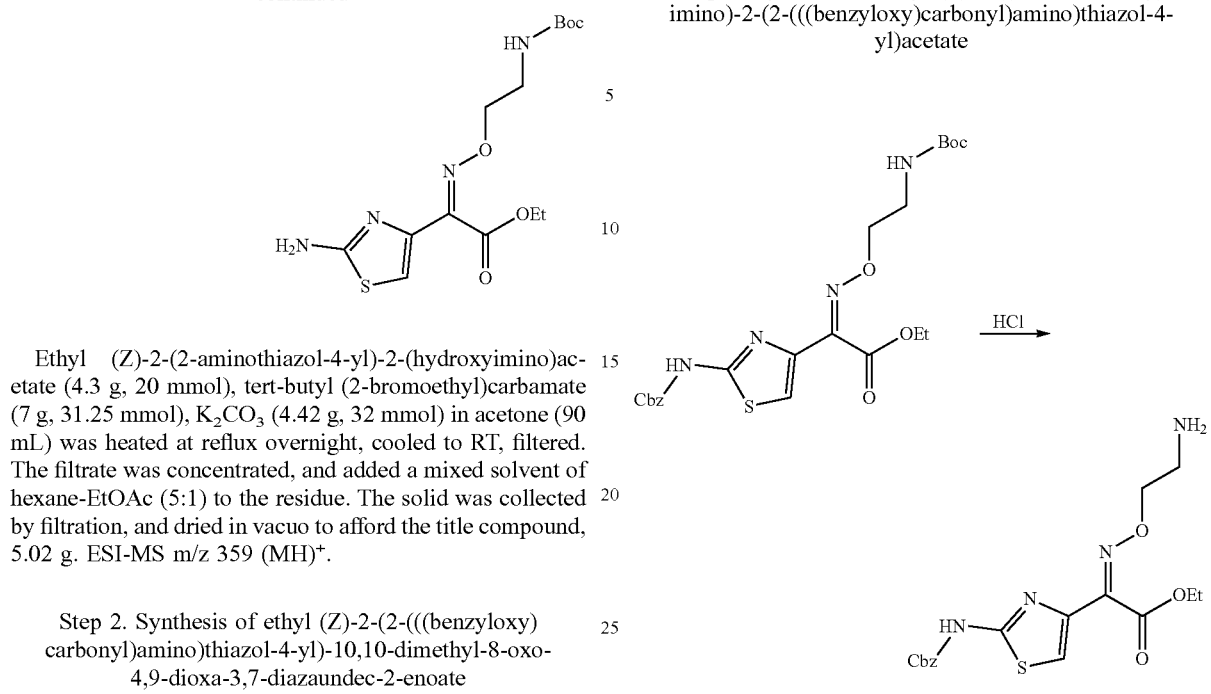

Ethyl (Z)-2-(2-aminothiazol-4-yl)-2-(hydroxyimino)acetate (4.3 g, 20 mmol), tert-butyl (2-bromoethyl)carbamate (7 g, 31.25 mmol), K$_2$CO$_3$ (4.42 g, 32 mmol) in acetone (90 mL) was heated at reflux overnight, cooled to RT, filtered. The filtrate was concentrated, and added a mixed solvent of hexane-EtOAc (5:1) to the residue. The solid was collected by filtration, and dried in vacuo to afford the title compound, 5.02 g. ESI-MS m/z 359 (MH)$^+$.

Step 2. Synthesis of ethyl (Z)-2-(2-(((benzyloxy)carbonyl)amino)thiazol-4-yl)-10,10-dimethyl-8-oxo-4,9-dioxa-3,7-diazaundec-2-enoate By following the same procedures described in Step 2 of Example 113, the title compound was prepared. ESI-MS m/z 493 (MH)$^+$.

Step 3. Synthesis of ethyl (Z)-2-((2-aminoethoxy)imino)-2-(2-(((benzyloxy)carbonyl)amino)thiazol-4-yl)acetate

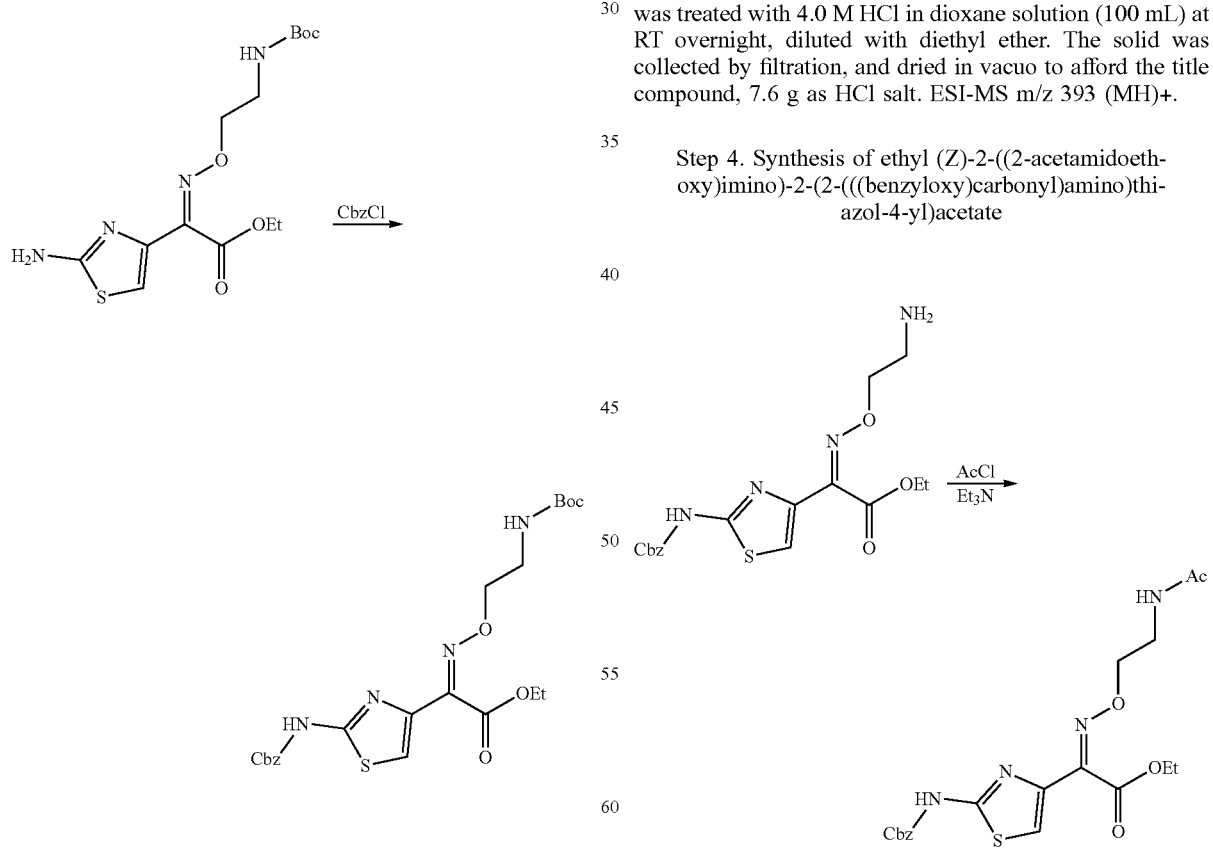

The above product (8.8 g, 17.9 mmol) in DCM (100 mL) was treated with 4.0 M HCl in dioxane solution (100 mL) at RT overnight, diluted with diethyl ether. The solid was collected by filtration, and dried in vacuo to afford the title compound, 7.6 g as HCl salt. ESI-MS m/z 393 (MH)+.

Step 4. Synthesis of ethyl (Z)-2-((2-acetamidoethoxy)imino)-2-(2-(((benzyloxy)carbonyl)amino)thiazol-4-yl)acetate To the above product (2.15 g, 5 mmol) in DCM (60 mL) at 0° C. was added triethylamine (1.95 mL, 14 mmol), followed by acetyl chloride (0.57 mL, 8 mmol). The reaction mixture was stirred at 0° C. for 20 min, and at RT for 1 h, then washed with aqueous saturated NaHCO₃, dried over Na₂SO₄, concentrated to yield the title compound, 2.17 g. ESI-MS m/z 435 (MH)⁺.

Step 5. Synthesis of (R,Z)-3-(2-((2-acetamidoethoxy)imino)-2-(2-aminothiazol-4-yl)acetamido)-2-hydroxy-3,4-dihydro-2H-benzo[e][1,2]oxaborinine-8-carboxylic Acid

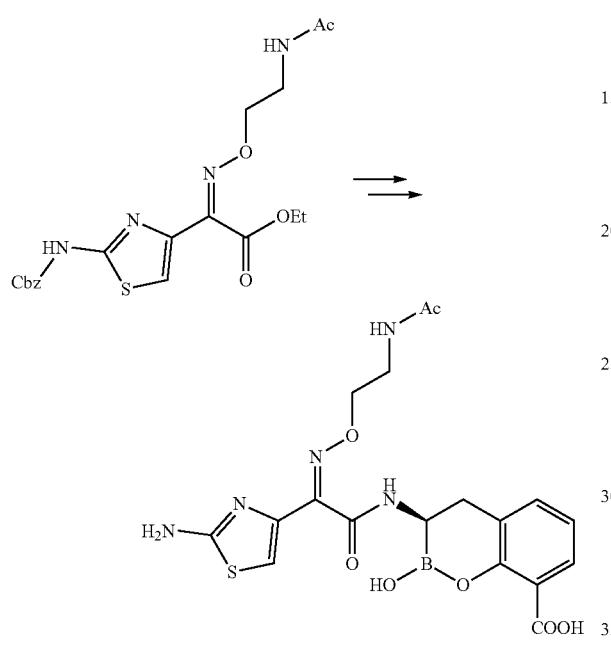

In a similar manner to the synthesis of Example 6, the title compound was prepared from the above product. ESI-MS m/z 462 (MH)⁺.

Example 120: (R,Z)-3-(2-(2-aminothiazol-4-yl)-2-((2-(methylsulfonamido)ethoxy)imino)acetamido)-2-hydroxy-3,4-dihydro-2H-benzo[e][1,2]oxaborinine-8-carboxylic Acid

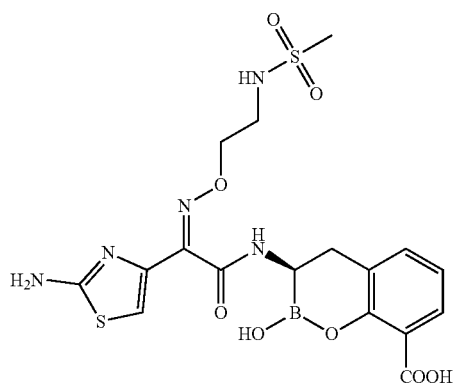 [SMILES: CS(=O)(=O)NCCO/N=C(\C(=O)N[C@H]1Cc2cccc(C(=O)O)c2OB1O)c1csc(N)n1]

The title compound was prepared according to the method of Example 119, utilizing methanesulfonyl chloride in place of acetyl chloride in Step 4. ESI-MS m/z 498 (MH)⁺.

Example 121: (R,Z)-2-hydroxy-3-(2-(hydroxyimino)-2-(2-((pyridin-2-ylmethyl)amino)thiazol-4-yl)acetamido)-3,4-dihydro-2H-benzo[e][1,2]oxaborinine-8-carboxylic Acid

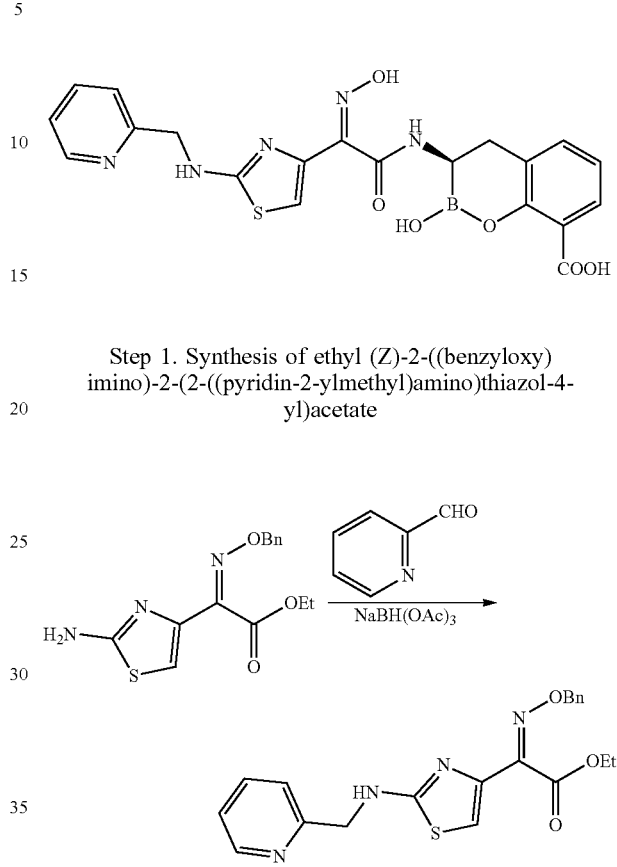

Step 1. Synthesis of ethyl (Z)-2-((benzyloxy)imino)-2-(2-((pyridin-2-ylmethyl)amino)thiazol-4-yl)acetate To a solution of ethyl (Z)-2-(2-aminothiazol-4-yl)-2-((benzyloxy)imino)acetate (2.44 g, 8 mmol) (from Step 1 of Example 10) in DCE (100 mL) was added pyridine-2-carboxaldehyde (1.72 g, 16 mmol) followed by HOAc (2.76 mL, 48 mmol). The reaction mixture was stirred at RT for 15 min, then added NaBH(OAc)₃ (4.76 g, 22.4 mmol). The reaction mixture was stirred at RT overnight, added more aldehyde (428 mg, 4 mmol) and NaBH(OAc)₃ (846 mg, 4 mmol). The reaction mixture was stirred at RT for an additional 6 h, then washed with aqueous saturated NaHCO₃, dried over Na₂SO₄, concentrated, and purified by flash chromatography on silica gel (hexane-EtOAc, 10:1-1:4) to afford the product, 1 g. ESI-MS m/z 397 (MH)⁺.

Step 2. Synthesis of (R,Z)-2-hydroxy-3-(2-(hydroxyimino)-2-(2-((pyridin-2-ylmethyl)amino)thiazol-4-yl)acetamido)-3,4-dihydro-2H-benzo[e][1,2]oxaborinine-8-carboxylic Acid

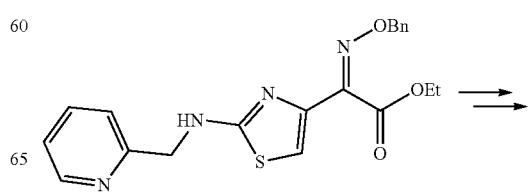

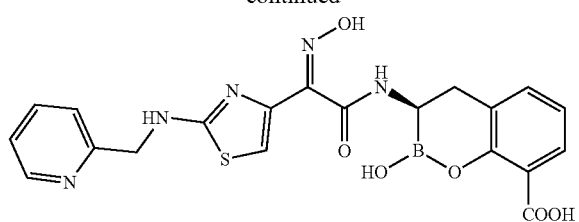

In a similar manner to the synthesis of Example 6, the title compound was prepared from the above product from Step 1. ESI-MS m/z 468 (MH)$^+$.

Example 122: (R,Z)-2-hydroxy-3-(2-(hydroxyimino)-2-(2-((2-(pyridin-2-yl)ethyl)amino)thiazol-4-yl)acetamido)-3,4-dihydro-2H-benzo[e][1,2]oxaborinine-8-carboxylic Acid

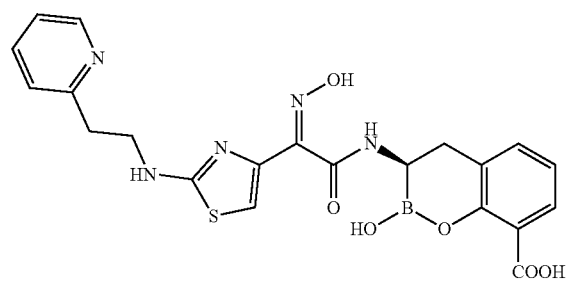 [SMILES: O=C(N[C@H]1Cc2cccc(C(=O)O)c2OB1O)/C(=N\O)c1csc(NCCc2ccccn2)n1]

The title compound was prepared according to the method of Example 93, utilizing 2-(2-pyridyl)ethylamine in place of imidazole in Step 1. ESI-MS m/z 482 (MH)$^+$.

Example 123: (R,Z)-2-hydroxy-3-(2-(hydroxyimino)-2-(2-((2-(pyridin-4-yl)ethyl)amino)thiazol-4-yl)acetamido)-3,4-dihydro-2H-benzo[e][1,2]oxaborinine-8-carboxylic Acid

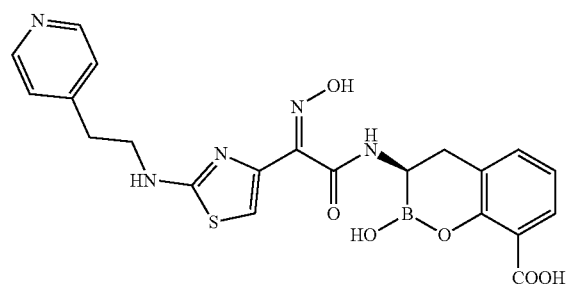 [SMILES: O=C(N[C@H]1Cc2cccc(C(=O)O)c2OB1O)/C(=N\O)c1csc(NCCc2ccncc2)n1]

Example 124: (R,E)-2-hydroxy-3-(2-(hydroxyimino)-2-(2-((2-(pyridin-4-yl)ethyl)amino)thiazol-4-yl)acetamido)-3,4-dihydro-2H-benzo[e][1,2]oxaborinine-8-carboxylic Acid

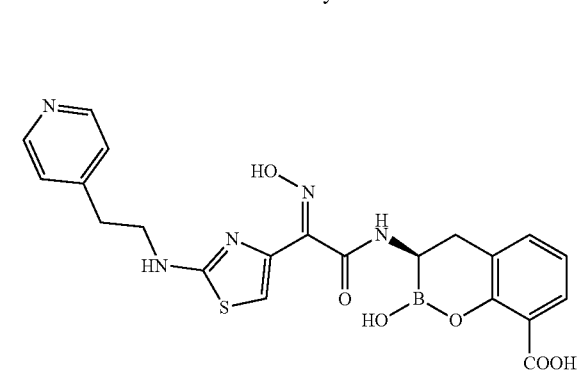

The title compounds, Example 123 and Example 124, were prepared according to the method of Example 93, utilizing 4-(2-aminoethyl)pyridine in place of imidazole in Step 1. ESI-MS m/z 482 (MH)$^+$.

Example 125: (R)-3-(2-(2-aminothiazol-4-yl)-2-((2-(3-(5,5-difluoro-7,9-dimethyl-5H-4$\lambda^4$,5$\lambda^4$-dipyrrolo[1,2-c:2',1'-f][1,3,2]diazaborinin-3-yl)propanamido)ethoxy)imino)acetamido)-2-hydroxy-3,4-dihydro-2H-benzo[e][1,2]oxaborinine-8-carboxylic Acid

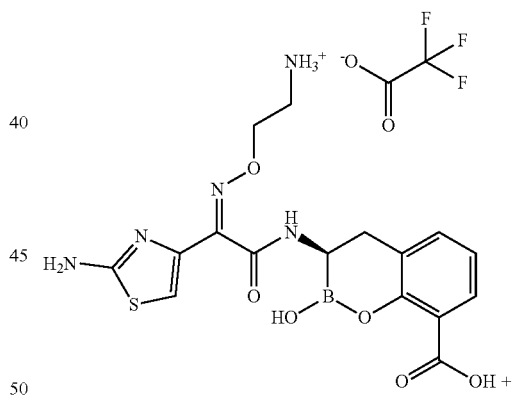

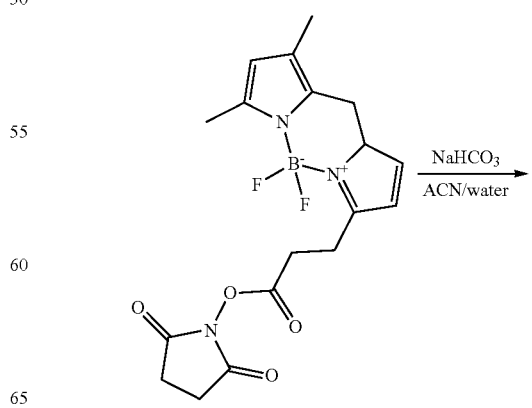

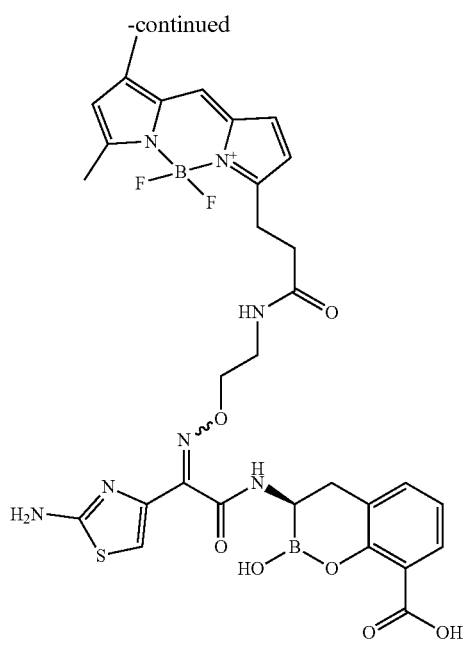

The title compound was prepared using an adaptation of a literature procedure (Li, Z., et al., *Proc. Nat. Acad. Sci.* 2013, 100, 414-419). To a stirred solution of the compound of Example 105(TFA salt, 15.8 mg. 0.03 mmol) and 2,5-dioxopyrrolidin-1-yl 3-(5,5-difluoro-7,9-dimethyl-5H-4$\lambda^4$,5$\lambda^4$-dipyrrolo[1,2-c:2',1'-f][1,3,2]diazaborinin-3-yl)propanoate (BODIPY® FL succinimidyl ester; 7.8 mg, 0.02 mmol) in 1 mL of a 9/1 (v/v) mixture of acetonitrile and water, was added a 1 M aqueous solution of NaHCO$_3$ (0.1 mL, 0.1 mmol) at 0° C. The reaction mixture was allowed to warm to room temperature and stirred for 5 h. The desired product was isolated by submitting the reaction mixture directly to reverse-phase flash chromatography (C18-Silica gel, water-acetonitrile 0-50% gradient, modified with 0.1% TFA) followed by lyophilization: 12.3 mg orange-red solid (yield: 88%), 1/1 mixture of E/Z oxime-ether diastereomers; ESI-MS m/z 694.2 (M+H)$^+$.

Example 126: (R,Z)-2-hydroxy-3-(2-(hydroxyimino)-3-(1H-1,2,4-triazol-1-yl)propanamido)-3,4-dihydro-2H-benzo[e][1,2]oxaborinine-8-carboxylic Acid

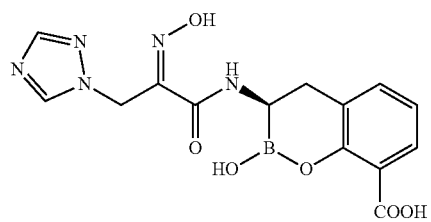 [SMILES: O=C(N[C@H]1Cc2cccc(C(=O)O)c2OB1O)/C(Cn1cncn1)=N\O]

The title compound was made in analogy to Example 112. ESI-MS m/z 360 (MH)$^+$.

Example 127: (R,Z)-2-hydroxy-3-(2-(hydroxyimino)-3-(2H-1,2,3-triazol-2-yl)propanamido)-3,4-dihydro-2H-benzo[e][1,2]oxaborinine-8-carboxylic Acid

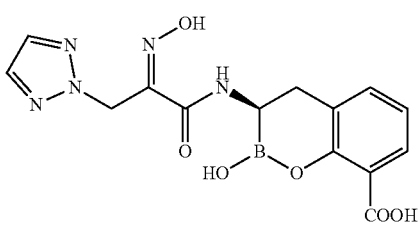 [SMILES: O=C(N[C@H]1Cc2cccc(C(=O)O)c2OB1O)/C(Cn1nccn1)=N\O]

The title compound was made in analogy to Example 112. ESI-MS m/z 360 (MH)$^+$.

TABLE 1

Example compounds

| Ex. | Structure | MW | ESI-MS (m/z) for [MH]$^+$ |
|---|---|---|---|
| 1 | ![structure] | 390.177 | 391 |
| 2 | ![structure] | 391.165 | 392 |

TABLE 1-continued

Example compounds

| Ex. | Structure | MW | ESI-MS (m/z) for [MH]+ |
|---|---|---|---|
| 3 | 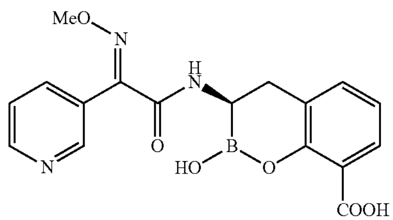 [SMILES: CO/N=C(/C(=O)N[C@H]1Cc2cccc(C(=O)O)c2OB1O)c1cccnc1] | 369.14 | 370 |
| 4 | 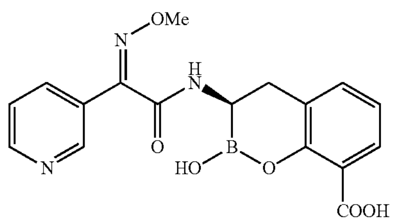 [SMILES: CO/N=C(\C(=O)N[C@H]1Cc2cccc(C(=O)O)c2OB1O)c1cccnc1] | 369.14 | 370 |
| 5 | 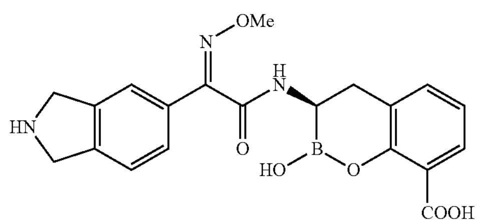 [SMILES: CO/N=C(\C(=O)N[C@H]1Cc2cccc(C(=O)O)c2OB1O)c1ccc2c(c1)CNC2] | 409.205 | 410 |
| 6 | 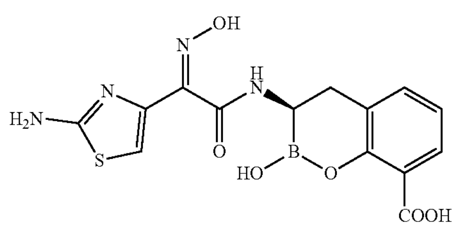 [SMILES: Nc1nc(/C(=N/O)C(=O)N[C@H]2Cc3cccc(C(=O)O)c3OB2O)cs1] | 376.15 | 377 |
| 7 | 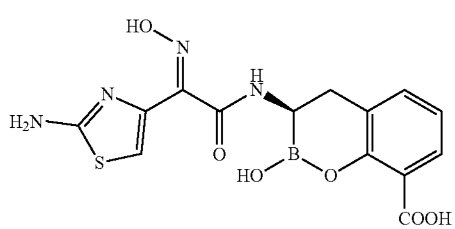 | 376.15 | 377 |
| 8 | 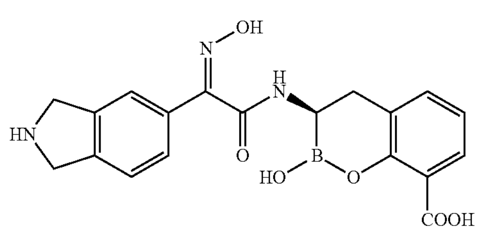 [SMILES: O=C(N[C@H]1Cc2cccc(C(=O)O)c2OB1O)/C(=N\O)c1ccc2c(c1)CNC2] | 395.178 | 396 |

TABLE 1-continued

Example compounds

| Ex. | Structure | MW | ESI-MS (m/z) for [MH]+ |
|---|---|---|---|
| 9 | 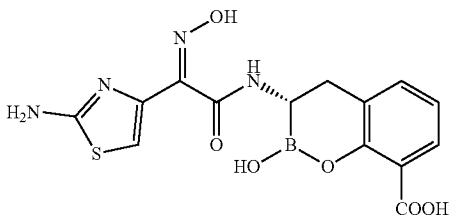 [SMILES: Nc1nc(/C(=N/O)C(=O)N[C@@H]2Cc3cccc(C(=O)O)c3OB2O)cs1] | 376.15 | 377 |
| 10 | 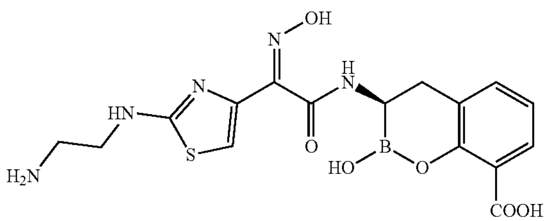 [SMILES: NCCNc1nc(/C(=N/O)C(=O)N[C@H]2Cc3cccc(C(=O)O)c3OB2O)cs1] | 419.219 | 420 |
| 11 | 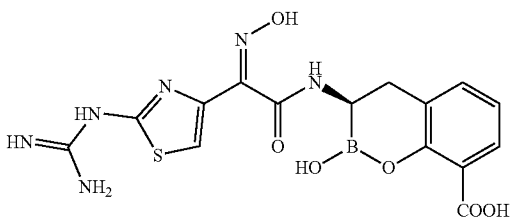 [SMILES: N=C(N)Nc1nc(/C(=N/O)C(=O)N[C@H]2Cc3cccc(C(=O)O)c3OB2O)cs1] | 418.191 | 419 |
| 12 | 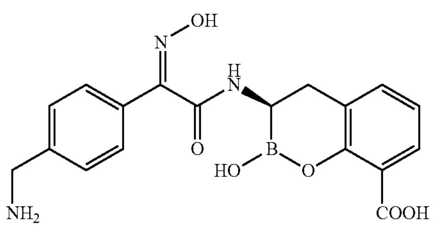 [SMILES: NCc1ccc(/C(=N/O)C(=O)N[C@H]2Cc3cccc(C(=O)O)c3OB2O)cc1] | 383.167 | 384 |
| 13 | 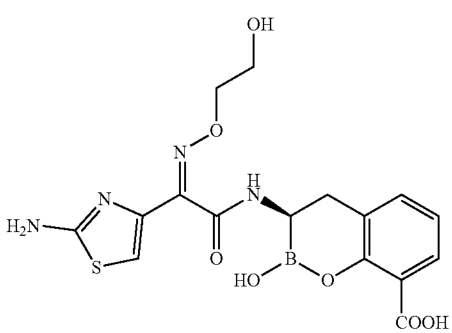 | 420.203 | 421 |
| 14 | 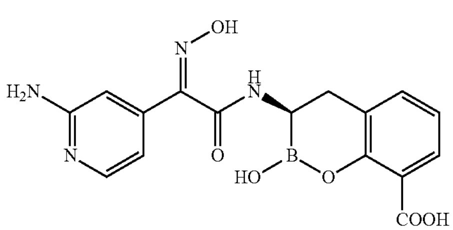 [SMILES: Nc1cc(/C(=N/O)C(=O)N[C@H]2Cc3cccc(C(=O)O)c3OB2O)ccn1] | 370.128 | 371 |

TABLE 1-continued

Example compounds

| Ex. | Structure | MW | ESI-MS (m/z) for [MH]+ |
|---|---|---|---|
| 15 | 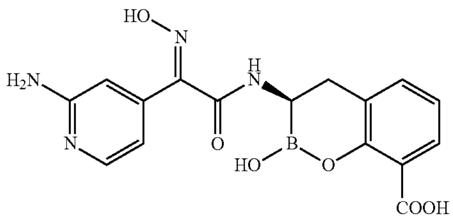 [SMILES: Nc1cc(/C(=N\O)C(=O)N[C@H]2Cc3cccc(C(=O)O)c3OB2O)ccn1] | 370.128 | 371 |
| 16 | 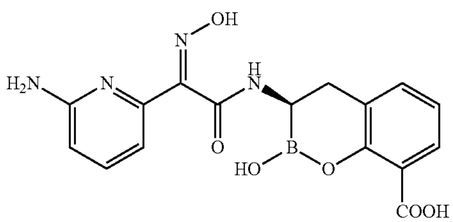 [SMILES: Nc1cccc(/C(=N/O)C(=O)N[C@H]2Cc3cccc(C(=O)O)c3OB2O)n1] | 370.128 | 371 |
| 17 | 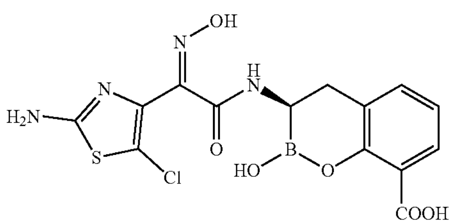 [SMILES: Nc1nc(/C(=N/O)C(=O)N[C@H]2Cc3cccc(C(=O)O)c3OB2O)c(Cl)s1] | 410.592 | 411 |
| 18 | 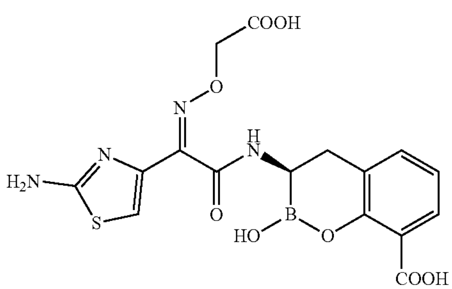 [SMILES: Nc1nc(/C(=N/OCC(=O)O)C(=O)N[C@H]2Cc3cccc(C(=O)O)c3OB2O)cs1] | 434.186 | 435 |
| 19 | 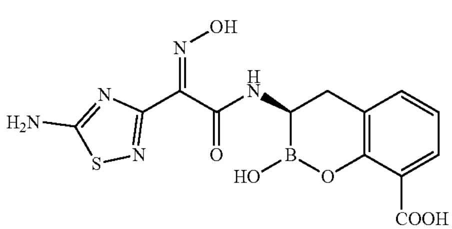 | 377.138 | 378 |
| 20 | 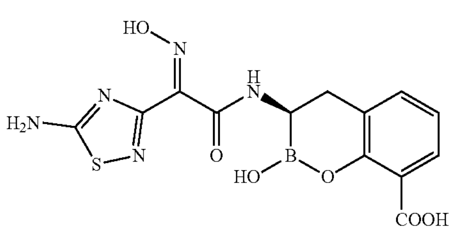 | 377.138 | 378 |

TABLE 1-continued

Example compounds

| Ex. | Structure | MW | ESI-MS (m/z) for [MH]+ |
|---|---|---|---|
| 21 | (2-aminothiazolyl)-C(=NOH)-C(=O)-NH-[benzoxaborinine with 7-OH, 8-COOH] | 392.149 | 393 |
| 22 | (2-methylaminothiazolyl)-C(=NOH)-C(=O)-N(Me)-[benzoxaborinine with 8-COOH] | 404.204 | 406 |
| 23 | (2-methylaminothiazolyl)-C(=NOBn)-C(=O)-N(Me)-[benzoxaborinine with 8-COOH] | 494.329 | 496 |
| 24 | (2-aminothiazolyl)-C(=NOH)-C(=O)-NH-[benzoxaborinine with 7-CHO, 8-COOH] | 404.16 | 405 |
| 25 | (2-aminothiazolyl)-C(=NOH)-C(=O)-NH-[benzoxaborinine with 7-CH$_2$-pyrrolidinyl, 8-COOH] | 459.284 | 460 |
| 26 | (2-aminothiazolyl)-C(=NOH)-C(=O)-NH-[benzoxaborinine with 7-CH$_2$-(N-methylpyrrolidinium), 8-COO$^-$] | 473.311 | 474 |

TABLE 1-continued
Example compounds
| Ex. | Structure | MW | ESI-MS (m/z) for [MH]+ |
|---|---|---|---|
| 27 | 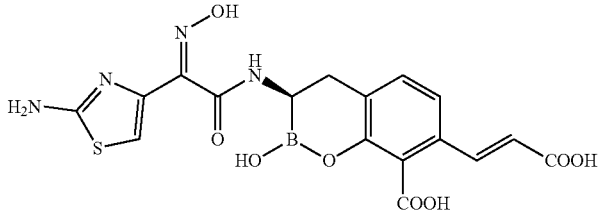 [SMILES: Nc1nc(/C(=N/O)C(=O)N[C@H]2Cc3ccc(/C=C/C(=O)O)c(C(=O)O)c3OB2O)cs1] | 446.197 | 447 |
| 28 | 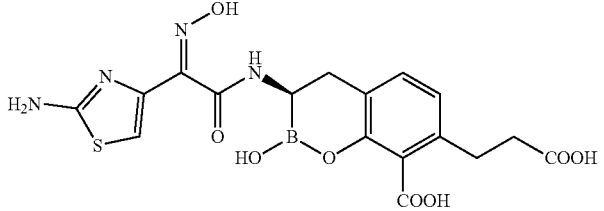 [SMILES: Nc1nc(/C(=N/O)C(=O)N[C@H]2Cc3ccc(CCC(=O)O)c(C(=O)O)c3OB2O)cs1] | 448.213 | 449 |
| 29 | 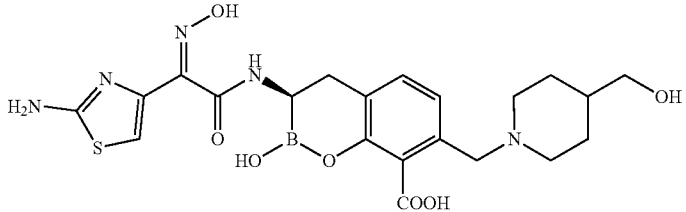 [SMILES: Nc1nc(/C(=N/O)C(=O)N[C@H]2Cc3ccc(CN4CCC(CO)CC4)c(C(=O)O)c3OB2O)cs1] | 503.337 | 504 |
| 30 | 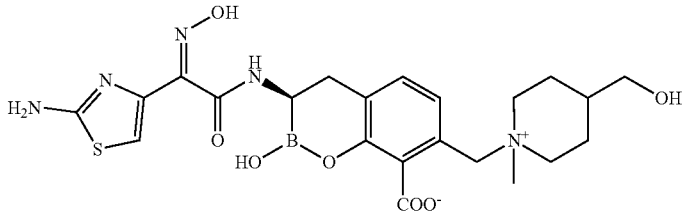 | 517.364 | 518 |
| 31 | 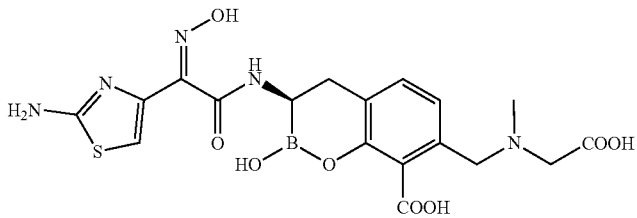 [SMILES: CN(CC(=O)O)Cc1ccc2c(c1C(=O)O)OB(O)[C@@H](NC(=O)/C(=N\O)c1csc(N)n1)C2] | 477.255 | 478 |
| 32 | 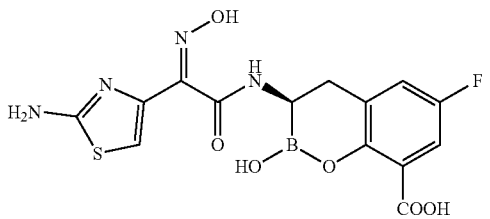 [SMILES: Nc1nc(/C(=N/O)C(=O)N[C@H]2Cc3cc(F)cc(C(=O)O)c3OB2O)cs1] | 394.140 | 395 |

US 11,267,826 B2
227                                                                                             228
TABLE 1-continued
Example compounds
| Ex. | Structure | MW | ESI-MS (m/z) for [MH]+ |
|---|---|---|---|
| 33 | 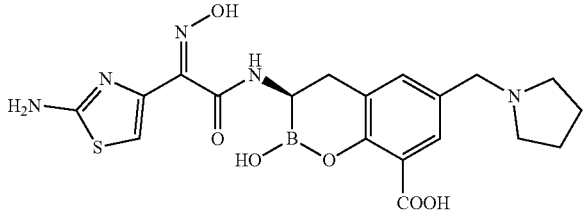 [SMILES: Nc1nc(/C(=N/O)C(=O)N[C@H]2Cc3cc(CN4CCCC4)cc(C(=O)O)c3OB2O)cs1] | 459.284 | 460 |
| 34 | 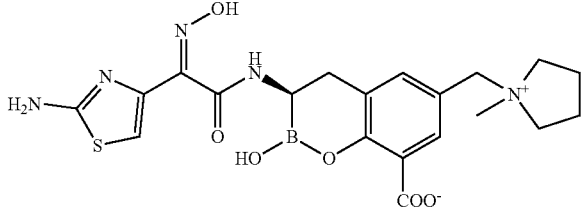 | 473.311 | 474 |
| 35 | 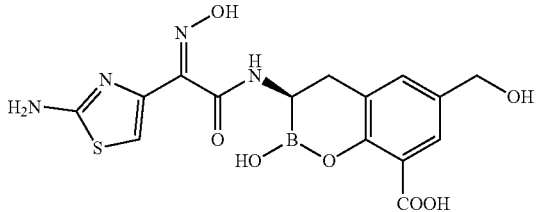 [SMILES: Nc1nc(/C(=N/O)C(=O)N[C@H]2Cc3cc(CO)cc(C(=O)O)c3OB2O)cs1] | 406.176 | 407 |
| 36 | 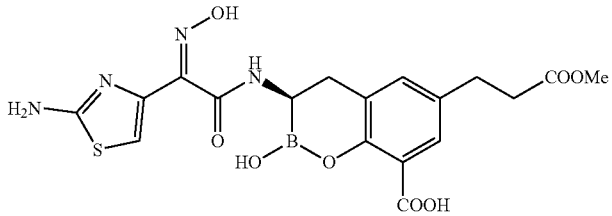 [SMILES: COC(=O)CCc1cc2c(c(C(=O)O)c1)OB(O)[C@@H](NC(=O)/C(=N\O)c1csc(N)n1)C2] | 462.24 | 463 |
| 37 | 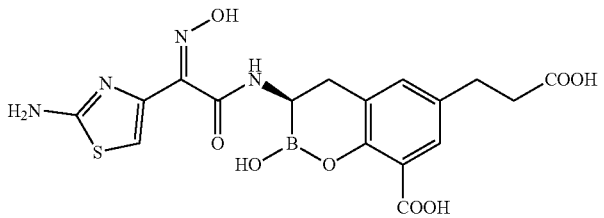 [SMILES: Nc1nc(/C(=N/O)C(=O)N[C@H]2Cc3cc(CCC(=O)O)cc(C(=O)O)c3OB2O)cs1] | 448.213 | 449 |
| 38 | 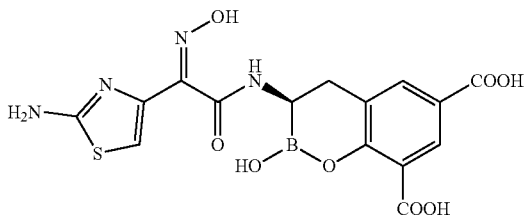 [SMILES: Nc1nc(/C(=N/O)C(=O)N[C@H]2Cc3cc(C(=O)O)cc(C(=O)O)c3OB2O)cs1] | 420.159 | 421 |

TABLE 1-continued

Example compounds

| Ex. | Structure | MW | ESI-MS (m/z) for [MH]+ |
|---|---|---|---|
| 39 | 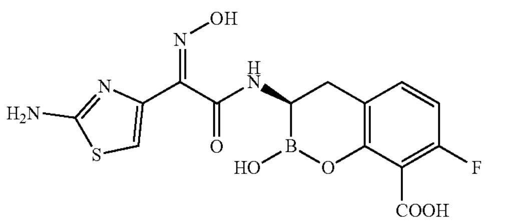 [SMILES: Nc1nc(/C(=N/O)C(=O)N[C@H]2Cc3ccc(F)c(C(=O)O)c3OB2O)cs1] | 394.140 | 395 |
| 40 | 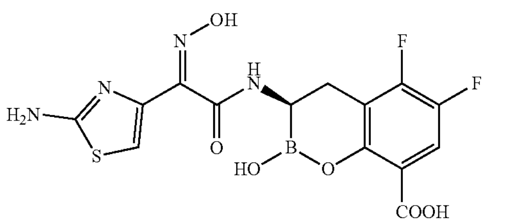 [SMILES: Nc1nc(/C(=N/O)C(=O)N[C@H]2Cc3c(F)c(F)cc(C(=O)O)c3OB2O)cs1] | 412.131 | 413 |
| 41 | 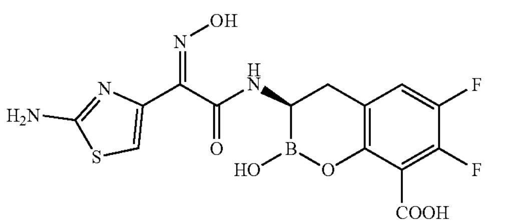 [SMILES: Nc1nc(/C(=N/O)C(=O)N[C@H]2Cc3cc(F)c(F)c(C(=O)O)c3OB2O)cs1] | 412.131 | 413 |
| 42 | 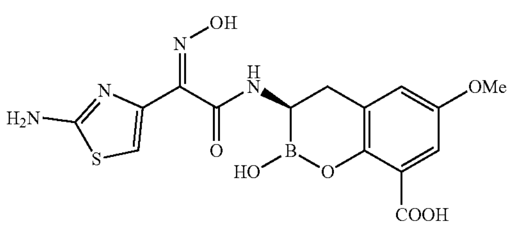 [SMILES: COc1cc2c(c(C(=O)O)c1)OB(O)[C@@H](NC(=O)/C(=N\O)c1csc(N)n1)C2] | 406.176 | 407 |
| 43 | 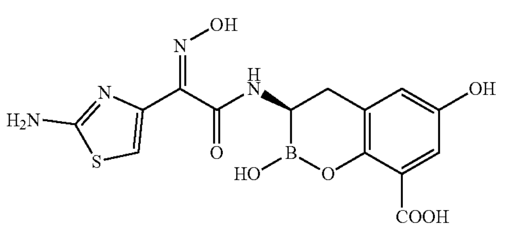 [SMILES: Nc1nc(/C(=N/O)C(=O)N[C@H]2Cc3cc(O)cc(C(=O)O)c3OB2O)cs1] | 392.149 | 393 |
| 44 | 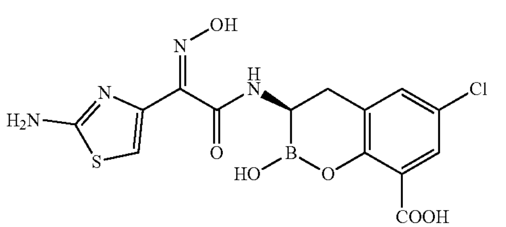 [SMILES: Nc1nc(/C(=N/O)C(=O)N[C@H]2Cc3cc(Cl)cc(C(=O)O)c3OB2O)cs1] | 410.592 | 411 |

TABLE 1-continued
Example compounds
| Ex. | Structure | MW | ESI-MS (m/z) for [MH]+ |
|---|---|---|---|
| 45 | 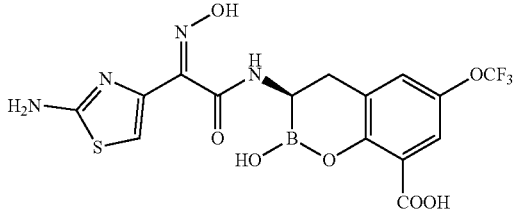 [SMILES: Nc1nc(/C(=N/O)C(=O)N[C@H]2Cc3cc(OC(F)(F)F)cc(C(=O)O)c3OB2O)cs1] | 460.147 | 461 |
| 46 | 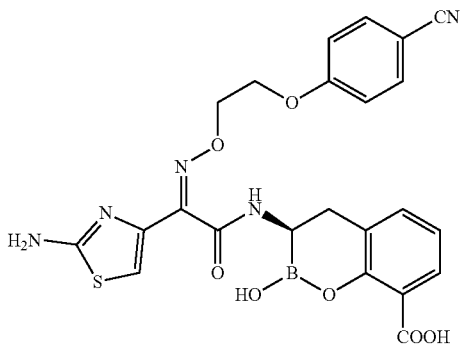 [SMILES: N#Cc1ccc(OCCO/N=C(\C(=O)N[C@H]2Cc3cccc(C(=O)O)c3OB2O)c2csc(N)n2)cc1] | 521.311 | 522 |
| 47 | 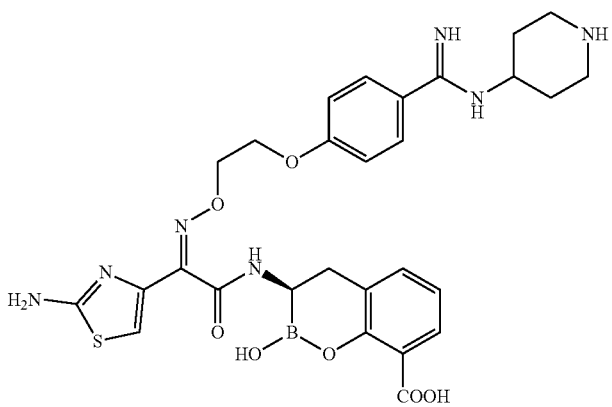 [SMILES: N=C(NC1CCNCC1)c1ccc(OCCO/N=C(\C(=O)N[C@H]2Cc3cccc(C(=O)O)c3OB2O)c2csc(N)n2)cc1] | 621.476 | 622 |
| 48 | 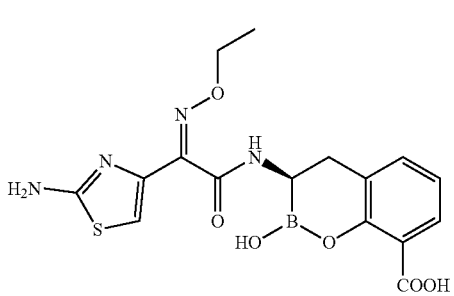 [SMILES: CCO/N=C(\C(=O)N[C@H]1Cc2cccc(C(=O)O)c2OB1O)c1csc(N)n1] | 404.204 | 405 |

TABLE 1-continued

Example compounds

| Ex. | Structure | MW | ESI-MS (m/z) for [MH]+ |
|---|---|---|---|
| 49 | 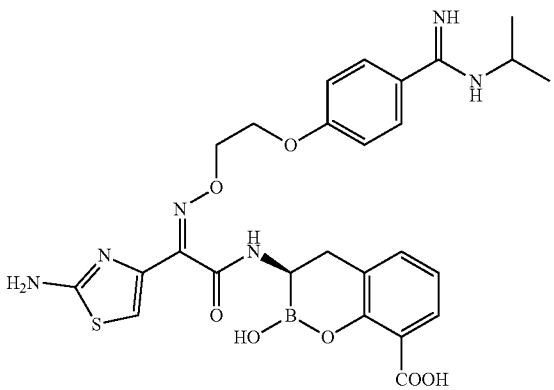 [SMILES: CC(C)NC(=N)c1ccc(OCCO/N=C(\C(=O)N[C@H]2Cc3cccc(C(=O)O)c3OB2O)c2csc(N)n2)cc1] | 580.423 | 581 |
| 50 | 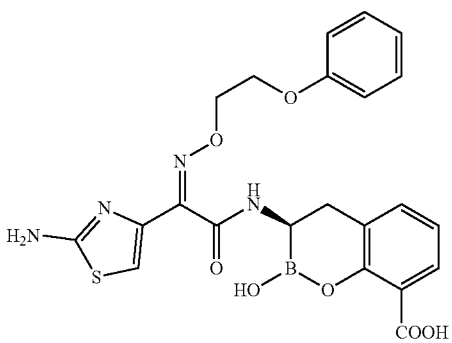 [SMILES: Nc1nc(/C(=N/OCCOc2ccccc2)C(=O)N[C@H]2Cc3cccc(C(=O)O)c3OB2O)cs1] | 496.301 | 497 |
| 51 | 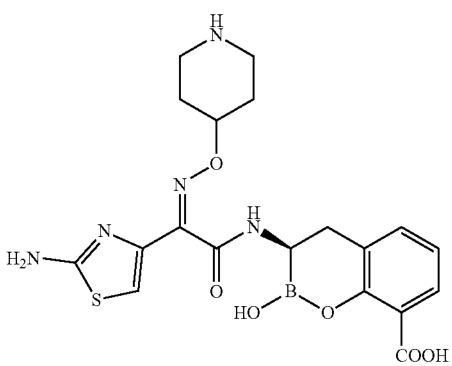 [SMILES: Nc1nc(/C(=N/OC2CCNCC2)C(=O)N[C@H]2Cc3cccc(C(=O)O)c3OB2O)cs1] | 459.284 | 460 |
| 52 | 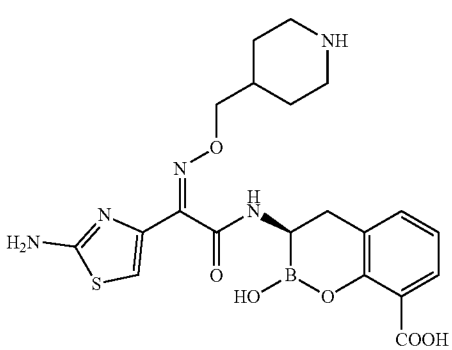 [SMILES: Nc1nc(/C(=N/OCC2CCNCC2)C(=O)N[C@H]2Cc3cccc(C(=O)O)c3OB2O)cs1] | 473.311 | 474 |

TABLE 1-continued
| | Example compounds | | |
|---|---|---|---|
| Ex. | Structure | MW | ESI-MS (m/z) for [MH]+ |
| 53 | 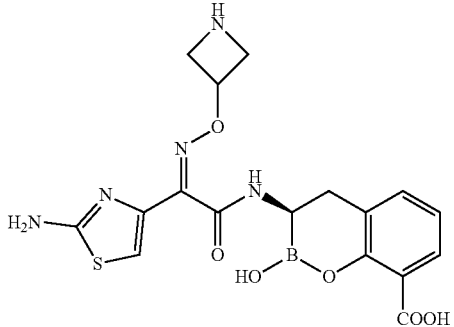 [SMILES: Nc1nc(/C(=N/OC2CNC2)C(=O)N[C@H]2Cc3cccc(C(=O)O)c3OB2O)cs1] | 431.23 | 432 |
| 54 | 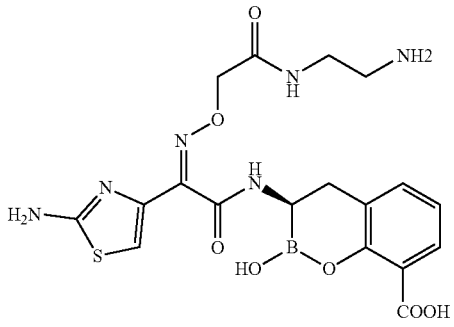 [SMILES: NCCNC(=O)CO/N=C(\C(=O)N[C@H]1Cc2cccc(C(=O)O)c2OB1O)c1csc(N)n1] | 476.271 | 477 |
| 55 | 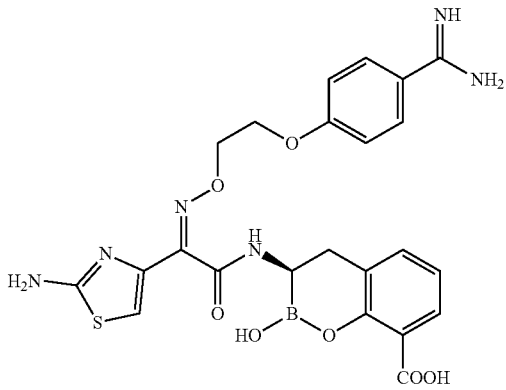 [SMILES: N=C(N)c1ccc(OCCO/N=C(\C(=O)N[C@H]2Cc3cccc(C(=O)O)c3OB2O)c2csc(N)n2)cc1] | 538.342 | 539 |
| 56 | 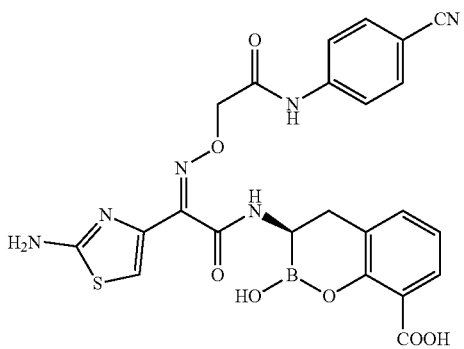 [SMILES: N#Cc1ccc(NC(=O)CO/N=C(\C(=O)N[C@H]2Cc3cccc(C(=O)O)c3OB2O)c2csc(N)n2)cc1] | 534.31 | 535 |

TABLE 1-continued
Example compounds
| Ex. | Structure | MW | ESI-MS (m/z) for [MH]+ |
|---|---|---|---|
| 57 | 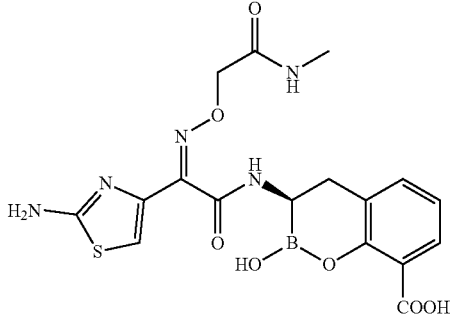 [SMILES: CNC(=O)CO/N=C(\C(=O)N[C@H]1Cc2cccc(C(=O)O)c2OB1O)c1csc(N)n1] | 447.229 | 448 |
| 58 | 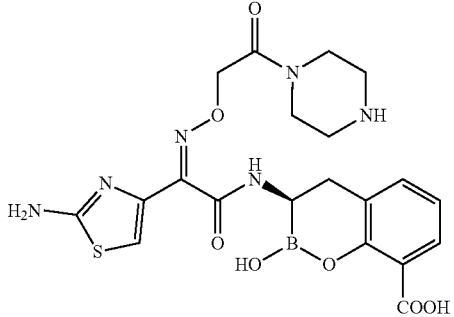 [SMILES: Nc1nc(/C(=N/OCC(=O)N2CCNCC2)C(=O)N[C@H]2Cc3cccc(C(=O)O)c3OB2O)cs1] | 502.309 | 503 |
| 59 | 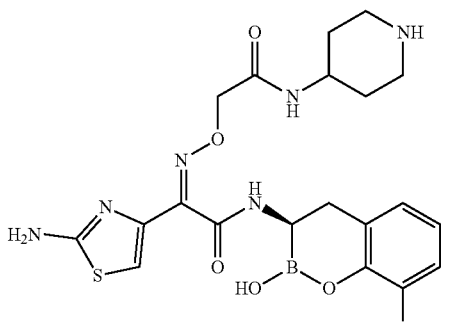 | 516.336 | 517 |
| 60 | 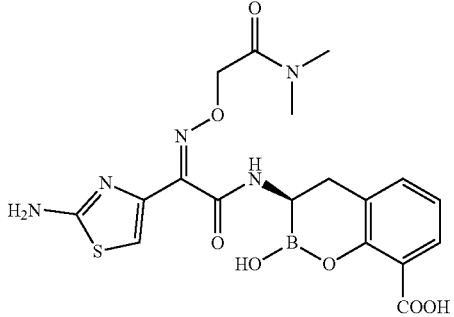 [SMILES: CN(C)C(=O)CO/N=C(\C(=O)N[C@H]1Cc2cccc(C(=O)O)c2OB1O)c1csc(N)n1] | 461.256 | 462 |

TABLE 1-continued
Example compounds
| Ex. | Structure | MW | ESI-MS (m/z) for [MH]+ |
|---|---|---|---|
| 61 | 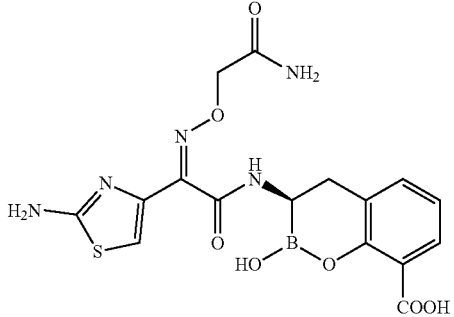 [SMILES: NC(=O)CO/N=C(\C(=O)N[C@H]1Cc2cccc(C(=O)O)c2OB1O)c1csc(N)n1] | 433.202 | 434 |
| 62 | 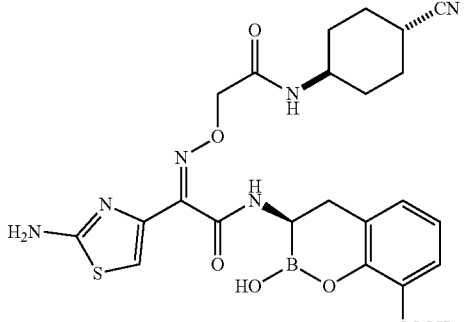 | 540.358 | 541 |
| 63 | 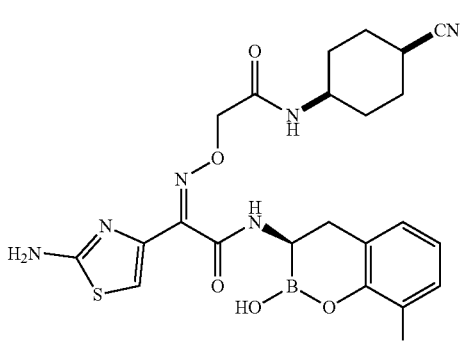 | 540.358 | 541 |
| 64 | 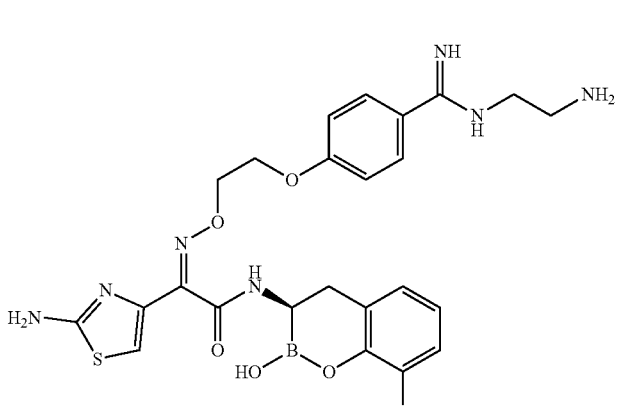 | 581.411 | 582 |

TABLE 1-continued

Example compounds

| Ex. | Structure | MW | ESI-MS (m/z) for [MH]+ |
|---|---|---|---|
| 65 | 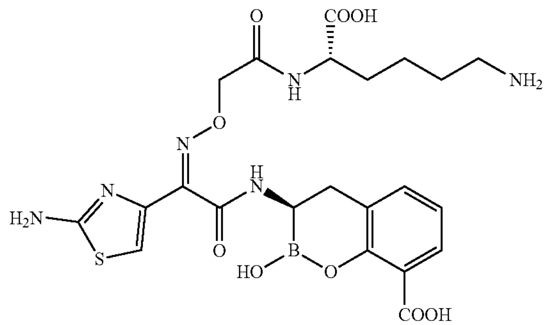 [SMILES: NCCCC[C@H](NC(=O)CO/N=C(\C(=O)N[C@H]1Cc2cccc(C(=O)O)c2OB1O)c1csc(N)n1)C(=O)O] | 562.361 | 563 |
| 66 | 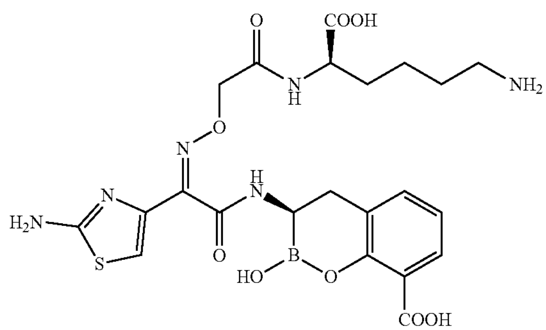 [SMILES: NCCCC[C@@H](NC(=O)CO/N=C(\C(=O)N[C@H]1Cc2cccc(C(=O)O)c2OB1O)c1csc(N)n1)C(=O)O] | 562.361 | 563 |
| 67 | 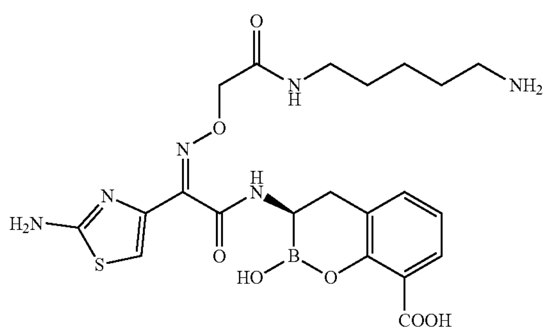 [SMILES: NCCCCCNC(=O)CO/N=C(\C(=O)N[C@H]1Cc2cccc(C(=O)O)c2OB1O)c1csc(N)n1] | 518.352 | 519 |
| 68 | 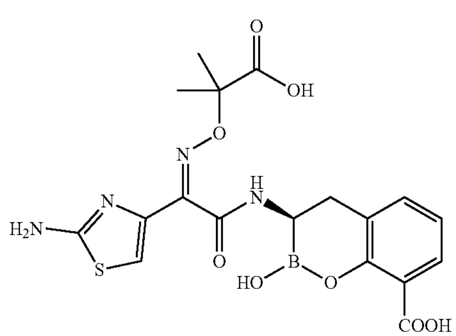 [SMILES: CC(C)(O/N=C(\C(=O)N[C@H]1Cc2cccc(C(=O)O)c2OB1O)c1csc(N)n1)C(=O)O] | 462.24 | 463 |

TABLE 1-continued

Example compounds

| Ex. | Structure | MW | ESI-MS (m/z) for [MH]+ |
|---|---|---|---|
| 69 | 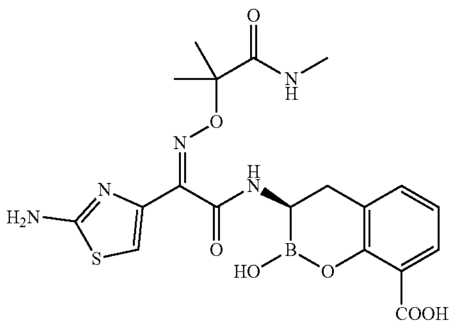 [SMILES: CNC(=O)C(C)(C)O/N=C(\C(=O)N[C@H]1Cc2cccc(C(=O)O)c2OB1O)c1csc(N)n1] | 475.283 | 476 |
| 70 | 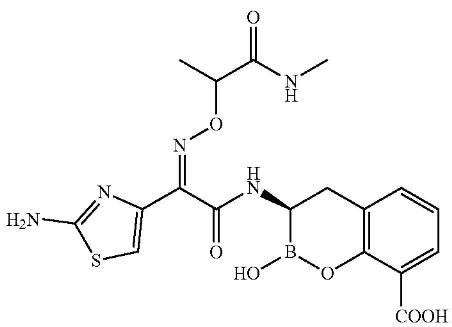 [SMILES: CNC(=O)C(C)O/N=C(\C(=O)N[C@H]1Cc2cccc(C(=O)O)c2OB1O)c1csc(N)n1] | 461.256 | 462 |
| 71 | 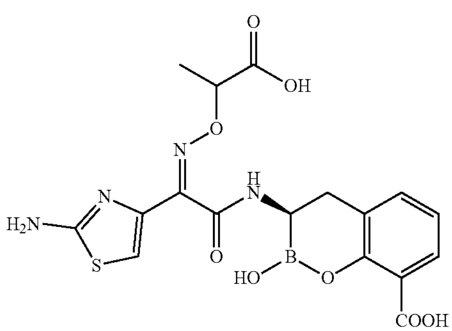 [SMILES: CC(O/N=C(\C(=O)N[C@H]1Cc2cccc(C(=O)O)c2OB1O)c1csc(N)n1)C(=O)O] | 448.213 | 449 |
| 72 | 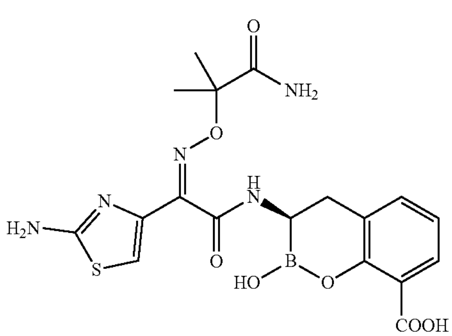 [SMILES: CC(C)(O/N=C(\C(=O)N[C@H]1Cc2cccc(C(=O)O)c2OB1O)c1csc(N)n1)C(N)=O] | 461.256 | 462 |

TABLE 1-continued

Example compounds

| Ex. | Structure | MW | ESI-MS (m/z) for [MH]+ |
|---|---|---|---|
| 73 | 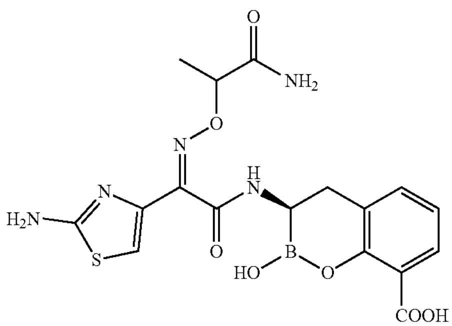 | 447.229 | 448 |
| 74 | 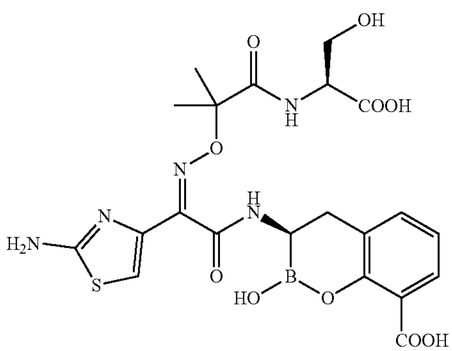 [SMILES: CC(C)(O/N=C(\C(=O)N[C@H]1Cc2cccc(C(=O)O)c2OB1O)c1csc(N)n1)C(=O)N[C@@H](CO)C(=O)O] | 549.318 | 550 |
| 75 | 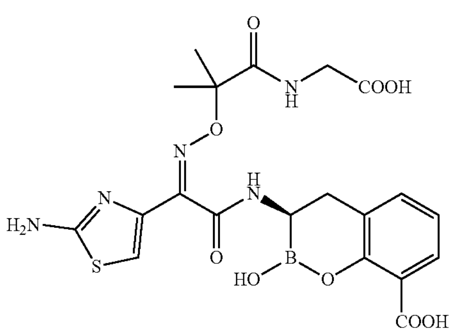 [SMILES: CC(C)(O/N=C(\C(=O)N[C@H]1Cc2cccc(C(=O)O)c2OB1O)c1csc(N)n1)C(=O)NCC(=O)O] | 519.292 | 520 |
| 76 | 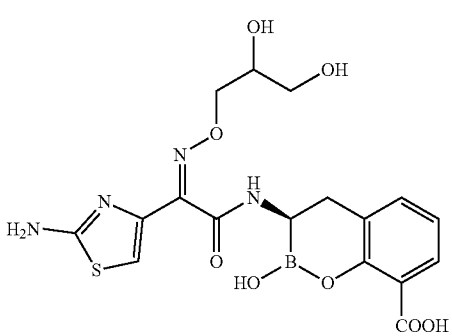 [SMILES: Nc1nc(/C(=N/OCC(O)CO)C(=O)N[C@H]2Cc3cccc(C(=O)O)c3OB2O)cs1] | 450.229 | 451 |

TABLE 1-continued

Example compounds

| Ex. | Structure | MW | ESI-MS (m/z) for [MH]+ |
|---|---|---|---|
| 77 | 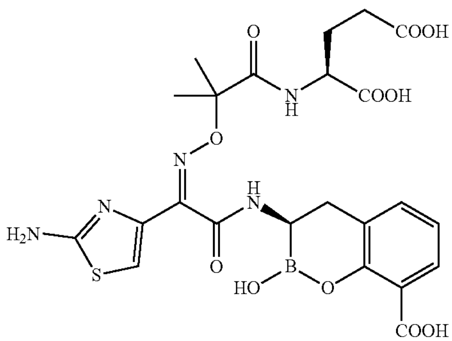 [SMILES: CC(C)(O/N=C(\C(=O)N[C@H]1Cc2cccc(C(=O)O)c2OB1O)c1csc(N)n1)C(=O)N[C@@H](CCC(=O)O)C(=O)O] | 591.355 | 592 |
| 78 | 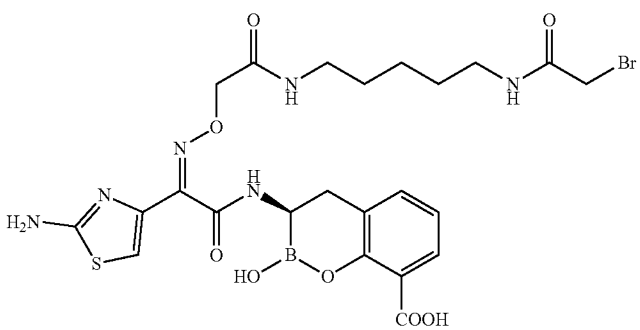 [SMILES: Nc1nc(/C(=N/OCC(=O)NCCCCCNC(=O)CBr)C(=O)N[C@H]2Cc3cccc(C(=O)O)c3OB2O)cs1] | 639.285 | 639, 641 |
| 79 | 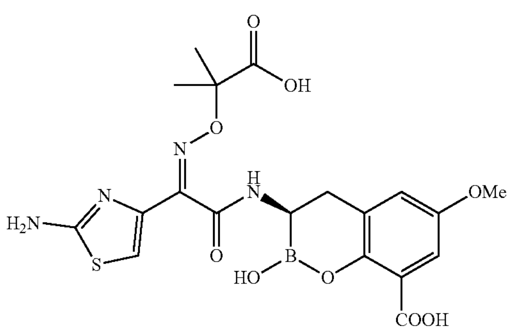 [SMILES: COc1cc2c(c(C(=O)O)c1)OB(O)[C@@H](NC(=O)/C(=N\OC(C)(C)C(=O)O)c1csc(N)n1)C2] | 492.266 | 493 |
| 80 | 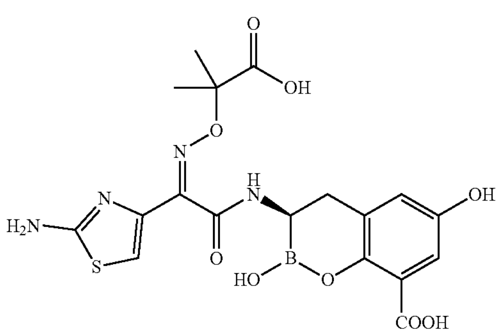 [SMILES: CC(C)(O/N=C(\C(=O)N[C@H]1Cc2cc(O)cc(C(=O)O)c2OB1O)c1csc(N)n1)C(=O)O] | 478.239 | 479 |

TABLE 1-continued

Example compounds

| Ex. | Structure | MW | ESI-MS (m/z) for [MH]+ |
|---|---|---|---|
| 81 | 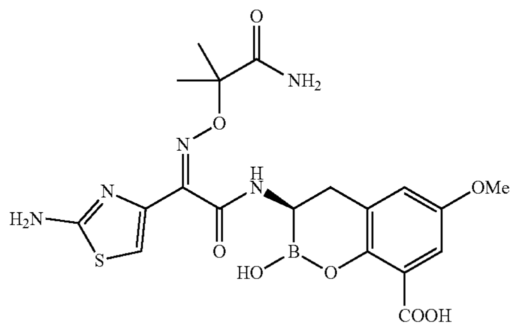 [SMILES: COc1cc2c(c(C(=O)O)c1)OB(O)[C@@H](NC(=O)/C(=N\OC(C)(C)C(N)=O)c1csc(N)n1)C2] | 491.282 | 492 |
| 82 | 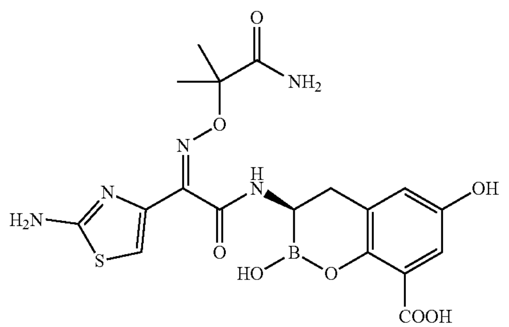 [SMILES: CC(C)(O/N=C(\C(=O)N[C@H]1Cc2cc(O)cc(C(=O)O)c2OB1O)c1csc(N)n1)C(N)=O] | 477.255 | 478 |
| 83 | 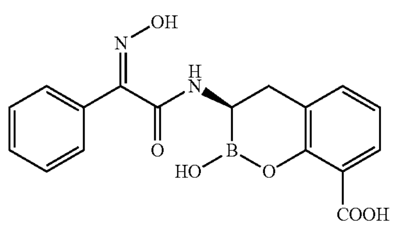 [SMILES: O=C(N[C@H]1Cc2cccc(C(=O)O)c2OB1O)/C(=N\O)c1ccccc1] | 354.125 | 355 |
| 84 | 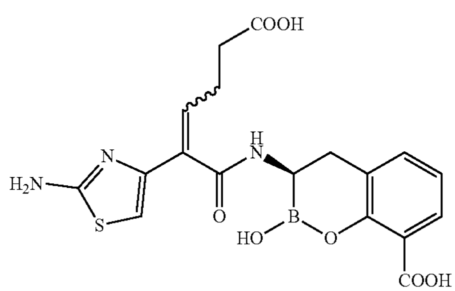 [SMILES: Nc1nc(C(=CCCC(=O)O)C(=O)N[C@H]2Cc3cccc(C(=O)O)c3OB2O)cs1] | 431.226 | 432 |
| 85 | 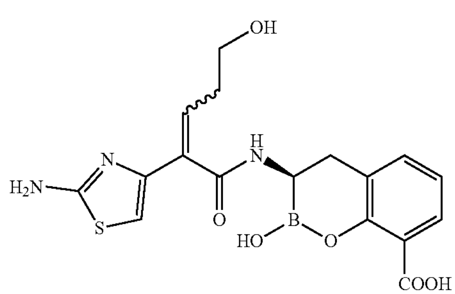 [SMILES: Nc1nc(C(=CCCO)C(=O)N[C@H]2Cc3cccc(C(=O)O)c3OB2O)cs1] | 403.216 | 404 |

TABLE 1-continued

Example compounds

| Ex. | Structure | MW | ESI-MS (m/z) for [MH]+ |
|---|---|---|---|
| 86 | 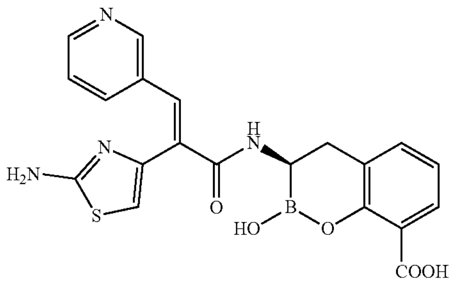 [SMILES: Nc1nc(/C(=C\c2cccnc2)C(=O)N[C@H]2Cc3cccc(C(=O)O)c3OB2O)cs1] | 436.249 | 437 |
| 87 | 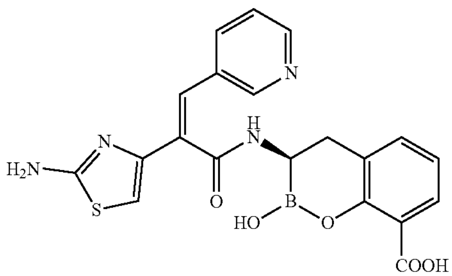 [SMILES: Nc1nc(/C(=C/c2cccnc2)C(=O)N[C@H]2Cc3cccc(C(=O)O)c3OB2O)cs1] | 436.249 | 437 |
| 88 | 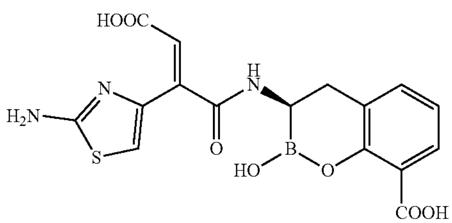 [SMILES: Nc1nc(/C(=C\C(=O)O)C(=O)N[C@H]2Cc3cccc(C(=O)O)c3OB2O)cs1] | 403.172 | 404 |
| 89 | 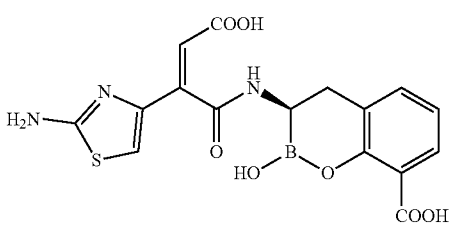 [SMILES: Nc1nc(/C(=C/C(=O)O)C(=O)N[C@H]2Cc3cccc(C(=O)O)c3OB2O)cs1] | 403.172 | 404 |
| 90 | 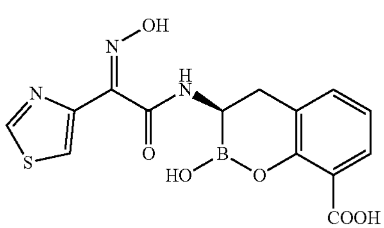 [SMILES: O=C(N[C@H]1Cc2cccc(C(=O)O)c2OB1O)/C(=N\O)c1cscn1] | 361.1 | 362 |
| 91 | 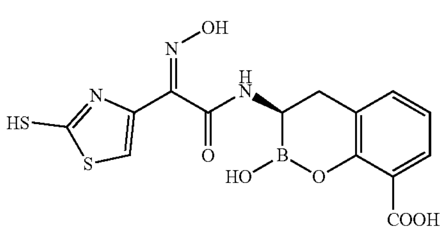 [SMILES: O=C(N[C@H]1Cc2cccc(C(=O)O)c2OB1O)/C(=N\O)c1csc(S)n1] | 393.2 | 394 |

TABLE 1-continued

Example compounds

| Ex. | Structure | MW | ESI-MS (m/z) for [MH]+ |
|---|---|---|---|
| 92 | 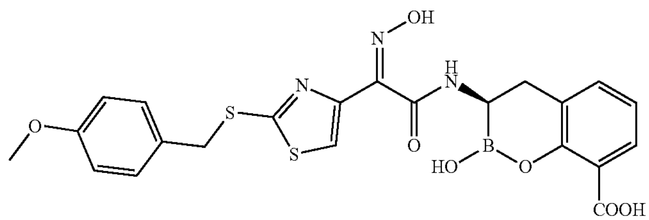 [SMILES: COc1ccc(CSc2nc(/C(=N/O)C(=O)N[C@H]3Cc4cccc(C(=O)O)c4OB3O)cs2)cc1] | 513.3 | 514 |
| 93 | 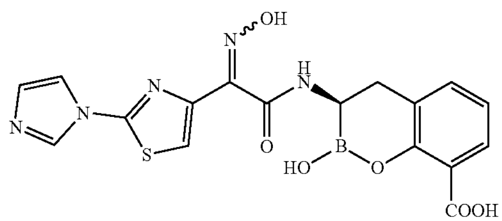 [SMILES: O=C(N[C@H]1Cc2cccc(C(=O)O)c2OB1O)C(=NO)c1csc(-n2ccnc2)n1] | 427.2 | 428 |
| 94 | 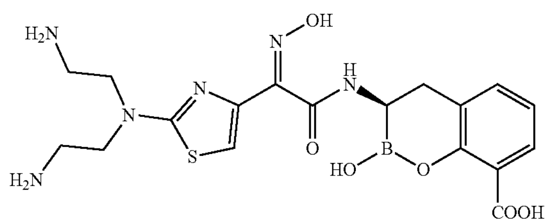 [SMILES: NCCN(CCN)c1nc(/C(=N/O)C(=O)N[C@H]2Cc3cccc(C(=O)O)c3OB2O)cs1] | 462.3 | 463 |
| 95 | 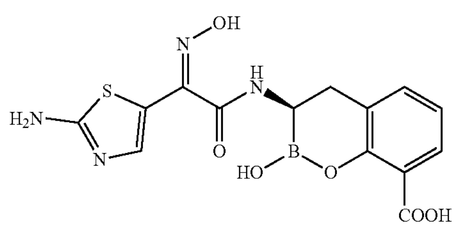 [SMILES: Nc1ncc(/C(=N/O)C(=O)N[C@H]2Cc3cccc(C(=O)O)c3OB2O)s1] | 376.2 | 377 |
| 96 | 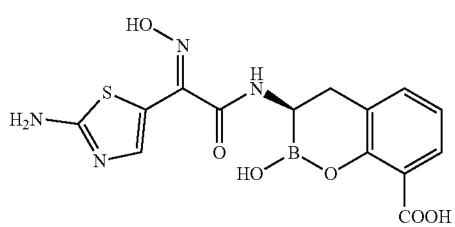 [SMILES: Nc1ncc(/C(=N\O)C(=O)N[C@H]2Cc3cccc(C(=O)O)c3OB2O)s1] | 376.2 | 377 |
| 97 | 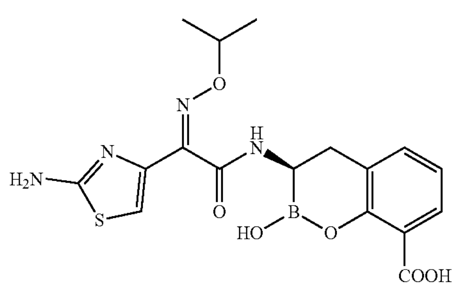 [SMILES: CC(C)O/N=C(\C(=O)N[C@H]1Cc2cccc(C(=O)O)c2OB1O)c1csc(N)n1] | 418.2 | 419 |

TABLE 1-continued

Example compounds

| Ex. | Structure | MW | ESI-MS (m/z) for [MH]+ |
|---|---|---|---|
| 98 | 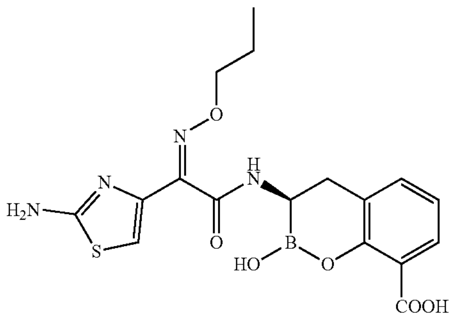 [SMILES: CCCO/N=C(\C(=O)N[C@H]1Cc2cccc(C(=O)O)c2OB1O)c1csc(N)n1] | 418.2 | 419 |
| 99 | 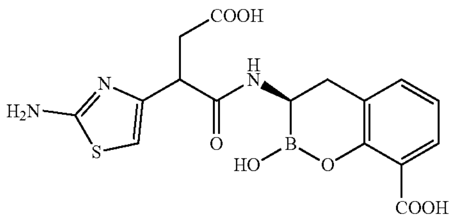 [SMILES: Nc1nc(C(CC(=O)O)C(=O)N[C@H]2Cc3cccc(C(=O)O)c3OB2O)cs1] | 405.2 | 406 |
| 100 | 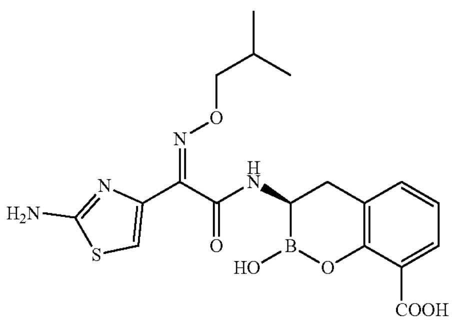 [SMILES: CC(C)CO/N=C(\C(=O)N[C@H]1Cc2cccc(C(=O)O)c2OB1O)c1csc(N)n1] | 432.3 | 433 |
| 101 | 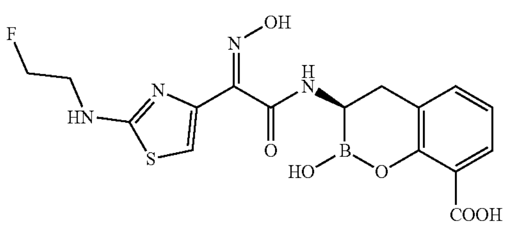 [SMILES: O=C(N[C@H]1Cc2cccc(C(=O)O)c2OB1O)/C(=N\O)c1csc(NCCF)n1] | 422.2 | 423 |
| 102 | 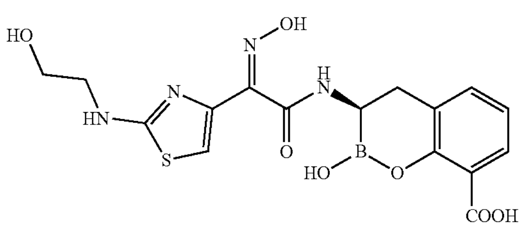 [SMILES: O=C(N[C@H]1Cc2cccc(C(=O)O)c2OB1O)/C(=N\O)c1csc(NCCO)n1] | 420.2 | 421 |
| 103 | 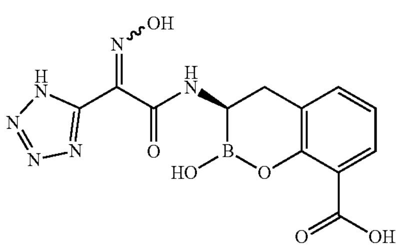 [SMILES: O=C(N[C@H]1Cc2cccc(C(=O)O)c2OB1O)C(=NO)c1nnn[nH]1] | 346.1 | 347 |

TABLE 1-continued
Example compounds
| Ex. | Structure | MW | ESI-MS (m/z) for [MH]+ |
|---|---|---|---|
| 104 | 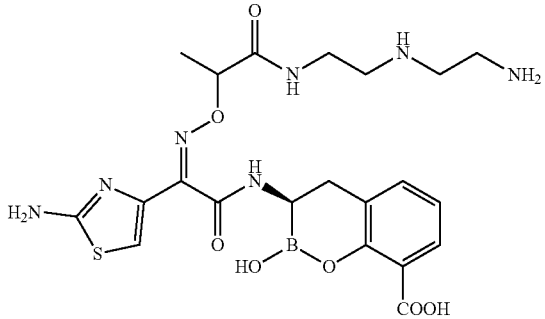 [SMILES: CC(O/N=C(\C(=O)N[C@H]1Cc2cccc(C(=O)O)c2OB1O)c1csc(N)n1)C(=O)NCCNCCN] | 533.4 | 534 |
| 105 | 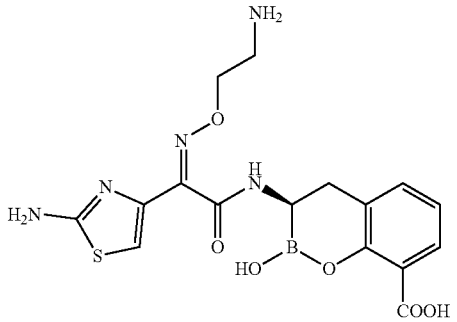 | 419.2 | 420 |
| 106 | 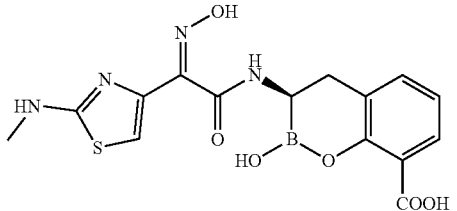 [SMILES: CNc1nc(/C(=N/O)C(=O)N[C@H]2Cc3cccc(C(=O)O)c3OB2O)cs1] | 390.2 | 391 |
| 107 | 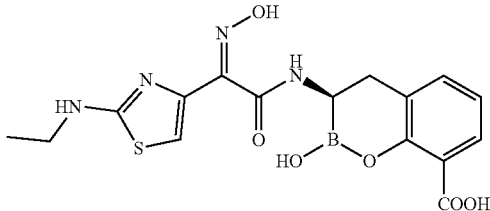 [SMILES: CCNc1nc(/C(=N/O)C(=O)N[C@H]2Cc3cccc(C(=O)O)c3OB2O)cs1] | 404.2 | 405 |
| 108 | 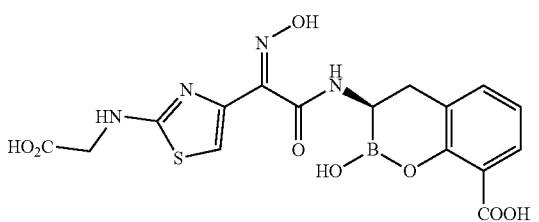 [SMILES: O=C(O)CNc1nc(/C(=N/O)C(=O)N[C@H]2Cc3cccc(C(=O)O)c3OB2O)cs1] | 434.2 | 435 |

TABLE 1-continued
Example compounds
| Ex. | Structure | MW | ESI-MS (m/z) for [MH]+ |
|---|---|---|---|
| 109 | 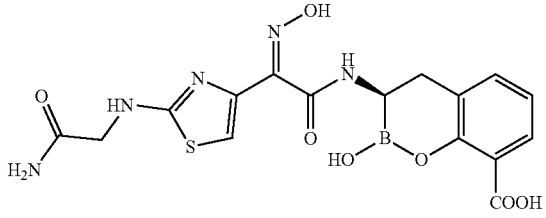 [SMILES: NC(=O)CNc1nc(/C(=N/O)C(=O)N[C@H]2Cc3cccc(C(=O)O)c3OB2O)cs1] | 433.2 | 434 |
| 110 | 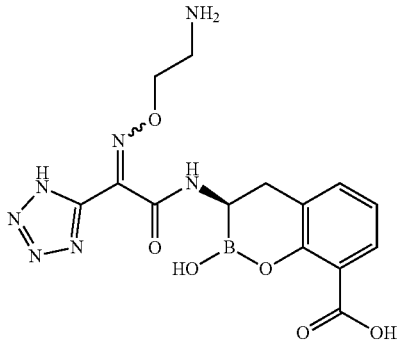 [SMILES: NCCON=C(C(=O)N[C@H]1Cc2cccc(C(=O)O)c2OB1O)c1nnn[nH]1] | 389.1 | 390 |
| 111 | 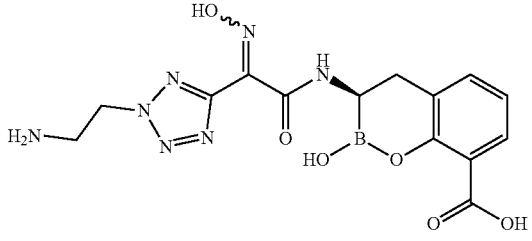 [SMILES: NCCn1nnc(C(=NO)C(=O)N[C@H]2Cc3cccc(C(=O)O)c3OB2O)n1] | 389.1 | 390 |
| 112 | 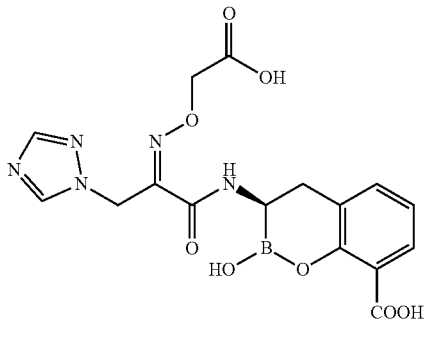 [SMILES: O=C(O)CO/N=C(/Cn1cncn1)C(=O)N[C@H]1Cc2cccc(C(=O)O)c2OB1O] | 417.1 | 418 |
| 113 | 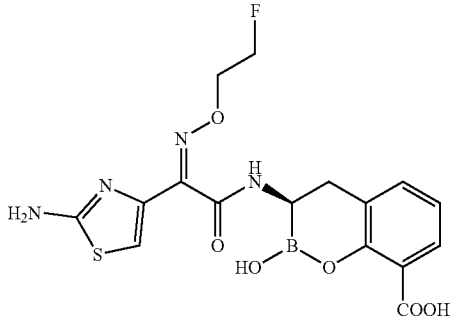 [SMILES: Nc1nc(/C(=N/OCCF)C(=O)N[C@H]2Cc3cccc(C(=O)O)c3OB2O)cs1] | 422.2 | 423 |

TABLE 1-continued
Example compounds
| Ex. | Structure | MW | ESI-MS (m/z) for [MH]+ |
|---|---|---|---|
| 114 | 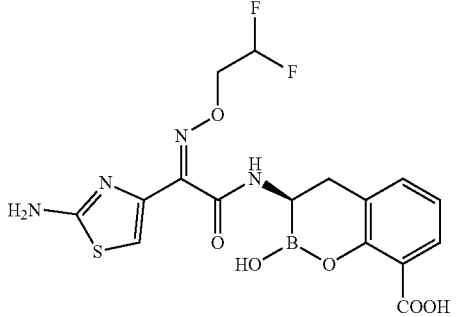 [SMILES: Nc1nc(/C(=N/OCC(F)F)C(=O)N[C@H]2Cc3cccc(C(=O)O)c3OB2O)cs1] | 440.2 | 441 |
| 115 | 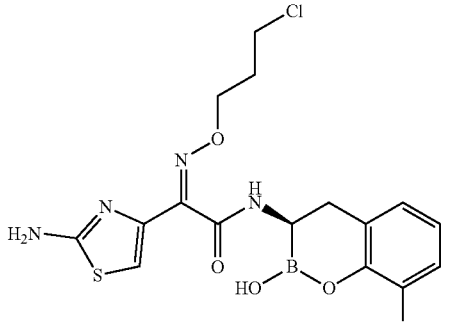 | 452.7 | 453, 455 |
| 116 | 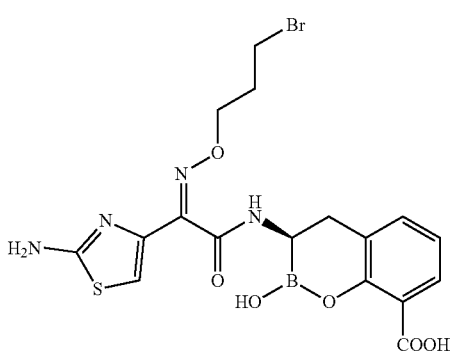 | 497.1 | 497, 499 |
| 117 | 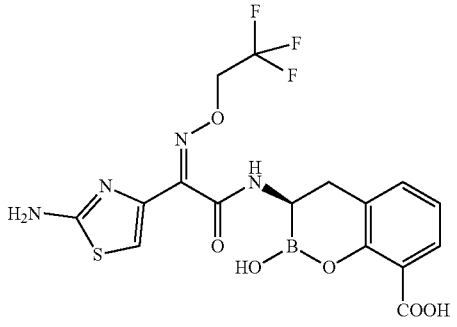 [SMILES: Nc1nc(/C(=N/OCC(F)(F)F)C(=O)N[C@H]2Cc3cccc(C(=O)O)c3OB2O)cs1] | 458.2 | 459 |

TABLE 1-continued

Example compounds

| Ex. | Structure | MW | ESI-MS (m/z) for [MH]+ |
|---|---|---|---|
| 118 | 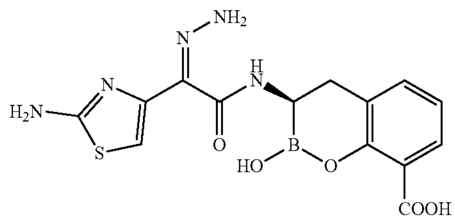 | 375.2 | 376 |
| 119 | 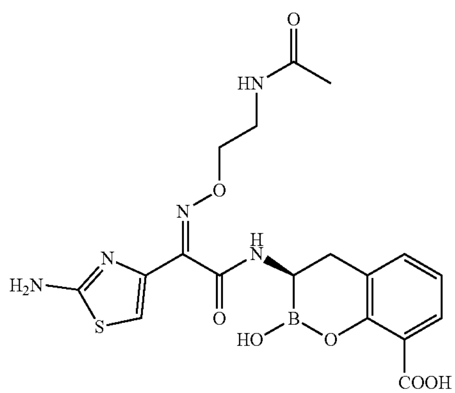 [SMILES: CC(=O)NCCO/N=C(\C(=O)N[C@H]1Cc2cccc(C(=O)O)c2OB1O)c1csc(N)n1] | 461.3 | 462 |
| 120 | 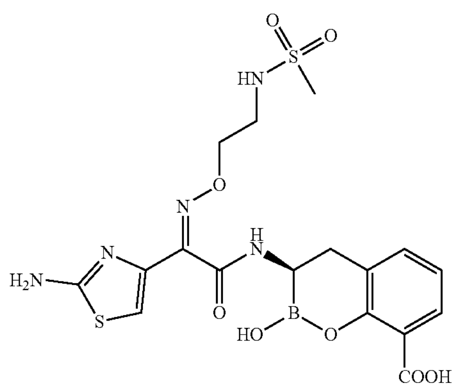 [SMILES: CS(=O)(=O)NCCO/N=C(\C(=O)N[C@H]1Cc2cccc(C(=O)O)c2OB1O)c1csc(N)n1] | 497.3 | 498 |
| 121 | 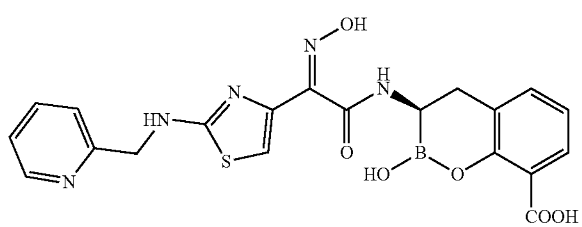 [SMILES: O=C(N[C@H]1Cc2cccc(C(=O)O)c2OB1O)/C(=N\O)c1csc(NCc2ccccn2)n1] | 467.3 | 468 |
| 122 | 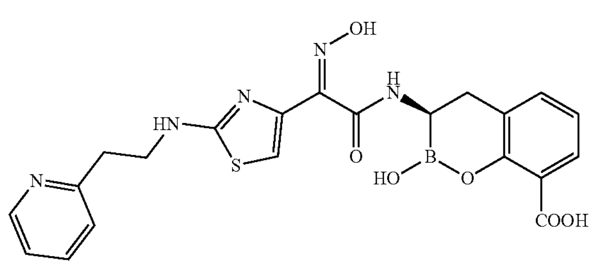 [SMILES: O=C(N[C@H]1Cc2cccc(C(=O)O)c2OB1O)/C(=N\O)c1csc(NCCc2ccccn2)n1] | 481.3 | 482 |

TABLE 1-continued

Example compounds

| Ex. | Structure | MW | ESI-MS (m/z) for [MH]+ |
|---|---|---|---|
| 123 | 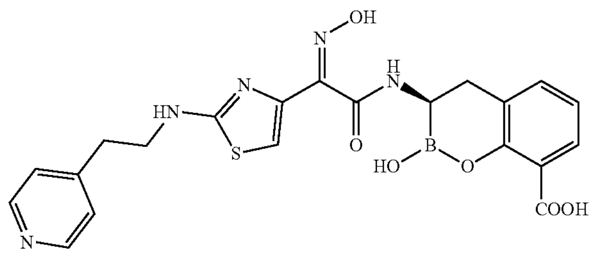 [SMILES: O=C(N[C@H]1Cc2cccc(C(=O)O)c2OB1O)/C(=N\O)c1csc(NCCc2ccncc2)n1] | 481.3 | 482 |
| 124 | 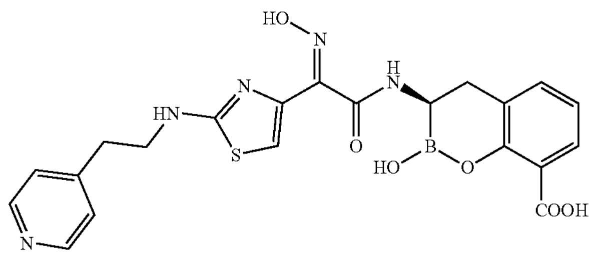 [SMILES: O=C(N[C@H]1Cc2cccc(C(=O)O)c2OB1O)/C(=N/O)c1csc(NCCc2ccncc2)n1] | 481.3 | 482 |
| 125 | 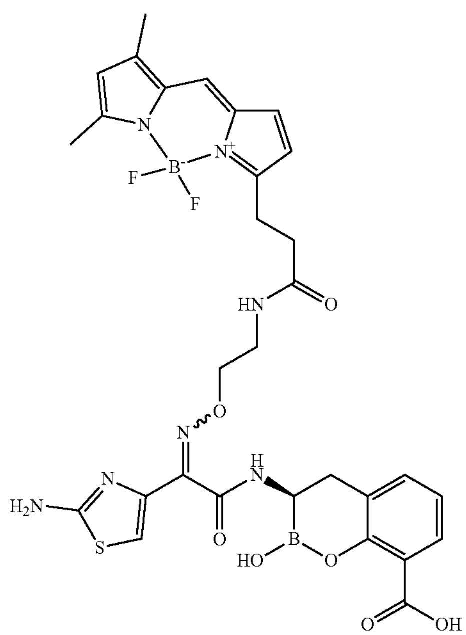 [SMILES: Cc1cc(C)n2c1C=C1C=CC(CCC(=O)NCCON=C(C(=O)N[C@H]3Cc4cccc(C(=O)O)c4OB3O)c3csc(N)n3)=[N+]1[B-]2(F)F] | 693.3 | 694 |
| 126 | 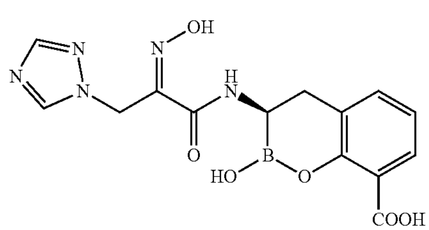 [SMILES: O=C(N[C@H]1Cc2cccc(C(=O)O)c2OB1O)/C(Cn1cncn1)=N\O] | 359.1 | 360 |

TABLE 1-continued

Example compounds

| Ex. | Structure | MW | ESI-MS (m/z) for [MH]+ |
|---|---|---|---|
| 127 | 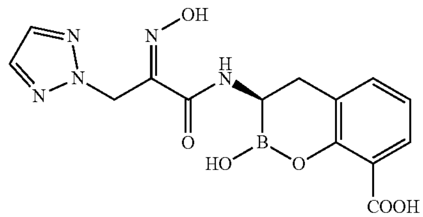 [SMILES: O=C(N[C@H]1Cc2cccc(C(=O)O)c2OB1O)/C(Cn1nccn1)=N\O] | 359.1 | 360 |

Example A1: Parenteral Composition of a Compounds of Formula (Ia)-(IVa) or (Ib)-(IVb)

To prepare a parenteral pharmaceutical composition suitable for administration by injection, 100 mg of a compound of Formula (Ia)-(IVa) or (Ib)-(IVb), or a water soluble pharmaceutically acceptable salt thereof, is dissolved in DMSO and then mixed with 10 ml of 0.9% sterile saline solution. The mixture is incorporated into a dosage unit suitable for administration by injection.

Example A2: Oral Composition of a Compounds of Formula (Ia)-(IVa) or (Ib)-(IVb)

To prepare a pharmaceutical composition for oral delivery, 400 mg of compound of Formula (Ia)-(IVa) or (Ib)-(IVb) and the following ingredients are mixed intimately and pressed into single scored tablets.

Tablet Formulation

| Ingredient | Quantity per tablet (mg) |
|---|---|
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

Capsule Formulation

| Ingredient | Quantity per capsule (mg) |
|---|---|
| compound | 200 |
| lactose spray dried | 148 |
| magnesium stearate | 2 |

BIOLOGICAL EXAMPLES

Example I: Experimental Method for Penicillin-Binding Protein Binding Assays To determine the ability of test compounds to bind Penicillin Binding Proteins (PBPs), a competition binding assay using Bocillin FL (fluorescent derivative of penicillin V) was adapted from the classical method used to assess PBP potency of beta-lactams.

Penicillin binding proteins were isolated from *Escherichia coli* K12 by growth of *Escherichia coli* K12 from a single colony in 4 L of Luria-Bertani (LB) broth at 35° C. and 250 rpm to an $OD_{600\ nm}$ of 0.5. The cells were harvested by centrifugation at 7,000×g for 10 min. at 4° C. Cells were resuspended and washed in 50 mM potassium phosphate pH 7.5. The cells were re-suspended in sonication buffer [50 mM Tris-HCl pH 7.5, 1 mM $MgCl_2$, 1 mM beta-mercaptoethanol, and 5 μg/mL DNAse I] and sonicated by 4 passes of 30 seconds at 45 W on ice. The sample was clarified by centrifugation at 3,000×g to remove cell debris and unbroken cells and supernatant containing the membrane proteins was retained. The membrane proteins including the PBPs were further purified from soluble constituents by an ultracentrifugation step at 100,000×g for 30 min. at 4° C. The membrane proteins are washed twice with 10 mM sodium phosphate pH 7, resuspended in a volume of 5 mL, quantitated by BCA assay, adjusted to 10 μg/mL and frozen at −80° C. until use.

The adapted Bocillin FL competition binding method described herein incorporates a 15 min. pre-incubation of test compound with isolated PBPs to attempt to balance the difference in mechanism of inhibition between beta-lactams (largely irreversible covalent bond to active site Serine) and the boron-containing PBP inhibitor test compounds (reversible covalent bond to active site Serine). Briefly, 50 μL reactions consisted of 100 μg's of total membrane protein extracts containing PBPs incubated with a dilution series of test compound ranging from 0.005 μg/mL to 2,480 μg/mL in 10 mM sodium phosphate pH7 containing 350 mM NaCl. Thirty minute reactions at 35° C. were initiated by addition of 10 mM Bocillin FL, quenched by addition of SDS-PAGE loading buffer containing sodium dodecyl sulfate (SDS) and heated for 15 minutes at 95° C. to denature proteins in preparation for SDS-polyacrylamide gel electrophoresis. The Bocillin FL labeled PBPs are then separated by SDS-PAGE in Novex NuPage 10% Bis-Tris pre-cast gels (Invitrogen). The SDS-PAGE gel, post-electrophoresis, is then washed in water to remove excess SDS for 10 minutes at room temperature and placed on the scanning bed of a GE Healthcare/Amersham Biosciences Storm 860 fluorescence scanner. The excitation wavelength is in the blue spectrum at 450 nm and the emission at 520 nm is captured by the instrument. Effective PBP inhibitors are detected by a reduction in Bocillin FL labeling of the particular PBP over the dose range of test compound in a dose-responsive manner. High molecular weight PBP 1a/1b are not resolved by these gels, thus we report HMW PBP binding results in μg/mL for PBPs 1a/1b combined as well as for PBP2 and PBP3.

Representative results are shown in Table 2, where A represents a potency of >1000 µg/mL, B represents a potency between 64 and 1000 µg/mL inclusive, and C represents a potency of <64 µg/mL. NT=Not Tested.

TABLE 2

Inhibition of Penicillin-Binding Proteins by Exemplary Compounds

| Ex. | E. coli K12 PBP1a/b Potency (µg/mL) | E. coli PBP2 Potency (µg/mL) | E. coli PBP3 Potency (µg/mL) |
|---|---|---|---|
| 1 | C | A | C |
| 6 | C | B | B |
| 7 | A | B | A |
| 12 | B | B | B |
| 17 | B | B | B |
| 35 | C | A | B |
| 37 | B | C | B |
| 41 | B | B | B |
| 42 | C | C | C |
| 44 | B | B | B |
| 46 | C | C | B |
| 47 | B | B | B |
| 48 | B | B | B |
| 49 | B | B | B |
| 50 | B | B | B |
| 52 | A | A | A |
| 55 | C | B | C |
| 56 | B | C | C |
| 57 | C | B | C |
| 58 | B | C | C |
| 59 | B | C | C |
| 60 | B | C | C |
| 61 | C | B | C |
| 62 | B | B | C |
| 63 | B | B | C |
| 64 | C | B | C |
| 65 | C | B | C |
| 66 | C | B | C |
| 67 | B | B | C |
| 68 | C | C | C |
| 69 | C | C | C |
| 70 | C | C | C |
| 71 | C | C | C |
| 72 | C | C | C |
| 73 | C | C | C |
| 74 | C | C | C |
| 75 | C | C | C |
| 78 | B | B | B |
| 87 | A | B | B |
| 88 | A | B | B |
| 89 | A | C | C |

Example II: In Vitro Antibacterial Assays

To determine the ability of test compounds to potentiate the inhibition of the growth of bacterial strains, classic cell based broth microdilution MIC assays were employed. MIC assays are performed according to CLSI methods except where otherwise noted (CLSI, 2011 and CLSI, 2009). The reference strain S. aureus ATCC 29213 and the hyperpermeable E. coli 901C were used to determine the ability of the PBP compounds to inhibit bacterial growth. Briefly, cryo-preserved bacterial cultures of clinical strains are streaked for isolation on appropriate agar medium, in this case Mueller Hinton II agar. Following incubation to allow formation of colonies these plates are sealed with parafilm and stored refrigerated for up to two weeks. For preparation of assay inocula and to ensure low variability, at least 5 colonies are picked from the agar plates with an inoculating loop and aseptically transferred to a culture tube containing 3 mL of Mueller-Hinton Broth (supplemented with divalent cations to required levels based on Manufacturers' certification). The broth culture is grown for 3-5 hours at 37° C. with shaking at 200 rpm. Meanwhile, 2-fold serial dilutions of test compounds are conducted in a 96 well plate with a final volume of 75 µL per well at 2-fold the final desired concentration. After the dilution plates are set up the growing cultures are then diluted in a cuvette containing MH II broth and the optical density is measured at 600 nm. Inocula are diluted such that 75 µL of this culture in Mueller-Hinton Broth results in a starting bacterial concentration of $5 \times 10^5$ CFU/mL when added to the dilution plates. The plates are incubated 16-20 hours at 37° C. The MIC is read visually as the lowest concentration well with no bacterial growth.

Representative results are shown in Table 3 where A represents an MIC >128 µg/mL, B represents an MIC between 64 and 128 µg/mL inclusive, and C represents an MIC of <64 µg/mL. NT=Not Tested.

TABLE 3

Inhibition of bacterial growth. Minimum Inhibitory Concentrations of Exemplary Compounds

| Ex. | S. aureus 29213 MIC (µg/mL) | E. coli 901C MIC (µg/mL) |
|---|---|---|
| 1 | B | C |
| 2 | A | C |
| 3 | A | A |
| 4 | B | A |
| 5 | A | A |
| 6 | C | C |
| 7 | B | C |
| 8 | C | C |
| 9 | A | A |
| 10 | B | A |
| 11 | C | A |
| 12 | C | A |
| 13 | B | A |
| 14 | C | A |
| 15 | B | A |
| 16 | C | B |
| 17 | C | B |
| 18 | A | C |
| 19 | B | A |
| 20 | A | A |
| 21 | B | A |
| 22 | A | A |
| 23 | A | A |
| 24 | B | A |
| 25 | C | A |
| 26 | C | NT |
| 27 | A | B |
| 28 | A | A |
| 29 | A | NT |
| 30 | C | NT |
| 31 | A | NT |
| 32 | C | C |
| 33 | C | A |
| 34 | C | NT |
| 35 | B | A |
| 36 | C | NT |
| 37 | B | C |
| 38 | A | NT |
| 39 | C | C |
| 40 | C | A |
| 41 | B | C |
| 42 | C | C |
| 43 | C | B |
| 44 | C | C |
| 45 | C | C |
| 46 | B | C |
| 47 | B | C |
| 48 | B | C |
| 49 | B | C |
| 50 | B | C |
| 51 | A | B |
| 52 | A | C |
| 53 | A | B |
| 54 | A | C |

TABLE 3-continued

Inhibition of bacterial growth. Minimum Inhibitory Concentrations of Exemplary Compounds

| Ex. | S. aureus 29213 MIC (µg/mL) | E. coli 901C MIC (µg/mL) |
|---|---|---|
| 55 | A | C |
| 56 | B | C |
| 57 | A | C |
| 58 | A | C |
| 59 | A | C |
| 60 | A | C |
| 61 | B | C |
| 62 | A | C |
| 63 | A | C |
| 64 | A | C |
| 65 | A | C |
| 66 | A | C |
| 67 | A | C |
| 68 | A | C |
| 69 | A | C |
| 70 | A | C |
| 71 | A | C |
| 72 | A | C |
| 73 | A | C |
| 74 | A | C |
| 75 | A | C |
| 76 | B | C |
| 77 | A | C |
| 78 | NT | A |
| 79 | A | C |
| 80 | A | C |
| 81 | A | C |
| 82 | A | C |
| 83 | C | A |
| 84 | A | C |
| 85 | B | B |
| 86 | B | C |
| 87 | B | C |
| 88 | A | B |
| 89 | A | B |
| 90 | C | B |
| 91 | C | A |
| 92 | C | A |
| 93 | C | A |
| 94 | C | A |
| 95 | C | A |
| 96 | B | A |
| 97 | B | A |
| 98 | C | C |
| 99 | A | B |
| 100 | C | C |
| 101 | A | B |
| 102 | A | A |
| 103 | A | A |
| 104 | A | C |
| 105 | A | C |
| 106 | A | A |
| 107 | A | A |
| 108 | A | A |
| 109 | A | A |
| 110 | A | A |
| 111 | A | A |
| 112 | A | A |
| 113 | B | C |
| 114 | B | C |
| 115 | A | C |
| 116 | A | A |
| 117 | B | C |
| 118 | A | B |
| 119 | A | B |
| 120 | A | B |
| 121 | C | A |
| 122 | C | A |
| 123 | C | A |
| 124 | A | A |
| 125 | A | A |
| 126 | A | A |
| 127 | A | A |

Example III: Boronate Compounds are not Inhibited by Known β-Lactamases

To determine if test compounds were affected by various known β-lactamases, the inhibition of the growth of engineered strains of Escherichia coli harboring select single β-lactamases were tested. These strains were constructed by cloning the gene encoding the particular β-lactamase into the NdeI and BamHI restriction endonuclease sites of plasmid pLBII, placing the gene(s) under the control of the Lac promoter. The constructed expression plasmids for SHV-5, CTX-M15, TEM-24, KPC-2, OXA-48, VIM-2, NDM-1 and IMP-18 were used to transform competent E. coli DH5a cells to make each engineered strain, including a control strain possessing the pLBII plasmid with no β-lactamase gene encoded. The classic cell based broth microdilution MIC assay was employed as described above with the addition of control antibiotics, known to be degraded by β-lactamases (Ceftazidime-Avibactam and Aztreonam). Examples 1 and 6 display the same MIC values in strains regardless of the β-lactamase expressed, whereas β-lactams antibiotics, aztreonam and ceftazidime-avibactam, have weaker MICs in those strains.

TABLE 4

Inhibition of growth of engineered Escherichia coli strains harboring select β-lactamase genes. Minimum Inhibitory Concentrations of Exemplary Compounds as compared to β-lactams antibiotics

| Compound MIC (µg/mL) | β-lactamase | | | | | | | | |
|---|---|---|---|---|---|---|---|---|---|
|  | None | SHV | CTXM | TEM | KPC | VIM | NDM | OXA | IMP |
| Ex. 1 | 8 | 8 | 8 | 8 | 4 | 8 | 8 | 8 | 8 |
| Ex. 6 | 16 | 16 | 16 | 16 | 16 | 16 | 16 | 16 | 16 |
| Ceftazidime-Avibactam | 0.06 | 0.25 | 0.125 | 0.25 | 0.25 | 4 | 8 | 0.125 | 128 |
| Aztreonam | 0.06 | 8 | 32 | 1 | 2 | 0.06 | 0.06 | 0.125 | 0.06 |

Example IV. Experimental Method for Penicillin-Binding Protein Binding Assay with Example 125 (Bodipy FL-Labeled Boronic Acid PBP Inhibitor/Probe)

To determine the ability of boronic acid-based test PBP inhibitors to bind Penicillin Binding Proteins (PBPs), a competition binding assay using a Bodipy-FL-labeled boronic acid PBP inhibitor (Example 125) was adapted from the classical method used to assess PBP potency of beta-lactams using Bocillin-FL (fluorescently-labeled penicillin V). The method is identical to that described in Example I for the Bocillin-FL competition binding assay with the following exceptions, the Bodipy-FL boronic acid probe (Example 125) is used at a final concentration of 30 μM, pre-incubation time of test compound with PBP enzymes is 10 minutes and reaction time is set for 10 minutes and reactions are prepared for SDS-PAGE analysis by simply adding SDS-containing loading buffer. Representative results are shown in Table 5, where A represents a potency of >1000 μg/mL, B represents a potency between 64 and 1000 μg/mL inclusive, and C represents a potency of <64 μg/mL. NT=Not Tested.

TABLE 5

Binding affinity to *E. coli* PBP1b by Exemplary Compounds in competition binding assay using Bodipy-FL boronic acid probe (Example 125).

| Ex. | *E. coli* K12 PBP1b Potency (μg/mL) |
|---|---|
| 6 | C |
| 47 | B |
| 48 | B |
| 49 | A |
| 52 | B |
| 59 | B |
| 61 | C |
| 68 | C |
| 76 | B |
| 82 | B |
| 113 | B |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (IIa) or (IIb), or a pharmaceutically acceptable salt, solvate, stereoisomer, tautomer, N-oxide, dimer, or trimer thereof:

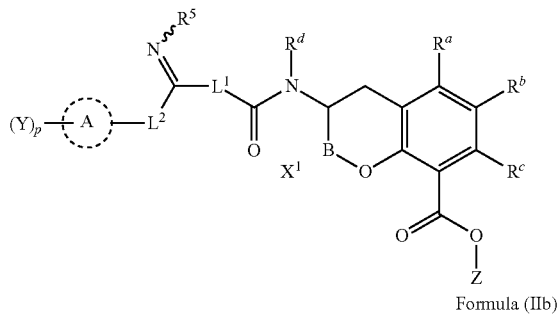

Formula (IIa)

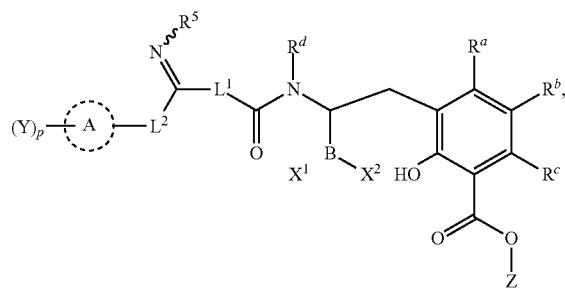

Formula (IIb)

wherein:
$L^1$ is —$(CR^1R^2)_n$-;
$L^2$ is —$(CR^1R^2)_m$-;
Ring A is cycloalkyl, heterocycloalkyl, aryl, or heteroaryl;
each $R^1$ and $R^2$ are independently hydrogen, halogen, optionally substituted alkyl, —OH, —$OR^{34}$, —$SR^{35}$, —$NR^{32}R^{33}$, —$NR^{32}C(=O)R^{34}$, —$C(=O)NR^{32}R^{33}$, —$NR^{32}S(=O)_2R^{34}$, —$C(=O)OH$, —$C(=O)OR^{34}$, optionally substituted cycloalkyl, optionally substituted heterocycloalkyl, optionally substituted aryl, or optionally substituted heteroaryl; or
$R^1$ and $R^2$ are taken together with the carbon to which they are attached to form an optionally substituted cycloalkyl;
$R^5$ is —$OR^{10}$, —$NR^{11}R^{12}$, or —$S(=O)_{0,1,2}R^{13}$;
$R^{10}$ is hydrogen, optionally substituted alkyl, optionally substituted cycloalkyl, optionally substituted heterocycloalkyl, optionally substituted aryl, optionally substituted heteroaryl, —$(CR^{40d}R^{41d})_vNR^{42d}R^{43d}$, —$(CR^{40d}R^{41d})_vC(=O)NR^{42d}R^{43d}$, —$(CR^{40d}R^{41d})_vC(=O)NR^{42d}(CR^{40d}R^{41d})_wNR^{42d}C(=O)R^{44d}$, —$(CR^{40d}R^{41d})_vC(=O)NR^{42d}(CR^{40d}R^{41d})_vNR^{42d}R^{43d}$, —$(CR^{40d}R^{41d})_vC(=O)NR^{42d}(CR^{40d}R^{41d})_wNR^{42d}(CR^{40d}R^{41d})_wNR^{42d}R^{43d}$, —$(CR^{40d}R^{41d})_vC(=O)NR^{42d}(CR^{40d}R^{41d})_vC(=O)OH$, —$(CR^{41d}R^{41d})_vC(=O)NR^{42d}(CR^{40d}R^{41d})_vC(=O)OR^{44d}$, —$(CR^{40d}R^{41d})_vNR^{42d}C(=O)R^{44d}$, —$(CR^{40d}R^{41d})_vNR^{42d}S(=O)_{0,1,2}R^{44d}$, —$(CR^{40d}R^{41d})_vOH$, —$(CR_{40d}R^{41d})_vOR^{44d}$, —$(CR^{40d}R^{41d})_vC(=O)OH$, —$(CR^{40d}R^{41d})_vC(=O)OR^{44d}$, —$(CR^{40d}R^{41d})_v$heteroaryl, or —$(CR^{40d}R^{41d})_v$heterocycloalkyl;
$R^{11}$ and $R^{12}$ are independently hydrogen, —$S(=O)_2R^{44e}$, —$S(=O)_2NR^{42e}R^{43e}$, optionally substituted alkyl, optionally substituted cycloalkyl, optionally substituted heterocycloalkyl, optionally substituted aryl, or optionally substituted heteroaryl; or
$R^{11}$ and $R^{12}$ are taken together with the nitrogen to which they are attached to form an optionally substituted heterocycloalkyl;

$R^{13}$ is optionally substituted alkyl, optionally substituted cycloalkyl, optionally substituted heterocycloalkyl, optionally substituted aryl, or optionally substituted heteroaryl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40d}$, $R^{41d}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40d}$ and $R^{41d}$, or $R^{50}$ and $R^{51}$ are taken together with the carbon atom to which they are attached form an optionally substituted cycloalkyl; or two $R^{30}$, two $R^{40d}$, or two $R^{50}$ on adjacent carbons are taken together to form an alkenyl; or two $R^{30}$ and two $R^{31}$, two $R^{40d}$ and two $R^{41d}$, or two $R^{50}$ and two $R^{51}$ on adjacent carbons are taken together to form an alkynyl;

$R^{32}$, $R^{33}$, $R^{42d}$, $R^{43d}$, $R^{42e}$, $R^{43e}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, $R^{42d}$ and $R^{43d}$, $R^{42e}$ and $R^{43e}$, or $R^{52}$ and $R^{53}$ are taken together with the nitrogen to which they are attached to form an optionally substituted heterocycloalkyl;

$R^{34}$, $R^{44d}$, $R^{44e}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)-, —C(CH$_3$)$_2$-,or optionally substituted 1, cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_w$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_v$OH, —S(CR$^{50}$R$^{51}$)$_v$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_w$NR$^{52}$C(=NR$^{56}$), —(CR$^{50}$R$^{51}$)$_w$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocyclalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_w$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_w$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S (=O)$_{0,1,2}$NR$^{32}$R$_{33}$, —OC(=O)R$^{34}$, —OC(=O)(CR$^{30}$R$^{31}$)$_v$NR$^{32}$R$^{33}$, —OC(=O)NR$^{32}$R$_{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(cR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(cR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$—(CR$^{30}$R$^{31}$)$_v$S(=O)$_{0,1,2}$NR$^{32}$R$^{33}$, —(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$—SR$^{35}$, S(=O)$_{0,1,2}$(cR$^{30}$R$^{31}$)$_w$NR$^{32}$R$^{33}$, —S(=O)$_{0,1,2}$(cR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_v$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(cR$_{30}$R$_{31}$)$_v$NR$^{32}$R$^{33}$R$^{34+}$Q$^-$, —NR$^{32}$(cR$_{30}$R$^{31}$)$_w$NR$^{32}$R$^{33}$R$^{34+}$Q$^-$, NR$^{32}$R$^{34+}$(CR$_{30}$R$^{31}$)$_w$NR$^{32}$R$^{33}$R$^{34+}$Q$^-$$_2$, —(CR$^{30}$R$^{31}$)$_v$(T)$^+$Q, or —O(CR$_{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5;

provided that the compound is not: (Z)-3-(2-(2-aminothiazol-4-yl)-2-(hydroxyimino)acetamido)-2-hydroxy-3,4-dihydro-2H-benzo[e][1,2]oxaborinine-8-carboxylic acid/(Z)-3-(2-(2-(2-aminothiazol-4-yl)-2-(hydroxyimino)acetamido)-2-boronoethyl)-2-hydroxybenzoic acid; (Z)-3-(2-(2-(2-aminothiazol-4-yl)-2-(((2-carboxypropan-2-yl)oxy)imino)acetamido)-2-hydroxy-3,4-dihydro-2H-benzo[e][1,2]oxaborinine-8-carboxylic acid/(Z)-5-(2-aminothiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(((2-carboxypropan-2-yl)oxy)imino)acetamido)-2-hydroxy-3,4-dihydro-2H-benzo[e][1,2]oxaborinine-8-carboxylic acid/(Z)-5-(2-(2-aminoacetamido)thiazol-4-yl)-2-(3-carboxy-2-hydroxybenzyl)-1,1-dihydroxy-8-methyl-4-oxo-7-oxa-3,6-diaza-1-boranon-5-ene-8-carboxylic acid; (Z)-3-(2-(2-(2-aminoacetamido)thiazol-4-yl)-2-(methoxyimino)acetamido)-2-hydroxy-3,4-dihydro-2H-benzo[e][1,2]oxaborinine-8-carboxylic acid/(Z)-3-(2-(2-(2-(2-aminoacetamido)thiazol-4-yl)-2-(methoxyimino)acetamido)-2-boronoethyl)-2-hydroxybenzoic acid; (Z)-3-(2-(2-(2,6-diaminohexanamido)thiazol-4-yl)-2-(methoxyimino)acetamido)-2-hydroxy-3,4-dihydro-2H-benzo[e][1,2]oxaborinine-8-carboxylic acid/(Z)-3-(2-borono-2-(2-(2-(2,6-diaminohexanamido)thiazol-4-yl)-2-(methoxyimino)acetamido)ethyl)-2-hydroxybenzoic acid; or (Z)-3-(2-(4-(aminomethyl)phenyl)-2-(hydroxyimino)acetamido)-2-hydroxy-3,4-dihydro-2H-benzo[e][1,2]oxaborinine-8-carboxylic acid/(Z)-3-(2-(2-(4-(aminomethyl)phenyl)-2-(hydroxyimino)acetamido)-2-boronoethyl)-2-hydroxybenzoic acid.

2. The compound of claim 1, wherein R$^5$ is —OR$^{10}$ and R$^{10}$ is C$_2$-C$_6$ alkyl, optionally substituted heterocycloalkyl, —(CR$^{40d}$R$^{41d}$)$_v$NR$^{42d}$R$^{43d}$, (CR$^{40d}$R$^{41d}$)$_v$C(=O)NR$^{42d}$R$^{43d}$, —(CR$^{40d}$R$^{41d}$)$_v$C(=O)NR$^{42d}$(CR$^{40d}$R$^{41d}$)$_w$NR$^{42d}$R$^{43d}$—(CR$^{40d}$R$^{41d}$)$_v$C(=O)NR$^{42d}$(CR$^{40d}$R$^{41d}$)$_v$C(=O)OH, —(CR$^{42d}$R$^{43d}$)$_v$C(=O)NR$^{42d}$(cR$^{40d}$R$^{41d}$)$_w$NR$^{42d}$C(=O)R$^{44d}$, —(CR$^{40d}$R$^{41d}$)$_v$C(=O)NR$^{42d}$(CR$^{40d}$R$^{41d}$)$_w$NR$^{42d}$(CR$^{40d}$R$^{41d}$)$_w$NR$^{42d}$R$^{43d}$, —(CR$^{40d}$R$^{41d}$)$_v$NR$^{42d}$C(=O)R$^{44d}$, —(CR$^{40d}$R$^{41d}$)$_v$NR$^{42d}$S(=O)$_{0,1,2}$R$^{44d}$, —(CR$_{40d}$R$^{41d}$)$_v$OH, —(CR$^{40d}$R$^{41d}$)$_v$OR$^{44d}$, —(CR$^{40d}$R$^{41d}$)$_v$C(=O)OH, —(CR$^{40d}$R$^{41d}$)$_v$C(=O)OR$^{44d}$, or —(CR$^{40d}$R$^{41d}$)$_v$heterocycloalkyl; provided that R$^{10}$ is not —C(CH$_3$)$_2$C(=O)OH.

3. The compound of claim 1, wherein

R$^{40d}$ and R$^{41d}$ are independently hydrogen, fluoro, chloro, bromo, —OH, alkyl, hydroxyalkyl, aminoalkyl, haloalkyl, or —C(=O)OH;

R$^{42d}$ and R$^{43d}$ are independently hydrogen, alkyl, optionally substituted aryl, optionally substituted cycloalkyl, or optionally substituted heterocycloalkyl; or R$^{42d}$ and R⁴³ᵈ are taken together with the nitrogen to which they are attached to form an optionally substituted heterocycloalkyl; and R⁴⁴ᵈ is optionally substituted alkyl or optionally substituted aryl.

4. The compound of claim 1, wherein R¹⁰ is

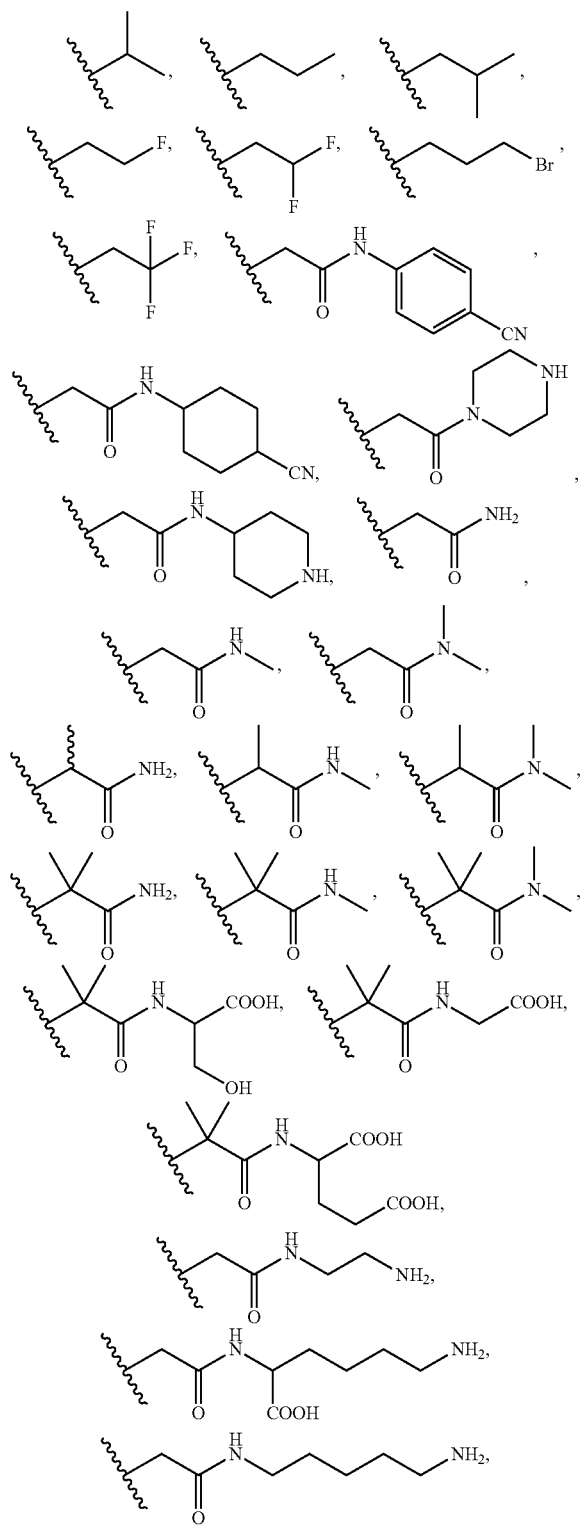

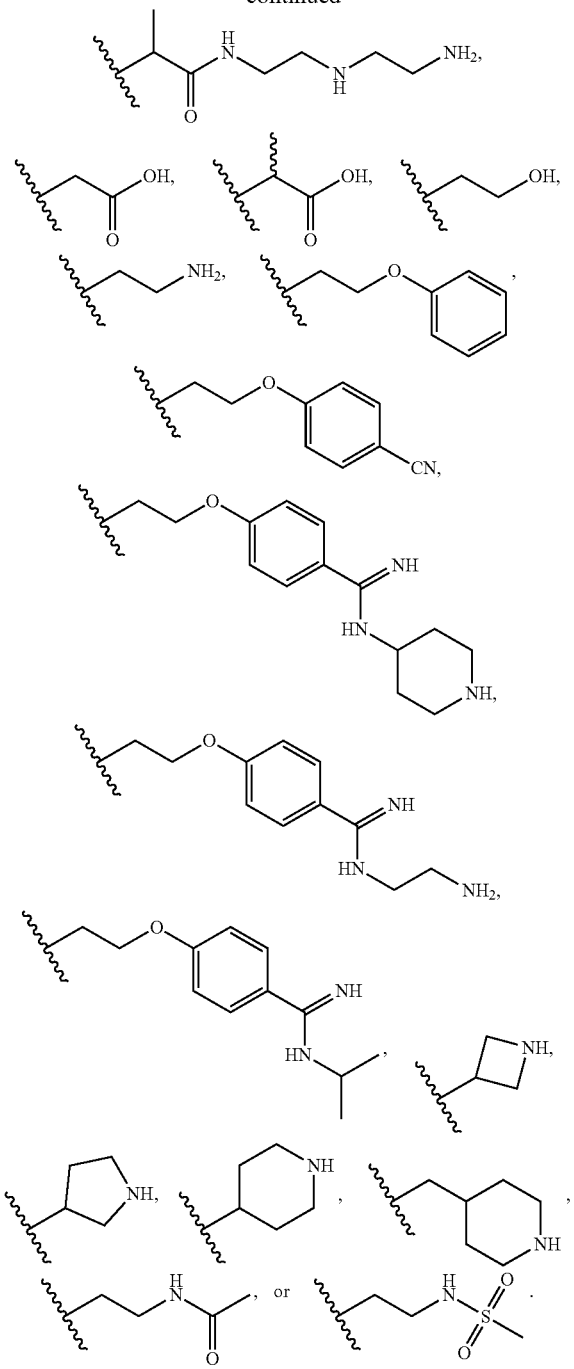

5. The compound of claim 1, wherein Ring A is benzene, pyridine, thiazole, triazole, tetrazole, oxadiazole, or thiadiazole.

6. The compound of claim 1, wherein Ring A is thiazole.

7. The compound of claim 1, wherein $R^a$, $R^b$, and $R^c$ are independently hydrogen, fluoro, chloro, optionally substituted alkyl, —(CR⁵⁰R⁵¹)ᵥC(=O)OH, or —(CR⁵⁰R⁵¹)ᵥheterocycloalkyl.

8. The compound of claim 1, wherein $R^a$, $R^b$, and $R^c$ are hydrogen.

9. The compound of claim 1, wherein X¹ is —OH and X² is —OH when present.

10. The compound of claim 1, wherein $R^d$ is alkyl or hydrogen.

11. The compound of claim 1, wherein n is 0, 1, or 2 and m is 0, 1, or 2.

12. The compound of claim 1, wherein each $R^1$ and $R^2$ are independently hydrogen, fluoro, chloro, bromo, or optionally substituted alkyl.

13. The compound of claim 1, wherein each $R^1$ and $R^2$ are hydrogen.

14. The compound of claim 1, wherein Z is hydrogen.

15. The compound of claim 1, wherein at least one Y is halogen, optionally substituted heteroaryl, —$NR^{32}R^{33}$, —OH, —$OR^{34}$, —$NR^{32}(cR^{30}R^{31})_wNR^{32}R^{33}$, $NR^{32}C(=NR^{36})NR^{32}R^{33}$, —$(CR^{30}R^{31})dNR^{32}R^{33}$, —$SR^{35}$, —$NR^{32}(CR^{31}R^{31})_vCO_2H$, —$NR^{32}(cR^{30}R^{31})_vC(=O)NR^{32}R^{33}$, or —$NR^{32}(CR^{30}R^{31})_v$heteroaryl; or two Ys taken together with the atoms to which they are attached form an optionally substituted heterocycloalkyl.

16. The compound of claim 1, wherein $R^{30}$ and $R^{31}$ are independently hydrogen or optionally substituted alkyl; or two $R^{30}$ on adjacent carbon form an alkenyl; $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl; $R^{34}$ is optionally substituted alkyl; $R^{35}$ is hydrogen or optionally substituted alkyl; $R^{36}$ is hydrogen or optionally substituted alkyl; each v is independently 1 or 2; and each w is independently 2 or 3.

17. The compound of claim 1, wherein p is 1 or 2.

18. A pharmaceutical composition comprising a compound of claim 1, or a pharmaceutically acceptable salt, solvate, stereoisomer, tautomer, N-oxide, dimer, or trimer thereof, and a pharmaceutically acceptable excipient.

19. A method of treating a bacterial infection in a subject, comprising administering to the subject an effective amount of a compound of claim 1, or a pharmaceutically acceptable salt, solvate, stereoisomer, tautomer, N-oxide, dimer, or trimer thereof.

20. The compound of claim 1, selected from:

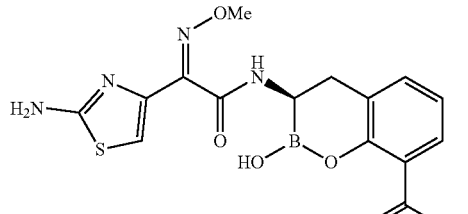

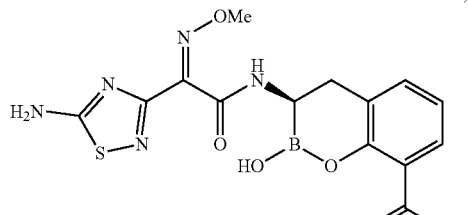

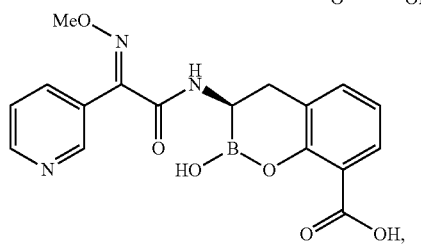

-continued

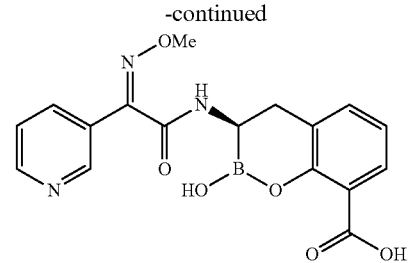

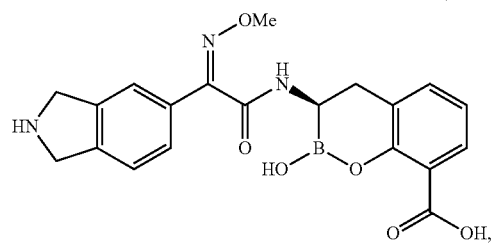

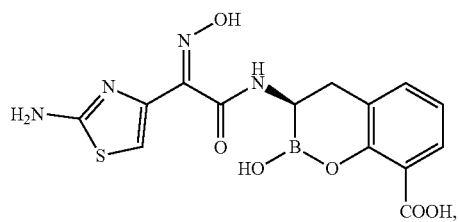

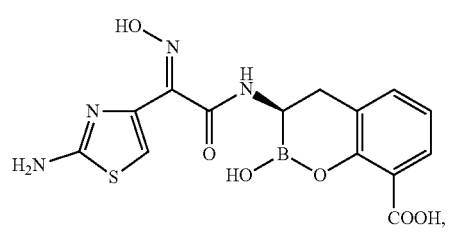

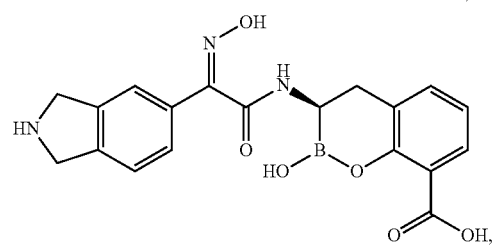

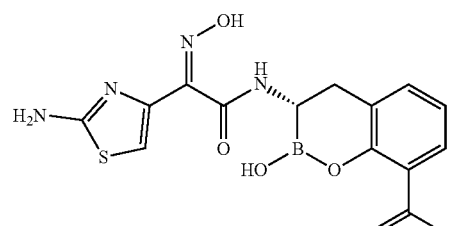

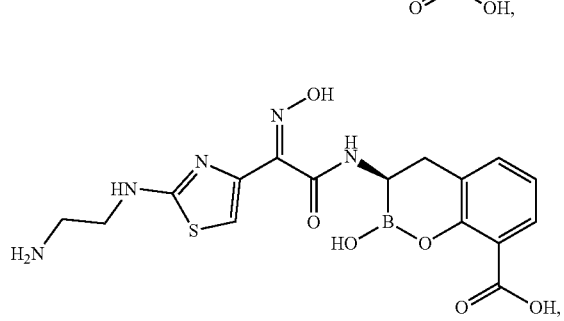

-continued
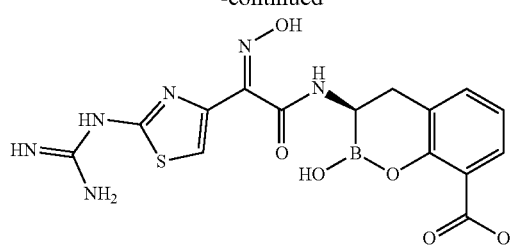
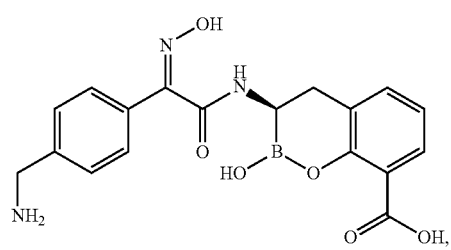
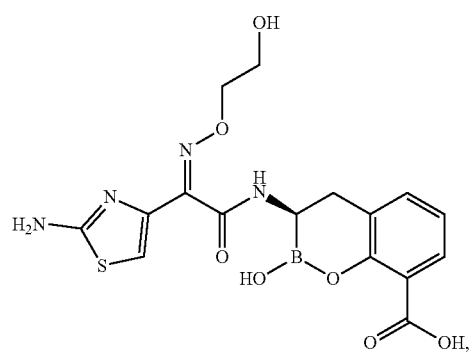
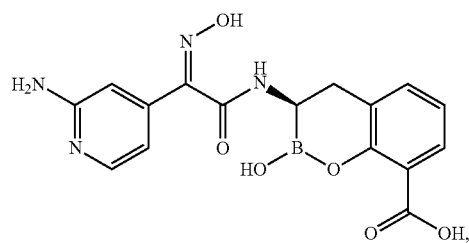
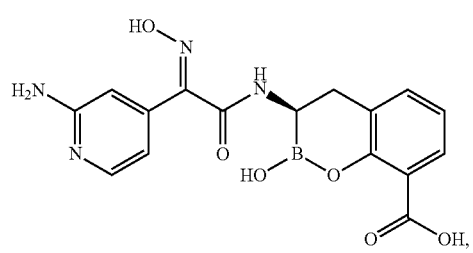
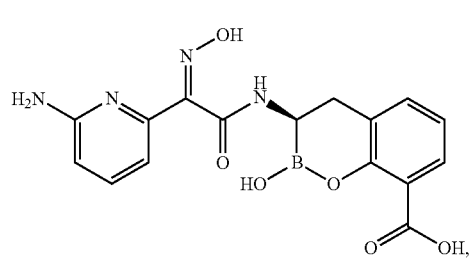
-continued
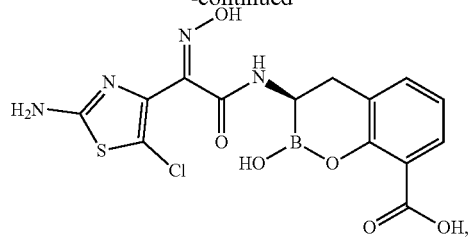
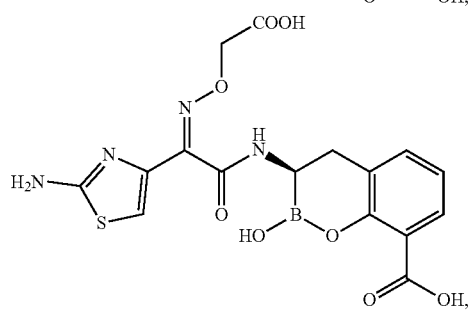
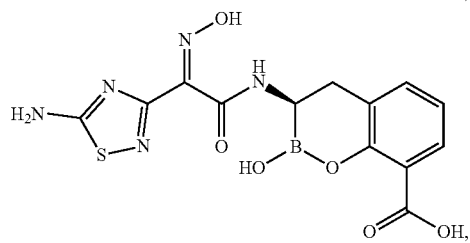
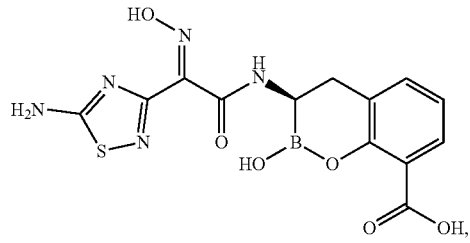
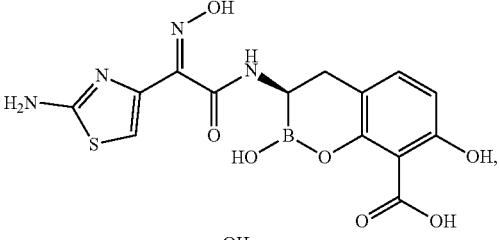
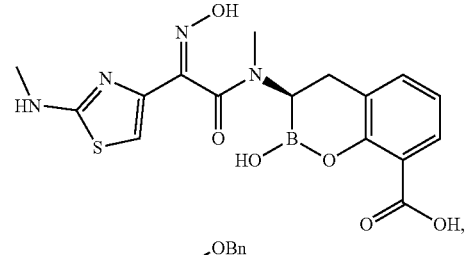
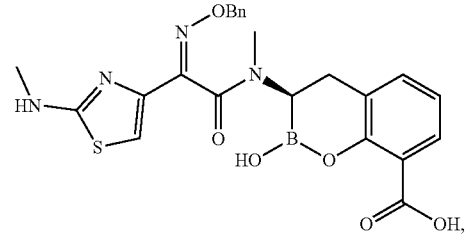

-continued

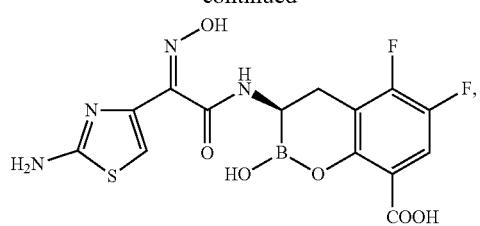
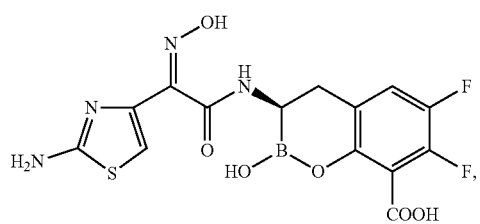
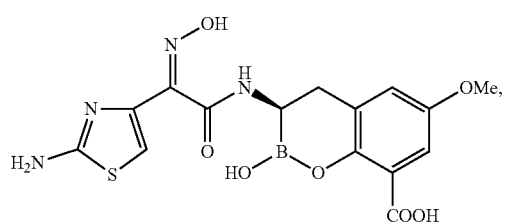
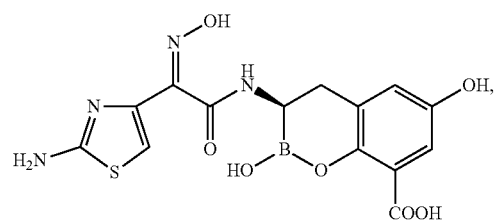
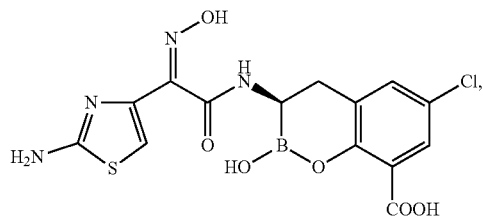
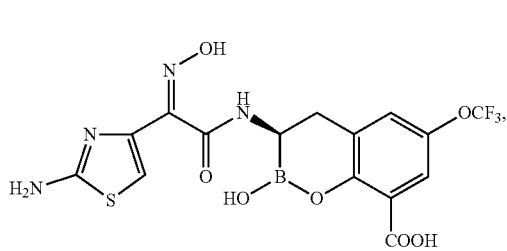
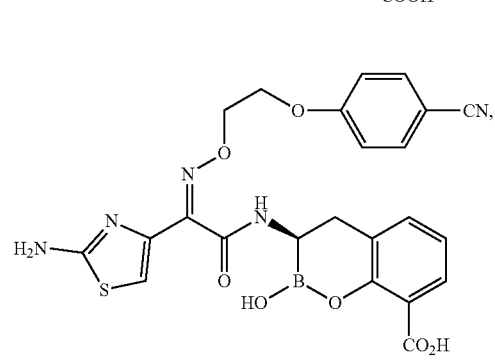
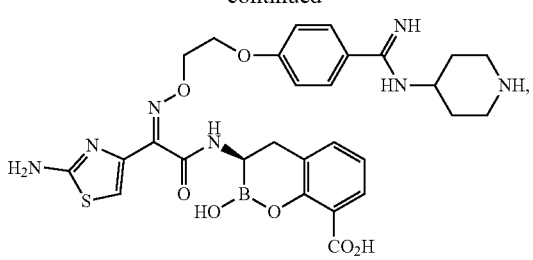
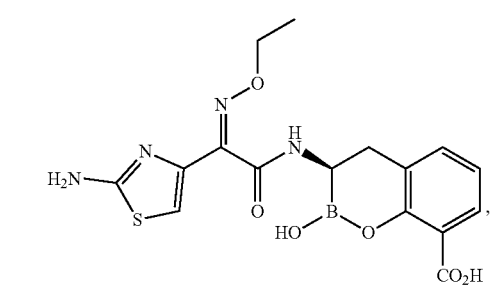
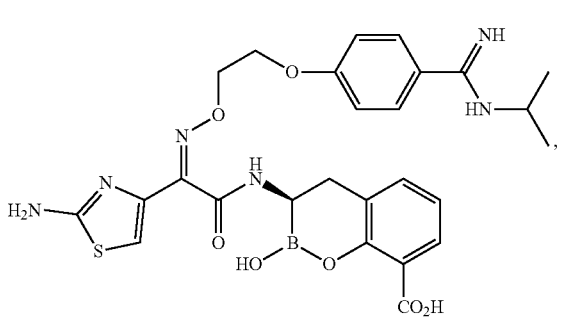
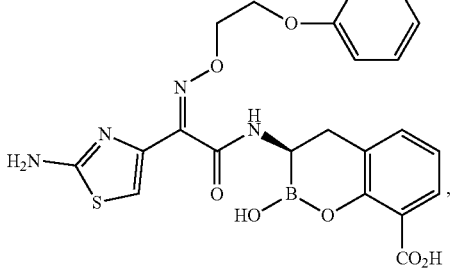
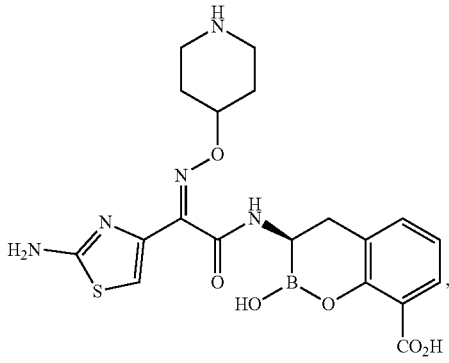

289 290
-continued -continued
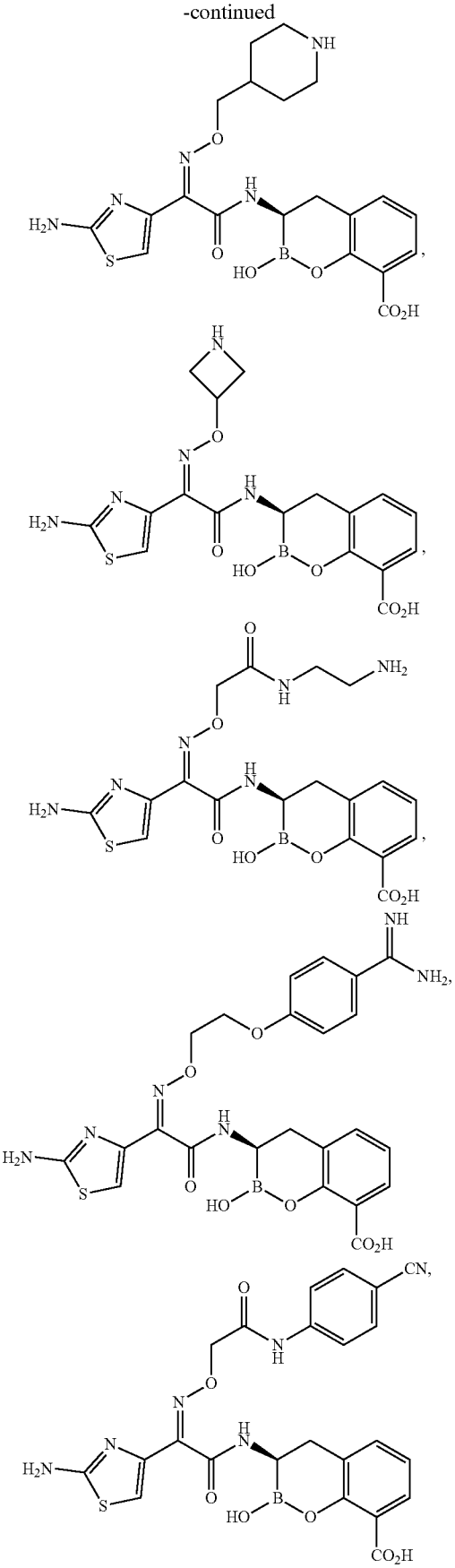
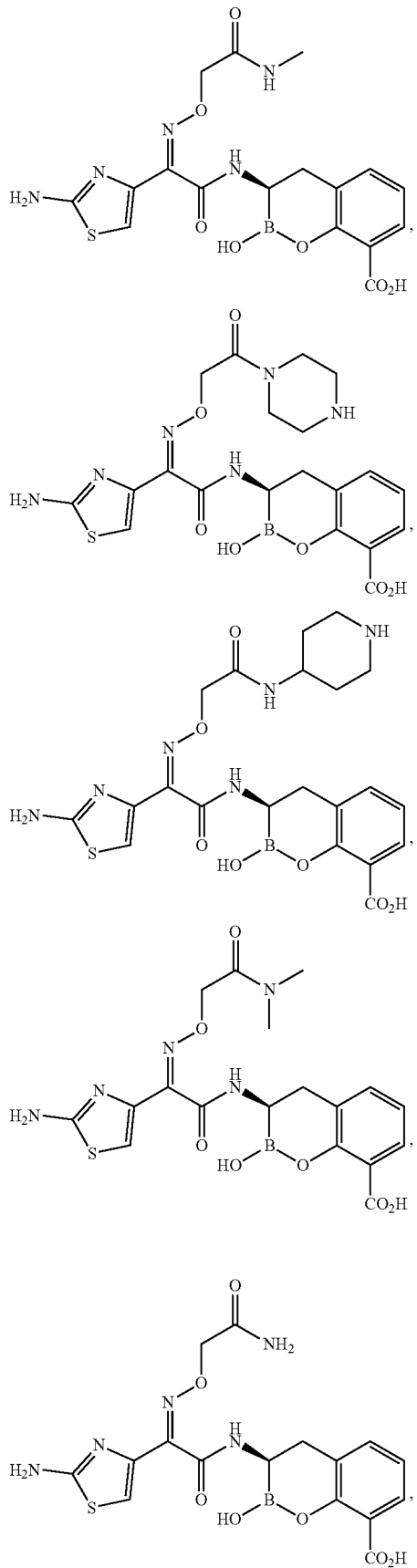

291
-continued
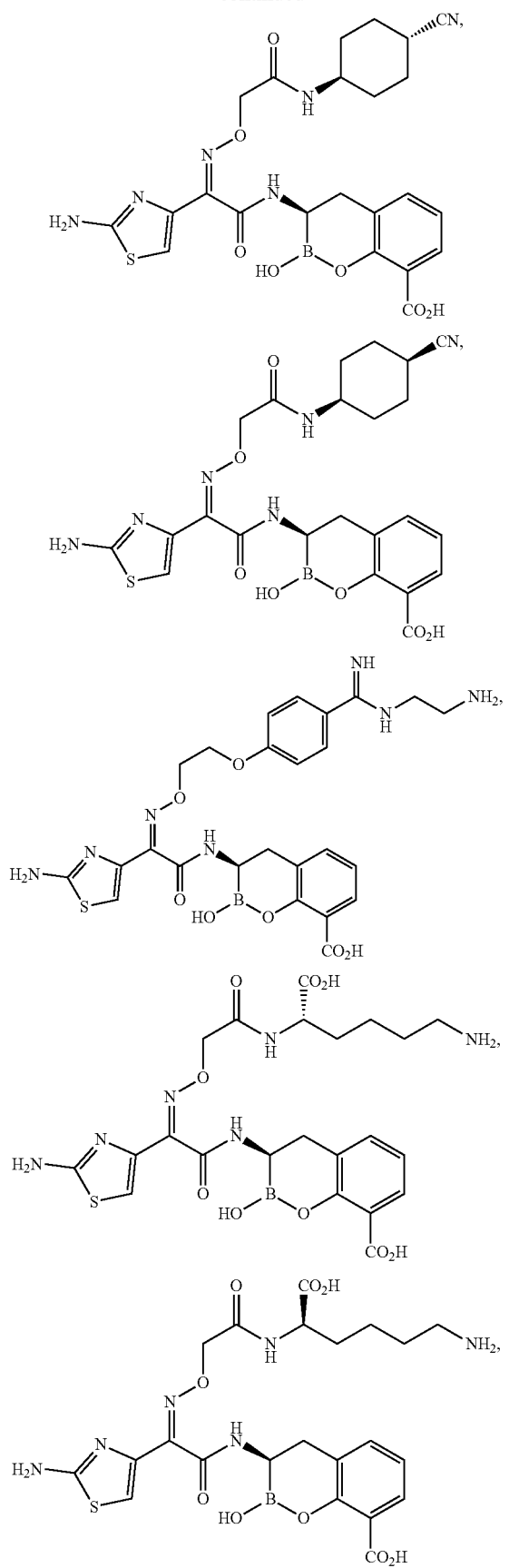
292
-continued
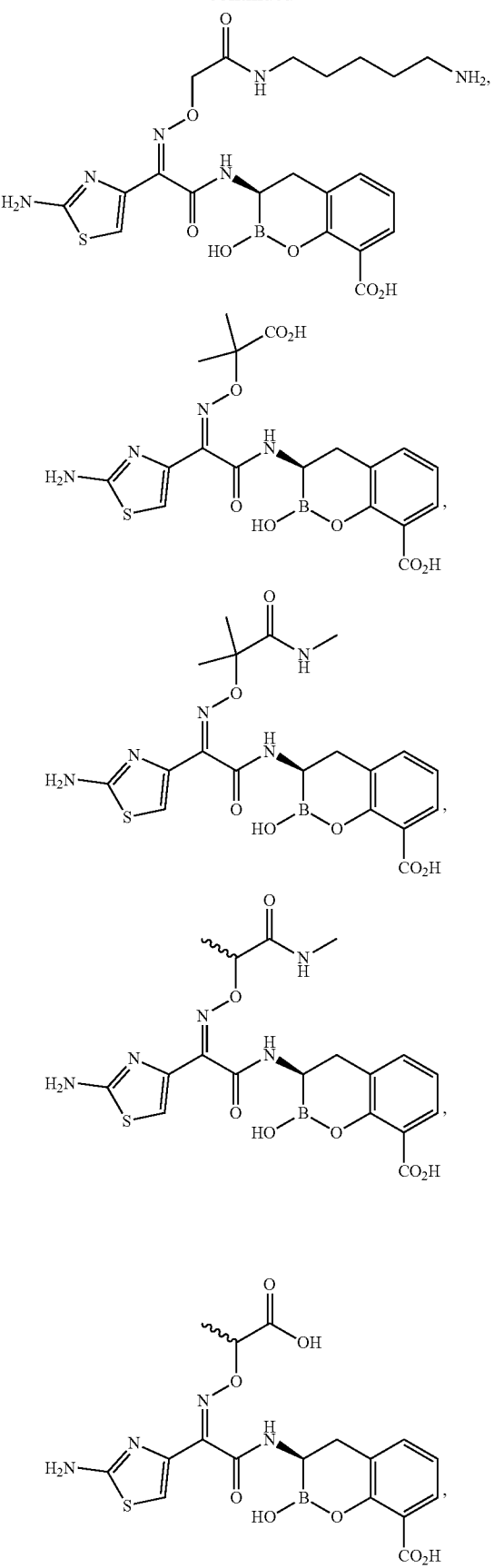

293
-continued
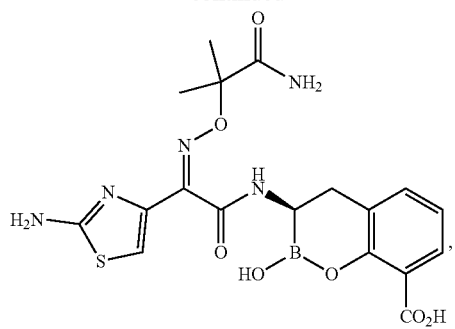
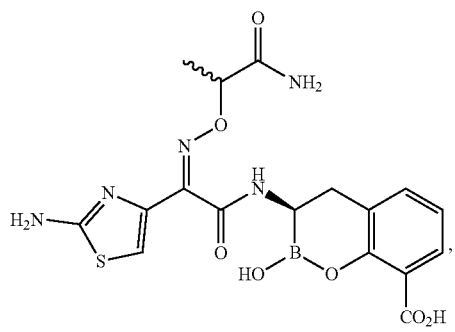
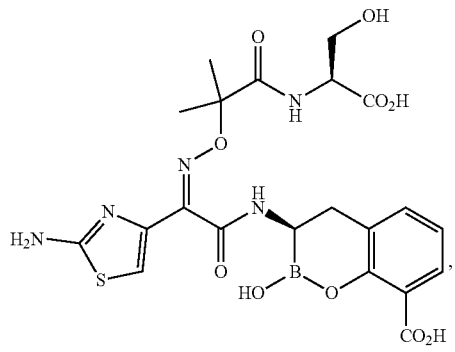
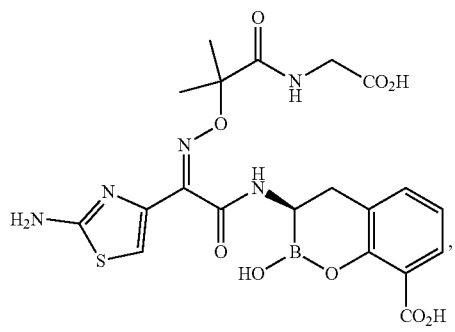
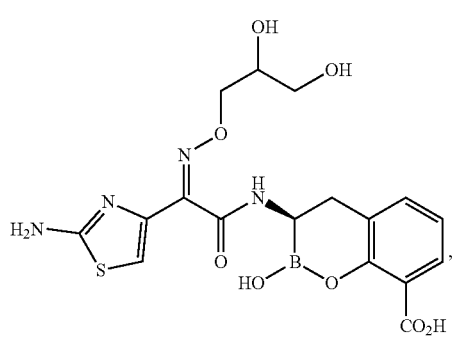
294
-continued
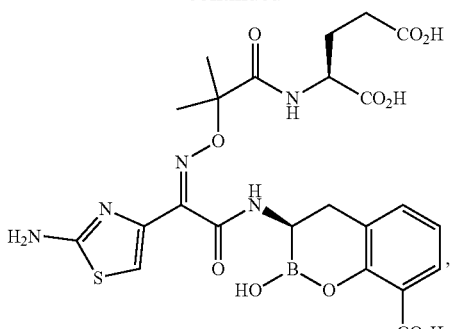
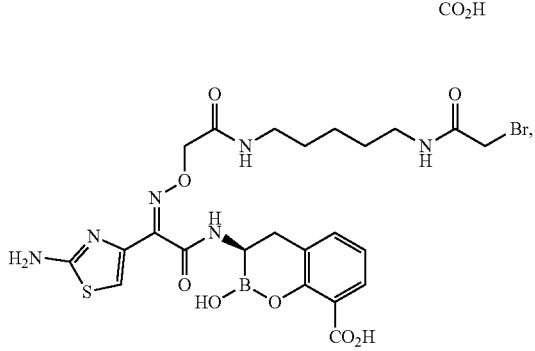
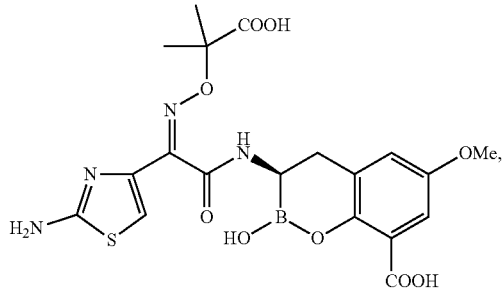
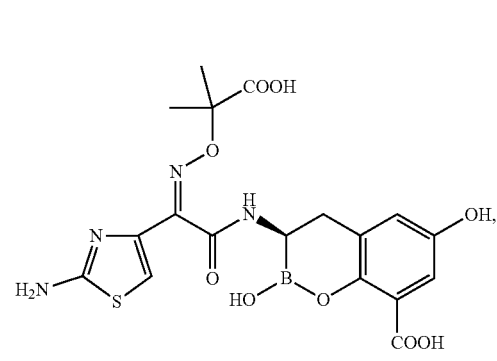
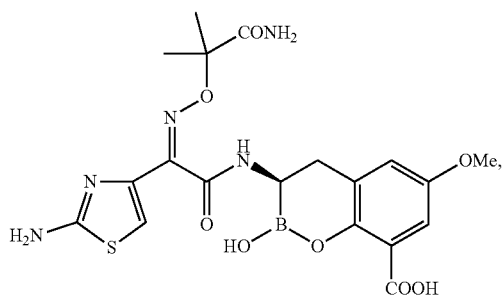

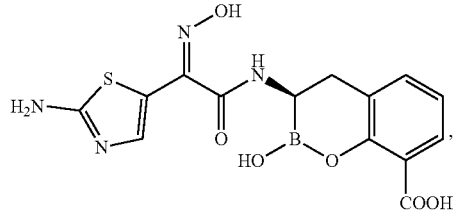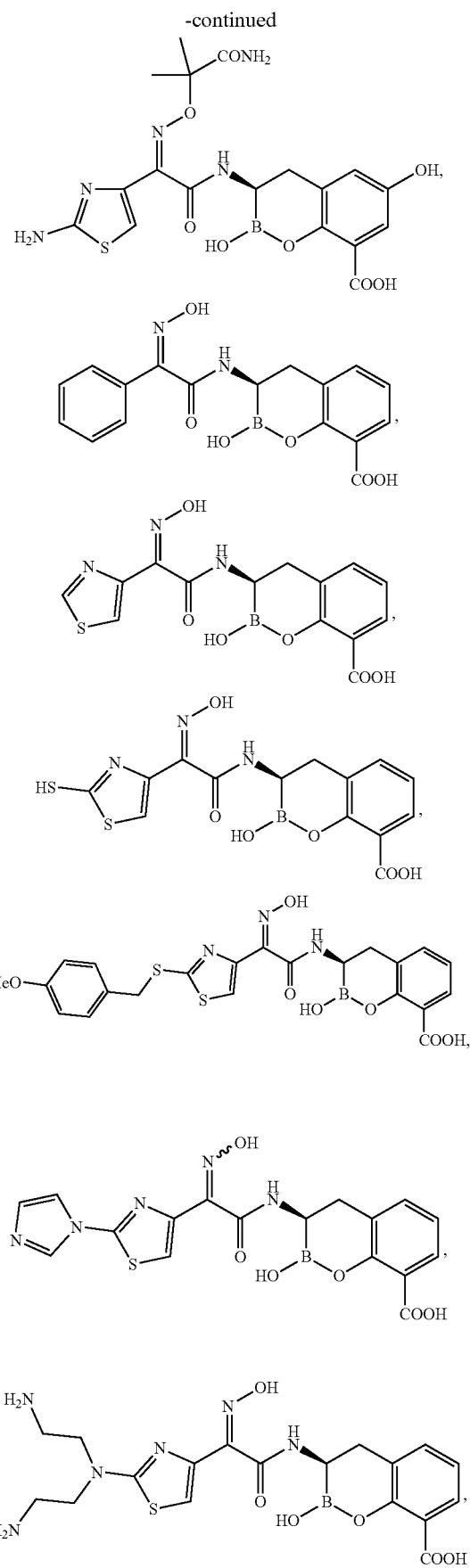

-continued
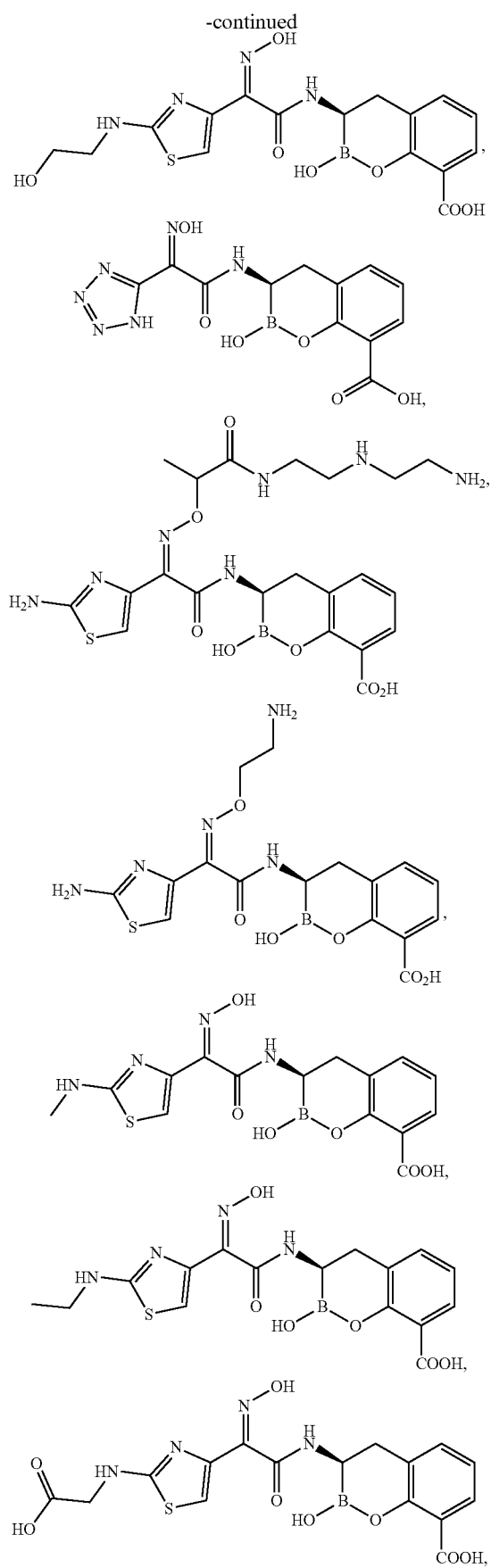
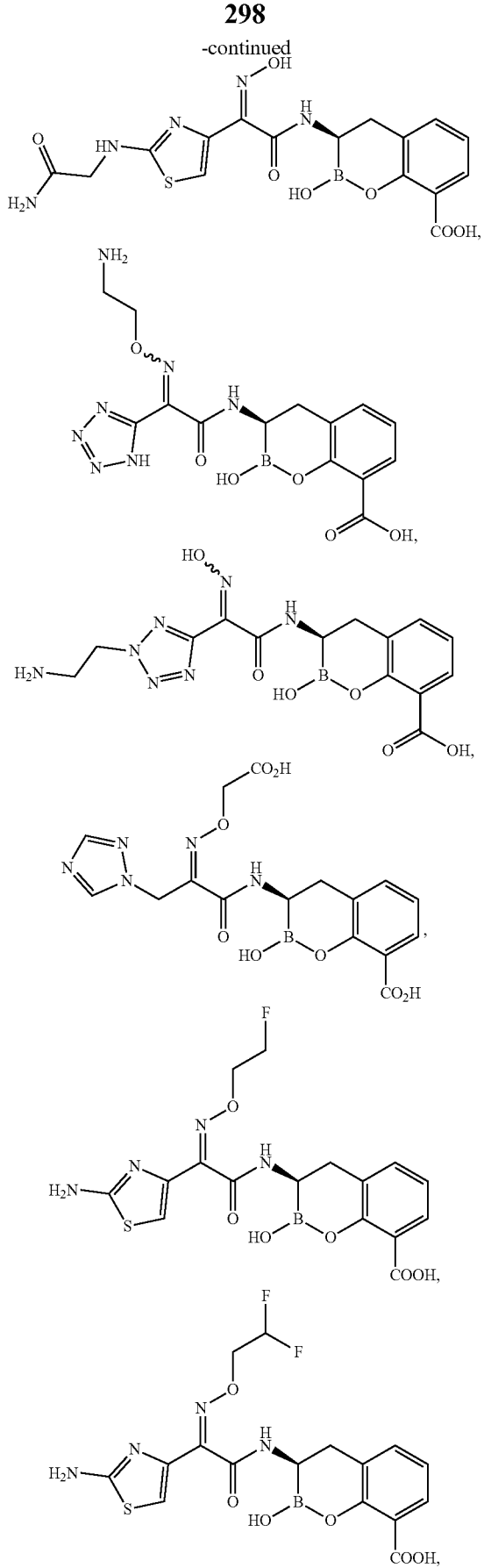

299
-continued
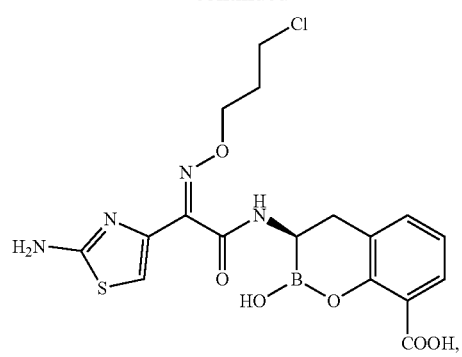
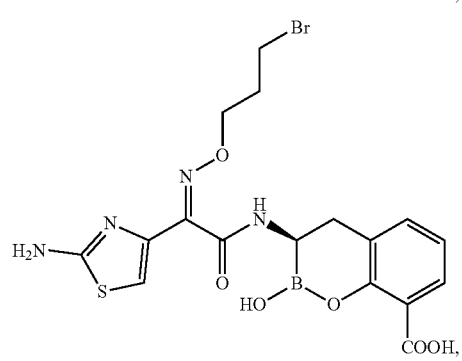
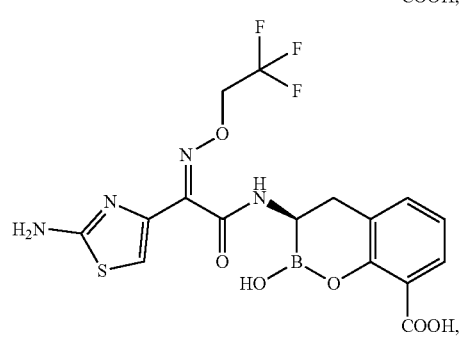
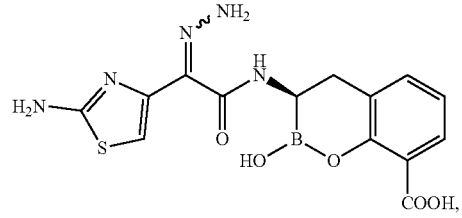
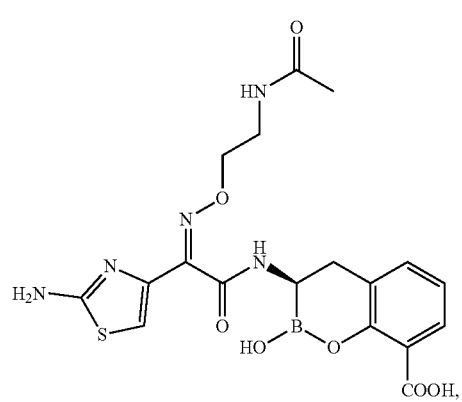
300
-continued
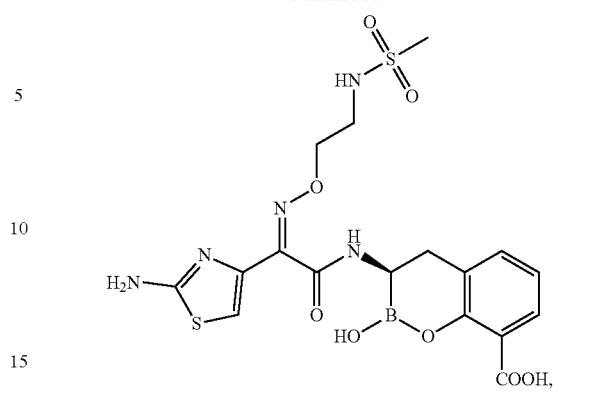
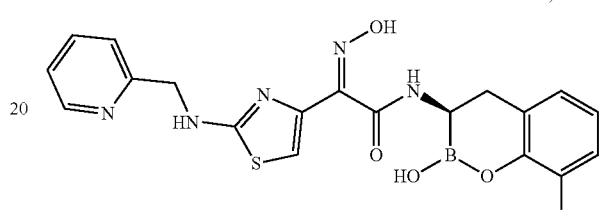
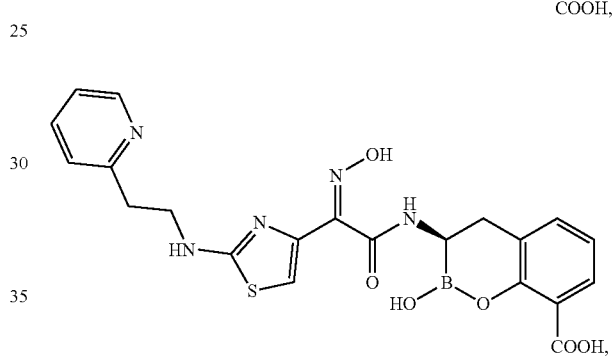
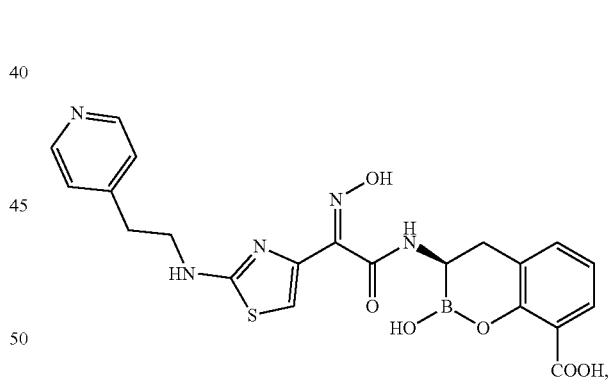
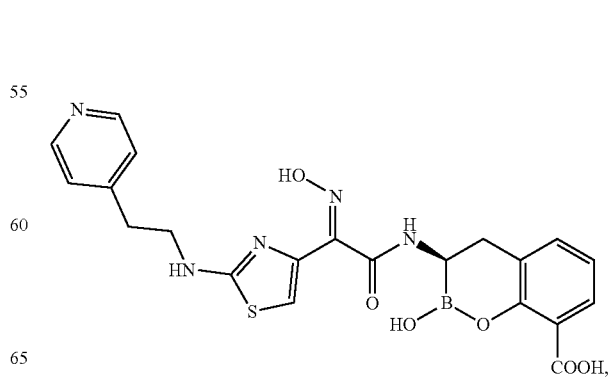

301
-continued
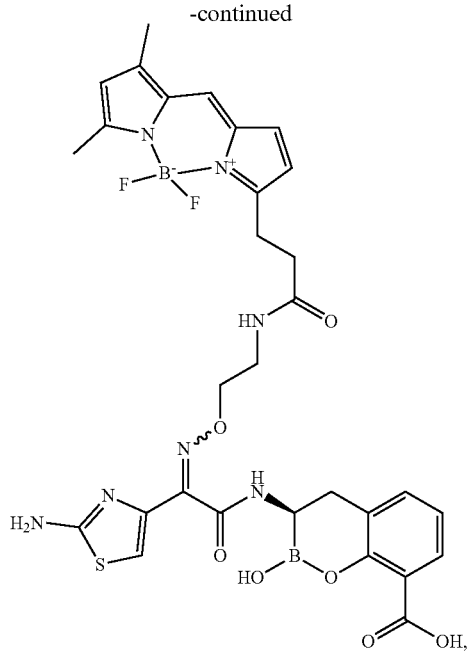
302
-continued
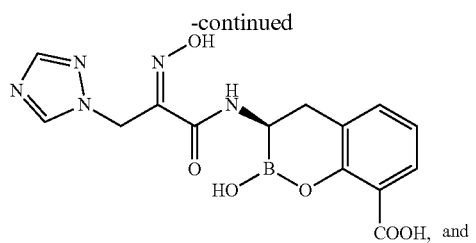
or a pharmaceutically acceptable salt, solvate, stereoisomer, tautomer, N-oxide, dimer, or trimer thereof.
* * * * *

UNITED STATES PATENT AND TRADEMARK OFFICE
CERTIFICATE OF CORRECTION

PATENT NO. : 11,267,826 B2  
APPLICATION NO. : 16/616382  
DATED : March 8, 2022  
INVENTOR(S) : Burns et al.

Page 1 of 3

It is certified that error appears in the above-identified patent and that said Letters Patent is hereby corrected as shown below:

In the Claims

Column 274, Lines 1-15:

In Claim 1, replace " 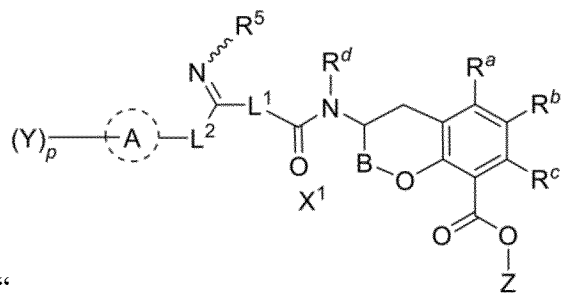 " with

--

Column 274, Lines 15-27:

In Claim 1, replace " 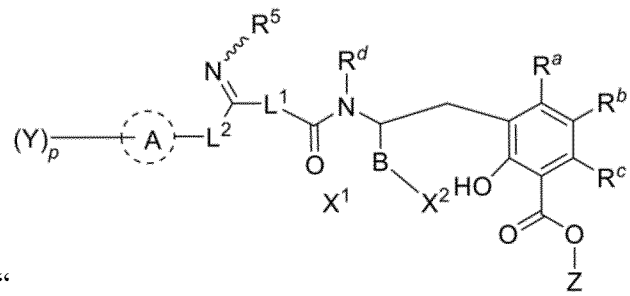 " with

Signed and Sealed this  
Twenty-eighth Day of June, 2022

Katherine Kelly Vidal  
*Director of the United States Patent and Trademark Office*

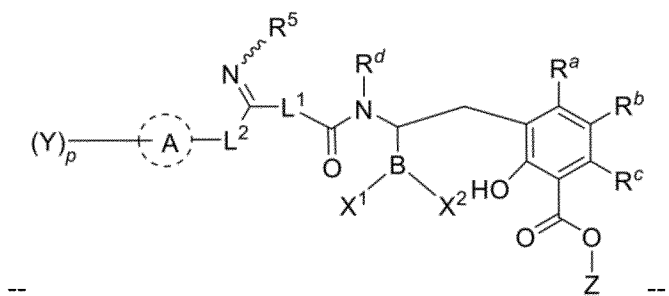

Column 274, Lines 53-54:
In Claim 1, replace "-(CR$^{4ld}$R$^{4ld}$)$_v$C(=O)NR$^{42d}$(CR$^{40d}$R$^{41d}$)$_v$C(=O)OR$^{44d}$" with -- -CR$^{40d}$R$^{4ld}$)$_v$C(=O)NR$^{42d}$(CR$^{40d}$R$^{41d}$)$_v$C(=O)OR$^{44d}$--

Column 274, Line 56:
In Claim 1, replace "-(CR$_{40d}$R$^{4ld}$)$_v$OR$^{44d}$" with -- -(CR$^{40d}$R$^{41d}$)$_v$OR$^{44d}$--

Column 275, Line 30:
In Claim 1, replace "attached form an optionally substituted" with --attached to form an optionally substituted--

Column 275, Line 55:
In Claim 1, replace "aryl, optionally substituted heteroaryl" with --aryl, or optionally substituted heteroaryl--

Column 276, Line 25:
In Claim 1, replace "-S(CR$^{50}$R$^{51}$)$_v$OH" with -- -S(CR$^{50}$R$^{51}$)$_w$OH--

Column 276, Lines 43-44:
In Claim 1, replace "(poly-ethylene-glycol)-ethyl, an optionally substituted saccharide" with --(poly-ethylene-glycol)-ethyl, or an optionally substituted saccharide--

Column 276, Line 55:
In Claim 1, replace "heterocyclalkyl" with --heterocycloalkyl--

Column 276, Line 67 to Column 277, Line 1:
In Claim 1, replace "-O(CR$^{30}$R$^{31}$)$_w$S(=O)$_{0,1,2}$NR$^{32}$R$_{33}$" with -- -O(CR$^{30}$R$^{31}$)$_w$S(=O)$_{0,1,2}$NR$^{32}$R$^{33}$--

Column 277, Line 2:
In Claim 1, replace "-OC(=O)NR$^{32}$R$_{33}$" with -- -OC(=O)NR$^{32}$R$^{33}$--

Column 277, Lines 4-5:
In Claim 1, replace "O(CR$^{30}$R$^{31}$),heteroaryl" with -- -O(CR$^{30}$R$^{31}$)$_v$heteroaryl--

Column 277, Line 5:
In Claim 1, replace "-O(CR$^{30}$R$^{31}$),heterocycloalkyl" with -- -O(CR$^{30}$R$^{31}$)$_v$heterocycloalkyl--

CERTIFICATE OF CORRECTION (continued)
U.S. Pat. No. 11,267,826 B2

Column 277, Lines 15-16:
In Claim 1, replace "-NR$^{32}$(cR$^{30}$R$^{31}$)$_w$NR$^{32}$S(=O)$_{0,1,2}$NR$^{32}$R$^{33}$" with
-- -NR$^{32}$(CR$^{30}$R$^{31}$)$_w$NR$^{32}$S(=O)$_{0,1,2}$NR$^{32}$R$^{33}$--

Column 277, Line 27:
In Claim 1, replace "-NR$^{32}$(cR$^{30}$R$^{31}$)$_w$NR$^{32}$-heteroaryl" with -- -NR$^{32}$(CR$^{30}$R$^{31}$)$_w$NR$^{32}$-heteroaryl--

Column 277, Line 59:
In Claim 1, replace "S(=O)$_{0,1,2}$(cR$^{30}$R$^{31}$)$_w$NR$^{32}$R$^{33}$" with -- -S(=O)$_{0,1,2}$(CR$^{30}$R$^{31}$)$_w$NR$^{32}$R$^{33}$--

Column 277, Line 60:
In Claim 1, replace "-S(=O)$_{0,1,2}$(cR$^{30}$R$^{3}$)$_w$OH" with -- -S(=O)$_{0,1,2}$(cR$^{30}$R$^{31}$)$_w$OH--

Column 278, Lines 1-4:
In Claim 1, replace "–(cR$_{30}$R$_{31}$)$_v$NR$^{32}$R$^{33}$R$^{34+}$Q$^-$, –NR$^{32}$(cR$_{30}$R$^{31}$)$_w$NR$^{32}$R$^{33}$R$^{34+}$Q$^-$, NR$^{32}$R$^{34+}$(CR$_{30}$R$^{31}$)$_w$NR$^{32}$R$^{33}$R$^{34+}$Q$^-_2$, –(CR$^{30}$R$^{31}$)$_v$(T)$^+$Q, or –O(CR$_{30}$R$^{31}$)$_w$NR$^{32}$R$^{33}$R$^{34+}$Q$^-$" with
-- –(CR$^{30}$R$^{31}$)$_v$NR$^{32}$R$^{33}$R$^{34+}$Q$^-$, –NR$^{32}$(CR$^{30}$R$^{31}$)$_w$NR$^{32}$R$^{33}$R$^{34+}$Q$^-$, –NR$^{32}$R$^{34+}$(CR$^{30}$R$^{31}$)$_w$NR$^{32}$R$^{33}$R$^{34+}$Q$^-_2$, –(CR$^{30}$R$^{31}$)$_v$(T)$^+$Q$^-$, or –O(CR$^{30}$R$^{31}$)$_w$NR$^{32}$R$^{33}$R$^{34+}$Q$^-$--

Column 278, Lines 50-54:
In Claim 2, replace "(CR$^{40d}$R$^{41d}$)$_v$C(=O)NR$^{42d}$R$^{43d}$, -(CR$^{40d}$R$^{41d}$)$_v$C(=O)NR$^{42d}$(CR$^{40d}$R$^{41d}$)$_w$NR$^{42d}$R$^{43d}$-(CR$^{40d}$R$^{41d}$)$_v$C(=O)NR$^{42d}$(CR$^{40d}$R$^{41d}$)$_v$C(=O)OH, -CR$^{42d}$R$^{43d}$)$_v$C(=O)NR$^{42d}$(cR$^{40d}$R$^{41d}$)$_w$NR$^{42d}$C(=O)R$^{44d}$"
with -- -(CR$^{40d}$R$^{41d}$)$_v$C(=O)NR$^{42d}$R$^{43d}$, -(CR$^{40d}$R$^{41d}$)$_v$C(=O)NR$^{42d}$(CR$^{40d}$R$^{41d}$)$_w$NR$^{42d}$R$^{43d}$,
-(CR$^{40d}$R$^{41d}$)$_v$C(=O)NR$^{42d}$(CR$^{40d}$R$^{41d}$)$_v$C(=O)OH,
-(CR$^{42d}$R$^{43d}$)$_v$C(=O)NR$^{42d}$(CR$^{40d}$R$^{41d}$)$_w$NR$^{42d}$C(=O)R$^{44d}$--

Column 278, Line 57:
In Claim 2, replace "-(CR$_{40d}$R$^{41d}$)$_v$OH" with -- -(CR$^{40d}$R$^{41d}$)$_v$OH--

Column 280, Lines 62-63:
In Claim 7, replace "–(CR$^{50}$R$^{51}$),heterocycloalkyl" with -- –(CR$^{50}$R$^{51}$)$_v$heterocycloalkyl--

Column 281, Line 13:
In Claim 15, replace "-NR$^{32}$(cR$^{30}$R$^{31}$)$_w$NR$^{32}$R$^{33}$" with -- -NR$^{32}$(CR$^{30}$R$^{31}$)$_w$NR$^{32}$R$^{33}$--

Column 281, Line 14:
In Claim 15, replace "-(CR$^{30}$R$^{31}$)dNR$^{32}$R$^{33}$" with -- -(CR$^{30}$R$^{31}$)$_v$NR$^{32}$R$^{33}$--

Column 281, Line 15:
In Claim 15, replace "-NR$^{32}$(cR$^{30}$R$^{31}$)$_v$C(=O)NR$^{32}$R$^{33}$" with -- -NR$^{32}$(CR$^{30}$R$^{31}$)$_v$C(=O)NR$^{32}$R$^{33}$--